United States Patent
Yam et al.

(10) Patent No.: US 11,993,658 B2
(45) Date of Patent: May 28, 2024

(54) ANTI-BCMA ANTIBODIES AND TREATMENT METHODS

(71) Applicant: SUTRO BIOPHARMA, INC., South San Francisco, CA (US)

(72) Inventors: Alice Yam, South San Francisco, CA (US); Ryan Stafford, South San Francisco, CA (US); Xiaofan Li, South San Francisco, CA (US); Junhao Yang, South San Francisco, CA (US); Stephanie Armstrong, South San Francisco, CA (US); Abigail Yu, South San Francisco, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 216 days.

(21) Appl. No.: 17/041,349

(22) PCT Filed: Mar. 25, 2019

(86) PCT No.: PCT/US2019/023844
§ 371 (c)(1),
(2) Date: Sep. 24, 2020

(87) PCT Pub. No.: WO2019/190969
PCT Pub. Date: Oct. 3, 2019

(65) Prior Publication Data
US 2021/0130483 A1 May 6, 2021

Related U.S. Application Data

(60) Provisional application No. 62/648,266, filed on Mar. 26, 2018.

(51) Int. Cl.
*A61K 39/395* (2006.01)
*C07K 16/28* (2006.01)

(52) U.S. Cl.
CPC ...... *C07K 16/2878* (2013.01); *C07K 2317/55* (2013.01); *C07K 2317/622* (2013.01); *C07K 2317/73* (2013.01); *C07K 2317/92* (2013.01)

(58) Field of Classification Search
None
See application file for complete search history.

(56) References Cited

U.S. PATENT DOCUMENTS 10,072,088 B2 * 9/2018 Pillarisetti .......... C07K 16/2878
10,465,009 B2 * 11/2019 Armitage ................ A61N 5/10
10,683,369 B2 * 6/2020 Vu ........................... A61P 35/02
2022/0323599 A1 * 10/2022 Lee .................... C07K 16/2896
2022/0362394 A1 * 11/2022 Lee ........................ A61P 35/00
2022/0401569 A1 * 12/2022 Wu ..................... C07K 16/2878

FOREIGN PATENT DOCUMENTS

| WO | WO 2014/089335 A2 | 6/2014 |
| WO | WO 2016/090327 A2 | 6/2016 |
| WO | WO 2016/166629 A1 | 10/2016 |

OTHER PUBLICATIONS

Mohyuddin et al., Rethinking mechanisms of neurotoxicity with BCMA directed therapy, Crit. Rev. Oncol. Hematol. 166:103453, doi.org/10.1016/j.critrevonc.2021.103453, 5 pages, Aug. 2021.*
Chen et al., Enhancement and destruction of antibody function by somatic mutation: unequal occurrence is controlled by V gene combinatorial associations, EMBO J., 14 (12): 2784-2794, 1995.*
MacCallum et al., Antibody-antigen interactions: contact analysis and binding site topography, J. Mol. Biol. 262:732-745, 1996.*
Lamminmaki et al., Chrystal structure of a recombinant anti-estradiol Fab fragment in complex with the 17beta-estradiol, J. Blol. Chem. 276:36687-94, 2001.*
Herold et al., Determinants of the assembly and function of antibody variable domains, Scientific Reports, 7:12276, DOI:10.1038/s41598-017-12519-9, Sep. 2017.*
Nezlin, RS, Biochemistry of Antibodies, Plenum Press:New York, p. 160, 1970.*
Kranz et al., Restricted reassociation of heavy and light chains from hapten-specific monoclonal antibodies, Proc. Natl. Acad. Sci., USA, 78(9):5807-5811, 1981.*
Mohan et al., Risk of Infections with BCMA-Directed Immunotherapy in Multiple Myeloma, Blood, 138 (Suppl 1):1626, doi.org/10.1182/blood-2021-148223, 2021.*
International Search Report and Written Opinion of PCT/US2019/023844 dated Sep. 3, 2019; 19 pages.
Fellouse et al., "High-throughput Generation of Synthetic Antibodies from Highly Functional Minimalist Phage-displayed Libraries", Journal of Molecular Biology, Academic Press, United Kingdom, Oct. 3, 2007, vol. 373, No. 4, pp. 924-940.
Sidhu et al., "Phage-displayed Antibody Libraries of Synthetic Heavy Chain Complementarity Determining Regions", Journal of Molecular Bio, Academic Press, United Kingdom, Apr. 23, 2004, vol. 338, No. 2, pp. 299-310.

* cited by examiner

*Primary Examiner* — Claire Kaufman
(74) *Attorney, Agent, or Firm* — SQUIRE PATTON BOGGS (US) LLP

(57) ABSTRACT

The present disclosure relates to antibodies that selectively bind to B-cell maturation antigen (BCMA) and its isoforms and homologs, and compositions comprising the antibodies. Also provided are methods of using the antibodies, such as therapeutic and diagnostic methods.

16 Claims, 4 Drawing Sheets
Specification includes a Sequence Listing.

| SEQ ID NO: | Molecule | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 411 | 2137-C07 | E | V | Q | L | V | E | S | G | G | G | L | V | Q | P | G | G | S | L | R | L | S | C | A | A | S | G | F | N | I | S | G | S | G | I | H | W | V | R | Q | A | P | G |
| 412 | 2265-F06 | E | V | Q | L | V | E | S | G | G | G | L | V | Q | P | G | G | S | L | R | L | S | C | A | A | S | G | F | N | I | S | Y | P | G | I | H | W | V | R | Q | A | P | G |
| 413 | 2265-F05 | E | V | Q | L | V | E | S | G | G | G | L | V | Q | P | G | G | S | L | R | L | S | C | A | A | S | G | F | N | I | I | A | P | G | I | H | W | V | R | Q | A | P | G |
| 414 | 2265-F02 | E | V | Q | L | V | E | S | G | G | G | L | V | Q | P | G | G | S | L | R | L | S | C | A | A | S | G | F | N | I | S | A | P | G | I | H | W | V | R | Q | A | P | G |
| 415 | 2265-B06 | E | V | Q | L | V | E | S | G | G | G | L | V | Q | P | G | G | S | L | R | L | S | C | A | A | S | G | F | N | I | R | V | S | G | I | H | W | V | R | Q | A | P | G |
| 416 | 2265-A09 | E | V | Q | L | V | E | S | G | G | G | L | V | Q | P | G | G | S | L | R | L | S | C | A | A | S | G | F | N | I | I | G | P | G | I | H | W | V | R | Q | A | P | G |
| 417 | 2265-F03 | E | V | Q | L | V | E | S | G | G | G | L | V | Q | P | G | G | S | L | R | L | S | C | A | A | S | G | F | N | I | R | G | P | G | I | H | W | V | R | Q | A | P | G |
| 418 | 2265-E02 | E | V | Q | L | V | E | S | G | G | G | L | V | Q | P | G | G | S | L | R | L | S | C | A | A | S | G | F | N | I | Y | V | S | G | I | H | W | V | R | Q | A | P | G |
| 419 | 2265-D11 | E | V | Q | L | V | E | S | G | G | G | L | V | Q | P | G | G | S | L | R | L | S | C | A | A | S | G | F | N | I | S | G | P | G | I | H | W | V | R | Q | A | P | G |
| 420 | 2265-D05 | E | V | Q | L | V | E | S | G | G | G | L | V | Q | P | G | G | S | L | R | L | S | C | A | A | S | G | F | N | I | S | G | P | G | I | H | W | V | R | Q | A | P | G |
| 421 | 2265-C03 | E | V | Q | L | V | E | S | G | G | G | L | V | Q | P | G | G | S | L | R | L | S | C | A | A | P | G | F | N | I | S | Y | P | G | I | H | W | V | R | Q | A | P | G |
| 422 | 2265-C02 | E | V | Q | L | V | E | S | G | G | G | L | V | Q | P | G | G | S | L | R | L | S | C | A | A | S | G | F | N | I | G | V | S | G | I | H | W | V | R | Q | A | P | G |
| 423 | 2265-A06 | E | V | Q | L | V | E | S | G | G | G | L | V | Q | P | G | G | S | L | R | L | S | C | A | A | S | G | F | N | I | Y | R | S | G | I | H | W | V | R | Q | A | P | G |
| 424 | 2137-A05 | E | V | Q | L | V | E | S | G | G | G | L | V | Q | P | G | G | S | L | R | L | S | C | A | A | S | G | F | N | I | N | N | S | Y | I | H | W | V | R | Q | A | P | G |
| 425 | 2288-A03 | E | V | Q | L | V | E | S | G | G | G | L | V | Q | P | G | G | S | L | R | L | S | C | A | A | S | G | F | N | I | N | N | S | W | I | H | W | V | R | Q | A | P | G |
| 426 | 2190-B01 | E | V | Q | L | V | E | S | G | G | G | L | V | Q | P | G | G | S | L | R | L | S | C | A | A | S | G | F | N | I | S | S | Y | W | I | H | W | V | R | Q | A | P | G |
| 427 | 2290-G01 | E | V | Q | L | V | E | S | G | G | G | L | V | Q | P | G | G | S | L | R | L | S | C | A | A | S | G | F | N | I | S | P | Y | W | I | H | W | V | R | Q | A | P | G |
| 428 | 2290-D02 | E | V | Q | L | V | E | S | G | G | G | L | V | Q | P | G | G | S | L | R | L | S | C | A | A | S | G | F | N | I | S | S | Y | W | I | H | W | V | R | Q | A | P | G |
| 429 | 2290-C07 | E | V | Q | L | V | E | S | G | G | G | L | V | Q | P | G | G | S | L | R | L | S | C | A | A | S | G | F | N | I | T | Y | D | W | I | H | W | V | R | Q | A | P | G |
| 430 | 2290-D05 | E | V | Q | L | V | E | S | G | G | G | L | V | Q | P | G | G | S | L | R | L | S | C | A | A | S | G | F | N | I | A | S | R | W | I | H | W | V | R | Q | A | P | G |
| 431 | 2290-C08 | E | V | Q | L | V | E | S | G | G | G | L | V | Q | P | G | G | S | L | R | L | S | C | A | A | S | G | F | N | I | Q | P | Y | W | I | H | W | V | R | Q | A | P | G |
| 432 | 2290-A02 | E | V | Q | L | V | E | S | G | G | G | L | V | Q | P | G | G | S | L | R | L | S | C | A | A | S | G | F | N | I | S | T | R | W | I | H | W | V | R | Q | A | P | G |
| 433 | 2213-A06 | E | V | Q | L | V | E | S | G | G | G | L | V | Q | P | G | G | S | L | R | L | S | C | A | A | S | G | F | N | I | S | S | Y | A | I | H | W | V | R | Q | A | P | G |
| 434 | 2291-G05 | E | V | Q | L | V | E | S | G | G | G | L | V | Q | P | G | G | S | L | R | L | S | C | A | A | S | G | F | N | I | A | A | Y | T | I | H | W | V | R | Q | A | P | G |
| 435 | 2291-E06 | E | V | Q | L | V | E | S | G | G | G | L | V | Q | P | G | G | S | L | R | L | S | C | A | A | S | G | F | N | I | S | P | Y | T | I | H | W | V | R | Q | A | P | G |

| SEQ ID NO: | Molecule | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 411 | 2137-C07 | K | G | L | E | W | V | G | F | I | N | P | : | A | G | G | Y | T | D | Y | A | D | S | V | K | G | R | F | T | I | S | A | D | T | S | K | N | T | A | Y | L | Q | M | N |
| 412 | 2265-F06 | K | G | L | E | W | V | G | F | I | N | P | : | A | G | G | Y | T | D | Y | A | D | S | V | K | G | R | F | T | I | S | A | D | T | S | K | N | T | A | Y | L | Q | M | N |
| 413 | 2265-F05 | K | G | L | E | W | V | G | F | I | N | P | : | A | G | G | Y | T | D | Y | A | D | S | V | K | G | R | F | T | I | S | A | D | T | S | K | N | T | A | Y | L | Q | M | N |
| 414 | 2265-F02 | K | G | L | E | W | V | G | F | I | N | P | : | A | G | G | Y | T | D | Y | A | D | S | V | K | G | R | F | T | I | S | A | D | T | S | K | N | T | A | Y | L | Q | M | N |
| 415 | 2265-B06 | K | G | L | E | W | V | G | F | I | N | P | : | A | G | G | Y | T | D | Y | A | D | S | V | K | G | R | F | T | I | S | A | D | T | S | K | N | T | A | Y | L | Q | M | N |
| 416 | 2265-A09 | K | G | L | E | W | V | G | F | I | N | P | : | A | G | G | Y | T | D | Y | A | D | S | V | K | G | R | F | T | I | S | A | D | T | S | K | N | T | A | Y | L | Q | M | N |
| 417 | 2265-F03 | K | G | L | E | W | V | G | F | I | S | P | : | A | A | G | Y | T | D | Y | A | D | S | V | K | G | R | F | T | I | S | A | D | T | S | K | N | T | A | Y | L | Q | M | N |
| 418 | 2265-E02 | K | G | L | E | W | V | G | F | I | N | P | : | A | G | G | Y | T | D | Y | A | D | S | V | K | G | R | F | T | I | S | A | D | T | S | K | N | T | A | Y | L | Q | T | N |
| 419 | 2265-D11 | K | G | L | E | W | V | G | F | I | N | P | : | A | A | G | Y | T | D | Y | A | D | S | V | K | G | R | F | T | I | S | A | D | T | S | K | N | T | A | Y | L | Q | M | N |
| 420 | 2265-D05 | K | G | L | E | W | V | G | F | I | N | P | : | A | A | G | Y | T | D | Y | A | D | S | V | K | G | R | F | A | I | S | A | D | T | S | K | N | T | A | Y | L | Q | M | N |
| 421 | 2265-C03 | K | G | L | E | W | V | G | F | I | N | P | : | A | G | G | Y | T | D | Y | A | D | S | V | K | G | R | F | T | I | S | A | D | T | S | K | N | T | A | Y | L | Q | M | N |
| 422 | 2265-C02 | K | G | L | E | W | V | G | F | I | N | P | : | A | G | G | Y | T | D | Y | A | G | S | V | K | G | R | F | T | I | S | A | D | T | S | K | N | T | A | Y | L | Q | M | N |
| 423 | 2265-A06 | K | G | L | E | W | V | G | F | I | N | P | : | A | G | G | Y | T | D | Y | A | D | S | V | K | G | R | F | T | I | S | A | D | T | S | K | N | T | A | Y | L | Q | M | N |
| 424 | 2137-A05 | K | G | L | E | W | V | G | W | I | Y | P | : | Y | S | G | Y | T | N | Y | A | D | S | V | K | G | R | F | T | I | S | A | D | T | S | K | N | T | A | Y | L | Q | M | N |
| 425 | 2288-A03 | K | G | L | E | W | V | G | W | I | Y | P | : | Y | I | G | F | T | E | Y | A | D | S | V | K | G | R | F | T | I | S | A | D | T | S | K | N | T | A | Y | L | Q | M | N |
| 426 | 2190-B01 | K | G | L | E | W | V | G | V | I | T | P | : | S | G | G | Y | T | Y | Y | A | D | S | V | K | G | R | F | T | I | S | A | D | T | S | K | N | T | A | Y | L | Q | M | N |
| 427 | 2290-G01 | K | G | L | E | W | V | G | V | I | T | P | : | P | S | G | F | T | Y | Y | A | D | S | V | K | G | R | F | T | I | S | A | D | T | S | K | N | T | A | Y | L | Q | V | N |
| 428 | 2290-D02 | K | G | L | E | W | M | G | V | I | T | P | : | A | A | G | Y | T | Y | Y | A | D | S | V | K | G | R | F | T | I | S | A | D | T | S | K | N | T | A | Y | L | Q | M | N |
| 429 | 2290-C07 | K | G | L | E | W | V | G | V | I | T | P | : | F | D | G | Y | T | Y | Y | A | D | S | V | K | G | H | F | T | I | S | A | D | T | S | K | N | T | A | Y | L | Q | M | N |
| 430 | 2290-D05 | K | G | L | E | W | V | G | V | I | T | P | : | S | A | G | Y | T | Y | Y | A | D | S | V | K | G | R | F | T | I | S | A | D | T | S | K | N | T | A | Y | L | Q | M | N |
| 431 | 2290-C08 | K | G | L | E | W | V | G | V | I | T | P | : | P | S | G | Y | T | Y | Y | A | D | S | V | K | G | R | F | T | I | S | A | D | T | S | K | N | T | A | Y | L | Q | M | N |
| 432 | 2290-A02 | K | G | L | E | W | V | G | V | I | T | P | : | S | A | G | Y | T | H | Y | A | D | S | V | K | G | R | F | T | I | S | A | G | T | S | K | N | T | A | Y | L | Q | M | N |
| 433 | 2213-A06 | K | G | L | E | W | V | G | V | I | S | P | : | Y | G | G | Y | T | E | Y | A | D | S | V | K | G | R | F | T | I | S | A | D | T | S | K | N | T | A | Y | L | Q | M | N |
| 434 | 2291-G05 | K | G | L | E | W | V | G | W | I | T | P | : | Y | G | G | Y | T | E | Y | A | D | S | V | K | G | R | F | T | I | S | A | D | T | S | K | N | T | A | Y | L | Q | M | N |
| 435 | 2291-E06 | K | G | L | E | W | V | A | H | I | F | P | : | S | G | G | Y | T | D | Y | A | D | S | V | K | G | R | F | T | I | S | A | D | T | S | K | N | T | A | Y | L | Q | M | N |

| SEQ ID NO: | Molecule | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 | 126 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 411 | 2137-C07 | S | L | R | A | E | D | T | A | V | Y | Y | C | A | R | D | Y | V | Y | Q | Y | W | : | : | : | T | Y | V | L | D | Y | W | G | Q | G | T | L | V | T | V | S | S |
| 412 | 2265-F06 | S | L | R | A | E | D | T | A | V | Y | Y | C | A | R | D | Y | I | L | Q | Y | W | : | : | : | T | Y | V | L | D | Y | W | G | Q | G | T | L | V | T | V | S | S |
| 413 | 2265-F05 | S | L | R | A | E | D | T | A | V | Y | Y | C | A | R | D | Y | V | N | A | Y | W | : | : | : | T | Y | V | L | D | Y | W | G | Q | G | T | L | V | T | V | S | S |
| 414 | 2265-F02 | S | L | R | A | E | D | T | A | V | Y | Y | C | A | R | D | Y | I | R | Q | Y | W | : | : | : | T | Y | V | L | D | Y | W | G | Q | G | T | L | V | T | V | S | S |
| 415 | 2265-B06 | S | L | R | A | E | D | T | A | V | Y | Y | C | A | R | D | Y | V | Q | A | Y | W | : | : | : | T | Y | V | L | D | Y | W | G | Q | G | T | L | V | T | V | S | S |
| 416 | 2265-A09 | S | L | R | A | E | D | T | A | V | Y | Y | C | A | R | D | Y | V | V | N | Y | W | : | : | : | T | Y | V | L | D | Y | W | G | Q | G | T | L | V | T | V | S | S |
| 417 | 2265-F03 | S | L | R | A | E | D | T | A | V | Y | Y | C | A | R | D | F | V | Q | S | Y | W | : | : | : | T | Y | V | L | D | Y | W | G | Q | G | T | L | V | T | V | S | S |
| 418 | 2265-E02 | S | L | R | A | E | D | T | A | V | Y | Y | C | A | R | D | Y | V | V | Q | Y | W | : | : | : | T | Y | V | L | D | Y | W | G | Q | G | T | L | V | T | V | S | S |
| 419 | 2265-D11 | S | L | R | A | E | D | T | A | V | Y | Y | C | A | R | D | Y | I | Y | Q | Y | W | : | : | : | T | Y | V | L | D | Y | W | G | Q | G | T | L | V | T | V | S | S |
| 420 | 2265-D05 | S | L | R | A | E | D | T | A | V | Y | Y | C | A | R | D | F | V | V | A | Y | W | : | : | : | T | Y | V | L | D | Y | W | G | Q | G | T | L | V | T | V | S | S |
| 421 | 2265-C03 | S | L | R | A | E | D | T | A | V | Y | Y | C | A | R | D | Y | V | P | Q | Y | W | : | : | : | T | Y | V | L | D | Y | W | G | Q | G | T | L | V | T | V | S | S |
| 422 | 2265-C02 | S | L | R | A | E | D | T | A | V | Y | Y | C | A | R | D | Y | I | Y | S | Y | W | : | : | : | T | Y | V | L | D | Y | W | G | Q | G | T | L | V | T | V | S | S |
| 423 | 2265-A06 | S | L | R | A | E | D | T | A | V | Y | Y | C | A | R | D | Y | V | P | Q | Y | W | : | : | : | T | Y | V | L | D | Y | W | G | Q | G | T | L | V | T | V | S | S |
| 424 | 2137-A05 | S | L | R | A | E | D | T | A | V | Y | Y | C | A | R | D | Y | G | P | W | Y | G | : | : | : | T | G | V | L | D | Y | W | G | Q | G | T | L | V | T | V | S | S |
| 425 | 2288-A03 | S | L | R | A | E | D | T | A | V | Y | Y | C | A | R | D | Y | D | L | R | Y | L | : | : | : | T | G | V | L | D | Y | W | G | Q | G | T | L | V | T | V | S | S |
| 426 | 2190-B01 | S | L | R | A | E | D | T | A | V | Y | Y | C | A | R | D | L | G | G | G | Y | W | : | : | : | V | G | F | F | D | Y | W | G | Q | G | T | L | V | T | V | S | S |
| 427 | 2290-G01 | S | L | R | A | E | D | T | A | V | Y | Y | C | A | R | D | L | G | S | R | Y | W | : | : | : | V | G | F | S | D | Y | W | G | Q | G | T | L | V | T | V | S | S |
| 428 | 2290-D02 | S | L | R | A | E | D | T | A | V | Y | Y | C | A | R | D | L | G | H | R | Y | W | : | : | : | V | G | F | S | D | Y | W | G | Q | G | T | L | V | T | V | S | S |
| 429 | 2290-C07 | S | L | R | A | E | D | T | A | V | Y | Y | C | A | R | D | M | G | V | G | Y | W | : | : | : | V | G | F | S | D | Y | W | G | Q | G | T | L | V | T | V | S | S |
| 430 | 2290-D05 | S | L | R | A | E | D | T | A | V | Y | Y | C | A | R | D | L | G | Y | G | Y | W | : | : | : | V | G | F | S | D | Y | W | G | Q | G | T | L | V | T | V | S | S |
| 431 | 2290-C08 | S | L | R | A | E | D | T | A | V | Y | Y | C | A | R | D | W | G | V | G | Y | W | : | : | : | V | G | F | S | D | Y | W | G | Q | G | T | L | V | T | V | S | S |
| 432 | 2290-A02 | S | L | R | A | E | D | T | A | V | Y | Y | C | A | R | D | L | G | S | R | Y | W | : | : | : | V | G | F | V | D | Y | W | G | Q | G | T | L | V | T | V | S | S |
| 433 | 2213-A06 | S | L | R | A | E | D | T | A | V | Y | Y | C | A | R | D | F | Y | D | R | Y | S | : | : | : | T | Y | V | L | D | Y | W | G | Q | G | T | L | V | T | V | S | S |
| 434 | 2291-G05 | S | L | R | A | E | D | T | A | V | Y | Y | C | A | R | D | F | H | D | R | Y | A | : | : | : | T | F | V | L | D | Y | W | G | Q | G | T | L | V | T | V | S | S |
| 435 | 2291-E06 | S | L | R | A | E | D | T | A | V | Y | Y | C | A | R | D | F | Y | D | R | Y | A | : | : | : | T | Y | V | L | D | Y | W | G | Q | G | T | L | V | T | V | S | S |

":" represents a gap in the sequence alignment

FIG 2

| SEQ ID NO: | Molecule | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 436 | 2291-D07 | E | V | Q | L | V | E | S | G | G | G | L | V | Q | P | G | G | S | L | R | L | S | C | A | A | S | G | F | N | I | K | D | T | Y | I | H | W | V | R | Q | A | P | G |
| 437 | 2291-F10 | E | V | Q | L | V | E | S | G | G | G | L | V | Q | P | G | G | S | L | R | L | S | C | A | A | S | G | F | N | I | D | P | Y | T | I | H | W | V | R | Q | A | P | G |
| 438 | 2291-A04 | E | V | Q | L | V | E | S | G | G | G | L | V | Q | P | G | G | S | L | R | L | S | C | A | A | S | G | F | N | I | S | S | Y | G | I | H | W | V | R | Q | A | P | G |
| 439 | 2291-A01 | E | V | Q | L | V | E | S | G | G | G | L | V | Q | P | G | G | S | L | R | L | S | C | A | A | S | G | F | N | I | Q | P | Y | T | I | H | W | A | R | Q | A | P | G |
| 440 | 9A8 | A | V | T | L | D | E | S | G | G | G | L | Q | T | P | G | G | T | L | S | L | V | C | K | A | S | G | F | T | F | S | S | F | N | M | F | W | V | R | Q | A | P | G |
| 441 | 10G5 | A | V | T | L | D | E | S | G | G | G | L | Q | T | P | G | G | V | L | S | L | V | C | K | A | S | G | F | T | F | S | S | F | N | M | F | W | V | R | Q | A | P | G |
| 442 | 11D6 | A | V | T | L | D | E | S | G | G | G | L | Q | T | P | G | G | T | L | S | L | V | C | K | A | S | G | F | T | F | S | S | F | N | M | F | W | V | R | Q | A | P | G |
| 443 | h11D6-Hc4 | E | V | Q | L | V | E | S | G | G | G | L | V | Q | P | G | G | S | L | R | L | S | C | A | A | S | G | F | T | F | S | S | F | N | M | F | W | V | R | Q | A | P | G |
| 444 | h11D6-Hc3 | Q | V | Q | L | V | E | S | G | G | G | V | V | Q | P | G | R | S | L | R | L | S | C | A | A | S | G | F | T | F | S | S | F | N | M | F | W | V | R | Q | A | P | G |
| 445 | h11D6-Hc2 | E | V | Q | L | L | E | S | G | G | G | L | V | Q | P | G | G | S | L | R | L | S | C | A | A | S | G | F | T | F | S | S | F | N | M | F | W | V | R | Q | A | P | G |
| 446 | h11D6-Hc1 | E | V | Q | L | V | E | S | G | G | G | L | V | K | P | G | G | S | L | R | L | S | C | A | A | S | G | F | T | F | S | S | F | N | M | F | W | V | R | Q | A | P | G |
| 447 | 10F4 | A | V | T | L | D | E | S | G | G | G | L | Q | T | P | G | G | A | L | S | L | V | C | K | A | S | G | F | T | F | S | G | Y | N | M | G | W | V | R | Q | A | P | G |
| 448 | h10F4-Hc4 | E | V | Q | L | V | E | S | G | G | G | L | V | Q | P | G | G | S | L | R | L | S | C | A | A | S | G | F | T | F | S | G | Y | N | M | G | W | V | R | Q | A | P | G |
| 449 | h10F4-Hc3 | Q | V | Q | L | V | E | S | G | G | G | V | V | Q | P | G | R | S | L | R | L | S | C | A | A | S | G | F | T | F | S | G | Y | N | M | G | W | V | R | Q | A | P | G |
| 450 | h10F4-Hc2 | E | V | Q | L | L | E | S | G | G | G | L | V | Q | P | G | G | S | L | R | L | S | C | A | A | S | G | F | T | F | S | G | Y | N | M | G | W | V | R | Q | A | P | G |
| 451 | h10F4-Hc1 | E | V | Q | L | V | E | S | G | G | G | L | V | K | P | G | G | S | L | R | L | S | C | A | A | S | G | F | T | F | S | G | Y | N | M | G | W | V | R | Q | A | P | G |
| 452 | 9A5 | A | V | T | L | D | E | S | G | G | G | L | Q | T | P | G | G | A | V | S | L | V | C | K | A | S | G | F | S | I | S | D | Y | G | M | G | W | M | R | Q | A | P | G |
| 453 | 9E12 | A | V | T | L | D | E | S | G | G | G | L | Q | T | P | G | G | L | S | L | V | C | K | A | S | G | F | T | F | S | D | Y | G | L | G | W | M | R | Q | A | P | G | |
| 454 | 9H1 | A | V | T | L | D | E | S | G | G | G | L | Q | T | P | G | G | A | L | S | L | V | C | K | G | S | G | F | T | F | S | D | Y | G | M | G | W | M | R | Q | A | P | G |
| 455 | 10H1 | A | V | T | L | D | E | S | G | G | G | L | Q | T | P | G | G | A | L | S | L | V | C | K | A | S | G | F | T | F | S | G | Y | G | M | G | W | M | R | Q | A | P | G |
| 456 | 10E10 | A | V | T | L | D | E | S | G | G | G | L | Q | T | P | G | G | G | L | S | L | V | C | K | A | S | G | F | T | F | S | G | Y | G | M | G | W | M | R | Q | A | P | G |
| 457 | h10H1-Hc4 | E | V | Q | L | V | E | S | G | G | G | L | V | Q | P | G | G | S | L | R | L | S | C | A | A | S | G | F | T | F | S | G | Y | G | M | G | W | V | R | Q | A | P | G |
| 458 | h10H1-Hc3 | Q | V | Q | L | V | E | S | G | G | G | V | V | Q | P | G | R | S | L | R | L | S | C | A | A | S | G | F | T | F | S | G | Y | G | M | G | W | V | R | Q | A | P | G |
| 459 | h10H1-Hc2 | E | V | Q | L | L | E | S | G | G | G | L | V | Q | P | G | G | S | L | R | L | S | C | A | A | S | G | F | T | F | S | G | Y | G | M | G | W | V | R | Q | A | P | G |
| 460 | h10H1-Hc1 | E | V | Q | L | V | E | S | G | G | G | L | V | K | P | G | G | S | L | R | L | S | C | A | A | S | G | F | T | F | S | G | Y | G | M | G | W | V | R | Q | A | P | G |

| SEQ ID NO: | Molecule | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 436 | 2291-D07 | K | G | L | E | W | V | G | V | I | S | P | : | Y | D | G | Y | T | E | Y | A | D | S | V | K | G | R | F | T | I | S | A | D | T | S | K | N | T | A | Y | L | Q | M | N |
| 437 | 2291-F10 | K | G | L | E | W | V | G | W | I | S | P | : | Y | D | G | Y | T | E | Y | A | D | S | V | K | G | R | F | T | I | S | A | D | T | S | K | N | T | A | Y | L | Q | M | N |
| 438 | 2291-A04 | K | G | L | E | W | V | G | F | I | S | P | : | Y | D | G | Y | T | E | Y | A | D | S | V | K | G | R | F | T | I | S | A | G | T | S | K | N | T | A | Y | L | Q | M | N |
| 439 | 2291-A01 | K | G | L | E | W | V | A | H | I | S | P | : | Y | D | G | Y | T | D | Y | A | D | S | V | K | G | R | F | T | I | S | A | D | T | S | K | N | T | A | Y | L | Q | M | N |
| 440 | 9A8 | K | G | L | E | W | V | A | Y | I | R | N | D | : | G | N | S | A | S | Y | G | P | A | V | K | G | R | A | T | I | S | R | D | N | G | Q | S | T | V | R | L | Q | L | N |
| 441 | 10G5 | K | G | L | E | W | V | A | Y | I | S | N | D | : | G | S | S | T | S | Y | G | P | A | V | K | G | R | A | T | I | S | R | D | N | G | Q | S | T | V | R | L | Q | L | N |
| 442 | 11D6 | E | G | L | E | W | V | A | Y | I | R | N | D | : | G | R | S | T | S | Y | G | P | A | V | K | G | R | A | T | I | S | R | D | N | G | Q | S | T | V | R | L | Q | L | N |
| 443 | h11D6-Hc4 | K | G | L | E | W | V | A | Y | I | R | N | : | D | G | R | S | T | S | Y | V | D | S | V | K | G | R | F | T | I | S | R | D | N | A | K | S | S | V | Y | Y | Q | M | N |
| 444 | h11D6-Hc3 | K | G | L | E | W | V | A | Y | I | R | N | : | D | G | R | S | T | S | Y | A | D | S | V | K | G | R | F | T | I | S | R | D | N | S | K | S | T | V | Y | Y | Q | M | N |
| 445 | h11D6-Hc2 | K | G | L | E | W | V | A | Y | I | R | N | : | D | G | R | S | T | S | Y | A | D | S | V | K | G | R | F | T | I | S | R | D | N | S | K | S | T | V | V | Y | Q | M | N |
| 446 | h11D6-Hc1 | K | G | L | E | W | V | A | Y | I | R | N | : | D | G | R | S | T | S | Y | A | A | P | V | K | G | R | F | T | I | S | R | D | N | S | K | S | T | V | V | Y | Q | M | N |
| 447 | 10F4 | K | G | L | E | Y | V | A | G | I | T | Y | G | T | G | S | Y | T | A | Y | G | A | A | V | K | G | R | A | T | I | S | R | D | N | G | Q | S | T | L | R | L | Q | L | N |
| 448 | h10F4-Hc4 | K | G | L | E | W | V | A | G | I | T | Y | G | T | G | S | Y | T | A | Y | V | D | S | V | K | G | R | F | T | I | S | R | D | N | A | K | S | S | L | Y | Y | Q | M | N |
| 449 | h10F4-Hc3 | K | G | L | E | W | V | A | G | I | T | Y | G | T | G | S | Y | T | A | Y | A | D | S | V | K | G | R | F | T | I | S | R | D | N | S | K | S | T | L | Y | Y | Q | M | N |
| 450 | h10F4-Hc2 | K | G | L | E | W | V | A | G | I | T | Y | G | T | G | S | Y | T | A | Y | A | D | S | V | K | G | R | F | T | I | S | R | D | N | S | K | S | T | L | Y | Y | Q | M | N |
| 451 | h10F4-Hc1 | K | G | L | E | W | V | A | G | I | T | Y | G | T | G | S | Y | T | A | Y | A | A | P | V | K | G | R | F | T | I | S | R | D | N | S | K | S | T | L | Y | Y | Q | M | N |
| 452 | 9A5 | K | G | L | Q | Y | V | A | R | I | D | H | D | : | G | R | Y | T | D | Y | G | A | V | V | K | G | R | A | T | I | S | R | D | N | G | Q | S | T | V | R | L | Q | L | N |
| 453 | 9E12 | K | G | L | E | Y | V | A | R | I | N | S | A | : | G | S | G | T | Y | Y | G | S | A | V | D | G | R | A | T | I | S | R | D | N | G | Q | S | T | V | R | L | Q | L | N |
| 454 | 9H1 | K | G | L | Q | Y | V | A | R | I | N | S | A | : | G | S | D | T | N | Y | G | S | A | V | V | K | G | R | A | T | I | S | R | D | D | G | Q | S | T | V | R | L | Q | L | S |
| 455 | 10H1 | K | G | L | E | Y | V | A | R | I | N | S | A | : | G | S | D | T | D | Y | G | A | A | V | K | G | R | A | T | I | S | R | D | N | G | Q | S | T | V | R | L | Q | L | N |
| 456 | 10E10 | K | G | L | E | Y | V | A | R | I | N | S | G | G | S | S | Y | T | D | Y | G | S | A | V | K | G | R | A | T | I | S | R | D | D | G | Q | S | T | V | R | L | Q | L | N |
| 457 | h10H1-Hc4 | K | G | L | E | W | V | A | R | I | N | S | : | A | G | S | D | T | D | Y | V | D | S | V | K | G | R | F | T | I | S | R | D | N | A | K | S | S | V | Y | Y | Q | M | N |
| 458 | h10H1-Hc3 | K | G | L | E | W | V | A | R | I | N | S | : | A | G | S | D | T | D | Y | A | D | S | V | K | G | R | F | T | I | S | R | D | N | S | K | S | T | V | Y | Y | Q | M | N |
| 459 | h10H1-Hc2 | K | G | L | E | W | V | A | R | I | N | S | : | A | G | S | D | T | D | Y | A | D | S | V | K | G | R | F | T | I | S | R | D | N | S | K | S | T | V | Y | Y | Q | M | N |
| 460 | h10H1-Hc1 | K | G | L | E | W | V | A | R | I | N | S | : | A | G | S | D | T | D | Y | A | A | P | V | K | G | R | F | T | I | S | R | D | N | S | K | S | T | V | Y | Y | Q | M | N |

| SEQ ID NO: | Molecule | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 | 126 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 436 | 2291-D07 | S | L | R | A | E | D | T | A | V | Y | Y | C | A | H | D | F | Y | D | R | Y | S | : | : | : | T | Y | V | L | D | Y | W | G | Q | G | T | L | V | T | V | S | S |
| 437 | 2291-F10 | S | L | R | A | E | D | T | A | V | Y | Y | C | A | R | D | F | Y | D | R | Y | S | : | : | : | T | Y | V | L | D | Y | W | G | Q | G | T | L | V | T | V | S | S |
| 438 | 2291-A04 | S | L | R | A | E | D | T | A | V | Y | Y | C | A | R | D | F | N | D | R | Y | F | : | : | : | T | Y | V | L | D | Y | W | G | Q | G | T | L | V | T | V | S | S |
| 439 | 2291-A01 | S | L | R | A | E | D | T | A | V | Y | Y | C | A | R | D | F | Y | D | R | Y | S | : | : | : | T | Y | V | L | D | Y | W | G | Q | G | T | L | V | T | V | S | S |
| 440 | 9A8 | N | L | R | A | E | D | T | A | T | Y | Y | C | A | K | T | T | C | I | G | S | G | G | C | : | : | : | : | I | D | T | W | G | H | G | T | E | V | I | V | S | S |
| 441 | 10G5 | N | L | R | A | E | D | T | A | T | Y | F | C | A | K | T | T | C | I | G | S | G | G | C | : | : | : | : | I | D | T | W | G | H | G | T | E | V | I | V | S | S |
| 442 | 11D6 | N | L | R | A | E | D | T | G | T | Y | F | C | A | K | T | T | C | V | G | S | G | G | C | : | : | : | : | I | D | T | W | G | H | G | T | E | V | I | V | S | S |
| 443 | h11D6-Hc4 | S | L | R | A | E | D | T | A | V | Y | Y | C | A | K | T | T | C | V | G | S | G | G | C | : | : | : | : | I | D | T | W | G | Q | G | T | L | V | T | V | S | S |
| 444 | h11D6-Hc3 | S | L | R | A | E | D | T | A | V | Y | Y | C | A | K | T | T | C | V | G | S | G | G | C | : | : | : | : | I | D | T | W | G | Q | G | T | L | V | T | V | S | S |
| 445 | h11D6-Hc2 | S | L | R | A | E | D | T | A | V | Y | Y | C | A | K | T | T | C | V | G | S | G | G | C | : | : | : | : | I | D | T | W | G | Q | G | T | L | V | T | V | S | S |
| 446 | h11D6-Hc1 | S | L | K | T | E | D | T | A | V | Y | Y | C | A | K | T | T | C | V | G | S | G | G | C | : | : | : | : | I | D | T | W | G | Q | G | T | L | V | T | V | S | S |
| 447 | 10F4 | N | L | R | A | E | D | T | A | T | Y | Y | C | A | R | G | G | G | L | N | S | Y | G | C | S | G | A | N | I | D | A | W | G | H | G | T | E | V | I | V | S | S |
| 448 | h10F4-Hc4 | S | L | R | A | E | D | T | A | V | Y | Y | C | A | R | G | G | G | L | N | S | Y | G | C | S | G | A | N | I | D | A | W | G | Q | G | T | L | V | T | V | S | S |
| 449 | h10F4-Hc3 | S | L | R | A | E | D | T | A | V | Y | Y | C | A | R | G | G | G | L | N | S | Y | G | C | S | G | A | N | I | D | A | W | G | Q | G | T | L | V | T | V | S | S |
| 450 | h10F4-Hc2 | S | L | R | A | E | D | T | A | V | Y | Y | C | A | R | G | G | G | L | N | S | Y | G | C | S | G | A | N | I | D | A | W | G | Q | G | T | L | V | T | V | S | S |
| 451 | h10F4-Hc1 | S | L | K | T | E | D | T | A | V | Y | Y | C | A | R | G | G | G | L | N | S | Y | G | C | S | G | A | N | I | D | A | W | G | Q | G | T | L | V | T | V | S | S |
| 452 | 9A5 | N | L | R | A | E | D | T | G | T | Y | Y | C | T | R | G | G | G | : | : | : | : | : | : | : | : | A | A | S | I | D | T | W | G | H | G | T | E | V | I | V | S | S |
| 453 | 9E12 | N | L | R | A | E | D | T | G | T | Y | Y | C | T | R | G | G | G | : | : | : | : | : | : | : | : | G | A | S | I | D | G | W | G | H | G | T | E | V | I | V | S | S |
| 454 | 9H1 | S | L | R | A | E | D | T | G | T | Y | Y | C | T | R | G | G | G | : | : | : | : | : | : | : | : | G | A | S | I | D | G | W | G | H | G | T | E | V | I | V | S | S |
| 455 | 10H1 | N | L | R | A | E | D | T | A | T | Y | F | C | T | R | G | G | G | : | : | : | : | : | : | : | : | G | A | S | I | D | G | W | G | H | G | T | E | V | I | V | S | S |
| 456 | 10E10 | N | L | R | A | E | D | T | G | T | Y | Y | C | T | R | G | G | G | : | : | : | : | : | : | : | : | G | A | S | I | D | G | W | G | H | G | T | E | V | I | V | S | S |
| 457 | h10H1-Hc4 | S | L | R | A | E | D | T | A | V | Y | Y | C | T | R | G | G | G | : | : | : | : | : | : | : | : | G | A | S | I | D | G | W | G | Q | G | T | L | V | T | V | S | S |
| 458 | h10H1-Hc3 | S | L | R | A | E | D | T | A | V | Y | Y | C | T | R | G | G | G | : | : | : | : | : | : | : | : | G | A | S | I | D | G | W | G | Q | G | T | L | V | T | V | S | S |
| 459 | h10H1-Hc2 | S | L | R | A | E | D | T | A | V | Y | Y | C | T | R | G | G | G | : | : | : | : | : | : | : | : | G | A | S | I | D | G | W | G | Q | G | T | L | V | T | V | S | S |
| 460 | h10H1-Hc1 | S | L | K | T | E | D | T | A | V | Y | Y | C | T | R | G | G | G | : | : | : | : | : | : | : | : | G | A | S | I | D | G | W | G | Q | G | T | L | V | T | V | S | S |

":" represents a gap in the sequence alignment

Table 1 (positions 1-45):

| SEQ ID NO: | Molecule | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 461 | trastuzumab | D | I | Q | M | T | Q | S | P | S | S | L | S | A | S | V | G | D | R | V | T | I | T | C | R | A | S | Q | D | V | : | : | : | N | T | A | V | A | W | Y | Q | Q | K | : | P | G | K |
| 462 | 9A8 | : | : | A | L | T | Q | : | P | S | S | V | S | A | N | P | G | E | T | V | K | I | T | C | S | G | G | S | S | : | : | : | : | : | D | Y | G | W | F | Q | Q | K | S | P | G | S |
| 463 | 10G5 | : | : | A | L | T | Q | : | P | S | S | V | S | A | N | P | G | E | T | V | K | I | T | C | S | G | G | N | Y | : | : | : | : | : | D | Y | G | W | Y | Q | Q | K | S | P | G | S |
| 464 | 11D6 | : | : | A | L | T | Q | : | P | S | S | V | S | A | N | P | G | E | T | V | K | I | T | C | S | G | G | N | S | : | : | : | : | : | D | Y | G | W | F | Q | Q | K | S | P | G | S |
| 465 | h11D6-Lc4 | S | Y | V | L | T | Q | : | P | P | S | V | S | V | A | P | G | K | T | A | R | I | T | C | S | G | G | N | S | : | : | : | : | : | D | Y | G | W | Y | Q | Q | K | : | P | G | Q |
| 466 | h11D6-Lc3 | S | Y | E | L | T | Q | : | P | P | S | V | S | V | S | P | G | Q | T | A | S | I | T | C | S | G | G | N | S | : | : | : | : | : | D | Y | G | W | Y | Q | Q | K | : | P | G | Q |
| 467 | h11D6-Lc2 | Q | S | V | L | T | Q | : | P | P | S | V | S | A | A | P | G | Q | K | V | T | I | S | C | S | G | G | N | S | : | : | : | : | : | D | Y | G | W | Y | Q | Q | L | : | P | G | T |
| 468 | h11D6-Lc1 | D | I | Q | M | T | Q | S | P | S | S | V | S | A | S | V | G | D | R | V | T | I | T | C | S | G | G | N | S | : | : | : | : | : | D | Y | G | W | Y | Q | Q | K | : | P | G | K |
| 469 | 10F4 | : | : | A | L | T | Q | : | P | S | S | V | S | A | N | L | G | G | T | V | K | I | T | C | S | G | G | N | Y | F | G | S | Y | Y | Y | G | W | Y | Q | Q | K | A | P | G | S |
| 470 | h10F4-Lc4 | S | Y | V | L | T | Q | : | P | P | S | V | S | V | A | P | G | K | T | A | R | I | T | C | S | G | G | N | Y | F | G | S | Y | Y | Y | G | W | Y | Q | Q | K | : | P | G | Q |
| 471 | h10F4-Lc3 | S | Y | E | L | T | Q | : | P | P | S | V | S | V | S | P | G | Q | T | A | S | I | T | C | S | G | G | N | Y | F | G | S | Y | Y | Y | G | W | Y | Q | Q | K | : | P | G | Q |
| 472 | h10F4-Lc2 | Q | S | V | L | T | Q | : | P | P | S | V | S | A | A | P | G | Q | K | V | T | I | S | C | S | G | G | N | Y | F | G | S | Y | Y | Y | G | W | Y | Q | Q | L | : | P | G | T |
| 473 | h10F4-Lc1 | D | I | Q | M | T | Q | S | P | S | S | V | S | A | S | V | G | D | R | V | T | I | T | C | S | G | G | N | Y | F | G | S | Y | Y | Y | G | W | Y | Q | Q | K | : | P | G | K |
| 474 | 9A5 | : | : | A | L | T | Q | : | P | S | S | V | S | A | N | P | G | E | T | V | K | I | T | C | S | G | G | N | V | G | G | Y | Y | Y | Y | G | W | Y | Q | Q | K | A | P | G | S |
| 475 | 9E12 | : | : | A | L | T | Q | : | P | S | S | V | S | A | N | P | G | E | T | V | K | I | T | C | S | G | G | S | Y | Y | G | S | Y | Y | Y | G | W | Y | Q | Q | K | S | P | G | S |
| 476 | 9H1 | : | : | A | L | T | Q | : | P | S | S | V | S | A | N | P | G | E | T | V | K | I | T | C | S | G | G | S | Y | Y | G | S | Y | Y | Y | G | W | Y | Q | Q | K | S | P | G | S |
| 477 | 10H1 | : | : | A | L | T | Q | : | P | S | S | V | S | A | N | P | G | E | T | V | K | I | T | C | S | G | G | N | Y | Y | G | S | Y | Y | Y | G | W | Y | Q | Q | K | A | P | G | S |
| 478 | 10E10 | : | : | A | L | T | Q | : | P | S | S | V | S | A | N | P | G | E | T | V | K | I | T | C | S | G | G | N | Y | A | G | S | Y | Y | Y | G | W | Y | Q | Q | K | S | P | G | S |
| 479 | h10H1-Lc4 | S | Y | V | L | T | Q | : | P | P | S | V | S | V | A | P | G | K | T | A | R | I | T | C | S | G | G | N | Y | Y | G | S | Y | Y | Y | G | W | Y | Q | Q | K | : | P | G | Q |
| 480 | h10H1-Lc3 | S | Y | E | L | T | Q | : | P | P | S | V | S | V | S | P | G | Q | T | A | S | I | T | C | S | G | G | N | Y | Y | G | S | Y | Y | Y | G | W | Y | Q | Q | K | : | P | G | Q |
| 481 | h10H1-Lc2 | Q | S | V | L | T | Q | : | P | P | S | V | S | A | A | P | G | Q | K | V | T | I | S | C | S | G | G | N | Y | Y | G | S | Y | Y | Y | G | W | Y | Q | Q | L | : | P | G | T |
| 482 | h10H1-Lc1 | D | I | Q | M | T | Q | S | P | S | S | V | S | A | S | V | G | D | R | V | T | I | T | C | S | G | G | N | Y | Y | G | S | Y | Y | Y | G | W | Y | Q | Q | K | : | P | G | K |

Table 2 (positions 46-83):

| SEQ ID NO: | Molecule | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 |
|---|---|---|---|---|---|---|---|---|---|---|---|---|---|---|---|---|---|---|---|---|---|---|---|---|---|---|---|---|---|---|---|---|---|---|---|---|---|---|---|
| 461 | trastuzumab | A | P | K | L | L | I | Y | S | A | S | F | L | Y | S | G | V | P | S | R | F | S | G | S | R | S | G | T | D | F | T | L | T | I | S | S | L | Q | P |
| 462 | 9A8 | A | P | V | T | V | I | Y | S | N | N | Q | R | P | S | G | I | P | S | R | F | S | G | S | K | S | G | S | T | G | L | L | T | I | T | G | V | Q | A |
| 463 | 10G5 | A | P | V | T | L | I | Y | Y | N | N | K | R | P | S | D | I | P | S | R | F | S | G | S | K | S | G | S | T | G | T | L | T | I | T | G | V | Q | A |
| 464 | 11D6 | A | P | V | T | V | I | Y | R | N | N | Q | R | P | S | D | I | P | S | R | F | S | G | S | G | S | G | S | T | N | T | L | T | I | T | G | V | Q | A |
| 465 | h11D6-Lc4 | A | P | V | L | V | V | Y | R | N | N | Q | R | P | S | G | I | P | E | R | F | S | G | S | G | S | G | S | T | N | T | L | T | I | S | G | T | Q | A |
| 466 | h11D6-Lc3 | S | P | V | L | V | I | Y | R | N | N | Q | R | P | S | G | I | P | E | R | F | S | G | S | G | S | G | S | T | N | T | L | T | I | S | G | T | Q | A |
| 467 | h11D6-Lc2 | A | P | K | L | L | I | Y | R | N | N | Q | R | P | S | G | I | P | D | R | F | S | G | S | G | S | G | S | T | N | T | L | G | I | T | G | L | Q | T |
| 468 | h11D6-Lc1 | A | P | K | L | L | I | Y | R | N | N | Q | R | P | S | G | V | P | S | R | F | S | G | S | G | S | G | S | T | N | T | L | T | I | S | S | L | Q | P |
| 469 | 10F4 | A | P | V | T | V | I | Y | N | N | N | N | R | P | S | D | I | P | S | R | F | S | G | S | T | S | G | T | S | T | L | T | I | T | S | G | V | R | A |
| 470 | h10F4-Lc4 | A | P | V | L | V | V | Y | N | N | N | N | R | P | S | G | I | P | E | R | F | S | G | S | T | S | G | T | S | T | L | L | T | I | S | G | T | Q | A |
| 471 | h10F4-Lc3 | S | P | V | L | V | I | Y | N | N | N | N | R | P | S | G | I | P | E | R | F | S | G | S | T | S | G | T | S | T | L | L | T | I | S | G | T | Q | A |
| 472 | h10F4-Lc2 | A | P | K | L | L | I | Y | N | N | N | N | R | P | S | G | I | P | D | R | F | S | G | S | T | S | G | T | S | T | L | G | I | T | G | L | Q | T |  |
| 473 | h10F4-Lc1 | A | P | K | L | L | I | Y | N | N | N | N | R | P | S | G | V | P | S | R | F | S | G | S | T | S | G | T | S | T | L | T | I | S | S | L | Q | P |  |
| 474 | 9A5 | A | L | V | T | L | I | Y | N | N | N | N | R | P | S | N | I | P | S | R | F | S | G | S | T | S | G | S | T | S | T | L | L | T | I | T | G | V | R | A |
| 475 | 9E12 | A | P | V | T | L | I | Y | N | N | N | N | R | P | S | D | I | P | S | R | F | S | G | S | T | S | G | S | T | G | T | L | L | T | I | T | G | V | Q | A |
| 476 | 9H1 | A | P | V | T | L | I | Y | N | N | N | N | R | P | S | D | I | P | S | R | F | S | G | S | T | S | G | T | G | T | L | L | T | I | T | G | V | R | A |
| 477 | 10H1 | A | P | V | T | V | I | Y | N | N | N | N | R | P | S | N | I | P | S | R | F | S | G | S | K | S | G | S | T | G | T | L | L | T | I | T | G | V | Q | A |
| 478 | 10E10 | A | P | L | T | V | I | Y | N | S | N | N | R | P | S | D | I | P | S | R | F | S | G | S | L | S | G | S | T | G | T | L | L | T | I | T | G | V | R | A |
| 479 | h10H1-Lc4 | A | P | V | L | V | V | Y | N | N | N | N | R | P | S | G | I | P | E | R | F | S | G | S | K | S | G | S | T | G | T | L | L | T | I | S | G | T | Q | A |
| 480 | h10H1-Lc3 | S | P | V | L | V | I | Y | N | N | N | N | R | P | S | G | I | P | E | R | F | S | G | S | K | S | G | S | T | G | T | L | L | T | I | S | G | T | Q | A |
| 481 | h10H1-Lc2 | A | P | K | L | L | I | Y | N | N | N | N | R | P | S | G | I | P | D | R | F | S | G | S | K | S | G | S | T | G | T | L | G | I | T | G | L | Q | T |
| 482 | h10H1-Lc1 | A | P | K | L | L | I | Y | N | N | N | N | R | P | S | G | V | P | S | R | F | S | G | S | K | S | G | S | T | G | T | L | L | T | I | S | S | L | Q | P |

Table 3 (positions 84-111):

| SEQ ID NO: | Molecule | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 |
|---|---|---|---|---|---|---|---|---|---|---|---|---|---|---|---|---|---|---|---|---|---|---|---|---|---|---|---|---|---|
| 461 | trastuzumab | E | D | F | A | T | Y | Y | C | Q | Q | : | H | Y | T | T | P | P | T | F | G | Q | G | T | K | V | E | I | K |
| 462 | 9A8 | E | D | E | A | I | Y | Y | C | A | N | V | D | : | Y | T | D | D | V | F | G | A | G | T | T | L | T | V | L |
| 463 | 10G5 | E | D | E | A | I | Y | Y | C | A | N | V | D | : | S | T | D | D | V | F | G | A | G | T | T | L | T | V | L |
| 464 | 11D6 | E | D | E | A | I | Y | Y | C | G | N | V | D | : | F | T | D | D | V | F | G | A | G | T | T | L | T | V | L |
| 465 | h11D6-Lc4 | M | D | E | A | D | Y | Y | C | G | G | F | D | S | S | S | D | A | I | F | G | G | G | T | K | L | T | V | L |
| 466 | h11D6-Lc3 | M | D | E | A | D | Y | Y | C | G | G | F | D | S | S | S | D | A | I | F | G | G | G | T | K | L | T | V | L |
| 467 | h11D6-Lc2 | G | D | E | A | D | Y | Y | C | G | G | F | D | S | S | S | D | A | I | F | G | G | G | T | K | L | T | V | L |
| 468 | h11D6-Lc1 | E | D | F | A | T | Y | Y | C | G | G | F | D | S | S | S | D | A | I | F | G | Q | G | T | K | V | E | I | K |
| 469 | 10F4 | E | D | E | A | V | Y | Y | F | G | G | F | D | S | S | T | D | A | I | F | G | A | G | T | T | L | T | V | L |
| 470 | h10F4-Lc4 | M | D | E | A | D | Y | Y | C | G | G | F | D | S | S | T | D | A | I | F | G | G | G | T | K | L | T | V | L |
| 471 | h10F4-Lc3 | M | D | E | A | D | Y | Y | C | G | G | F | D | S | S | T | D | A | I | F | G | G | G | T | K | L | T | V | L |
| 472 | h10F4-Lc2 | G | D | E | A | D | Y | Y | C | G | G | F | D | S | S | T | D | A | I | F | G | G | G | T | K | L | T | V | L |
| 473 | h10F4-Lc1 | E | D | F | A | T | Y | Y | C | G | G | F | D | S | S | T | D | A | I | F | G | Q | G | T | K | V | E | I | K |
| 474 | 9A5 | E | D | E | A | V | Y | Y | C | G | S | F | D | S | S | T | D | A | I | F | G | A | G | T | T | L | T | V | L |
| 475 | 9E12 | E | D | E | A | V | Y | Y | C | G | S | F | D | S | S | T | D | A | I | F | G | A | G | T | T | L | T | V | L |
| 476 | 9H1 | E | D | E | A | V | Y | Y | C | G | S | F | D | S | S | T | D | A | I | F | G | A | G | T | T | L | T | V | L |
| 477 | 10H1 | E | D | E | A | V | Y | Y | F | G | G | F | D | S | S | T | D | A | I | F | G | A | G | T | T | L | T | V | L |
| 478 | 10E10 | E | D | E | A | V | Y | Y | F | G | G | F | D | S | S | T | D | A | I | F | G | A | G | T | T | L | T | V | L |
| 479 | h10H1-Lc4 | M | D | E | A | D | Y | Y | C | G | G | F | D | S | S | T | D | A | I | F | G | G | G | T | K | L | T | V | L |
| 480 | h10H1-Lc3 | M | D | E | A | D | Y | Y | C | G | G | F | D | S | S | T | D | A | I | F | G | G | G | T | K | L | T | V | L |
| 481 | h10H1-Lc2 | G | D | E | A | D | Y | Y | C | G | G | F | D | S | S | S | D | A | I | F | G | G | G | T | K | L | T | V | L |
| 482 | h10H1-Lc1 | E | D | F | A | T | Y | Y | C | G | G | F | D | S | S | S | D | A | I | F | G | Q | G | T | K | V | E | I | K |

":" represents a gap in the sequence alignment

FIG 4

SEQUENCE LISTING

<160> NUMBER OF SEQ ID NOS: 275

<210> SEQ ID NO 1
<211> LENGTH: 184
<212> TYPE: PRT
<213> ORGANISM: Homo sapiens
<220> FEATURE:
<221> NAME/KEY: misc_feature
<222> LOCATION: (1)..(184)
<223> OTHER INFORMATION: Human BCMA (Isoform 1)

<400> SEQUENCE: 1

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
            85                  90                  95

Leu Gly Met Ala Asn Ile Asp Leu Glu Lys Ser Arg Thr Gly Asp Glu
        100                 105                 110

Ile Ile Leu Pro Arg Gly Leu Glu Tyr Thr Val Glu Glu Cys Thr Cys
    115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
            165                 170                 175

Ile Glu Lys Ser Ile Ser Ala Arg
        180

<210> SEQ ID NO 2
<211> LENGTH: 135
<212> TYPE: PRT
<213> ORGANISM: Homo sapiens
<220> FEATURE:
<221> NAME/KEY: misc_feature
<222> LOCATION: (1)..(135)
<223> OTHER INFORMATION: Human BCMA (Isoform 2)

<400> SEQUENCE: 2

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Arg Ser Gly Leu Leu
        35                  40                  45

Gly Met Ala Asn Ile Asp Leu Glu Lys Ser Arg Thr Gly Asp Glu Ile
    50                  55                  60

Ile Leu Pro Arg Gly Leu Glu Tyr Thr Val Glu Glu Cys Thr Cys Glu
65                  70                  75                  80

Asp Cys Ile Lys Ser Lys Pro Lys Val Asp Ser Asp His Cys Phe Pro
            85                  90                  95

-continued

```
Leu Pro Ala Met Glu Glu Gly Ala Thr Ile Leu Val Thr Thr Lys Thr
            100                 105                 110

Asn Asp Tyr Cys Lys Ser Leu Pro Ala Ala Leu Ser Ala Thr Glu Ile
        115                 120                 125

Glu Lys Ser Ile Ser Ala Arg
    130                 135

<210> SEQ ID NO 3
<211> LENGTH: 183
<212> TYPE: PRT
<213> ORGANISM: Macaca mulatta
<220> FEATURE:
<221> NAME/KEY: misc_feature
<222> LOCATION: (1)..(183)
<223> OTHER INFORMATION: Cynomolgus BCMA

<400> SEQUENCE: 3

Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
            20                  25                  30

Pro Leu Thr Cys Gln Arg Tyr Cys Asn Ala Ser Met Thr Asn Ser Val
        35                  40                  45

Lys Gly Met Asn Ala Ile Leu Trp Thr Cys Leu Gly Leu Ser Leu Ile
    50                  55                  60

Ile Ser Leu Ala Val Phe Val Leu Thr Phe Leu Leu Arg Lys Met Ser
65                  70                  75                  80

Ser Glu Pro Leu Lys Asp Glu Phe Lys Asn Thr Gly Ser Gly Leu Leu
                85                  90                  95

Gly Met Ala Asn Ile Asp Leu Glu Lys Gly Arg Thr Gly Asp Glu Ile
            100                 105                 110

Val Leu Pro Arg Gly Leu Glu Tyr Thr Val Glu Glu Cys Thr Cys Glu
        115                 120                 125

Asp Cys Ile Lys Asn Lys Pro Lys Val Asp Ser Asp His Cys Phe Pro
    130                 135                 140

Leu Pro Ala Met Glu Glu Gly Ala Thr Ile Leu Val Thr Thr Lys Thr
145                 150                 155                 160

Asn Asp Tyr Cys Asn Ser Leu Ser Ala Ala Leu Ser Val Thr Glu Ile
                165                 170                 175

Glu Lys Ser Ile Ser Ala Arg
            180

<210> SEQ ID NO 4
<211> LENGTH: 185
<212> TYPE: PRT
<213> ORGANISM: Mus musculus
<220> FEATURE:
<221> NAME/KEY: misc_feature
<222> LOCATION: (1)..(185)
<223> OTHER INFORMATION: Murine BCMA

<400> SEQUENCE: 4

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Ala Thr Cys
            20                  25                  30

Gln Pro Tyr Cys Asp Pro Ser Val Thr Ser Ser Val Lys Gly Thr Tyr
        35                  40                  45
```

```
Thr Val Leu Trp Ile Phe Leu Gly Leu Thr Leu Val Leu Ser Leu Ala
 50                  55                  60

Leu Phe Thr Ile Ser Phe Leu Leu Arg Lys Met Asn Pro Glu Ala Leu
 65                  70                  75                  80

Lys Asp Glu Pro Gln Ser Pro Gly Gln Leu Asp Gly Ser Ala Gln Leu
                 85                  90                  95

Asp Lys Ala Asp Thr Glu Leu Thr Arg Ile Arg Ala Gly Asp Asp Arg
            100                 105                 110

Ile Phe Pro Arg Ser Leu Glu Tyr Thr Val Glu Cys Thr Cys Glu
            115                 120                 125

Asp Cys Val Lys Ser Lys Pro Lys Gly Asp Ser Asp His Phe Phe Pro
        130                 135                 140

Leu Pro Ala Met Glu Glu Gly Ala Thr Ile Leu Val Thr Thr Lys Thr
145                 150                 155                 160

Gly Asp Tyr Gly Lys Ser Ser Val Pro Thr Ala Leu Gln Ser Val Met
                    165                 170                 175

Gly Met Glu Lys Pro Thr His Thr Arg
            180                 185

<210> SEQ ID NO 5
<211> LENGTH: 7
<212> TYPE: PRT
<213> ORGANISM: Artificial Sequence
<220> FEATURE:
<223> OTHER INFORMATION: Synthetic: 108843.00220_ST25 - v1

<400> SEQUENCE: 5

Gly Phe Asn Ile Ser Gly Ser
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic: 2265-F06; CDR-H1; Chothia

<400> SEQUENCE: 6

Gly Phe Asn Ile Ser Tyr Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic: 2265-F05; CDR-H1; Chothia

<400> SEQUENCE: 7

Gly Phe Asn Ile Ile Ala Pro
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic: 2265-F02; CDR-H1; Chothia

<400> SEQUENCE: 8

Gly Phe Asn Ile Ser Ala Pro
1               5
```

```
<210> SEQ ID NO 9
<211> LENGTH: 7
<212> TYPE: PRT
<213> ORGANISM: Artificial Sequence
<220> FEATURE:
<223> OTHER INFORMATION: Synthetic: 2265-B06; CDR-H1; Chothia

<400> SEQUENCE: 9

Gly Phe Asn Ile Arg Val Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic: 2265-A09; CDR-H1; Chothia

<400> SEQUENCE: 10

Gly Phe Asn Ile Ile Gly Pro
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic: 2265-F03; CDR-H1; Chothia

<400> SEQUENCE: 11

Gly Phe Asn Ile Arg Gly Pro
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic: 2265-E02; CDR-H1; Chothia

<400> SEQUENCE: 12

Gly Phe Asn Ile Tyr Val Ser
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic: 2265-D11; CDR-H1; Chothia

<400> SEQUENCE: 13

Gly Phe Asn Ile Ser Gly Pro
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic: 2265-C03; CDR-H1; Chothia

<400> SEQUENCE: 14

Gly Phe Asn Ile Ser Val Pro
1               5
```

```
<210> SEQ ID NO 15
<211> LENGTH: 7
<212> TYPE: PRT
<213> ORGANISM: Artificial Sequence
<220> FEATURE:
<223> OTHER INFORMATION: Synthetic: 2265-C02; CDR-H1; Chothia

<400> SEQUENCE: 15

Gly Phe Asn Ile Gly Val Ser
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic: 2265-A06; CDR-H1; Chothia

<400> SEQUENCE: 16

Gly Phe Asn Ile Tyr Arg Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic: 2137-A05; CDR-H1; Chothia

<400> SEQUENCE: 17

Gly Phe Asn Ile Asn Asn Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic: 2190-B01; CDR-H1; Chothia

<400> SEQUENCE: 18

Gly Phe Asn Ile Ser Ser Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic: 2290-G01; CDR-H1; Chothia

<400> SEQUENCE: 19

Gly Phe Asn Ile Ser Pro Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic: 2290-C07; CDR-H1; Chothia

<400> SEQUENCE: 20

Gly Phe Asn Ile Thr Tyr Asp
1               5

<210> SEQ ID NO 21
```

```
<211> LENGTH: 7
<212> TYPE: PRT
<213> ORGANISM: Artificial Sequence
<220> FEATURE:
<223> OTHER INFORMATION: Synthetic: 2290-D05; CDR-H1; Chothia

<400> SEQUENCE: 21

Gly Phe Asn Ile Ala Ser Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic: 2290-C08; CDR-H1; Chothia

<400> SEQUENCE: 22

Gly Phe Asn Ile Gln Pro Tyr
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic: 2290-A02; CDR-H1; Chothia

<400> SEQUENCE: 23

Gly Phe Asn Ile Ser Thr Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic: 2291-G05; CDR-H1; Chothia

<400> SEQUENCE: 24

Gly Phe Asn Ile Ala Ala Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic: 2291-D07; CDR-H1; Chothia

<400> SEQUENCE: 25

Gly Phe Asn Ile Lys Asp Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic: 2291-F10; CDR-H1; Chothia

<400> SEQUENCE: 26

Gly Phe Asn Ile Asp Pro Tyr
1               5

<210> SEQ ID NO 27
<211> LENGTH: 7
```

```
<212> TYPE: PRT
<213> ORGANISM: Artificial Sequence
<220> FEATURE:
<223> OTHER INFORMATION: Synthetic: 9A8; CDR-H1; Chothia

<400> SEQUENCE: 27

Gly Phe Thr Phe Ser Ser Phe
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic: 10F4; CDR-H1; Chothia

<400> SEQUENCE: 28

Gly Phe Thr Phe Ser Gly Tyr
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic: 9A5; CDR-H1; Chothia

<400> SEQUENCE: 29

Gly Phe Ser Ile Ser Asp Tyr
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic: 9E12; CDR-H1; Chothia

<400> SEQUENCE: 30

Gly Phe Thr Phe Ser Asp Tyr
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic: 10E10; CDR-H1; Chothia

<400> SEQUENCE: 31

Gly Phe Thr Phe Ser Ser Tyr
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic: 2137-C07; CDR-H1; Kabat

<400> SEQUENCE: 32

Gly Ser Gly Ile His
1               5

<210> SEQ ID NO 33
<211> LENGTH: 5
<212> TYPE: PRT
```

<213> ORGANISM: Artificial Sequence
<220> FEATURE:
<223> OTHER INFORMATION: Synthetic: 2265-F06; CDR-H1; Kabat

<400> SEQUENCE: 33

Tyr Pro Gly Ile His
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic: 2265-F05; CDR-H1; Kabat

<400> SEQUENCE: 34

Ala Pro Gly Ile His
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic: 2265-B06; CDR-H1; Kabat

<400> SEQUENCE: 35

Val Ser Gly Ile His
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic: 2265-A09; CDR-H1; Kabat

<400> SEQUENCE: 36

Gly Pro Gly Ile His
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic: 2265-C03; CDR-H1; Kabat

<400> SEQUENCE: 37

Val Pro Gly Ile His
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic: 2265-A06; CDR-H1; Kabat

<400> SEQUENCE: 38

Arg Ser Gly Ile His
1               5

<210> SEQ ID NO 39
<211> LENGTH: 5
<212> TYPE: PRT
<213> ORGANISM: Artificial Sequence

```
<220> FEATURE:
<223> OTHER INFORMATION: Synthetic: 2137-A05; CDR-H1; Kabat

<400> SEQUENCE: 39

Asn Ser Tyr Ile His
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic: 2288-A03; CDR-H1; Kabat

<400> SEQUENCE: 40

Asn Ser Trp Ile His
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic: 2190-B01; CDR-H1; Kabat

<400> SEQUENCE: 41

Ser Tyr Trp Ile His
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic: 2290-G01; CDR-H1; Kabat

<400> SEQUENCE: 42

Pro Tyr Trp Ile His
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic: 2290-C07; CDR-H1; Kabat

<400> SEQUENCE: 43

Tyr Asp Trp Ile His
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic: 2290-D05; CDR-H1; Kabat

<400> SEQUENCE: 44

Ser Arg Trp Ile His
1               5

<210> SEQ ID NO 45
<211> LENGTH: 5
<212> TYPE: PRT
<213> ORGANISM: Artificial Sequence
<220> FEATURE:
```

<223> OTHER INFORMATION: Synthetic: 2290-A02; CDR-H1; Kabat

<400> SEQUENCE: 45

Thr Arg Trp Ile His
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic: 2213-A06; CDR-H1; Kabat

<400> SEQUENCE: 46

Ser Tyr Ala Ile His
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic: 2291-G05; CDR-H1; Kabat

<400> SEQUENCE: 47

Ala Tyr Thr Ile His
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic: 2291-E06; CDR-H1; Kabat

<400> SEQUENCE: 48

Pro Tyr Thr Ile His
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic: 2291-D07; CDR-H1; Kabat

<400> SEQUENCE: 49

Asp Thr Tyr Ile His
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic: 2291-A04; CDR-H1; Kabat

<400> SEQUENCE: 50

Ser Tyr Gly Ile His
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic: 9A8; CDR-H1; Kabat

```
<400> SEQUENCE: 51

Ser Phe Asn Met Phe
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic: 10F4; CDR-H1; Kabat

<400> SEQUENCE: 52

Gly Tyr Asn Met Gly
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic: 9A5; CDR-H1; Kabat

<400> SEQUENCE: 53

Asp Tyr Gly Met Gly
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic: 9E12; CDR-H1; Kabat

<400> SEQUENCE: 54

Asp Tyr Gly Leu Gly
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic: 10H1; CDR-H1; Kabat

<400> SEQUENCE: 55

Gly Tyr Gly Met Gly
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic: 10E10; CDR-H1; Kabat

<400> SEQUENCE: 56

Ser Tyr Gly Met Gly
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic: 2137-C07; CDR-H2; Chothia
```

```
<400> SEQUENCE: 57

Asn Pro Ala Gly Gly Tyr
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic: 2265-F03; CDR-H2; Chothia

<400> SEQUENCE: 58

Ser Pro Ala Ala Gly Tyr
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic: 2265-D11; CDR-H2; Chothia

<400> SEQUENCE: 59

Asn Pro Ala Ala Gly Tyr
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic: 2137-A05; CDR-H2; Chothia

<400> SEQUENCE: 60

Tyr Pro Tyr Ser Gly Tyr
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic: 2288-A03; CDR-H2; Chothia

<400> SEQUENCE: 61

Tyr Pro Tyr Ile Gly Phe
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic: 2190-B01; CDR-H2; Chothia

<400> SEQUENCE: 62

Thr Pro Ser Gly Gly Tyr
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic: 2290-G01; CDR-H2; Chothia

<400> SEQUENCE: 63
```

Thr Pro Pro Ser Gly Phe
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic: 2290-D02; CDR-H2; Chothia

<400> SEQUENCE: 64

Thr Pro Ala Ala Gly Tyr
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic: 2290-C07; CDR-H2; Chothia

<400> SEQUENCE: 65

Thr Pro Phe Asp Gly Tyr
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic: 2290-D05; CDR-H2; Chothia

<400> SEQUENCE: 66

Thr Pro Ser Ala Gly Tyr
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic: 2290-C08; CDR-H2; Chothia

<400> SEQUENCE: 67

Thr Pro Pro Ser Gly Tyr
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic: 2213-A06; CDR-H2; Chothia

<400> SEQUENCE: 68

Ser Pro Tyr Gly Gly Tyr
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic: 2291-E06; CDR-H2; Chothia

<400> SEQUENCE: 69

Phe Pro Ser Gly Gly Tyr
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic: 2291-D07; CDR-H2; Chothia

<400> SEQUENCE: 70

Ser Pro Tyr Asp Gly Tyr
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic: 9A8; CDR-H2; Chothia

<400> SEQUENCE: 71

Arg Asn Asp Gly Asn Ser
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic: 10G5; CDR-H2; Chothia

<400> SEQUENCE: 72

Ser Asn Asp Gly Ser Ser
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic: 11D6; CDR-H2; Chothia

<400> SEQUENCE: 73

Arg Asn Asp Gly Arg Ser
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic: 10F4; CDR-H2; Chothia

<400> SEQUENCE: 74

Thr Tyr Gly Thr Gly Ser Tyr
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic: 9A5; CDR-H2; Chothia

<400> SEQUENCE: 75

Asp His Asp Gly Arg Tyr

```
<210> SEQ ID NO 76
<211> LENGTH: 6
<212> TYPE: PRT
<213> ORGANISM: Artificial Sequence
<220> FEATURE:
<223> OTHER INFORMATION: Synthetic: 9E12; CDR-H2; Chothia

<400> SEQUENCE: 76

Asn Ser Ala Gly Ser Gly
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic: 9H1; CDR-H2; Chothia

<400> SEQUENCE: 77

Asn Ser Ala Gly Ser Asp
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic: 10E10; CDR-H2; Chothia

<400> SEQUENCE: 78

Asn Ser Gly Gly Ser Ser Tyr
1               5

<210> SEQ ID NO 79
<211> LENGTH: 17
<212> TYPE: PRT
<213> ORGANISM: Artificial Sequence
<220> FEATURE:
<223> OTHER INFORMATION: Synthetic: 2137-C07; CDR-H2; Kabat

<400> SEQUENCE: 79

Phe Ile Asn Pro Ala Gly Gly Tyr Thr Asp Tyr Ala Asp Ser Val Lys
1               5                   10                  15
Gly

<210> SEQ ID NO 80
<211> LENGTH: 17
<212> TYPE: PRT
<213> ORGANISM: Artificial Sequence
<220> FEATURE:
<223> OTHER INFORMATION: Synthetic: 2265-F03; CDR-H2; Kabat

<400> SEQUENCE: 80

Phe Ile Ser Pro Ala Ala Gly Tyr Thr Asp Tyr Ala Asp Ser Val Lys
1               5                   10                  15
Gly

<210> SEQ ID NO 81
<211> LENGTH: 17
<212> TYPE: PRT
<213> ORGANISM: Artificial Sequence
<220> FEATURE:
<223> OTHER INFORMATION: Synthetic: 2265-D11; CDR-H2; Kabat
```

```
<400> SEQUENCE: 81

Phe Ile Asn Pro Ala Ala Gly Tyr Thr Asp Tyr Ala Asp Ser Val Lys
1               5                   10                  15

Gly

<210> SEQ ID NO 82
<211> LENGTH: 17
<212> TYPE: PRT
<213> ORGANISM: Artificial Sequence
<220> FEATURE:
<223> OTHER INFORMATION: Synthetic: 2137-A05; CDR-H2; Kabat

<400> SEQUENCE: 82

Trp Ile Tyr Pro Tyr Ser Gly Tyr Thr Asn Tyr Ala Asp Ser Val Lys
1               5                   10                  15

Gly

<210> SEQ ID NO 83
<211> LENGTH: 17
<212> TYPE: PRT
<213> ORGANISM: Artificial Sequence
<220> FEATURE:
<223> OTHER INFORMATION: Synthetic: 2288-A03; CDR-H2; Kabat

<400> SEQUENCE: 83

Trp Ile Tyr Pro Tyr Ile Gly Phe Thr Glu Tyr Ala Asp Ser Val Lys
1               5                   10                  15

Gly

<210> SEQ ID NO 84
<211> LENGTH: 17
<212> TYPE: PRT
<213> ORGANISM: Artificial Sequence
<220> FEATURE:
<223> OTHER INFORMATION: Synthetic: 2190-B01; CDR-H2; Kabat

<400> SEQUENCE: 84

Val Ile Thr Pro Ser Gly Gly Tyr Thr Tyr Tyr Ala Asp Ser Val Lys
1               5                   10                  15

Gly

<210> SEQ ID NO 85
<211> LENGTH: 17
<212> TYPE: PRT
<213> ORGANISM: Artificial Sequence
<220> FEATURE:
<223> OTHER INFORMATION: Synthetic: 2290-G01; CDR-H2; Kabat

<400> SEQUENCE: 85

Val Ile Thr Pro Pro Ser Gly Phe Thr Tyr Tyr Ala Asp Ser Val Lys
1               5                   10                  15

Gly

<210> SEQ ID NO 86
<211> LENGTH: 17
<212> TYPE: PRT
<213> ORGANISM: Artificial Sequence
<220> FEATURE:
<223> OTHER INFORMATION: Synthetic: 2290-D02; CDR-H2; Kabat

<400> SEQUENCE: 86

Val Ile Thr Pro Ala Ala Gly Tyr Thr Tyr Tyr Ala Asp Ser Val Lys
1               5                   10                  15
```

Gly

<210> SEQ ID NO 87
<211> LENGTH: 17
<212> TYPE: PRT
<213> ORGANISM: Artificial Sequence
<220> FEATURE:
<223> OTHER INFORMATION: Synthetic: 2290-C07; CDR-H2; Kabat

<400> SEQUENCE: 87

Val Ile Thr Pro Phe Asp Gly Tyr Thr Tyr Tyr Ala Asp Ser Val Lys
1               5                   10                  15
Gly

<210> SEQ ID NO 88
<211> LENGTH: 17
<212> TYPE: PRT
<213> ORGANISM: Artificial Sequence
<220> FEATURE:
<223> OTHER INFORMATION: Synthetic: 2290-D05; CDR-H2; Kabat

<400> SEQUENCE: 88

Val Ile Thr Pro Ser Ala Gly Tyr Thr Tyr Tyr Ala Asp Ser Val Lys
1               5                   10                  15
Gly

<210> SEQ ID NO 89
<211> LENGTH: 17
<212> TYPE: PRT
<213> ORGANISM: Artificial Sequence
<220> FEATURE:
<223> OTHER INFORMATION: Synthetic: 2290-C08; CDR-H2; Kabat

<400> SEQUENCE: 89

Val Ile Thr Pro Pro Ser Gly Tyr Thr Tyr Tyr Ala Asp Ser Val Lys
1               5                   10                  15
Gly

<210> SEQ ID NO 90
<211> LENGTH: 17
<212> TYPE: PRT
<213> ORGANISM: Artificial Sequence
<220> FEATURE:
<223> OTHER INFORMATION: Synthetic: 2290-A02; CDR-H2; Kabat

<400> SEQUENCE: 90

Val Ile Thr Pro Ser Ala Gly Tyr Thr His Tyr Ala Asp Ser Val Lys
1               5                   10                  15
Gly

<210> SEQ ID NO 91
<211> LENGTH: 17
<212> TYPE: PRT
<213> ORGANISM: Artificial Sequence
<220> FEATURE:
<223> OTHER INFORMATION: Synthetic: 2213-A06; CDR-H2; Kabat

<400> SEQUENCE: 91

Val Ile Ser Pro Tyr Gly Gly Tyr Thr Glu Tyr Ala Asp Ser Val Lys
1               5                   10                  15
Gly

```
<210> SEQ ID NO 92
<211> LENGTH: 17
<212> TYPE: PRT
<213> ORGANISM: Artificial Sequence
<220> FEATURE:
<223> OTHER INFORMATION: Synthetic: 2291-G05; CDR-H2; Kabat

<400> SEQUENCE: 92

Trp Ile Ser Pro Tyr Gly Gly Tyr Thr Glu Tyr Ala Asp Ser Val Lys
1               5                   10                  15
Gly

<210> SEQ ID NO 93
<211> LENGTH: 17
<212> TYPE: PRT
<213> ORGANISM: Artificial Sequence
<220> FEATURE:
<223> OTHER INFORMATION: Synthetic: 2291-E06; CDR-H2; Kabat

<400> SEQUENCE: 93

His Ile Phe Pro Ser Gly Gly Tyr Thr Asp Tyr Ala Asp Ser Val Lys
1               5                   10                  15
Gly

<210> SEQ ID NO 94
<211> LENGTH: 17
<212> TYPE: PRT
<213> ORGANISM: Artificial Sequence
<220> FEATURE:
<223> OTHER INFORMATION: Synthetic: 2291-D07; CDR-H2; Kabat

<400> SEQUENCE: 94

Val Ile Ser Pro Tyr Asp Gly Tyr Thr Glu Tyr Ala Asp Ser Val Lys
1               5                   10                  15
Gly

<210> SEQ ID NO 95
<211> LENGTH: 17
<212> TYPE: PRT
<213> ORGANISM: Artificial Sequence
<220> FEATURE:
<223> OTHER INFORMATION: Synthetic: 2291-F10; CDR-H2; Kabat

<400> SEQUENCE: 95

Trp Ile Ser Pro Tyr Asp Gly Tyr Thr Glu Tyr Ala Asp Ser Val Lys
1               5                   10                  15
Gly

<210> SEQ ID NO 96
<211> LENGTH: 17
<212> TYPE: PRT
<213> ORGANISM: Artificial Sequence
<220> FEATURE:
<223> OTHER INFORMATION: Synthetic: 2291-A04; CDR-H2; Kabat

<400> SEQUENCE: 96

Phe Ile Ser Pro Tyr Asp Gly Tyr Thr Glu Tyr Ala Asp Ser Val Lys
1               5                   10                  15
Gly

<210> SEQ ID NO 97
<211> LENGTH: 17
<212> TYPE: PRT
<213> ORGANISM: Artificial Sequence
```

<220> FEATURE:
<223> OTHER INFORMATION: Synthetic: 2291-A01; CDR-H2; Kabat

<400> SEQUENCE: 97

His Ile Ser Pro Tyr Asp Gly Tyr Thr Asp Tyr Ala Asp Ser Val Lys
1               5                   10                  15
Gly

<210> SEQ ID NO 98
<211> LENGTH: 17
<212> TYPE: PRT
<213> ORGANISM: Artificial Sequence
<220> FEATURE:
<223> OTHER INFORMATION: Synthetic: 9A8; CDR-H2; Kabat

<400> SEQUENCE: 98

Tyr Ile Arg Asn Asp Gly Asn Ser Ala Ser Tyr Gly Pro Ala Val Lys
1               5                   10                  15
Gly

<210> SEQ ID NO 99
<211> LENGTH: 17
<212> TYPE: PRT
<213> ORGANISM: Artificial Sequence
<220> FEATURE:
<223> OTHER INFORMATION: Synthetic: 10G5; CDR-H2; Kabat

<400> SEQUENCE: 99

Tyr Ile Ser Asn Asp Gly Ser Ser Thr Ser Tyr Gly Pro Ala Val Lys
1               5                   10                  15
Gly

<210> SEQ ID NO 100
<211> LENGTH: 17
<212> TYPE: PRT
<213> ORGANISM: Artificial Sequence
<220> FEATURE:
<223> OTHER INFORMATION: Synthetic: 11D6; CDR-H2; Kabat

<400> SEQUENCE: 100

Tyr Ile Arg Asn Asp Gly Arg Ser Thr Ser Tyr Gly Pro Ala Val Lys
1               5                   10                  15
Gly

<210> SEQ ID NO 101
<211> LENGTH: 17
<212> TYPE: PRT
<213> ORGANISM: Artificial Sequence
<220> FEATURE:
<223> OTHER INFORMATION: Synthetic: h11D6-Hc4; CDR-H2; Kabat

<400> SEQUENCE: 101

Tyr Ile Arg Asn Asp Gly Arg Ser Thr Ser Tyr Val Asp Ser Val Lys
1               5                   10                  15
Gly

<210> SEQ ID NO 102
<211> LENGTH: 17
<212> TYPE: PRT
<213> ORGANISM: Artificial Sequence
<220> FEATURE:
<223> OTHER INFORMATION: Synthetic: h11D6-Hc3; CDR-H2; Kabat

<400> SEQUENCE: 102

Tyr Ile Arg Asn Asp Gly Arg Ser Thr Ser Tyr Ala Asp Ser Val Lys
1               5                   10                  15

Gly

<210> SEQ ID NO 103
<211> LENGTH: 17
<212> TYPE: PRT
<213> ORGANISM: Artificial Sequence
<220> FEATURE:
<223> OTHER INFORMATION: Synthetic: h11D6-Hc1; CDR-H2; Kabat

<400> SEQUENCE: 103

Tyr Ile Arg Asn Asp Gly Arg Ser Thr Ser Tyr Ala Ala Pro Val Lys
1               5                   10                  15

Gly

<210> SEQ ID NO 104
<211> LENGTH: 18
<212> TYPE: PRT
<213> ORGANISM: Artificial Sequence
<220> FEATURE:
<223> OTHER INFORMATION: Synthetic: 10F4; CDR-H2; Kabat

<400> SEQUENCE: 104

Gly Ile Thr Tyr Gly Thr Gly Ser Tyr Thr Ala Tyr Gly Ala Ala Val
1               5                   10                  15

Lys Gly

<210> SEQ ID NO 105
<211> LENGTH: 18
<212> TYPE: PRT
<213> ORGANISM: Artificial Sequence
<220> FEATURE:
<223> OTHER INFORMATION: Synthetic: h10F4-Hc4; CDR-H2; Kabat

<400> SEQUENCE: 105

Gly Ile Thr Tyr Gly Thr Gly Ser Tyr Thr Ala Tyr Val Asp Ser Val
1               5                   10                  15

Lys Gly

<210> SEQ ID NO 106
<211> LENGTH: 18
<212> TYPE: PRT
<213> ORGANISM: Artificial Sequence
<220> FEATURE:
<223> OTHER INFORMATION: Synthetic: h10F4-Hc3; CDR-H2; Kabat

<400> SEQUENCE: 106

Gly Ile Thr Tyr Gly Thr Gly Ser Tyr Thr Ala Tyr Ala Asp Ser Val
1               5                   10                  15

Lys Gly

<210> SEQ ID NO 107
<211> LENGTH: 18
<212> TYPE: PRT
<213> ORGANISM: Artificial Sequence
<220> FEATURE:
<223> OTHER INFORMATION: Synthetic: h10F4-Hc1; CDR-H2; Kabat

<400> SEQUENCE: 107

Gly Ile Thr Tyr Gly Thr Gly Ser Tyr Thr Ala Tyr Ala Ala Pro Val
1               5                   10                  15

Lys Gly

<210> SEQ ID NO 108
<211> LENGTH: 17
<212> TYPE: PRT
<213> ORGANISM: Artificial Sequence
<220> FEATURE:
<223> OTHER INFORMATION: Synthetic: 9A5; CDR-H2; Kabat

<400> SEQUENCE: 108

Arg Ile Asp His Asp Gly Arg Tyr Thr Asp Tyr Gly Ala Val Val Lys
1               5                   10                  15
Gly

<210> SEQ ID NO 109
<211> LENGTH: 17
<212> TYPE: PRT
<213> ORGANISM: Artificial Sequence
<220> FEATURE:
<223> OTHER INFORMATION: Synthetic: 9E12; CDR-H2; Kabat

<400> SEQUENCE: 109

Arg Ile Asn Ser Ala Gly Ser Gly Thr Tyr Tyr Gly Ser Ala Val Asp
1               5                   10                  15
Gly

<210> SEQ ID NO 110
<211> LENGTH: 17
<212> TYPE: PRT
<213> ORGANISM: Artificial Sequence
<220> FEATURE:
<223> OTHER INFORMATION: Synthetic: 9H1; CDR-H2; Kabat

<400> SEQUENCE: 110

Arg Ile Asn Ser Ala Gly Ser Asp Thr Asn Tyr Gly Ser Ala Val Lys
1               5                   10                  15
Gly

<210> SEQ ID NO 111
<211> LENGTH: 17
<212> TYPE: PRT
<213> ORGANISM: Artificial Sequence
<220> FEATURE:
<223> OTHER INFORMATION: Synthetic: 10H1; CDR-H2; Kabat

<400> SEQUENCE: 111

Arg Ile Asn Ser Ala Gly Ser Asp Thr Asp Tyr Gly Ala Ala Val Lys
1               5                   10                  15
Gly

<210> SEQ ID NO 112
<211> LENGTH: 18
<212> TYPE: PRT
<213> ORGANISM: Artificial Sequence
<220> FEATURE:
<223> OTHER INFORMATION: Synthetic: 10E10; CDR-H2; Kabat

<400> SEQUENCE: 112

Arg Ile Asn Ser Gly Gly Ser Ser Tyr Thr Asp Tyr Gly Ser Ala Val
1               5                   10                  15
Lys Gly

<210> SEQ ID NO 113

```
<211> LENGTH: 17
<212> TYPE: PRT
<213> ORGANISM: Artificial Sequence
<220> FEATURE:
<223> OTHER INFORMATION: Synthetic: h10H1-Hc4; CDR-H2; Kabat

<400> SEQUENCE: 113

Arg Ile Asn Ser Ala Gly Ser Asp Thr Asp Tyr Val Asp Ser Val Lys
1               5                   10                  15
Gly

<210> SEQ ID NO 114
<211> LENGTH: 17
<212> TYPE: PRT
<213> ORGANISM: Artificial Sequence
<220> FEATURE:
<223> OTHER INFORMATION: Synthetic: h10H1-Hc3; CDR-H2; Kabat

<400> SEQUENCE: 114

Arg Ile Asn Ser Ala Gly Ser Asp Thr Asp Tyr Ala Asp Ser Val Lys
1               5                   10                  15
Gly

<210> SEQ ID NO 115
<211> LENGTH: 17
<212> TYPE: PRT
<213> ORGANISM: Artificial Sequence
<220> FEATURE:
<223> OTHER INFORMATION: Synthetic: h10H1-Hc1; CDR-H2; Kabat

<400> SEQUENCE: 115

Arg Ile Asn Ser Ala Gly Ser Asp Thr Asp Tyr Ala Ala Pro Val Lys
1               5                   10                  15
Gly

<210> SEQ ID NO 116
<211> LENGTH: 13
<212> TYPE: PRT
<213> ORGANISM: Artificial Sequence
<220> FEATURE:
<223> OTHER INFORMATION: Synthetic: 2137-C07; CDR-H3

<400> SEQUENCE: 116

Asp Tyr Val Tyr Gln Tyr Trp Thr Tyr Val Leu Asp Tyr
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Synthetic: 2265-F06; CDR-H3

<400> SEQUENCE: 117

Asp Tyr Ile Leu Gln Tyr Trp Thr Tyr Val Leu Asp Tyr
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Synthetic: 2265-F05; CDR-H3

<400> SEQUENCE: 118
```

```
Asp Tyr Val Asn Ala Tyr Trp Thr Tyr Val Leu Asp Tyr
1               5                   10
```

<210> SEQ ID NO 119
<211> LENGTH: 13
<212> TYPE: PRT
<213> ORGANISM: Artificial Sequence
<220> FEATURE:
<223> OTHER INFORMATION: Synthetic: 2265-F02; CDR-H3

<400> SEQUENCE: 119

```
Asp Tyr Ile Arg Gln Tyr Trp Thr Tyr Val Leu Asp Tyr
1               5                   10
```

<210> SEQ ID NO 120
<211> LENGTH: 13
<212> TYPE: PRT
<213> ORGANISM: Artificial Sequence
<220> FEATURE:
<223> OTHER INFORMATION: Synthetic: 2265-B06; CDR-H3

<400> SEQUENCE: 120

```
Asp Tyr Val Gln Ala Tyr Trp Thr Tyr Val Leu Asp Tyr
1               5                   10
```

<210> SEQ ID NO 121
<211> LENGTH: 13
<212> TYPE: PRT
<213> ORGANISM: Artificial Sequence
<220> FEATURE:
<223> OTHER INFORMATION: Synthetic: 2265-A09; CDR-H3

<400> SEQUENCE: 121

```
Asp Tyr Val Tyr Asn Tyr Trp Thr Tyr Val Leu Asp Tyr
1               5                   10
```

<210> SEQ ID NO 122
<211> LENGTH: 13
<212> TYPE: PRT
<213> ORGANISM: Artificial Sequence
<220> FEATURE:
<223> OTHER INFORMATION: Synthetic: 2265-F03; CDR-H3

<400> SEQUENCE: 122

```
Asp Phe Val Gln Ser Tyr Trp Thr Tyr Val Leu Asp Tyr
1               5                   10
```

<210> SEQ ID NO 123
<211> LENGTH: 13
<212> TYPE: PRT
<213> ORGANISM: Artificial Sequence
<220> FEATURE:
<223> OTHER INFORMATION: Synthetic: 2265-D11; CDR-H3

<400> SEQUENCE: 123

```
Asp Tyr Ile Tyr Gln Tyr Trp Thr Tyr Val Leu Asp Tyr
1               5                   10
```

<210> SEQ ID NO 124
<211> LENGTH: 13
<212> TYPE: PRT
<213> ORGANISM: Artificial Sequence
<220> FEATURE:
<223> OTHER INFORMATION: Synthetic: 2265-D05; CDR-H3

<400> SEQUENCE: 124

```
Asp Phe Val Tyr Ala Tyr Trp Thr Tyr Val Leu Asp Tyr
```

```
1               5                   10
```

<210> SEQ ID NO 125
<211> LENGTH: 13
<212> TYPE: PRT
<213> ORGANISM: Artificial Sequence
<220> FEATURE:
<223> OTHER INFORMATION: Synthetic: 2265-C03; CDR-H3

<400> SEQUENCE: 125

```
Asp Tyr Val Pro Gln Tyr Trp Thr Tyr Val Leu Asp Tyr
1               5                   10
```

<210> SEQ ID NO 126
<211> LENGTH: 13
<212> TYPE: PRT
<213> ORGANISM: Artificial Sequence
<220> FEATURE:
<223> OTHER INFORMATION: Synthetic: 2265-C02; CDR-H3

<400> SEQUENCE: 126

```
Asp Tyr Ile Tyr Ser Tyr Trp Thr Tyr Val Leu Asp Tyr
1               5                   10
```

<210> SEQ ID NO 127
<211> LENGTH: 13
<212> TYPE: PRT
<213> ORGANISM: Artificial Sequence
<220> FEATURE:
<223> OTHER INFORMATION: Synthetic: 2137-A05; CDR-H3

<400> SEQUENCE: 127

```
Asp Tyr Gly Pro Trp Tyr Gly Thr Gly Val Leu Asp Tyr
1               5                   10
```

<210> SEQ ID NO 128
<211> LENGTH: 13
<212> TYPE: PRT
<213> ORGANISM: Artificial Sequence
<220> FEATURE:
<223> OTHER INFORMATION: Synthetic: 2288-A03; CDR-H3

<400> SEQUENCE: 128

```
Asp Tyr Asp Leu Arg Tyr Leu Thr Gly Val Leu Asp Tyr
1               5                   10
```

<210> SEQ ID NO 129
<211> LENGTH: 13
<212> TYPE: PRT
<213> ORGANISM: Artificial Sequence
<220> FEATURE:
<223> OTHER INFORMATION: Synthetic: 2190-B01; CDR-H3

<400> SEQUENCE: 129

```
Asp Leu Gly Gly Gly Tyr Trp Val Gly Phe Phe Asp Tyr
1               5                   10
```

<210> SEQ ID NO 130
<211> LENGTH: 13
<212> TYPE: PRT
<213> ORGANISM: Artificial Sequence
<220> FEATURE:
<223> OTHER INFORMATION: Synthetic: 2290-G01; CDR-H3

<400> SEQUENCE: 130

```
Asp Leu Gly Val Gly Tyr Trp Val Gly Phe Ser Asp Tyr
1               5                   10
```

```
<210> SEQ ID NO 131
<211> LENGTH: 13
<212> TYPE: PRT
<213> ORGANISM: Artificial Sequence
<220> FEATURE:
<223> OTHER INFORMATION: Synthetic: 2290-D02; CDR-H3

<400> SEQUENCE: 131

Asp Leu Gly His Arg Tyr Trp Val Gly Val Phe Asp Tyr
1               5                   10

<210> SEQ ID NO 132
<211> LENGTH: 13
<212> TYPE: PRT
<213> ORGANISM: Artificial Sequence
<220> FEATURE:
<223> OTHER INFORMATION: Synthetic: 2290-C07; CDR-H3

<400> SEQUENCE: 132

Asp Met Gly Val Gly Tyr Trp Val Gly Phe Ser Asp Tyr
1               5                   10

<210> SEQ ID NO 133
<211> LENGTH: 13
<212> TYPE: PRT
<213> ORGANISM: Artificial Sequence
<220> FEATURE:
<223> OTHER INFORMATION: Synthetic: 2290-D05; CDR-H3

<400> SEQUENCE: 133

Asp Leu Gly Tyr Gly Tyr Trp Val Gly Phe Ser Asp Tyr
1               5                   10

<210> SEQ ID NO 134
<211> LENGTH: 13
<212> TYPE: PRT
<213> ORGANISM: Artificial Sequence
<220> FEATURE:
<223> OTHER INFORMATION: Synthetic: 2290-C08; CDR-H3

<400> SEQUENCE: 134

Asp Trp Gly Val Gly Tyr Trp Val Gly Phe Ser Asp Tyr
1               5                   10

<210> SEQ ID NO 135
<211> LENGTH: 13
<212> TYPE: PRT
<213> ORGANISM: Artificial Sequence
<220> FEATURE:
<223> OTHER INFORMATION: Synthetic: 2290-A02; CDR-H3

<400> SEQUENCE: 135

Asp Leu Gly Ser Arg Tyr Trp Val Gly Val Phe Asp Tyr
1               5                   10

<210> SEQ ID NO 136
<211> LENGTH: 13
<212> TYPE: PRT
<213> ORGANISM: Artificial Sequence
<220> FEATURE:
<223> OTHER INFORMATION: Synthetic: 2213-A06; CDR-H3

<400> SEQUENCE: 136

Asp Phe Tyr Asp Arg Tyr Ser Thr Tyr Val Leu Asp Tyr
1               5                   10
```

<210> SEQ ID NO 137
<211> LENGTH: 13
<212> TYPE: PRT
<213> ORGANISM: Artificial Sequence
<220> FEATURE:
<223> OTHER INFORMATION: Synthetic: 2291-G05; CDR-H3

<400> SEQUENCE: 137

Asp Phe His Asp Arg Tyr Ala Thr Phe Val Leu Asp Tyr
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Synthetic: 2291-E06; CDR-H3

<400> SEQUENCE: 138

Asp Phe Tyr Asp Arg Tyr Ala Thr Tyr Val Leu Asp Tyr
1               5                   10

<210> SEQ ID NO 139
<211> LENGTH: 13
<212> TYPE: PRT
<213> ORGANISM: Artificial Sequence
<220> FEATURE:
<223> OTHER INFORMATION: Synthetic: 2291-F10; CDR-H3

<400> SEQUENCE: 139

Asp Tyr Tyr Asp Arg Tyr Ser Thr Tyr Val Leu Asp Tyr
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Synthetic: 2291-A04; CDR-H3

<400> SEQUENCE: 140

Asp Phe Asn Asp Arg Tyr Phe Thr Tyr Val Leu Asp Tyr
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Synthetic: 9A8; CDR-H3

<400> SEQUENCE: 141

Thr Thr Cys Ile Gly Ser Gly Gly Cys Ile Asp Thr
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic: 11D6; CDR-H3

<400> SEQUENCE: 142

Thr Thr Cys Val Gly Ser Gly Gly Cys Ile Asp Thr
1               5                   10

```
<210> SEQ ID NO 143
<211> LENGTH: 16
<212> TYPE: PRT
<213> ORGANISM: Artificial Sequence
<220> FEATURE:
<223> OTHER INFORMATION: Synthetic: 10F4; CDR-H3

<400> SEQUENCE: 143

Gly Gly Gly Leu Asn Ser Tyr Gly Cys Ser Gly Ala Asn Ile Asp Ala
1               5                   10                  15

<210> SEQ ID NO 144
<211> LENGTH: 9
<212> TYPE: PRT
<213> ORGANISM: Artificial Sequence
<220> FEATURE:
<223> OTHER INFORMATION: Synthetic: 9A5; CDR-H3

<400> SEQUENCE: 144

Gly Gly Gly Ala Ala Ser Ile Asp Thr
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic: 9E12; CDR-H3

<400> SEQUENCE: 145

Gly Gly Gly Gly Ala Ser Ile Asp Gly
1               5

<210> SEQ ID NO 146
<211> LENGTH: 11
<212> TYPE: PRT
<213> ORGANISM: Artificial Sequence
<220> FEATURE:
<223> OTHER INFORMATION: Synthetic: trastuzumab; CDR-L1

<400> SEQUENCE: 146

Arg Ala Ser Gln Asp Val Asn Thr Ala Val Ala
1               5                   10

<210> SEQ ID NO 147
<211> LENGTH: 8
<212> TYPE: PRT
<213> ORGANISM: Artificial Sequence
<220> FEATURE:
<223> OTHER INFORMATION: Synthetic: 9A8; CDR-L1

<400> SEQUENCE: 147

Ser Gly Gly Ser Ser Asp Tyr Gly
1               5

<210> SEQ ID NO 148
<211> LENGTH: 8
<212> TYPE: PRT
<213> ORGANISM: Artificial Sequence
<220> FEATURE:
<223> OTHER INFORMATION: Synthetic: 10G5; CDR-L1

<400> SEQUENCE: 148

Ser Gly Gly Asn Tyr Asp Tyr Gly
1               5

<210> SEQ ID NO 149
```

```
<211> LENGTH: 8
<212> TYPE: PRT
<213> ORGANISM: Artificial Sequence
<220> FEATURE:
<223> OTHER INFORMATION: Synthetic: 11D6; CDR-L1

<400> SEQUENCE: 149

Ser Gly Gly Asn Ser Asp Tyr Gly
1               5

<210> SEQ ID NO 150
<211> LENGTH: 13
<212> TYPE: PRT
<213> ORGANISM: Artificial Sequence
<220> FEATURE:
<223> OTHER INFORMATION: Synthetic: 10F4; CDR-L1

<400> SEQUENCE: 150

Ser Gly Gly Gly Asn Tyr Phe Gly Ser Tyr Tyr Tyr Gly
1               5                   10

<210> SEQ ID NO 151
<211> LENGTH: 13
<212> TYPE: PRT
<213> ORGANISM: Artificial Sequence
<220> FEATURE:
<223> OTHER INFORMATION: Synthetic: 9A5; CDR-L1

<400> SEQUENCE: 151

Ser Gly Gly Gly Asn Tyr Val Gly Gly Tyr Tyr Tyr Gly
1               5                   10

<210> SEQ ID NO 152
<211> LENGTH: 13
<212> TYPE: PRT
<213> ORGANISM: Artificial Sequence
<220> FEATURE:
<223> OTHER INFORMATION: Synthetic: 9E12; CDR-L1

<400> SEQUENCE: 152

Ser Gly Gly Gly Ser Tyr Tyr Gly Ser Tyr Tyr Tyr Gly
1               5                   10

<210> SEQ ID NO 153
<211> LENGTH: 13
<212> TYPE: PRT
<213> ORGANISM: Artificial Sequence
<220> FEATURE:
<223> OTHER INFORMATION: Synthetic: 10H1; CDR-L1

<400> SEQUENCE: 153

Ser Gly Gly Gly Asn Tyr Tyr Gly Ser Tyr Tyr Tyr Gly
1               5                   10

<210> SEQ ID NO 154
<211> LENGTH: 13
<212> TYPE: PRT
<213> ORGANISM: Artificial Sequence
<220> FEATURE:
<223> OTHER INFORMATION: Synthetic: 10E10; CDR-L1

<400> SEQUENCE: 154

Ser Gly Gly Gly Asn Tyr Ala Gly Ser Tyr Tyr Tyr Gly
1               5                   10

<210> SEQ ID NO 155
<211> LENGTH: 7
```

```
<212> TYPE: PRT
<213> ORGANISM: Artificial Sequence
<220> FEATURE:
<223> OTHER INFORMATION: Synthetic: trastuzumab; CDR-L2

<400> SEQUENCE: 155

Ser Ala Ser Phe Leu Tyr Ser
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic: 9A8; CDR-L2

<400> SEQUENCE: 156

Ser Asn Asn Gln Arg Pro Ser
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic: 10G5; CDR-L2

<400> SEQUENCE: 157

Tyr Asn Asn Lys Arg Pro Ser
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic: 11D6; CDR-L2

<400> SEQUENCE: 158

Arg Asn Asn Gln Arg Pro Ser
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic: 10F4; CDR-L2

<400> SEQUENCE: 159

Asn Asn Asn Asn Arg Pro Ser
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic: 10E10; CDR-L2

<400> SEQUENCE: 160

Asn Ser Asn Asn Arg Pro Ser
1               5

<210> SEQ ID NO 161
<211> LENGTH: 9
<212> TYPE: PRT
```

```
<213> ORGANISM: Artificial Sequence
<220> FEATURE:
<223> OTHER INFORMATION: Synthetic: trastuzumab; CDR-L3

<400> SEQUENCE: 161

Gln Gln His Tyr Thr Thr Pro Pro Thr
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic: 9A8; CDR-L3

<400> SEQUENCE: 162

Ala Asn Val Asp Tyr Thr Asp Asp Val
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic: 10G5; CDR-L3

<400> SEQUENCE: 163

Ala Asn Val Asp Ser Thr Asp Asp Val
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic: 11D6; CDR-L3

<400> SEQUENCE: 164

Gly Asn Val Asp Phe Thr Asp Asp Val
1               5

<210> SEQ ID NO 165
<211> LENGTH: 10
<212> TYPE: PRT
<213> ORGANISM: Artificial Sequence
<220> FEATURE:
<223> OTHER INFORMATION: Synthetic: h11D6-Lc4; CDR-L3

<400> SEQUENCE: 165

Gly Gly Phe Asp Ser Ser Ser Asp Ala Ile
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Synthetic: 10F4; CDR-L3

<400> SEQUENCE: 166

Gly Gly Phe Asp Ser Ser Thr Asp Ala Ile
1               5                   10

<210> SEQ ID NO 167
<211> LENGTH: 122
<212> TYPE: PRT
<213> ORGANISM: Artificial Sequence
```

```
<220> FEATURE:
<223> OTHER INFORMATION: Synthetic: 2137-C07; VH

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Gly Ser
            20                  25                  30

Gly Ile His Trp Val Arg Gln Ala Pro Gly Lys Gly Leu Glu Trp Val
        35                  40                  45

Gly Phe Ile Asn Pro Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Val Tyr Gln Tyr Trp Thr Tyr Val Leu Asp Tyr Trp
            100                 105                 110

Gly Gln Gly Thr Leu Val Thr Val Ser Ser
        115                 120

<210> SEQ ID NO 168
<211> LENGTH: 122
<212> TYPE: PRT
<213> ORGANISM: Artificial Sequence
<220> FEATURE:
<223> OTHER INFORMATION: Synthetic: 2265-F06; VH

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Pro
            20                  25                  30

Gly Ile His Trp Val Arg Gln Ala Pro Gly Lys Gly Leu Glu Trp Val
        35                  40                  45

Gly Phe Ile Asn Pro Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Ile Leu Gln Tyr Trp Thr Tyr Val Leu Asp Tyr Trp
            100                 105                 110

Gly Gln Gly Thr Leu Val Thr Val Ser Ser
        115                 120

<210> SEQ ID NO 169
<211> LENGTH: 122
<212> TYPE: PRT
<213> ORGANISM: Artificial Sequence
<220> FEATURE:
<223> OTHER INFORMATION: Synthetic: 2265-F05; VH

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ile Ala Pro
            20                  25                  30
```

Gly Ile His Trp Val Arg Gln Ala Pro Gly Lys Gly Leu Glu Trp Val
            35                  40                  45

Gly Phe Ile Asn Pro Ala Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Val Asn Ala Tyr Trp Thr Tyr Val Leu Asp Tyr Trp
            100                 105                 110

Gly Gln Gly Thr Leu Val Thr Val Ser Ser
            115                 120

<210> SEQ ID NO 170
<211> LENGTH: 122
<212> TYPE: PRT
<213> ORGANISM: Artificial Sequence
<220> FEATURE:
<223> OTHER INFORMATION: Synthetic: 2265-F02; VH

<400> SEQUENCE: 170

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ala Pro
            20                  25                  30

Gly Ile His Trp Val Arg Gln Ala Pro Gly Lys Gly Leu Glu Trp Val
            35                  40                  45

Gly Phe Ile Asn Pro Ala Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Ile Arg Gln Tyr Trp Thr Tyr Val Leu Asp Tyr Trp
            100                 105                 110

Gly Gln Gly Thr Leu Val Thr Val Ser Ser
            115                 120

<210> SEQ ID NO 171
<211> LENGTH: 122
<212> TYPE: PRT
<213> ORGANISM: Artificial Sequence
<220> FEATURE:
<223> OTHER INFORMATION: Synthetic: 2265-B06; VH

<400> SEQUENCE: 171

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Val Ser
            20                  25                  30

Gly Ile His Trp Val Arg Gln Ala Pro Gly Lys Gly Leu Glu Trp Val
            35                  40                  45

Gly Phe Ile Asn Pro Ala Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

```
Ala Arg Asp Tyr Val Gln Ala Tyr Trp Thr Tyr Val Leu Asp Tyr Trp
            100                 105                 110

Gly Gln Gly Thr Leu Val Thr Val Ser Ser
        115                 120

<210> SEQ ID NO 172
<211> LENGTH: 122
<212> TYPE: PRT
<213> ORGANISM: Artificial Sequence
<220> FEATURE:
<223> OTHER INFORMATION: Synthetic: 2265-A09; VH

<400> SEQUENCE: 172

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ile Gly Pro
            20                  25                  30

Gly Ile His Trp Val Arg Gln Ala Pro Gly Lys Gly Leu Glu Trp Val
        35                  40                  45

Gly Phe Ile Asn Pro Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Val Tyr Asn Tyr Trp Thr Tyr Val Leu Asp Tyr Trp
            100                 105                 110

Gly Gln Gly Thr Leu Val Thr Val Ser Ser
        115                 120

<210> SEQ ID NO 173
<211> LENGTH: 122
<212> TYPE: PRT
<213> ORGANISM: Artificial Sequence
<220> FEATURE:
<223> OTHER INFORMATION: Synthetic: 2265-F03; VH

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Gly Pro
            20                  25                  30

Gly Ile His Trp Val Arg Gln Ala Pro Gly Lys Gly Leu Glu Trp Val
        35                  40                  45

Gly Phe Ile Ser Pro Ala Ala Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Val Gln Ser Tyr Trp Thr Tyr Val Leu Asp Tyr Trp
            100                 105                 110

Gly Gln Gly Thr Leu Val Thr Val Ser Ser
        115                 120

<210> SEQ ID NO 174
<211> LENGTH: 122
<212> TYPE: PRT
```

<213> ORGANISM: Artificial Sequence
<220> FEATURE:
<223> OTHER INFORMATION: Synthetic: 2265-E02; VH

<400> SEQUENCE: 174

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Val Ser
            20                  25                  30

Gly Ile His Trp Val Arg Gln Ala Pro Gly Lys Gly Leu Glu Trp Val
        35                  40                  45

Gly Phe Ile Asn Pro Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Thr Asn Ser Leu Arg Ala Glu Asp Thr Ala Val Tyr Tyr Cys
                85                  90                  95

Ala Arg Asp Tyr Val Tyr Gln Tyr Trp Thr Tyr Val Leu Asp Tyr Trp
            100                 105                 110

Gly Gln Gly Thr Leu Val Thr Val Ser Ser
        115                 120
```

<210> SEQ ID NO 175
<211> LENGTH: 122
<212> TYPE: PRT
<213> ORGANISM: Artificial Sequence
<220> FEATURE:
<223> OTHER INFORMATION: Synthetic: 2265-D11; VH

<400> SEQUENCE: 175

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Gly Pro
            20                  25                  30

Gly Ile His Trp Val Arg Gln Ala Pro Gly Lys Gly Leu Glu Trp Val
        35                  40                  45

Gly Phe Ile Asn Pro Ala Ala Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Ile Tyr Gln Tyr Trp Thr Tyr Val Leu Asp Tyr Trp
            100                 105                 110

Gly Gln Gly Thr Leu Val Thr Val Ser Ser
        115                 120
```

<210> SEQ ID NO 176
<211> LENGTH: 122
<212> TYPE: PRT
<213> ORGANISM: Artificial Sequence
<220> FEATURE:
<223> OTHER INFORMATION: Synthetic: 2265-D05; VH

<400> SEQUENCE: 176

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Gly Pro
            20                  25                  30
```

```
Gly Ile His Trp Val Arg Gln Ala Pro Gly Lys Gly Leu Glu Trp Val
            35                  40                  45

Gly Phe Ile Asn Pro Ala Ala Gly Tyr Thr Asp Tyr Ala Asp Ser Val
        50                  55                  60

Lys Gly Arg Phe Ala Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Asp Phe Val Tyr Ala Tyr Trp Thr Tyr Val Leu Asp Tyr Trp
            100                 105                 110

Gly Gln Gly Thr Leu Val Thr Val Ser Ser
            115                 120
```

<210> SEQ ID NO 177
<211> LENGTH: 122
<212> TYPE: PRT
<213> ORGANISM: Artificial Sequence
<220> FEATURE:
<223> OTHER INFORMATION: Synthetic: 2265-C03; VH

<400> SEQUENCE: 177

```
Glu Val Gln Leu Val Glu Ser Gly Gly Gly Leu Val Gln Pro Gly Gly
 1               5                  10                  15

Ser Leu Arg Leu Ser Cys Ala Ala Pro Gly Phe Asn Ile Ser Val Pro
            20                  25                  30

Gly Ile His Trp Val Arg Gln Ala Pro Gly Lys Gly Leu Glu Trp Val
            35                  40                  45

Gly Phe Ile Asn Pro Ala Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Asp Tyr Val Pro Gln Tyr Trp Thr Tyr Val Leu Asp Tyr Trp
            100                 105                 110

Gly Gln Gly Thr Leu Val Thr Val Ser Ser
            115                 120
```

<210> SEQ ID NO 178
<211> LENGTH: 122
<212> TYPE: PRT
<213> ORGANISM: Artificial Sequence
<220> FEATURE:
<223> OTHER INFORMATION: Synthetic: 2265-C02; VH

<400> SEQUENCE: 178

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Gly Val Ser
            20                  25                  30

Gly Ile His Trp Val Arg Gln Ala Pro Gly Lys Gly Leu Glu Trp Val
            35                  40                  45

Gly Phe Ile Asn Pro Ala Gly Gly Tyr Thr Asp Tyr Ala Gly Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
```

```
                85                  90                  95
Ala Arg Asp Tyr Ile Tyr Ser Tyr Trp Thr Tyr Val Leu Asp Tyr Trp
            100                 105                 110
Gly Gln Gly Thr Leu Val Thr Val Ser Ser
        115                 120

<210> SEQ ID NO 179
<211> LENGTH: 122
<212> TYPE: PRT
<213> ORGANISM: Artificial Sequence
<220> FEATURE:
<223> OTHER INFORMATION: Synthetic: 2265-A06; VH

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Arg Ser
            20                  25                  30

Gly Ile His Trp Val Arg Gln Ala Pro Gly Lys Gly Leu Glu Trp Val
        35                  40                  45

Gly Phe Ile Asn Pro Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Val Pro Gln Tyr Trp Thr Tyr Val Leu Asp Tyr Trp
            100                 105                 110

Gly Gln Gly Thr Leu Val Thr Val Ser Ser
        115                 120

<210> SEQ ID NO 180
<211> LENGTH: 122
<212> TYPE: PRT
<213> ORGANISM: Artificial Sequence
<220> FEATURE:
<223> OTHER INFORMATION: Synthetic: 2137-A05; VH

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Asn Asn Ser
            20                  25                  30

Tyr Ile His Trp Val Arg Gln Ala Pro Gly Lys Gly Leu Glu Trp Val
        35                  40                  45

Gly Trp Ile Tyr Pro Tyr Ser Gly Tyr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Pro Trp Tyr Gly Thr Gly Val Leu Asp Tyr Trp
            100                 105                 110

Gly Gln Gly Thr Leu Val Thr Val Ser Ser
        115                 120

<210> SEQ ID NO 181
<211> LENGTH: 122
```

```
<212> TYPE: PRT
<213> ORGANISM: Artificial Sequence
<220> FEATURE:
<223> OTHER INFORMATION: Synthetic: 2288-A03; VH

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Asn Asn Ser
            20                  25                  30

Trp Ile His Trp Val Arg Gln Ala Pro Gly Lys Gly Leu Glu Trp Val
        35                  40                  45

Gly Trp Ile Tyr Pro Tyr Ile Gly Phe Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Leu Arg Tyr Leu Thr Gly Val Leu Asp Tyr Trp
            100                 105                 110

Gly Gln Gly Thr Leu Val Thr Val Ser Ser
        115                 120

<210> SEQ ID NO 182
<211> LENGTH: 122
<212> TYPE: PRT
<213> ORGANISM: Artificial Sequence
<220> FEATURE:
<223> OTHER INFORMATION: Synthetic: 2190-B01; VH

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Tyr
            20                  25                  30

Trp Ile His Trp Val Arg Gln Ala Pro Gly Lys Gly Leu Glu Trp Val
        35                  40                  45

Gly Val Ile Thr Pro Ser Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Gly Tyr Trp Val Gly Phe Phe Asp Tyr Trp
            100                 105                 110

Gly Gln Gly Thr Leu Val Thr Val Ser Ser
        115                 120

<210> SEQ ID NO 183
<211> LENGTH: 122
<212> TYPE: PRT
<213> ORGANISM: Artificial Sequence
<220> FEATURE:
<223> OTHER INFORMATION: Synthetic: 2290-G01; VH

<400> SEQUENCE: 183

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Pro Tyr
```

```
                20                  25                  30
Trp Ile His Trp Val Arg Gln Ala Pro Gly Lys Gly Leu Glu Trp Val
            35                  40                  45
Gly Val Ile Thr Pro Pro Ser Gly Phe Thr Tyr Tyr Ala Asp Ser Val
        50                  55                  60
Lys Gly Arg Phe Thr Ile Ser Ala Asp Thr Ser Lys Asn Thr Ala Tyr
65                  70                  75                  80
Leu Gln Val Asn Ser Leu Arg Ala Glu Asp Thr Ala Val Tyr Tyr Cys
                85                  90                  95
Ala Arg Asp Leu Gly Val Gly Tyr Trp Val Gly Phe Ser Asp Tyr Trp
            100                 105                 110
Gly Gln Gly Thr Leu Val Thr Val Ser Ser
            115                 120

<210> SEQ ID NO 184
<211> LENGTH: 122
<212> TYPE: PRT
<213> ORGANISM: Artificial Sequence
<220> FEATURE:
<223> OTHER INFORMATION: Synthetic: 2290-D02; VH

<400> SEQUENCE: 184

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Ser Ser Tyr
            20                  25                  30
Trp Ile His Trp Val Arg Gln Ala Pro Gly Lys Gly Leu Glu Trp Met
            35                  40                  45
Gly Val Ile Thr Pro Ala Ala Gly Tyr Thr Tyr Tyr Ala Asp Ser Val
        50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Asp Leu Gly His Arg Tyr Trp Val Gly Val Phe Asp Tyr Trp
            100                 105                 110
Gly Gln Gly Thr Leu Val Thr Val Ser Ser
            115                 120

<210> SEQ ID NO 185
<211> LENGTH: 122
<212> TYPE: PRT
<213> ORGANISM: Artificial Sequence
<220> FEATURE:
<223> OTHER INFORMATION: Synthetic: 2290-C07; VH

<400> SEQUENCE: 185

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Thr Tyr Asp
            20                  25                  30
Trp Ile His Trp Val Arg Gln Ala Pro Gly Lys Gly Leu Glu Trp Val
            35                  40                  45
Gly Val Ile Thr Pro Phe Asp Gly Tyr Thr Tyr Tyr Ala Asp Ser Val
        50                  55                  60
Lys Gly His Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ala Arg Asp Met Gly Val Gly Tyr Trp Val Gly Phe Asp Tyr Trp
            100                 105                 110

Gly Gln Gly Thr Leu Val Thr Val Ser Ser
        115                 120

<210> SEQ ID NO 186
<211> LENGTH: 122
<212> TYPE: PRT
<213> ORGANISM: Artificial Sequence
<220> FEATURE:
<223> OTHER INFORMATION: Synthetic: 2290-D05; VH

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ala Ser Arg
            20                  25                  30

Trp Ile His Trp Val Arg Gln Ala Pro Gly Lys Gly Leu Glu Trp Val
        35                  40                  45

Gly Val Ile Thr Pro Ser Ala Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Tyr Gly Tyr Trp Val Gly Phe Asp Tyr Trp
            100                 105                 110

Gly Gln Gly Thr Leu Val Thr Val Ser Ser
        115                 120

<210> SEQ ID NO 187
<211> LENGTH: 122
<212> TYPE: PRT
<213> ORGANISM: Artificial Sequence
<220> FEATURE:
<223> OTHER INFORMATION: Synthetic: 2290-C08; VH

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Gln Pro Tyr
            20                  25                  30

Trp Ile His Trp Val Arg Gln Ala Pro Gly Lys Gly Leu Glu Trp Val
        35                  40                  45

Gly Val Ile Thr Pro Pro Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Trp Gly Val Gly Tyr Trp Val Gly Phe Asp Tyr Trp
            100                 105                 110

Gly Gln Gly Thr Leu Val Thr Val Ser Ser
        115                 120

<210> SEQ ID NO 188
```

```
<211> LENGTH: 122
<212> TYPE: PRT
<213> ORGANISM: Artificial Sequence
<220> FEATURE:
<223> OTHER INFORMATION: Synthetic: 2290-A02; VH

<400> SEQUENCE: 188

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Thr Arg
            20                  25                  30

Trp Ile His Trp Val Arg Gln Ala Pro Gly Lys Gly Leu Glu Trp Val
        35                  40                  45

Gly Val Ile Thr Pro Ser Ala Gly Tyr Thr His Tyr Ala Asp Ser Val
    50                  55                  60

Lys Gly Arg Phe Thr Ile Ser Ala Gly Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Ser Arg Tyr Trp Val Gly Val Phe Asp Tyr Trp
            100                 105                 110

Gly Gln Gly Thr Leu Val Thr Val Ser Ser
        115                 120

<210> SEQ ID NO 189
<211> LENGTH: 122
<212> TYPE: PRT
<213> ORGANISM: Artificial Sequence
<220> FEATURE:
<223> OTHER INFORMATION: Synthetic: 2213-A06; VH

<400> SEQUENCE: 189

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Tyr
            20                  25                  30

Ala Ile His Trp Val Arg Gln Ala Pro Gly Lys Gly Leu Glu Trp Val
        35                  40                  45

Gly Val Ile Ser Pro Tyr Gly Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Tyr Asp Arg Tyr Ser Thr Tyr Val Leu Asp Tyr Trp
            100                 105                 110

Gly Gln Gly Thr Leu Val Thr Val Ser Ser
        115                 120

<210> SEQ ID NO 190
<211> LENGTH: 122
<212> TYPE: PRT
<213> ORGANISM: Artificial Sequence
<220> FEATURE:
<223> OTHER INFORMATION: Synthetic: 2291-G05; VH

<400> SEQUENCE: 190

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Asn Ile Ala Ala Tyr
            20                  25                  30

Thr Ile His Trp Val Arg Gln Ala Pro Gly Lys Gly Leu Glu Trp Val
            35                  40                  45

Gly Trp Ile Ser Pro Tyr Gly Gly Tyr Thr Glu Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asp Phe His Asp Arg Tyr Ala Thr Phe Val Leu Asp Tyr Trp
             100                 105                 110

Gly Gln Gly Thr Leu Val Thr Val Ser Ser
         115                 120

<210> SEQ ID NO 191
<211> LENGTH: 122
<212> TYPE: PRT
<213> ORGANISM: Artificial Sequence
<220> FEATURE:
<223> OTHER INFORMATION: Synthetic: 2291-E06; VH

<400> SEQUENCE: 191

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Asn Ile Ser Pro Tyr
            20                  25                  30

Thr Ile His Trp Val Arg Gln Ala Pro Gly Lys Gly Leu Glu Trp Val
            35                  40                  45

Ala His Ile Phe Pro Ser Gly Gly Tyr Thr Asp Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asp Phe Tyr Asp Arg Tyr Ala Thr Tyr Val Leu Asp Tyr Trp
             100                 105                 110

Gly Gln Gly Thr Leu Val Thr Val Ser Ser
         115                 120

<210> SEQ ID NO 192
<211> LENGTH: 122
<212> TYPE: PRT
<213> ORGANISM: Artificial Sequence
<220> FEATURE:
<223> OTHER INFORMATION: Synthetic: 2291-D07; VH

<400> SEQUENCE: 192

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Gly Val Ile Ser Pro Tyr Asp Gly Tyr Thr Glu Tyr Ala Asp Ser Val
 50                  55                  60

Lys Gly Arg Phe Thr Ile Ser Ala Asp Thr Ser Lys Asn Thr Ala Tyr
 65                  70                  75                  80

```
Leu Gln Met Asn Ser Leu Arg Ala Glu Asp Thr Ala Val Tyr Tyr Cys
                85                  90                  95

Ala His Asp Phe Tyr Asp Arg Tyr Ser Thr Tyr Val Leu Asp Tyr Trp
            100                 105                 110

Gly Gln Gly Thr Leu Val Thr Val Ser Ser
        115                 120

<210> SEQ ID NO 193
<211> LENGTH: 122
<212> TYPE: PRT
<213> ORGANISM: Artificial Sequence
<220> FEATURE:
<223> OTHER INFORMATION: Synthetic: 2291-F10; VH

<400> SEQUENCE: 193

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Asp Pro Tyr
            20                  25                  30

Thr Ile His Trp Val Arg Gln Ala Pro Gly Lys Gly Leu Glu Trp Val
        35                  40                  45

Gly Trp Ile Ser Pro Tyr Asp Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Arg Tyr Ser Thr Tyr Val Leu Asp Tyr Trp
            100                 105                 110

Gly Arg Gly Thr Leu Val Thr Val Ser Ser
        115                 120

<210> SEQ ID NO 194
<211> LENGTH: 122
<212> TYPE: PRT
<213> ORGANISM: Artificial Sequence
<220> FEATURE:
<223> OTHER INFORMATION: Synthetic: 2291-A04; VH

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Tyr
            20                  25                  30

Gly Ile His Trp Val Arg Gln Ala Pro Gly Lys Gly Leu Glu Trp Val
        35                  40                  45

Gly Phe Ile Ser Pro Tyr Asp Gly Tyr Thr Glu Tyr Ala Asp Ser Val
    50                  55                  60

Lys Gly Arg Phe Thr Ile Ser Ala Gly Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Asn Asp Arg Tyr Phe Thr Tyr Val Leu Asp Tyr Trp
            100                 105                 110

Gly Gln Gly Thr Leu Val Thr Val Ser Ser
        115                 120
```

```
<210> SEQ ID NO 195
<211> LENGTH: 122
<212> TYPE: PRT
<213> ORGANISM: Artificial Sequence
<220> FEATURE:
<223> OTHER INFORMATION: Synthetic: 2291-A01; VH

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Asp Pro Tyr
            20                  25                  30

Thr Ile His Trp Ala Arg Gln Ala Pro Gly Lys Gly Leu Glu Trp Val
        35                  40                  45

Ala His Ile Ser Pro Tyr Asp Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Tyr Asp Arg Tyr Ser Thr Tyr Val Leu Asp Tyr Trp
            100                 105                 110

Gly Gln Gly Thr Leu Val Thr Val Ser Ser
        115                 120

<210> SEQ ID NO 196
<211> LENGTH: 121
<212> TYPE: PRT
<213> ORGANISM: Artificial Sequence
<220> FEATURE:
<223> OTHER INFORMATION: Synthetic: 9A8; VH

<400> SEQUENCE: 196

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Phe
            20                  25                  30

Asn Met Phe Trp Val Arg Gln Ala Pro Gly Lys Gly Leu Glu Trp Val
        35                  40                  45

Ala Tyr Ile Arg Asn Asp Gly Asn Ser Ala Ser Tyr Gly Pro Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Thr Thr Cys Ile Gly Ser Gly Gly Cys Ile Asp Thr Trp Gly
            100                 105                 110

His Gly Thr Glu Val Ile Val Ser Ser
        115                 120

<210> SEQ ID NO 197
<211> LENGTH: 121
<212> TYPE: PRT
<213> ORGANISM: Artificial Sequence
<220> FEATURE:
<223> OTHER INFORMATION: Synthetic: 10G5; VH

<400> SEQUENCE: 197

Ala Val Thr Leu Asp Glu Ser Gly Gly Gly Leu Gln Thr Pro Gly Gly
1               5                   10                  15
```

-continued

Val Leu Ser Leu Val Cys Lys Ala Ser Gly Phe Thr Phe Ser Ser Phe
            20                  25                  30

Asn Met Phe Trp Val Arg Gln Ala Pro Gly Lys Gly Leu Glu Trp Val
        35                  40                  45

Ala Tyr Ile Ser Asn Asp Gly Ser Ser Thr Ser Tyr Gly Pro Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Phe Cys
                85                  90                  95

Ala Lys Thr Thr Cys Ile Gly Ser Gly Gly Cys Ile Asp Thr Trp Gly
            100                 105                 110

His Gly Thr Glu Val Ile Val Ser Ser
        115                 120

<210> SEQ ID NO 198
<211> LENGTH: 121
<212> TYPE: PRT
<213> ORGANISM: Artificial Sequence
<220> FEATURE:
<223> OTHER INFORMATION: Synthetic: 11D6; VH

<400> SEQUENCE: 198

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Phe
            20                  25                  30

Asn Met Phe Trp Val Arg Gln Ala Pro Gly Glu Gly Leu Glu Trp Val
        35                  40                  45

Ala Tyr Ile Arg Asn Asp Gly Arg Ser Thr Ser Tyr Gly Pro Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Lys Thr Thr Cys Val Gly Ser Gly Gly Cys Ile Asp Thr Trp Gly
            100                 105                 110

His Gly Thr Glu Val Ile Val Ser Ser
        115                 120

<210> SEQ ID NO 199
<211> LENGTH: 121
<212> TYPE: PRT
<213> ORGANISM: Artificial Sequence
<220> FEATURE:
<223> OTHER INFORMATION: Synthetic: h11D6-HC4; VH

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asn Met Phe Trp Val Arg Gln Ala Pro Gly Lys Gly Leu Glu Trp Val
        35                  40                  45

Ala Tyr Ile Arg Asn Asp Gly Arg Ser Thr Ser Tyr Val Asp Ser Val
    50                  55                  60

Lys Gly Arg Phe Thr Ile Ser Arg Asp Asn Ala Lys Ser Ser Val Tyr

```
                65                  70                  75                  80
Leu Gln Met Asn Ser Leu Arg Ala Glu Asp Thr Ala Val Tyr Tyr Cys
                    85                  90                  95

Ala Lys Thr Thr Cys Val Gly Ser Gly Gly Cys Ile Asp Thr Trp Gly
                100                 105                 110

Gln Gly Thr Leu Val Thr Val Ser Ser
            115                 120

<210> SEQ ID NO 200
<211> LENGTH: 121
<212> TYPE: PRT
<213> ORGANISM: Artificial Sequence
<220> FEATURE:
<223> OTHER INFORMATION: Synthetic: h11D6-HC3; VH

<400> SEQUENCE: 200

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Asn Met Phe Trp Val Arg Gln Ala Pro Gly Lys Gly Leu Glu Trp Val
        35                  40                  45

Ala Tyr Ile Arg Asn Asp Gly Arg Ser Thr Ser Tyr Ala Asp Ser Val
    50                  55                  60

Lys Gly Arg Phe Thr Ile Ser Arg Asp Asn Ser Lys Ser Thr Val Tyr
65                  70                  75                  80

Leu Gln Met Asn Ser Leu Arg Ala Glu Asp Thr Ala Val Tyr Tyr Cys
                85                  90                  95

Ala Lys Thr Thr Cys Val Gly Ser Gly Gly Cys Ile Asp Thr Trp Gly
            100                 105                 110

Gln Gly Thr Leu Val Thr Val Ser Ser
            115                 120

<210> SEQ ID NO 201
<211> LENGTH: 121
<212> TYPE: PRT
<213> ORGANISM: Artificial Sequence
<220> FEATURE:
<223> OTHER INFORMATION: Synthetic: h11D6-HC2; VH

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asn Met Phe Trp Val Arg Gln Ala Pro Gly Lys Gly Leu Glu Trp Val
        35                  40                  45

Ala Tyr Ile Arg Asn Asp Gly Arg Ser Thr Ser Tyr Ala Asp Ser Val
    50                  55                  60

Lys Gly Arg Phe Thr Ile Ser Arg Asp Asn Ser Lys Ser Thr Val Tyr
65                  70                  75                  80

Leu Gln Met Asn Ser Leu Arg Ala Glu Asp Thr Ala Val Tyr Tyr Cys
                85                  90                  95

Ala Lys Thr Thr Cys Val Gly Ser Gly Gly Cys Ile Asp Thr Trp Gly
            100                 105                 110

Gln Gly Thr Leu Val Thr Val Ser Ser
            115                 120
```

<210> SEQ ID NO 202
<211> LENGTH: 121
<212> TYPE: PRT
<213> ORGANISM: Artificial Sequence
<220> FEATURE:
<223> OTHER INFORMATION: Synthetic: h11D6-HC1; VH

<400> SEQUENCE: 202

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Asn Met Phe Trp Val Arg Gln Ala Pro Gly Lys Gly Leu Glu Trp Val
        35                  40                  45

Ala Tyr Ile Arg Asn Asp Gly Arg Ser Thr Ser Tyr Ala Ala Pro Val
    50                  55                  60

Lys Gly Arg Phe Thr Ile Ser Arg Asp Asn Ser Lys Ser Thr Val Tyr
65                  70                  75                  80

Leu Gln Met Asn Ser Leu Lys Thr Glu Asp Thr Ala Val Tyr Tyr Cys
                85                  90                  95

Ala Lys Thr Thr Cys Val Gly Ser Gly Gly Cys Ile Asp Thr Trp Gly
            100                 105                 110

Gln Gly Thr Leu Val Thr Val Ser Ser
        115                 120

<210> SEQ ID NO 203
<211> LENGTH: 126
<212> TYPE: PRT
<213> ORGANISM: Artificial Sequence
<220> FEATURE:
<223> OTHER INFORMATION: Synthetic: 10F4; VH

<400> SEQUENCE: 203

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Gly Tyr
            20                  25                  30

Asn Met Gly Trp Val Arg Gln Ala Pro Gly Lys Gly Leu Glu Tyr Val
        35                  40                  45

Ala Gly Ile Thr Tyr Gly Thr Gly Ser Tyr Thr Ala Tyr Gly Ala Ala
    50                  55                  60

Val Lys Gly Arg Ala Thr Ile Ser Arg Asp Asn Gly Gln Ser Thr Leu
65                  70                  75                  80

Arg Leu Gln Leu Asn Asn Leu Arg Ala Glu Asp Thr Ala Thr Tyr Tyr
                85                  90                  95

Cys Ala Arg Gly Gly Leu Asn Ser Tyr Gly Cys Ser Gly Ala Asn
            100                 105                 110

Ile Asp Ala Trp Gly His Gly Thr Glu Val Ile Val Ser Ser
        115                 120                 125

<210> SEQ ID NO 204
<211> LENGTH: 126
<212> TYPE: PRT
<213> ORGANISM: Artificial Sequence
<220> FEATURE:
<223> OTHER INFORMATION: Synthetic: h10F4-HC4; VH

<400> SEQUENCE: 204

Glu Val Gln Leu Val Glu Ser Gly Gly Gly Leu Val Gln Pro Gly Gly

```
                1               5                  10                  15
                Ser Leu Arg Leu Ser Cys Ala Ala Ser Gly Phe Thr Phe Ser Gly Tyr
                                20                  25                  30

Asn Met Gly Trp Val Arg Gln Ala Pro Gly Lys Gly Leu Glu Trp Val
                            35                  40                  45

Ala Gly Ile Thr Tyr Gly Thr Gly Ser Tyr Thr Ala Tyr Val Asp Ser
                        50                  55                  60

Val Lys Gly Arg Phe Thr Ile Ser Arg Asp Asn Ala Lys Ser Ser Leu
                65                  70                  75                  80

Tyr Leu Gln Met Asn Ser Leu Arg Ala Glu Asp Thr Ala Val Tyr Tyr
                                85                  90                  95

Cys Ala Arg Gly Gly Gly Leu Asn Ser Tyr Gly Cys Ser Gly Ala Asn
                                100                 105                 110

Ile Asp Ala Trp Gly Gln Gly Thr Leu Val Thr Val Ser Ser
                                115                 120                 125
```

<210> SEQ ID NO 205
<211> LENGTH: 126
<212> TYPE: PRT
<213> ORGANISM: Artificial Sequence
<220> FEATURE:
<223> OTHER INFORMATION: Synthetic: h10F4-HC3; VH

<400> SEQUENCE: 205

```
                Gln Val Gln Leu Val Glu Ser Gly Gly Gly Val Val Gln Pro Gly Arg
                1               5                   10                  15

Ser Leu Arg Leu Ser Cys Ala Ala Ser Gly Phe Thr Phe Ser Gly Tyr
                                20                  25                  30

Asn Met Gly Trp Val Arg Gln Ala Pro Gly Lys Gly Leu Glu Trp Val
                            35                  40                  45

Ala Gly Ile Thr Tyr Gly Thr Gly Ser Tyr Thr Ala Tyr Ala Asp Ser
                        50                  55                  60

Val Lys Gly Arg Phe Thr Ile Ser Arg Asp Asn Ser Lys Ser Thr Leu
                65                  70                  75                  80

Tyr Leu Gln Met Asn Ser Leu Arg Ala Glu Asp Thr Ala Val Tyr Tyr
                                85                  90                  95

Cys Ala Arg Gly Gly Gly Leu Asn Ser Tyr Gly Cys Ser Gly Ala Asn
                                100                 105                 110

Ile Asp Ala Trp Gly Gln Gly Thr Leu Val Thr Val Ser Ser
                                115                 120                 125
```

<210> SEQ ID NO 206
<211> LENGTH: 126
<212> TYPE: PRT
<213> ORGANISM: Artificial Sequence
<220> FEATURE:
<223> OTHER INFORMATION: Synthetic: h10F4-HC2; VH

<400> SEQUENCE: 206

```
                Glu Val Gln Leu Leu Glu Ser Gly Gly Gly Leu Val Gln Pro Gly Gly
                1               5                   10                  15

Ser Leu Arg Leu Ser Cys Ala Ala Ser Gly Phe Thr Phe Ser Gly Tyr
                                20                  25                  30

Asn Met Gly Trp Val Arg Gln Ala Pro Gly Lys Gly Leu Glu Trp Val
                            35                  40                  45

Ala Gly Ile Thr Tyr Gly Thr Gly Ser Tyr Thr Ala Tyr Ala Asp Ser
                        50                  55                  60
```

```
Val Lys Gly Arg Phe Thr Ile Ser Arg Asp Asn Ser Lys Ser Thr Leu
 65                  70                  75                  80

Tyr Leu Gln Met Asn Ser Leu Arg Ala Glu Asp Thr Ala Val Tyr Tyr
                 85                  90                  95

Cys Ala Arg Gly Gly Gly Leu Asn Ser Tyr Gly Cys Ser Gly Ala Asn
            100                 105                 110

Ile Asp Ala Trp Gly Gln Gly Thr Leu Val Thr Val Ser Ser
        115                 120                 125

<210> SEQ ID NO 207
<211> LENGTH: 126
<212> TYPE: PRT
<213> ORGANISM: Artificial Sequence
<220> FEATURE:
<223> OTHER INFORMATION: Synthetic: h10F4-HC1; VH

<400> SEQUENCE: 207

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Tyr
                 20                  25                  30

Asn Met Gly Trp Val Arg Gln Ala Pro Gly Lys Gly Leu Glu Trp Val
             35                  40                  45

Ala Gly Ile Thr Tyr Gly Thr Gly Ser Tyr Thr Ala Tyr Ala Ala Pro
         50                  55                  60

Val Lys Gly Arg Phe Thr Ile Ser Arg Asp Asn Ser Lys Ser Thr Leu
 65                  70                  75                  80

Tyr Leu Gln Met Asn Ser Leu Lys Thr Glu Asp Thr Ala Val Tyr Tyr
                 85                  90                  95

Cys Ala Arg Gly Gly Gly Leu Asn Ser Tyr Gly Cys Ser Gly Ala Asn
            100                 105                 110

Ile Asp Ala Trp Gly Gln Gly Thr Leu Val Thr Val Ser Ser
        115                 120                 125

<210> SEQ ID NO 208
<211> LENGTH: 118
<212> TYPE: PRT
<213> ORGANISM: Artificial Sequence
<220> FEATURE:
<223> OTHER INFORMATION: Synthetic: 9A5; VH

<400> SEQUENCE: 208

Ala Val Thr Leu Asp Glu Ser Gly Gly Gly Leu Gln Thr Pro Gly Gly
1               5                   10                  15

Ala Val Ser Leu Val Cys Lys Ala Ser Gly Phe Ser Ile Ser Asp Tyr
                 20                  25                  30

Gly Met Gly Trp Met Arg Gln Ala Pro Gly Lys Gly Leu Gln Tyr Val
             35                  40                  45

Ala Arg Ile Asp His Asp Gly Arg Tyr Thr Asp Tyr Gly Ala Val Val
         50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Tyr Tyr Tyr Cys
                 85                  90                  95

Thr Arg Gly Gly Gly Ala Ala Ser Ile Asp Thr Trp Gly His Gly Thr
            100                 105                 110

Glu Val Ile Val Ser Ser
        115
```

<210> SEQ ID NO 209
<211> LENGTH: 118
<212> TYPE: PRT
<213> ORGANISM: Artificial Sequence
<220> FEATURE:
<223> OTHER INFORMATION: Synthetic: 9E12; VH

<400> SEQUENCE: 209

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Asp Tyr
            20                  25                  30

Gly Leu Gly Trp Met Arg Gln Ala Pro Gly Lys Gly Leu Glu Tyr Val
        35                  40                  45

Ala Arg Ile Asn Ser Ala Gly Ser Gly Thr Tyr Tyr Gly Ser Ala Val
    50                  55                  60

Asp Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Thr Arg Gly Gly Gly Ala Ser Ile Asp Gly Trp Gly His Gly Thr
            100                 105                 110

Glu Val Ile Val Ser Ser
            115
```

<210> SEQ ID NO 210
<211> LENGTH: 118
<212> TYPE: PRT
<213> ORGANISM: Artificial Sequence
<220> FEATURE:
<223> OTHER INFORMATION: Synthetic: 9H1; VH

<400> SEQUENCE: 210

```
Ala Val Thr Leu Asp Glu Ser Gly Gly Gly Leu Gln Thr Pro Gly Gly
1               5                   10                  15

Ala Leu Ser Leu Val Cys Lys Gly Ser Gly Phe Thr Phe Ser Asp Tyr
            20                  25                  30

Gly Met Gly Trp Met Arg Gln Ala Pro Gly Lys Gly Leu Gln Tyr Val
        35                  40                  45

Ala Arg Ile Asn Ser Ala Gly Ser Asp Thr Asn Tyr Gly Ser Ala Val
    50                  55                  60

Lys Gly Arg Ala Thr Ile Ser Arg Asp Asp Gly Gln Ser Thr Val Arg
65                  70                  75                  80

Leu Gln Leu Ser Ser Leu Arg Ala Glu Asp Thr Gly Ile Tyr Tyr Cys
                85                  90                  95

Thr Arg Gly Gly Gly Ala Ser Ile Asp Gly Trp Gly His Gly Thr
            100                 105                 110

Glu Val Ile Val Ser Ser
            115
```

<210> SEQ ID NO 211
<211> LENGTH: 118
<212> TYPE: PRT
<213> ORGANISM: Artificial Sequence
<220> FEATURE:
<223> OTHER INFORMATION: Synthetic: 10H1; VH

<400> SEQUENCE: 211

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Gly Tyr
            20                  25                  30

Gly Met Gly Trp Met Arg Gln Ala Pro Gly Lys Gly Leu Glu Tyr Val
        35                  40                  45

Ala Arg Ile Asn Ser Ala Gly Ser Asp Thr Asp Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Phe Cys
                85                  90                  95

Thr Arg Gly Gly Gly Gly Ala Ser Ile Asp Gly Trp Gly His Gly Thr
                100                 105                 110

Glu Val Ile Val Ser Ser
            115
```

<210> SEQ ID NO 212
<211> LENGTH: 119
<212> TYPE: PRT
<213> ORGANISM: Artificial Sequence
<220> FEATURE:
<223> OTHER INFORMATION: Synthetic: 10E10; VH

<400> SEQUENCE: 212

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Tyr
            20                  25                  30

Gly Met Gly Trp Met Arg Gln Ala Pro Gly Lys Gly Leu Glu Phe Val
        35                  40                  45

Ala Arg Ile Asn Ser Gly Gly Ser Ser Tyr Thr Asp Tyr Gly Ser Ala
    50                  55                  60

Val Lys Gly Arg Ala Thr Ile Ser Arg Asp Asp Gly Gln Ser Thr Val
65                  70                  75                  80

Arg Leu Gln Leu Asn Asn Leu Arg Ala Glu Asp Thr Gly Ile Tyr Tyr
                85                  90                  95

Cys Thr Arg Gly Gly Gly Gly Ala Ser Ile Asp Gly Trp Gly His Gly
                100                 105                 110

Thr Glu Val Ile Val Ser Ser
        115
```

<210> SEQ ID NO 213
<211> LENGTH: 118
<212> TYPE: PRT
<213> ORGANISM: Artificial Sequence
<220> FEATURE:
<223> OTHER INFORMATION: Synthetic: h10H1-HC4; VH

<400> SEQUENCE: 213

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Gly Trp Val Arg Gln Ala Pro Gly Lys Gly Leu Glu Trp Val
        35                  40                  45

Ala Arg Ile Asn Ser Ala Gly Ser Asp Thr Asp Tyr Val Asp Ser Val
    50                  55                  60
```

Lys Gly Arg Phe Thr Ile Ser Arg Asp Asn Ala Lys Ser Ser Val Tyr
65                  70                  75                  80

Leu Gln Met Asn Ser Leu Arg Ala Glu Asp Thr Ala Val Tyr Tyr Cys
                85                  90                  95

Thr Arg Gly Gly Gly Gly Ala Ser Ile Asp Gly Trp Gly Gln Gly Thr
            100                 105                 110

Leu Val Thr Val Ser Ser
            115

<210> SEQ ID NO 214
<211> LENGTH: 118
<212> TYPE: PRT
<213> ORGANISM: Artificial Sequence
<220> FEATURE:
<223> OTHER INFORMATION: Synthetic: h10H1-HC3; VH

<400> SEQUENCE: 214

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Gly Tyr
                20                  25                  30

Gly Met Gly Trp Val Arg Gln Ala Pro Gly Lys Gly Leu Glu Trp Val
            35                  40                  45

Ala Arg Ile Asn Ser Ala Gly Ser Asp Thr Asp Tyr Ala Asp Ser Val
        50                  55                  60

Lys Gly Arg Phe Thr Ile Ser Arg Asp Asn Ser Lys Ser Thr Val Tyr
65                  70                  75                  80

Leu Gln Met Asn Ser Leu Arg Ala Glu Asp Thr Ala Val Tyr Tyr Cys
                85                  90                  95

Thr Arg Gly Gly Gly Gly Ala Ser Ile Asp Gly Trp Gly Gln Gly Thr
            100                 105                 110

Leu Val Thr Val Ser Ser
            115

<210> SEQ ID NO 215
<211> LENGTH: 118
<212> TYPE: PRT
<213> ORGANISM: Artificial Sequence
<220> FEATURE:
<223> OTHER INFORMATION: Synthetic: h10H1-HC2; VH

<400> SEQUENCE: 215

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
                20                  25                  30

Gly Met Gly Trp Val Arg Gln Ala Pro Gly Lys Gly Leu Glu Trp Val
            35                  40                  45

Ala Arg Ile Asn Ser Ala Gly Ser Asp Thr Asp Tyr Ala Asp Ser Val
        50                  55                  60

Lys Gly Arg Phe Thr Ile Ser Arg Asp Asn Ser Lys Ser Thr Val Tyr
65                  70                  75                  80

Leu Gln Met Asn Ser Leu Arg Ala Glu Asp Thr Ala Val Tyr Tyr Cys
                85                  90                  95

Thr Arg Gly Gly Gly Gly Ala Ser Ile Asp Gly Trp Gly Gln Gly Thr
            100                 105                 110

Leu Val Thr Val Ser Ser

```
                    115

<210> SEQ ID NO 216
<211> LENGTH: 118
<212> TYPE: PRT
<213> ORGANISM: Artificial Sequence
<220> FEATURE:
<223> OTHER INFORMATION: Synthetic: h10H1-HC1; VH

<400> SEQUENCE: 216

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Tyr
            20                  25                  30

Gly Met Gly Trp Val Arg Gln Ala Pro Gly Lys Gly Leu Glu Trp Val
        35                  40                  45

Ala Arg Ile Asn Ser Ala Gly Ser Asp Thr Asp Tyr Ala Ala Pro Val
    50                  55                  60

Lys Gly Arg Phe Thr Ile Ser Arg Asp Asn Ser Lys Ser Thr Val Tyr
65                  70                  75                  80

Leu Gln Met Asn Ser Leu Lys Thr Glu Asp Thr Ala Val Tyr Tyr Cys
                85                  90                  95

Thr Arg Gly Gly Gly Gly Ala Ser Ile Asp Gly Trp Gly Gln Gly Thr
            100                 105                 110

Leu Val Thr Val Ser Ser
            115

<210> SEQ ID NO 217
<211> LENGTH: 107
<212> TYPE: PRT
<213> ORGANISM: Artificial Sequence
<220> FEATURE:
<223> OTHER INFORMATION: Synthetic: trastuzumab; VL

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 218
<211> LENGTH: 102
<212> TYPE: PRT
<213> ORGANISM: Artificial Sequence
<220> FEATURE:
<223> OTHER INFORMATION: Synthetic: 9A8; VL

<400> SEQUENCE: 218

Ala Leu Thr Gln Pro Ser Ser Val Ser Ala Asn Pro Gly Glu Thr Val
1               5                   10                  15
```

Lys Ile Thr Cys Ser Gly Gly Ser Ser Asp Tyr Gly Trp Phe Gln Gln
            20                  25                  30

Lys Ser Pro Gly Ser Ala Pro Val Thr Val Ile Tyr Ser Asn Asn Gln
        35                  40                  45

Arg Pro Ser Gly Ile Pro Ser Arg Phe Ser Gly Ser Lys Ser Gly Ser
    50                  55                  60

Thr Gly Thr Leu Thr Ile Thr Gly Val Gln Ala Glu Asp Glu Ala Ile
65                  70                  75                  80

Tyr Tyr Cys Ala Asn Val Asp Tyr Thr Asp Asp Val Phe Gly Ala Gly
                85                  90                  95

Thr Thr Leu Thr Val Leu
            100

<210> SEQ ID NO 219
<211> LENGTH: 102
<212> TYPE: PRT
<213> ORGANISM: Artificial Sequence
<220> FEATURE:
<223> OTHER INFORMATION: Synthetic: 10G5; VL

<400> SEQUENCE: 219

Ala Leu Thr Gln Pro Ser Ser Val Ser Ala Asn Pro Gly Glu Thr Val
1               5                   10                  15

Lys Ile Thr Cys Ser Gly Gly Asn Tyr Asp Tyr Gly Trp Tyr Gln Gln
            20                  25                  30

Lys Ser Pro Gly Ser Ala Pro Val Thr Leu Ile Tyr Tyr Asn Asn Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Gln Ala Glu Asp Glu Ala Ile
65                  70                  75                  80

Tyr Tyr Cys Ala Asn Val Asp Ser Thr Asp Asp Val Phe Gly Ala Gly
                85                  90                  95

Thr Thr Leu Thr Val Leu
            100

<210> SEQ ID NO 220
<211> LENGTH: 102
<212> TYPE: PRT
<213> ORGANISM: Artificial Sequence
<220> FEATURE:
<223> OTHER INFORMATION: Synthetic: 11D6; VL

<400> SEQUENCE: 220

Ala Leu Thr Gln Pro Ser Ser Val Ser Ala Asn Pro Gly Glu Thr Val
1               5                   10                  15

Glu Ile Thr Cys Ser Gly Gly Asn Ser Asp Tyr Gly Trp Phe Gln Gln
            20                  25                  30

Lys Ser Pro Gly Ser Ala Pro Val Thr Val Ile Tyr Arg Asn Asn Gln
        35                  40                  45

Arg Pro Ser Asp Ile Pro Ser Arg Phe Ser Gly Ser Gly Ser Gly Ser
    50                  55                  60

Thr Asn Thr Leu Thr Ile Thr Gly Val Gln Ala Glu Asp Glu Ala Ile
65                  70                  75                  80

Tyr Tyr Cys Gly Asn Val Asp Phe Thr Asp Asp Val Phe Gly Ala Gly
                85                  90                  95

Thr Thr Leu Thr Val Leu

-continued

```
                100

<210> SEQ ID NO 221
<211> LENGTH: 104
<212> TYPE: PRT
<213> ORGANISM: Artificial Sequence
<220> FEATURE:
<223> OTHER INFORMATION: Synthetic: h11D6-LC4; VL

<400> SEQUENCE: 221

Ser Tyr Val Leu Thr Gln Pro Pro Ser Val Ser Val Ala Pro Gly Lys
1               5                   10                  15

Thr Ala Arg Ile Thr Cys Ser Gly Gly Asn Ser Asp Tyr Gly Trp Tyr
            20                  25                  30

Gln Gln Lys Pro Gly Gln Ala Pro Val Leu Val Val Tyr Arg Asn Asn
        35                  40                  45

Gln Arg Pro Ser Gly Ile Pro Glu Arg Phe Ser Gly Ser Gly Ser Gly
    50                  55                  60

Ser Thr Asn Thr Leu Thr Ile Ser Gly Thr Gln Ala Met Asp Glu Ala
65                  70                  75                  80

Asp Tyr Tyr Cys Gly Gly Phe Asp Ser Ser Asp Ala Ile Phe Gly
                85                  90                  95

Gly Gly Thr Lys Leu Thr Val Leu
            100

<210> SEQ ID NO 222
<211> LENGTH: 104
<212> TYPE: PRT
<213> ORGANISM: Artificial Sequence
<220> FEATURE:
<223> OTHER INFORMATION: Synthetic: h11D6-LC3; VL

<400> SEQUENCE: 222

Ser Tyr Glu Leu Thr Gln Pro Pro Ser Val Ser Val Ser Pro Gly Gln
1               5                   10                  15

Thr Ala Ser Ile Thr Cys Ser Gly Gly Asn Ser Asp Tyr Gly Trp Tyr
            20                  25                  30

Gln Gln Lys Pro Gly Gln Ser Pro Val Leu Val Ile Tyr Arg Asn Asn
        35                  40                  45

Gln Arg Pro Ser Gly Ile Pro Glu Arg Phe Ser Gly Ser Gly Ser Gly
    50                  55                  60

Ser Thr Asn Thr Leu Thr Ile Ser Gly Thr Gln Ala Met Asp Glu Ala
65                  70                  75                  80

Asp Tyr Tyr Cys Gly Gly Phe Asp Ser Ser Asp Ala Ile Phe Gly
                85                  90                  95

Gly Gly Thr Lys Leu Thr Val Leu
            100

<210> SEQ ID NO 223
<211> LENGTH: 104
<212> TYPE: PRT
<213> ORGANISM: Artificial Sequence
<220> FEATURE:
<223> OTHER INFORMATION: Synthetic: h11D6-LC2; VL

<400> SEQUENCE: 223

Gln Ser Val Leu Thr Gln Pro Pro Ser Val Ser Ala Ala Pro Gly Gln
1               5                   10                  15

Lys Val Thr Ile Ser Cys Ser Gly Gly Asn Ser Asp Tyr Gly Trp Tyr
            20                  25                  30
```

```
Gln Gln Leu Pro Gly Thr Ala Pro Lys Leu Leu Ile Tyr Arg Asn Asn
            35                  40                  45

Gln Arg Pro Ser Gly Ile Pro Asp Arg Phe Ser Gly Ser Gly Ser Gly
 50                  55                  60

Ser Thr Asn Thr Leu Gly Ile Thr Gly Leu Gln Thr Gly Asp Glu Ala
 65                  70                  75                  80

Asp Tyr Tyr Cys Gly Gly Phe Asp Ser Ser Asp Ala Ile Phe Gly
                 85                  90                  95

Gly Gly Thr Lys Leu Thr Val Leu
            100
```

```
<210> SEQ ID NO 224
<211> LENGTH: 105
<212> TYPE: PRT
<213> ORGANISM: Artificial Sequence
<220> FEATURE:
<223> OTHER INFORMATION: Synthetic: h11D6-LC1; VL

<400> SEQUENCE: 224

Asp Ile Gln Met Thr Gln Ser Pro Ser Ser Val Ser Ala Ser Val Gly
 1               5                  10                  15

Asp Arg Val Thr Ile Thr Cys Ser Gly Gly Asn Ser Asp Tyr Gly Trp
            20                  25                  30

Tyr Gln Gln Lys Pro Gly Lys Ala Pro Lys Leu Leu Ile Tyr Arg Asn
        35                  40                  45

Asn Gln Arg Pro Ser Gly Val Pro Ser Arg Phe Ser Gly Ser Gly Ser
 50                  55                  60

Gly Ser Thr Asn Thr Leu Thr Ile Ser Ser Leu Gln Pro Glu Asp Phe
 65                  70                  75                  80

Ala Thr Tyr Tyr Cys Gly Gly Phe Asp Ser Ser Asp Ala Ile Phe
                 85                  90                  95

Gly Gln Gly Thr Lys Val Glu Ile Lys
            100                 105
```

```
<210> SEQ ID NO 225
<211> LENGTH: 108
<212> TYPE: PRT
<213> ORGANISM: Artificial Sequence
<220> FEATURE:
<223> OTHER INFORMATION: Synthetic: 10F4; VL

<400> SEQUENCE: 225

Ala Leu Thr Gln Pro Ser Ser Val Ser Ala Asn Leu Gly Gly Thr Val
 1               5                  10                  15

Lys Ile Thr Cys Ser Gly Gly Gly Asn Tyr Phe Gly Ser Tyr Tyr Tyr
            20                  25                  30

Gly Trp Tyr Gln Gln Lys Ala Pro Gly Ser Ala Pro Val Thr Val Ile
        35                  40                  45

Tyr Asn Asn Asn Asn Arg Pro Ser Asp Ile Pro Ser Arg Phe Ser Gly
        50                  55                  60

Ser Thr Ser Gly Ser Thr Ser Thr Leu Thr Ile Ser Gly Val Arg Ala
 65                  70                  75                  80

Glu Asp Glu Ala Val Tyr Phe Cys Gly Gly Phe Asp Ser Ser Thr Asp
                 85                  90                  95

Ala Ile Phe Gly Ala Gly Thr Thr Leu Thr Val Leu
            100                 105
```

<210> SEQ ID NO 226
<211> LENGTH: 109
<212> TYPE: PRT
<213> ORGANISM: Artificial Sequence
<220> FEATURE:
<223> OTHER INFORMATION: Synthetic: h10F4-LC4; VL

<400> SEQUENCE: 226

```
Ser Tyr Val Leu Thr Gln Pro Pro Ser Val Ser Val Ala Pro Gly Lys
1               5                   10                  15

Thr Ala Arg Ile Thr Cys Ser Gly Gly Asn Tyr Phe Gly Ser Tyr
            20                  25                  30

Tyr Tyr Gly Trp Tyr Gln Gln Lys Pro Gly Gln Ala Pro Val Leu Val
        35                  40                  45

Val Tyr Asn Asn Asn Arg Pro Ser Gly Ile Pro Glu Arg Phe Ser
    50                  55                  60

Gly Ser Thr Ser Gly Ser Thr Ser Thr Leu Thr Ile Ser Gly Thr Gln
65                  70                  75                  80

Ala Met Asp Glu Ala Asp Tyr Tyr Cys Gly Gly Phe Asp Ser Ser Thr
                85                  90                  95

Asp Ala Ile Phe Gly Gly Gly Thr Lys Leu Thr Val Leu
            100                 105
```

<210> SEQ ID NO 227
<211> LENGTH: 109
<212> TYPE: PRT
<213> ORGANISM: Artificial Sequence
<220> FEATURE:
<223> OTHER INFORMATION: Synthetic: h10F4-LC3; VL

<400> SEQUENCE: 227

```
Ser Tyr Glu Leu Thr Gln Pro Pro Ser Val Ser Val Ser Pro Gly Gln
1               5                   10                  15

Thr Ala Ser Ile Thr Cys Ser Gly Gly Gly Asn Tyr Phe Gly Ser Tyr
            20                  25                  30

Tyr Tyr Gly Trp Tyr Gln Gln Lys Pro Gly Gln Ser Pro Val Leu Val
        35                  40                  45

Ile Tyr Asn Asn Asn Arg Pro Ser Gly Ile Pro Glu Arg Phe Ser
    50                  55                  60

Gly Ser Thr Ser Gly Ser Thr Ser Thr Leu Thr Ile Ser Gly Thr Gln
65                  70                  75                  80

Ala Met Asp Glu Ala Asp Tyr Tyr Cys Gly Gly Phe Asp Ser Ser Thr
                85                  90                  95

Asp Ala Ile Phe Gly Gly Gly Thr Lys Leu Thr Val Leu
            100                 105
```

<210> SEQ ID NO 228
<211> LENGTH: 109
<212> TYPE: PRT
<213> ORGANISM: Artificial Sequence
<220> FEATURE:
<223> OTHER INFORMATION: Synthetic: h10F4-LC2; VL

<400> SEQUENCE: 228

```
Gln Ser Val Leu Thr Gln Pro Pro Ser Val Ser Ala Ala Pro Gly Gln
1               5                   10                  15

Lys Val Thr Ile Ser Cys Ser Gly Gly Gly Asn Tyr Phe Gly Ser Tyr
            20                  25                  30

Tyr Tyr Gly Trp Tyr Gln Gln Leu Pro Gly Thr Ala Pro Lys Leu Leu
        35                  40                  45
```

Ile Tyr Asn Asn Asn Arg Pro Ser Gly Ile Pro Asp Arg Phe Ser
    50                  55                  60

Gly Ser Thr Ser Gly Ser Thr Ser Thr Leu Gly Ile Thr Gly Leu Gln
 65                  70                  75                  80

Thr Gly Asp Glu Ala Asp Tyr Tyr Cys Gly Gly Phe Asp Ser Ser Thr
                 85                  90                  95

Asp Ala Ile Phe Gly Gly Gly Thr Lys Leu Thr Val Leu
            100                 105

<210> SEQ ID NO 229
<211> LENGTH: 110
<212> TYPE: PRT
<213> ORGANISM: Artificial Sequence
<220> FEATURE:
<223> OTHER INFORMATION: Synthetic: h10F4-LC1; VL

<400> SEQUENCE: 229

Asp Ile Gln Met Thr Gln Ser Pro Ser Ser Val Ser Ala Ser Val Gly
 1               5                   10                  15

Asp Arg Val Thr Ile Thr Cys Ser Gly Gly Asn Tyr Phe Gly Ser
                 20                  25                  30

Tyr Tyr Tyr Gly Trp Tyr Gln Gln Lys Pro Gly Lys Ala Pro Lys Leu
             35                  40                  45

Leu Ile Tyr Asn Asn Asn Arg Pro Ser Gly Val Pro Ser Arg Phe
 50                  55                  60

Ser Gly Ser Thr Ser Gly Ser Thr Ser Thr Leu Thr Ile Ser Ser Leu
 65                  70                  75                  80

Gln Pro Glu Asp Phe Ala Thr Tyr Tyr Cys Gly Gly Phe Asp Ser Ser
                 85                  90                  95

Thr Asp Ala Ile Phe Gly Gln Gly Thr Lys Val Glu Ile Lys
            100                 105                 110

<210> SEQ ID NO 230
<211> LENGTH: 108
<212> TYPE: PRT
<213> ORGANISM: Artificial Sequence
<220> FEATURE:
<223> OTHER INFORMATION: Synthetic: 9A5; VL

<400> SEQUENCE: 230

Ala Leu Thr Gln Pro Ser Ser Val Ser Ala Asn Pro Gly Glu Thr Val
 1               5                   10                  15

Lys Ile Thr Cys Ser Gly Gly Gly Asn Tyr Val Gly Tyr Tyr Tyr
                 20                  25                  30

Gly Trp Tyr Gln Gln Lys Ala Pro Gly Ser Ala Leu Val Thr Leu Ile
             35                  40                  45

Tyr Asn Asn Asn Arg Pro Ser Asn Ile Pro Ser Arg Phe Ser Gly
 50                  55                  60

Ser Thr Ser Gly Ser Thr Ser Thr Leu Thr Ile Thr Gly Val Arg Ala
 65                  70                  75                  80

Glu Asp Glu Ala Val Tyr Phe Cys Gly Ser Phe Asp Ser Ser Thr Asp
                 85                  90                  95

Ala Ile Phe Gly Ala Gly Thr Thr Leu Thr Val Leu
            100                 105

<210> SEQ ID NO 231
<211> LENGTH: 108
<212> TYPE: PRT

<213> ORGANISM: Artificial Sequence
<220> FEATURE:
<223> OTHER INFORMATION: Synthetic: 9E12; VL

<400> SEQUENCE: 231

```
Ala Leu Thr Gln Pro Ser Ser Val Ser Ala Asn Pro Gly Glu Thr Val
1               5                   10                  15

Lys Ile Thr Cys Ser Gly Gly Ser Tyr Tyr Gly Ser Tyr Tyr Tyr
            20                  25                  30

Gly Trp Tyr Gln Gln Lys Ser Pro Gly Ser Ala Pro Val Thr Leu Ile
            35                  40                  45

Tyr Asn Asn Asn Arg Pro Ser Asp Ile Pro Ser Arg Phe Ser Gly
    50                  55                  60

Ser Thr Ser Gly Ser Thr Gly Thr Leu Thr Ile Thr Gly Val Arg Ala
65                  70                  75                  80

Glu Asp Glu Ala Val Tyr Tyr Cys Gly Ser Phe Asp Ser Ser Thr Asp
                85                  90                  95

Ala Ile Phe Gly Ala Gly Thr Thr Leu Thr Val Leu
            100                 105
```

<210> SEQ ID NO 232
<211> LENGTH: 108
<212> TYPE: PRT
<213> ORGANISM: Artificial Sequence
<220> FEATURE:
<223> OTHER INFORMATION: Synthetic: 9H1; VL

<400> SEQUENCE: 232

```
Ala Leu Thr Gln Pro Ser Ser Val Ser Ala Asn Pro Gly Glu Thr Val
1               5                   10                  15

Lys Ile Thr Cys Ser Gly Gly Ser Tyr Tyr Gly Ser Tyr Tyr Tyr
            20                  25                  30

Gly Trp Tyr Gln Gln Lys Ser Pro Gly Ser Ala Pro Val Thr Leu Ile
            35                  40                  45

Tyr Asn Asn Asn Arg Pro Ser Asp Ile Pro Ser Arg Phe Ser Gly
    50                  55                  60

Ser Thr Ser Gly Ser Thr Gly Thr Leu Thr Ile Thr Gly Val Arg Ala
65                  70                  75                  80

Glu Asp Glu Ala Val Tyr Tyr Cys Gly Ser Phe Asp Ser Ser Thr Asp
                85                  90                  95

Ala Ile Phe Gly Ala Gly Thr Thr Leu Thr Val Leu
            100                 105
```

<210> SEQ ID NO 233
<211> LENGTH: 108
<212> TYPE: PRT
<213> ORGANISM: Artificial Sequence
<220> FEATURE:
<223> OTHER INFORMATION: Synthetic: 10H1; VL

<400> SEQUENCE: 233

```
Ala Leu Thr Gln Pro Ser Ser Val Ser Ala Asn Pro Gly Glu Thr Val
1               5                   10                  15

Lys Ile Thr Cys Ser Gly Gly Gly Asn Tyr Tyr Gly Ser Tyr Tyr Tyr
            20                  25                  30

Gly Trp Tyr Gln Gln Lys Ala Pro Gly Ser Ala Pro Val Thr Val Ile
            35                  40                  45

Tyr Asn Asn Asn Arg Pro Ser Asn Ile Pro Ser Arg Phe Ser Gly
    50                  55                  60
```

```
Ser Lys Ser Gly Ser Thr Gly Thr Leu Thr Ile Thr Gly Val Gln Ala
 65                  70                  75                  80

Glu Asp Glu Ala Val Tyr Phe Cys Gly Gly Phe Asp Ser Ser Ser Asp
                 85                  90                  95

Ala Ile Phe Gly Ala Gly Thr Thr Leu Thr Val Leu
                100                 105
```

<210> SEQ ID NO 234
<211> LENGTH: 108
<212> TYPE: PRT
<213> ORGANISM: Artificial Sequence
<220> FEATURE:
<223> OTHER INFORMATION: Synthetic: 10E10; VL

<400> SEQUENCE: 234

```
Ala Leu Thr Gln Pro Ser Ser Val Ser Ala Asn Pro Gly Glu Thr Val
 1               5                  10                  15

Lys Ile Thr Cys Ser Gly Gly Asn Tyr Ala Gly Ser Tyr Tyr Tyr
             20                  25                  30

Gly Trp Tyr Gln Gln Lys Ser Pro Gly Ser Ala Pro Leu Thr Val Ile
         35                  40                  45

Tyr Asn Ser Asn Asn Arg Pro Ser Asp Ile Pro Ser Arg Phe Ser Gly
 50                  55                  60

Ser Leu Ser Gly Ser Thr Gly Thr Leu Thr Ile Thr Gly Val Arg Ala
 65                  70                  75                  80

Glu Asp Glu Ala Val Tyr Phe Cys Gly Gly Phe Asp Ser Ser Thr Asp
                 85                  90                  95

Ala Ile Phe Gly Ala Gly Thr Thr Leu Thr Val Leu
                100                 105
```

<210> SEQ ID NO 235
<211> LENGTH: 109
<212> TYPE: PRT
<213> ORGANISM: Artificial Sequence
<220> FEATURE:
<223> OTHER INFORMATION: Synthetic: h10H1-LC4; VL

<400> SEQUENCE: 235

```
Ser Tyr Val Leu Thr Gln Pro Pro Ser Val Ser Val Ala Pro Gly Lys
 1               5                  10                  15

Thr Ala Arg Ile Thr Cys Ser Gly Gly Asn Tyr Tyr Gly Ser Tyr
             20                  25                  30

Tyr Tyr Gly Trp Tyr Gln Gln Lys Pro Gly Gln Ala Pro Val Leu Val
         35                  40                  45

Val Tyr Asn Asn Asn Arg Pro Ser Gly Ile Pro Glu Arg Phe Ser
 50                  55                  60

Gly Ser Lys Ser Gly Ser Thr Gly Thr Leu Thr Ile Ser Gly Thr Gln
 65                  70                  75                  80

Ala Met Asp Glu Ala Asp Tyr Tyr Cys Gly Gly Phe Asp Ser Ser Ser
                 85                  90                  95

Asp Ala Ile Phe Gly Gly Gly Thr Lys Leu Thr Val Leu
                100                 105
```

<210> SEQ ID NO 236
<211> LENGTH: 109
<212> TYPE: PRT
<213> ORGANISM: Artificial Sequence
<220> FEATURE:
<223> OTHER INFORMATION: Synthetic: h10H1-LC3; VL

<400> SEQUENCE: 236

```
Ser Tyr Glu Leu Thr Gln Pro Pro Ser Val Ser Val Ser Pro Gly Gln
1               5                   10                  15

Thr Ala Ser Ile Thr Cys Ser Gly Gly Asn Tyr Tyr Gly Ser Tyr
            20                  25                  30

Tyr Tyr Gly Trp Tyr Gln Gln Lys Pro Gly Gln Ser Pro Val Leu Val
        35                  40                  45

Ile Tyr Asn Asn Asn Arg Pro Ser Gly Ile Pro Glu Arg Phe Ser
    50                  55                  60

Gly Ser Lys Ser Gly Ser Thr Gly Thr Leu Thr Ile Ser Gly Thr Gln
65                  70                  75                  80

Ala Met Asp Glu Ala Asp Tyr Tyr Cys Gly Gly Phe Asp Ser Ser
                85                  90                  95

Asp Ala Ile Phe Gly Gly Gly Thr Lys Leu Thr Val Leu
            100                 105
```

<210> SEQ ID NO 237
<211> LENGTH: 109
<212> TYPE: PRT
<213> ORGANISM: Artificial Sequence
<220> FEATURE:
<223> OTHER INFORMATION: Synthetic: h10H1-LC2; VL

<400> SEQUENCE: 237

```
Gln Ser Val Leu Thr Gln Pro Pro Ser Val Ser Ala Ala Pro Gly Gln
1               5                   10                  15

Lys Val Thr Ile Ser Cys Ser Gly Gly Asn Tyr Tyr Gly Ser Tyr
            20                  25                  30

Tyr Tyr Gly Trp Tyr Gln Gln Leu Pro Gly Thr Ala Pro Lys Leu Leu
        35                  40                  45

Ile Tyr Asn Asn Asn Arg Pro Ser Gly Ile Pro Asp Arg Phe Ser
    50                  55                  60

Gly Ser Lys Ser Gly Ser Thr Gly Thr Leu Gly Ile Thr Gly Leu Gln
65                  70                  75                  80

Thr Gly Asp Glu Ala Asp Tyr Tyr Cys Gly Gly Phe Asp Ser Ser Ser
                85                  90                  95

Asp Ala Ile Phe Gly Gly Gly Thr Lys Leu Thr Val Leu
            100                 105
```

<210> SEQ ID NO 238
<211> LENGTH: 110
<212> TYPE: PRT
<213> ORGANISM: Artificial Sequence
<220> FEATURE:
<223> OTHER INFORMATION: Synthetic: h10H1-LC1; VL

<400> SEQUENCE: 238

```
Asp Ile Gln Met Thr Gln Ser Pro Ser Val Ser Ala Ser Val Gly
1               5                   10                  15

Asp Arg Val Thr Ile Thr Cys Ser Gly Gly Asn Tyr Tyr Gly Ser
            20                  25                  30

Tyr Tyr Tyr Gly Trp Tyr Gln Gln Lys Pro Gly Lys Ala Pro Lys Leu
        35                  40                  45

Leu Ile Tyr Asn Asn Asn Arg Pro Ser Gly Val Pro Ser Arg Phe
    50                  55                  60

Ser Gly Ser Lys Ser Gly Ser Thr Gly Thr Leu Thr Ile Ser Ser Leu
65                  70                  75                  80
```

Gln Pro Glu Asp Phe Ala Thr Tyr Tyr Cys Gly Gly Phe Asp Ser Ser
                85                  90                  95

Ser Asp Ala Ile Phe Gly Gln Gly Thr Lys Val Glu Ile Lys
            100                 105                 110

<210> SEQ ID NO 239
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1 HC Constant

<400> SEQUENCE: 239

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

```
Gln Lys Ser Leu Ser Leu Ser Pro Gly Lys
            325                 330
```

<210> SEQ ID NO 240
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: Human IgG LC Constant Ckappa

<400> SEQUENCE: 240

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 241
<211> LENGTH: 323
<212> TYPE: PRT
<213> ORGANISM: Mus musculus
<220> FEATURE:
<221> NAME/KEY: misc_feature
<222> LOCATION: (1)..(323)
<223> OTHER INFORMATION: Mouse IgG1 HC Constant

<400> SEQUENCE: 241

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
```

```
                    165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly

<210> SEQ ID NO 242
<211> LENGTH: 107
<212> TYPE: PRT
<213> ORGANISM: Mus musculus
<220> FEATURE:
<221> NAME/KEY: misc_feature
<222> LOCATION: (1)..(107)
<223> OTHER INFORMATION: Mouse IgG LC Constant Ckappa

<400> SEQUENCE: 242

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 243
<211> LENGTH: 108
<212> TYPE: PRT
<213> ORGANISM: Artificial Sequence
<220> FEATURE:
<223> OTHER INFORMATION: Synthetic: Kappa LC

<400> SEQUENCE: 243

His Met Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30
```

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
 50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Thr His Gln Gly Leu Ser
                 85                  90                  95

Ser Pro Val Thr Lys Ser Phe Asn Arg Gly Glu Cys
            100                 105

<210> SEQ ID NO 244
<211> LENGTH: 106
<212> TYPE: PRT
<213> ORGANISM: Artificial Sequence
<220> FEATURE:
<223> OTHER INFORMATION: Synthetic: Lambda LD

<400> SEQUENCE: 244

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 245
<211> LENGTH: 20
<212> TYPE: PRT
<213> ORGANISM: Artificial Sequence
<220> FEATURE:
<223> OTHER INFORMATION: Synthetic: FlagHis Tag

<400> SEQUENCE: 245

Gly Ser Gly Asp Tyr Lys Asp Asp Asp Lys Gly Ser Gly His His
 1               5                  10                  15

His His His His
         20

<210> SEQ ID NO 246
<211> LENGTH: 15
<212> TYPE: PRT
<213> ORGANISM: Artificial Sequence
<220> FEATURE:
<223> OTHER INFORMATION: Synthetic: Linker

<400> SEQUENCE: 246

Gly Gly Gly Gly Ser Gly Gly Gly Gly Ser Gly Gly Gly Gly Ser
 1               5                  10                  15

<210> SEQ ID NO 247
<211> LENGTH: 11

```
<212> TYPE: PRT
<213> ORGANISM: Artificial Sequence
<220> FEATURE:
<223> OTHER INFORMATION: Synthetic: Linker

<400> SEQUENCE: 247

Ala Ala Gly Ser Asp Gln Glu Pro Lys Ser Ser
1               5                   10

<210> SEQ ID NO 248
<211> LENGTH: 13
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (2)..(2)
<223> OTHER INFORMATION: X is Y or F
<220> FEATURE:
<221> NAME/KEY: misc_feature
<222> LOCATION: (3)..(3)
<223> OTHER INFORMATION: X is V or I
<220> FEATURE:
<221> NAME/KEY: misc_feature
<222> LOCATION: (4)..(4)
<223> OTHER INFORMATION: X is Y, L, N, R, Q, or P
<220> FEATURE:
<221> NAME/KEY: misc_feature
<222> LOCATION: (5)..(5)
<223> OTHER INFORMATION: X is Q, A, N, or S

<400> SEQUENCE: 248

Asp Xaa Xaa Xaa Xaa Tyr Trp Thr Tyr Val Leu Asp Tyr
1               5                   10

<210> SEQ ID NO 249
<211> LENGTH: 13
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (3)..(3)
<223> OTHER INFORMATION: X is G or D
<220> FEATURE:
<221> NAME/KEY: misc_feature
<222> LOCATION: (4)..(4)
<223> OTHER INFORMATION: X is P or L
<220> FEATURE:
<221> NAME/KEY: misc_feature
<222> LOCATION: (5)..(5)
<223> OTHER INFORMATION: X is W or R
<220> FEATURE:
<221> NAME/KEY: misc_feature
<222> LOCATION: (7)..(7)
<223> OTHER INFORMATION: X is G or L

<400> SEQUENCE: 249

Asp Tyr Xaa Xaa Xaa Tyr Xaa Thr Gly Val Leu Asp Tyr
1               5                   10

<210> SEQ ID NO 250
<211> LENGTH: 13
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (2)..(2)
<223> OTHER INFORMATION: X is L, M, or W
```

```
<220> FEATURE:
<221> NAME/KEY: misc_feature
<222> LOCATION: (4)..(4)
<223> OTHER INFORMATION: X is G, V, H, Y, or S
<220> FEATURE:
<221> NAME/KEY: misc_feature
<222> LOCATION: (5)..(5)
<223> OTHER INFORMATION: X is G or R
<220> FEATURE:
<221> NAME/KEY: misc_feature
<222> LOCATION: (10)..(10)
<223> OTHER INFORMATION: X is F or V
<220> FEATURE:
<221> NAME/KEY: misc_feature
<222> LOCATION: (11)..(11)
<223> OTHER INFORMATION: X is F or S

<400> SEQUENCE: 250

Asp Xaa Gly Xaa Xaa Tyr Trp Val Gly Xaa Xaa Asp Tyr
1               5                   10

<210> SEQ ID NO 251
<211> LENGTH: 13
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (2)..(2)
<223> OTHER INFORMATION: X is F or Y
<220> FEATURE:
<221> NAME/KEY: misc_feature
<222> LOCATION: (3)..(3)
<223> OTHER INFORMATION: X is Y, H, or N
<220> FEATURE:
<221> NAME/KEY: misc_feature
<222> LOCATION: (7)..(7)
<223> OTHER INFORMATION: X is S, A, or F
<220> FEATURE:
<221> NAME/KEY: misc_feature
<222> LOCATION: (9)..(9)
<223> OTHER INFORMATION: X is Y or F

<400> SEQUENCE: 251

Asp Xaa Xaa Asp Arg Tyr Xaa Thr Xaa Val Leu Asp Tyr
1               5                   10

<210> SEQ ID NO 252
<211> LENGTH: 12
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (4)..(4)
<223> OTHER INFORMATION: X is I or V

<400> SEQUENCE: 252

Thr Thr Cys Xaa Gly Ser Gly Gly Cys Ile Asp Thr
1               5                   10

<210> SEQ ID NO 253
<211> LENGTH: 9
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (4)..(4)
<223> OTHER INFORMATION: X is A or G
```

```
<220> FEATURE:
<221> NAME/KEY: misc_feature
<222> LOCATION: (9)..(9)
<223> OTHER INFORMATION: X is T or G

<400> SEQUENCE: 253

Gly Gly Gly Xaa Ala Ser Ile Asp Xaa
1               5

<210> SEQ ID NO 254
<211> LENGTH: 7
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (5)..(5)
<223> OTHER INFORMATION: X is S, I, R, Y, or G
<220> FEATURE:
<221> NAME/KEY: misc_feature
<222> LOCATION: (6)..(6)
<223> OTHER INFORMATION: X is G, Y, A, V, or R
<220> FEATURE:
<221> NAME/KEY: misc_feature
<222> LOCATION: (7)..(7)
<223> OTHER INFORMATION: X is S or P

<400> SEQUENCE: 254

Gly Phe Asn Ile Xaa Xaa Xaa
1               5

<210> SEQ ID NO 255
<211> LENGTH: 7
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (5)..(5)
<223> OTHER INFORMATION: X is S, T, A, or Q
<220> FEATURE:
<221> NAME/KEY: misc_feature
<222> LOCATION: (6)..(6)
<223> OTHER INFORMATION: X is S, P, Y, or T
<220> FEATURE:
<221> NAME/KEY: misc_feature
<222> LOCATION: (7)..(7)
<223> OTHER INFORMATION: X is Y, D, or R

<400> SEQUENCE: 255

Gly Phe Asn Ile Xaa Xaa Xaa
1               5

<210> SEQ ID NO 256
<211> LENGTH: 7
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (5)..(5)
<223> OTHER INFORMATION: X is S, A, K, or D
<220> FEATURE:
<221> NAME/KEY: misc_feature
<222> LOCATION: (6)..(6)
<223> OTHER INFORMATION: X is S, A, P, or D
<220> FEATURE:
<221> NAME/KEY: misc_feature
<222> LOCATION: (7)..(7)
<223> OTHER INFORMATION: X is Y or T
```

```
<400> SEQUENCE: 256

Gly Phe Asn Ile Xaa Xaa Xaa
1               5

<210> SEQ ID NO 257
<211> LENGTH: 7
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (3)..(3)
<223> OTHER INFORMATION: X is S or T
<220> FEATURE:
<221> NAME/KEY: misc_feature
<222> LOCATION: (4)..(4)
<223> OTHER INFORMATION: X is I or F
<220> FEATURE:
<221> NAME/KEY: misc_feature
<222> LOCATION: (6)..(6)
<223> OTHER INFORMATION: X is D, G, or S

<400> SEQUENCE: 257

Gly Phe Xaa Xaa Ser Xaa Tyr
1               5

<210> SEQ ID NO 258
<211> LENGTH: 7
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (1)..(1)
<223> OTHER INFORMATION: X is N or S
<220> FEATURE:
<221> NAME/KEY: misc_feature
<222> LOCATION: (3)..(3)
<223> OTHER INFORMATION: X is absent
<220> FEATURE:
<221> NAME/KEY: misc_feature
<222> LOCATION: (5)..(5)
<223> OTHER INFORMATION: X is G or A

<400> SEQUENCE: 258

Xaa Pro Xaa Ala Xaa Gly Tyr
1               5

<210> SEQ ID NO 259
<211> LENGTH: 7
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (3)..(3)
<223> OTHER INFORMATION: X is absent
<220> FEATURE:
<221> NAME/KEY: misc_feature
<222> LOCATION: (5)..(5)
<223> OTHER INFORMATION: X is S or I
<220> FEATURE:
<221> NAME/KEY: misc_feature
<222> LOCATION: (7)..(7)
<223> OTHER INFORMATION: X is Y or F

<400> SEQUENCE: 259

Tyr Pro Xaa Tyr Xaa Gly Xaa
```

1               5

<210> SEQ ID NO 260
<211> LENGTH: 7
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (3)..(3)
<223> OTHER INFORMATION: X is absent
<220> FEATURE:
<221> NAME/KEY: misc_feature
<222> LOCATION: (4)..(4)
<223> OTHER INFORMATION: X is S, P, A, or F
<220> FEATURE:
<221> NAME/KEY: misc_feature
<222> LOCATION: (5)..(5)
<223> OTHER INFORMATION: X is G, S, A, or D
<220> FEATURE:
<221> NAME/KEY: misc_feature
<222> LOCATION: (7)..(7)
<223> OTHER INFORMATION: X is Y or F

<400> SEQUENCE: 260

Thr Pro Xaa Xaa Xaa Gly Xaa
1               5

<210> SEQ ID NO 261
<211> LENGTH: 7
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (1)..(1)
<223> OTHER INFORMATION: X is S or F
<220> FEATURE:
<221> NAME/KEY: misc_feature
<222> LOCATION: (3)..(3)
<223> OTHER INFORMATION: X is absent
<220> FEATURE:
<221> NAME/KEY: misc_feature
<222> LOCATION: (4)..(4)
<223> OTHER INFORMATION: X is Y or S
<220> FEATURE:
<221> NAME/KEY: misc_feature
<222> LOCATION: (5)..(5)
<223> OTHER INFORMATION: X is G or D

<400> SEQUENCE: 261

Xaa Pro Xaa Xaa Xaa Gly Tyr
1               5

<210> SEQ ID NO 262
<211> LENGTH: 7
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (1)..(1)
<223> OTHER INFORMATION: X is R or S
<220> FEATURE:
<221> NAME/KEY: misc_feature
<222> LOCATION: (4)..(4)
<223> OTHER INFORMATION: X is absent
<220> FEATURE:
<221> NAME/KEY: misc_feature
<222> LOCATION: (6)..(6)
<223> OTHER INFORMATION: X is N, S, or R

<400> SEQUENCE: 262

Xaa Asn Asp Xaa Gly Xaa Ser
1               5

<210> SEQ ID NO 263
<211> LENGTH: 5
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (3)..(3)
<223> OTHER INFORMATION: X is Y or W

<400> SEQUENCE: 263

Asn Ser Xaa Ile His
1               5

<210> SEQ ID NO 264
<211> LENGTH: 17
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (3)..(3)
<223> OTHER INFORMATION: X is N or S
<220> FEATURE:
<221> NAME/KEY: misc_feature
<222> LOCATION: (6)..(6)
<223> OTHER INFORMATION: X is G or A
<220> FEATURE:
<221> NAME/KEY: misc_feature
<222> LOCATION: (13)..(13)
<223> OTHER INFORMATION: X is D or G

<400> SEQUENCE: 264

Phe Ile Xaa Pro Ala Xaa Gly Tyr Thr Asp Tyr Ala Xaa Ser Val Lys
1               5                   10                  15

Gly

<210> SEQ ID NO 265
<211> LENGTH: 17
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (6)..(6)
<223> OTHER INFORMATION: X is S or I
<220> FEATURE:
<221> NAME/KEY: misc_feature
<222> LOCATION: (8)..(8)
<223> OTHER INFORMATION: X is Y or F
<220> FEATURE:
<221> NAME/KEY: misc_feature
<222> LOCATION: (10)..(10)
<223> OTHER INFORMATION: X is N or E

<400> SEQUENCE: 265

Trp Ile Tyr Pro Tyr Xaa Gly Xaa Thr Xaa Tyr Ala Asp Ser Val Lys
1               5                   10                  15

Gly

<210> SEQ ID NO 266

<211> LENGTH: 17
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (5)..(5)
<223> OTHER INFORMATION: X is S, P, A, or F
<220> FEATURE:
<221> NAME/KEY: misc_feature
<222> LOCATION: (6)..(6)
<223> OTHER INFORMATION: X is G, S, A, or D
<220> FEATURE:
<221> NAME/KEY: misc_feature
<222> LOCATION: (8)..(8)
<223> OTHER INFORMATION: X is Y or F
<220> FEATURE:
<221> NAME/KEY: misc_feature
<222> LOCATION: (10)..(10)
<223> OTHER INFORMATION: X is Y or H

<400> SEQUENCE: 266

Val Ile Thr Pro Xaa Xaa Gly Xaa Thr Xaa Tyr Ala Asp Ser Val Lys
1               5                   10                  15
Gly

<210> SEQ ID NO 267
<211> LENGTH: 17
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (1)..(1)
<223> OTHER INFORMATION: X is V, W, H, or F
<220> FEATURE:
<221> NAME/KEY: misc_feature
<222> LOCATION: (3)..(3)
<223> OTHER INFORMATION: X is S or F
<220> FEATURE:
<221> NAME/KEY: misc_feature
<222> LOCATION: (5)..(5)
<223> OTHER INFORMATION: X is Y or S
<220> FEATURE:
<221> NAME/KEY: misc_feature
<222> LOCATION: (6)..(6)
<223> OTHER INFORMATION: X is G or D
<220> FEATURE:
<221> NAME/KEY: misc_feature
<222> LOCATION: (10)..(10)
<223> OTHER INFORMATION: X is E or D

<400> SEQUENCE: 267

Xaa Ile Xaa Pro Xaa Xaa Gly Tyr Thr Xaa Tyr Ala Asp Ser Val Lys
1               5                   10                  15
Gly

<210> SEQ ID NO 268
<211> LENGTH: 17
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (3)..(3)
<223> OTHER INFORMATION: X is R or S
<220> FEATURE:
<221> NAME/KEY: misc_feature
<222> LOCATION: (7)..(7)
<223> OTHER INFORMATION: X is N, S, or R

```
<220> FEATURE:
<221> NAME/KEY: misc_feature
<222> LOCATION: (9)..(9)
<223> OTHER INFORMATION: X is A or T
<220> FEATURE:
<221> NAME/KEY: misc_feature
<222> LOCATION: (12)..(12)
<223> OTHER INFORMATION: X is G, V, or A
<220> FEATURE:
<221> NAME/KEY: misc_feature
<222> LOCATION: (13)..(13)
<223> OTHER INFORMATION: X is P, D, or A
<220> FEATURE:
<221> NAME/KEY: misc_feature
<222> LOCATION: (14)..(14)
<223> OTHER INFORMATION: X is A, S, or P

<400> SEQUENCE: 268

Tyr Ile Xaa Asn Asp Gly Xaa Ser Xaa Ser Tyr Xaa Xaa Xaa Val Lys
1               5                   10                  15

Gly

<210> SEQ ID NO 269
<211> LENGTH: 18
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (13)..(13)
<223> OTHER INFORMATION: X is G, V, or A
<220> FEATURE:
<221> NAME/KEY: misc_feature
<222> LOCATION: (14)..(14)
<223> OTHER INFORMATION: X is A or D
<220> FEATURE:
<221> NAME/KEY: misc_feature
<222> LOCATION: (15)..(15)
<223> OTHER INFORMATION: X is A, S, or P

<400> SEQUENCE: 269

Gly Ile Thr Tyr Gly Thr Gly Ser Tyr Thr Ala Tyr Xaa Xaa Xaa Val
1               5                   10                  15

Lys Gly

<210> SEQ ID NO 270
<211> LENGTH: 18
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (3)..(3)
<223> OTHER INFORMATION: X is D or N
<220> FEATURE:
<221> NAME/KEY: misc_feature
<222> LOCATION: (4)..(4)
<223> OTHER INFORMATION: X is H or S
<220> FEATURE:
<221> NAME/KEY: misc_feature
<222> LOCATION: (5)..(5)
<223> OTHER INFORMATION: X is D, A, G, or absent
<220> FEATURE:
<221> NAME/KEY: misc_feature
<222> LOCATION: (6)..(6)
<223> OTHER INFORMATION: X is G, A, or absent
<220> FEATURE:
<221> NAME/KEY: misc_feature
<222> LOCATION: (7)..(7)
<223> OTHER INFORMATION: X is G or S
<220> FEATURE:
```

```
<221> NAME/KEY: misc_feature
<222> LOCATION: (8)..(8)
<223> OTHER INFORMATION: X is R or S
<220> FEATURE:
<221> NAME/KEY: misc_feature
<222> LOCATION: (9)..(9)
<223> OTHER INFORMATION: X is Y, G, or D
<220> FEATURE:
<221> NAME/KEY: misc_feature
<222> LOCATION: (11)..(11)
<223> OTHER INFORMATION: X is D, Y, or N
<220> FEATURE:
<221> NAME/KEY: misc_feature
<222> LOCATION: (13)..(13)
<223> OTHER INFORMATION: X is G, V, or A
<220> FEATURE:
<221> NAME/KEY: misc_feature
<222> LOCATION: (14)..(14)
<223> OTHER INFORMATION: X is A, S, or D
<220> FEATURE:
<221> NAME/KEY: misc_feature
<222> LOCATION: (15)..(15)
<223> OTHER INFORMATION: X is V, A, S, or P
<220> FEATURE:
<221> NAME/KEY: misc_feature
<222> LOCATION: (17)..(17)
<223> OTHER INFORMATION: X is K or D

<400> SEQUENCE: 270

Arg Ile Xaa Xaa Xaa Xaa Xaa Xaa Xaa Thr Xaa Tyr Xaa Xaa Xaa Val
1               5                   10                  15

Xaa Gly

<210> SEQ ID NO 271
<211> LENGTH: 10
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (2)..(2)
<223> OTHER INFORMATION: X is S or G
<220> FEATURE:
<221> NAME/KEY: misc_feature
<222> LOCATION: (7)..(7)
<223> OTHER INFORMATION: X is T or S

<400> SEQUENCE: 271

Gly Xaa Phe Asp Ser Ser Xaa Asp Ala Ile
1               5                   10

<210> SEQ ID NO 272
<211> LENGTH: 7
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (1)..(1)
<223> OTHER INFORMATION: X is S, Y, or R
<220> FEATURE:
<221> NAME/KEY: misc_feature
<222> LOCATION: (4)..(4)
<223> OTHER INFORMATION: X is Q or K

<400> SEQUENCE: 272

Xaa Asn Asn Xaa Arg Pro Ser
1               5

<210> SEQ ID NO 273
```

```
<211> LENGTH: 7
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (2)..(2)
<223> OTHER INFORMATION: X is N or S

<400> SEQUENCE: 273

Asn Xaa Asn Asn Arg Pro Ser
1               5

<210> SEQ ID NO 274
<211> LENGTH: 8
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (4)..(4)
<223> OTHER INFORMATION: X is S or N
<220> FEATURE:
<221> NAME/KEY: misc_feature
<222> LOCATION: (5)..(5)
<223> OTHER INFORMATION: X is S or Y

<400> SEQUENCE: 274

Ser Gly Gly Xaa Xaa Asp Tyr Gly
1               5

<210> SEQ ID NO 275
<211> LENGTH: 13
<212> TYPE: PRT
<213> ORGANISM: Artificial Sequence
<220> FEATURE:
<223> OTHER INFORMATION: Synthetic: Consensus sequence
<220> FEATURE:
<221> NAME/KEY: misc_feature
<222> LOCATION: (5)..(5)
<223> OTHER INFORMATION: X is S or N
<220> FEATURE:
<221> NAME/KEY: misc_feature
<222> LOCATION: (7)..(7)
<223> OTHER INFORMATION: X is V, Y, or A
<220> FEATURE:
<221> NAME/KEY: misc_feature
<222> LOCATION: (9)..(9)
<223> OTHER INFORMATION: X is G or S

<400> SEQUENCE: 275

Ser Gly Gly Gly Xaa Tyr Xaa Gly Xaa Tyr Tyr Tyr Gly
1               5                   10
```

ANTI-BCMA ANTIBODIES AND TREATMENT METHODS

This application is the U.S. national stage entry of the PCT Application No. PCT/US2019/023844, filed on Mar. 25, 2019, which claims priority to U.S. Patent Application No. 62/648,266, filed on Mar. 26, 2018, the disclosures of the foregoing applications are incorporated herein by reference in their entirety.

SEQUENCE LISTING

This application incorporates the Sequence Listing text file electronically filed on Sep. 24, 2020, the contents of which are incorporated by reference in its entirety. The text file contains a sequence listing entitled "108843_00296_ST25.txt," created on Sep. 24, 2020, and is 146,652 bytes in size.

FIELD OF THE INVENTION

The present disclosure generally relates to antibodies with binding specificity for B-cell maturation antigen (BCMA) and compositions comprising the antibodies, including pharmaceutical compositions, diagnostic compositions, and kits. Also provided are methods of making anti-BCMA antibodies, and methods of using anti-BCMA antibodies, for example, for therapeutic purposes, diagnostic purposes, and research purposes.

BACKGROUND

B-cell maturation antigen (BCMA) is a member of the tumor necrosis factor (TNF) receptor superfamily which recognizes B-cell activating factor. The protein in humans is encoded by the tumor necrosis factor receptor superfamily member 17 (TNFRSF17) gene and is preferentially expressed in mature B lymphocytes.

BCMA plays an important role in regulating B-cell maturation and differentiation into plasma cells. It is closely related to BAFF receptor (BAFF-R) and transmembrane activator and calcium modulator and cyclophilin ligand interactor (TACI). While BCMA, BAFF-R, and TACI are type III transmembrane proteins that promote B-cell survival at distinct stages of development, BCMA is expressed exclusively in B-cell linage cells, such as, for example, plasmablasts and differentiated plasma cells (Avery et al. (2003) *J. Clin. Invest.* 112(2):286-297; O'Connor et al. (2004) *J. Exp. Med.* 199(1):91-98). It is selectively induced during plasma cell differentiation, which occurs concurrently with loss of BAFF-R expression in the differentiated cells (Darce et al. (2007) *J. Immunol.* 178(9):5612-5622). BCMA expression appears to support the survival of normal plasma cells and plasmablasts but is typically absent on naïve and most memory B cells. Thus, it does not appear to be needed for overall B-cell homeostasis but is required for optimal survival of long-lived plasma cells in the bone marrow (O'Connor et al. (2004) supra; Xu, S. and K. P. Lam (2001) *Mol. Cell. Biol.* 21(12):4067-4074).

In multiple myeloma, BCMA has been shown to be universally and widely expressed in malignant plasma cells at elevated levels; however, it is typically undetected on normal human tissues except for plasma cells. Due to its selective expression as a cell-surface receptor on multiple myeloma cell lines, BCMA can potentially be targeted in therapies to treat multiple myeloma. BCMA expression is also associated with leukemia and lymphoma. Accordingly, there is a need for improved methods of targeting and/or modulating the activity of BCMA.

SUMMARY

Provided herein are antibodies that selectively bind BCMA. In some embodiments, the antibodies bind human BCMA. In some embodiments, the antibodies also bind homologs of human BCMA.

In some embodiments, the antibodies comprise at least one CDR sequence defined by a consensus sequence provided in this disclosure. In some embodiments, the antibodies comprise an illustrative CDR, $V_H$, or $V_L$ sequence provided in this disclosure, or a variant thereof. In some aspects, the variant is a variant with one or more conservative amino acid substitutions.

Also provided are compositions and kits comprising the antibodies. In some embodiments, the compositions are pharmaceutical compositions. Any suitable pharmaceutical composition may be used. In some embodiments, the pharmaceutical composition is a composition for parenteral administration.

This disclosure also provides methods of using the anti-BCMA antibodies provided herein. In some embodiments, the method is a method of treatment. In some embodiments, the method is a diagnostic method. In some embodiments, the method is an analytical method. In some embodiments, the method is a method of purifying and/or quantifying BCMA.

In some embodiments, the antibodies are used to treat a disease or condition. In some aspects, the disease or condition is selected from a cancer, autoimmune disease, and infection. In some embodiments, the disease or condition is leukemia, lymphoma, or multiple myeloma These and other embodiments of the invention along with many of its features are described in more detail in conjunction with the text below and attached figures.

BRIEF DESCRIPTION OF THE FIGURES

FIGS. 2 and 3 provide alignments of the $V_H$ sequences (SEQ ID NOs: 167-216) from the variant antibodies provided herein. CDRs according to Chothia are highlighted, and CDRs according to Kabat are in boxes.

FIG. 4 provides alignments of the $V_L$ sequences (SEQ ID NOs: 217-238) from trastuzumab and the variant antibodies provided herein. CDRs according to Chothia are highlighted, and CDRs according to Kabat are in boxes.

DETAILED DESCRIPTION OF THE EMBODIMENTS

1. Definitions

Figure 1:
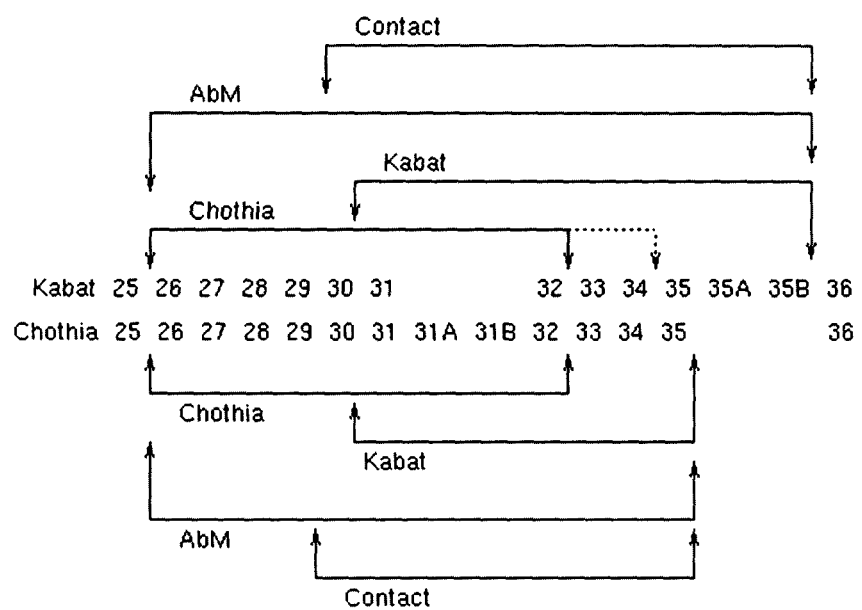
FIG. 1 provides a comparison of the Kabat and Chothia numbering systems for CDR-H1. Adapted from Martin A. C. R. (2010). Protein Sequence and Structure Analysis of Antibody Variable Domains. In R. Kontermann & S. Dübel (Eds.), *Antibody Engineering* vol. 2 (pp. 33-51). Springer-Verlag, Berlin Heidelberg.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Green & Sambrook, *Molecular Cloning: A Laboratory Manual* 4th ed. (2012), Cold Spring Harbor Laboratory Press, Cold Spring Harbor, NY; and Ausubel et al., *Current Protocols in Molecular Biology*, John Wiley & Sons. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value±10%, ±5%, or ±1%. In certain embodiments, the term "about" indicates the designated value±one standard deviation of that value.

The term "combinations thereof" includes every possible combination of elements to which the term refers to. For example, a sentence stating that "if $\alpha_2$ is A, then $\alpha_3$ is not D; as is not S; or $\alpha_6$ is not S; or combinations thereof" includes the following combinations when $\alpha_2$ is A: (1) $\alpha_3$ is not D; (2) as is not S; (3) $\alpha_6$ is not S; (4) $\alpha_3$ is not D; as is not S; and $\alpha_6$ is not S; (5) $\alpha_3$ is not D and $\alpha_5$ is not S; (6) $\alpha_3$ is not D and $\alpha_6$ is not S; and (7) $\alpha_5$ is not S and $\alpha_6$ is not S.

The terms "BCMA" and "B-cell maturation antigen" are used interchangeably herein. BCMA is also known by synonyms, including BCM, tumor necrosis factor receptor superfamily member 17 ("TNFRSF17"), CD269, TNFRSF13A, and TNF receptor superfamily member 17, among others. Unless specified otherwise, the terms include any variants, isoforms and species homologs of human BCMA that are naturally expressed by cells, or that are expressed by cells transfected with a BCMA or BCMA gene. BCMA proteins include, for example, human BCMA isoform 1 (SEQ ID NO: 1) and human BCMA isoform 2 (SEQ ID NO: 2). In some embodiments, BCMA proteins include cynomolgus monkey BCMA (SEQ ID NO: 3). In some embodiments, BCMA proteins include murine BCMA (SEQ ID NO: 4).

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, PA Briefly, each heavy chain typically comprises a heavy chain variable region ($V_H$ or VH) and a heavy chain constant region ($C_H$ or CH). The heavy chain constant region typically comprises three domains, abbreviated $C_H1$ (or CH1), $C_H2$ (or CH2), and $C_H3$ (or CH3). Each light chain typically comprises a light chain variable region ($V_L$ or VL) and a light chain constant region. The light chain constant region typically comprises one domain, abbreviated CL or CL.

The term "antibody" describes a type of immunoglobulin molecule and is used herein in its broadest sense. An antibody specifically includes intact antibodies (e.g., intact immunoglobulins), and antibody fragments. Antibodies comprise at least one antigen-binding domain. One example of an antigen-binding domain is an antigen binding domain formed by a $V_H$-$V_L$ dimer. A "BCMA antibody," "anti-BCMA antibody," "BCMA Ab," "BCMA-specific antibody," "anti-BCMA Ab," "BCMA antibody," "anti-BCMA antibody," "BCMA Ab," "BCMA-specific antibody," or "anti-BCMA Ab," or any iteration of these phrases where "BCMA" is substituted by "TNFSF17," is an antibody, as described herein, which binds specifically to BCMA. In some embodiments, the antibody binds the extracellular domain of BCMA.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, MD, incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

TABLE 1

Residues in CDRs according to Kabat and Chothia numbering schemes.

| CDR | Kabat | Chothia |
| --- | --- | --- |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1 when numbered using the Kabat numbering convention, varies between H32 and H34, depending on the length of the CDR, as illustrated in FIG. 1.

Unless otherwise specified, the numbering scheme used for identification of a particular CDR herein is the Kabat/Chothia numbering scheme. Where the residues encompassed by these two numbering schemes diverge (e.g., CDR-H1 and/or CDR-H2), the numbering scheme is specified as either Kabat or Chothia. For convenience, CDR-H3 is sometimes referred to herein as either Kabat or Chothia. However, this is not intended to imply differences in sequence where they do not exist, and one of skill in the art can readily confirm whether the sequences are the same or different by examining the sequences.

CDRs may be assigned, for example, using antibody numbering software, such as Abnum, available at bioinf.org.uk/abs/abnum/, and described in Abhinandan and Martin, Immunology, 2008, 45:3832-3839, incorporated by reference in its entirety.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain (CaO of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). In some embodiments, the linker is SEQ ID NO: 246. In some embodiments, the linker is SEQ ID NO: 247. Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminus of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG1 Fc domain. In some embodiments, the IgG1 Fc domain comprises SEQ ID NO: 239, or a portion thereof. SEQ ID NO: 239 provides the sequence of $C_H1$, $C_H2$, and $C_H3$ of the human IgG1 constant region.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is purified to at least 80%, 85%, 90%, 95%, or 99% by volume. In some embodiments, an isolated antibody is provided as a solution comprising at least 85%, 90%, 95%, 98%, 99% to 100% by weight. In some embodiments, an isolated antibody is provided as a solution comprising at least 85%, 90%, 95%, 98%, 99% to 100% by volume.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can be represented by the dissociation constant ($K_D$). Affinity can be measured by common methods known in the art, including those described herein. Affinity can be determined, for example, using surface plasmon resonance (SPR) technology, such as a Biacore® instrument. In some embodiments, the affinity is determined at 25° C.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that mimics the antibody binding site on the target. In that case, specific binding is indicated if the binding of the antibody to the target is competitively inhibited by the control molecule.

The term "$k_d$" or "$k_d$" ($sec^{-1}$), as used herein, refers to the dissociation rate constant of a particular antibody-antigen interaction. This value is also referred to as the $k_{off}$ value.

The term "$k_a$" or "$k_a$" ($M^{-1} \times sec^{-1}$), as used herein, refers to the association rate constant of a particular antibody-antigen interaction. This value is also referred to as the $k_{on}$ value.

The term "$K_D$" (also referred to as "Kd" or "KD," M or nM), as used herein, refers to the dissociation equilibrium constant of a particular antibody-antigen interaction. $K_D = k_d/k_a$. The value of $K_D$ is typically equal in magnitude to the concentration of ligand at which half the protein molecules are bound to ligand at equilibrium.

The term "$K_A$" or "$K_a$" ($M^{-1}$), as used herein, refers to the association equilibrium constant of a particular antibody-antigen interaction. $K_A = k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio/Technology*, 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.*, 1994, 91:3809-3813); Schier et al., *Gene*, 1995, 169:147-155; Yelton et al., *J. Immunol.*, 1995, 155:1994-2004; Jackson et al., *J. Immunol.*, 1995, 154:3310-33199; and Hawkins et al, *J. Mol. Biol.*, 1992, 226:889-896, each of which is incorporated by reference in its entirety.

When used herein in the context of two or more antibodies, the term "competes with" or "cross-competes with" indicates that the two or more antibodies compete for binding to an antigen (e.g., BCMA). In one exemplary assay, BCMA is coated on a plate and allowed to bind a first antibody, after which a second, labeled antibody is added. If the presence of the first antibody reduces binding of the second antibody, then the antibodies compete. In another exemplary assay, a first antibody is coated on a plate and allowed to bind the antigen, and then the second antibody is added. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to variants of BCMA with different point-mutations.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of an amino acid with a chemically or functionally similar amino acid. Conservative substitution tables providing similar amino acids are well known in the art. Polypeptide sequences having such substitutions are known as "conservatively modified variants." By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |

TABLE 2-continued

Selected groups of amino acids that are considered conservative substitutions for one another, in certain embodiments.

| | |
|---|---|
| Aromatic Residues | F, Y, and W |
| Alcohol Group-Containing Residues | S and T |
| Aliphatic Residues | I, L, V, and M |
| Cycloalkenyl-associated Residues | F, H, W, and Y |
| Hydrophobic Residues | A, C, F, G, H, I, L, M, R, T, V, W, and Y |
| Negatively Charged Residues | D and E |
| Polar Residues | C, D, E, H, K, N, Q, R, S, and T |
| Positively Charged Residues | H, K, and R |
| Small Residues | A, C, D, G, N, P, S, T, and V |
| Very Small Residues | A, G, and S |
| Residues Involved in Turn Formation | A, C, D, E, G, H, K, N, Q, R, S, P, and T |
| Flexible Residues | Q, T, K, S, G, P, D, E, and R |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, NY. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "therapeutically effective amount" or "effective amount" refers to an amount of an antibody or composition that when administered to a subject is effective to treat a disease or disorder.

As used herein, the term "subject" means a mammalian subject. Exemplary subjects include, but are not limited to humans, monkeys, dogs, cats, mice, rats, cows, horses, camels, avians, goats, and sheep. In certain embodiments, the subject is a human. In some embodiments, the subject has a disease that can be treated or diagnosed with an antibody provided herein. In some embodiments, the disease is leukemia, lymphoma, or multiple myeloma, a plasmacytoid dendritic cell tumor, a B-cell lineage malignancy, a plasma cell neoplasm, diffuse large B-cell lymophoma (DLBCL), a low-grade B-cell lymphoma, Burkitt's lymphoma, a plasmablastic lymphoma, or a follicular lymphoma.

2. Antibodies

Provided herein are antibodies that selectively bind human BCMA. In some aspects, the antibody selectively binds to the extracellular domain of human BCMA (human BCMA).

In some embodiments, the antibody binds to a homolog of human BCMA. In some aspects, the antibody binds to a homolog of human BCMA from a species selected from monkeys, mice, dogs, cats, rats, cows, horses, goats and sheep. In some aspects, the homolog is a cynomolgus monkey homolog. In some aspects, the homolog is a mouse or murine homolog.

In some embodiments, the antibody has one or more CDRs having particular lengths, in terms of the number of amino acid residues. In some embodiments, the Chothia CDR-H1 of the antibody is 6, 7, or 8 residues in length. In some embodiments, the Kabat CDR-H1 of the antibody is 4, 5, or 6 residues in length. In some embodiments, the Chothia CDR-H2 of the antibody is 5, 6, or 7 residues in length. In some embodiments, the Kabat CDR-H2 of the antibody is 16, 17, or 18 residues in length. In some embodiments, the Kabat/Chothia CDR-H3 of the antibody is 7, 8, 9, 10, 11, 12, 13, 14, 15, or 16 residues in length.

In some aspects, the Kabat/Chothia CDR-L1 of the antibody is 10, 11, 12, 13, 14, 15, or 16 residues in length. In some aspects, the Kabat/Chothia CDR-L2 of the antibody is 6, 7, or 8 residues in length. In some aspects, the Kabat/Chothia CDR-L3 of the antibody is 8, 9, or 10 residues in length.

In some embodiments, the antibody comprises a light chain. In some aspects, the light chain is a kappa light chain. In some aspects, the light chain is a lambda light chain.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')2 fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

In some embodiments, the antibody is an affinity matured antibody. In some aspects, the antibody is an affinity matured antibody derived from an illustrative sequence provided in this disclosure.

The antibodies provided herein may be useful for the treatment of a variety of diseases and conditions including cancers. In some embodiments, the antibodies provided herein may be useful for the treatment of cancers of solid tumors. For example, the antibodies provided herein can be useful for the treatment of colorectal cancer.

2.1 CDR-H3 Sequences

In some embodiments, the antibody comprises a CDR-H3 sequence comprising, consisting of, or consisting essentially of a CDR-H3 sequence of an illustrative antibody or $V_H$ sequence provided herein. In some aspects, the CDR-H3 sequence is a CDR-H3 sequence of a $V_H$ sequence provided in SEQ ID NOs: 167-216.

In some embodiments, the antibody comprises a CDR-H3 sequence comprising, consisting of, or consisting essentially of a sequence selected from SEQ ID NOs: 116-145. In some aspects, the antibody comprises a CDR-H3 sequence comprising, consisting of, or consisting essentially of SEQ ID NO: 116. In some aspects, the antibody comprises a CDR-H3 sequence comprising, consisting of, or consisting essentially of SEQ ID NO: 117. In some aspects, the antibody comprises a CDR-H3 sequence comprising, consisting of, or consisting essentially of SEQ ID NO: 118. In some aspects, the antibody comprises a CDR-H3 sequence comprising, consisting of, or consisting essentially of SEQ ID NO: 119. In some aspects, the antibody comprises a CDR-H3 sequence comprising, consisting of, or consisting essentially of SEQ ID NO: 120. In some aspects, the antibody comprises a CDR-H3 sequence comprising, consisting of, or consisting essentially of SEQ ID NO: 121. In some aspects, the antibody comprises a CDR-H3 sequence comprising, consisting of, or consisting essentially of SEQ ID NO: 122. In some aspects, the antibody comprises a CDR-H3 sequence comprising, consisting of, or consisting essentially of SEQ ID NO: 123. In some aspects, the antibody comprises a CDR-H3 sequence comprising, consisting of, or consisting essentially of SEQ ID NO: 124. In some aspects, the antibody comprises a CDR-H3 sequence comprising, consisting of, or consisting essentially of SEQ ID NO: 125. In some aspects, the antibody comprises a CDR-H3 sequence comprising, consisting of, or consisting essentially of SEQ ID NO: 126. In some aspects, the antibody comprises a CDR-H3 sequence comprising, consisting of, or consisting essentially of SEQ ID NO: 127. In some aspects, the antibody comprises a CDR-H3 sequence comprising, consisting of, or consisting essentially of SEQ ID NO: 128. In some aspects, the antibody comprises a CDR-H3 sequence comprising, consisting of, or consisting essentially of SEQ ID NO: 129. In some aspects, the antibody comprises a CDR-H3 sequence comprising, consisting of, or consisting essentially of SEQ ID NO: 130. In some aspects, the antibody comprises a CDR-H3 sequence comprising, consisting of, or consisting essentially of SEQ ID NO: 131. In some aspects, the antibody comprises a CDR-H3 sequence comprising, consisting of, or consisting essentially of SEQ ID NO: 132. In some aspects, the antibody comprises a CDR-H3 sequence comprising, consisting of, or consisting essentially of SEQ ID NO: 133. In some aspects, the antibody comprises a CDR-H3 sequence comprising, consisting of, or consisting essentially of SEQ ID NO: 134. In some aspects, the antibody comprises a CDR-H3 sequence comprising, consisting of, or consisting essentially of SEQ ID NO: 135. In some aspects, the antibody comprises a CDR-H3 sequence comprising, consisting of, or consisting essentially of SEQ ID NO: 136. In some aspects, the antibody comprises a CDR-H3 sequence comprising, consisting of, or consisting essentially of SEQ ID NO: 137. In some aspects, the antibody comprises a CDR-H3 sequence comprising, consisting of, or consisting essentially of SEQ ID NO: 138. In some aspects, the antibody comprises a CDR-H3 sequence comprising, consisting of, or consisting essentially of SEQ ID NO: 139. In some aspects, the antibody comprises a CDR-H3 sequence comprising, consisting of, or consisting essentially of SEQ ID NO: 140. In some aspects, the antibody comprises a CDR-H3 sequence comprising, consisting of, or consisting essentially of SEQ ID NO: 141. In some aspects, the antibody comprises a CDR-H3 sequence comprising, consisting of, or consisting essentially of SEQ ID NO: 142. In some aspects, the antibody comprises a CDR-H3 sequence comprising, consisting of, or consisting essentially of SEQ ID NO: 143. In some aspects, the antibody comprises a CDR-H3 sequence comprising, consisting of, or consisting essentially of SEQ ID NO: 144. In some aspects, the antibody comprises a CDR-H3 sequence comprising, consisting of, or consisting essentially of SEQ ID NO: 145.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

2.2 $V_H$ Sequences Comprising Illustrative CDRs

In some embodiments, the antibody comprises a $V_H$ sequence comprising one or more CDR-H3 sequences comprising, consisting of, or consisting essentially of one or more illustrative CDR-H3 sequences provided in this disclosure, and variants thereof. In some embodiments, the CDR-H3 sequences comprise, consist of, or consist essentially of one or more CDR-H3 sequences provided in a $V_H$ sequence selected from SEQ ID NOs: 167-216.

2.2.1. $V_H$ Sequences Comprising Illustrative Kabat CDRs

In some embodiments, the antibody comprises a $V_H$ sequence comprising one or more Kabat CDR-H3 sequences comprising, consisting of, or consisting essentially of one or more illustrative Kabat CDR-H3 sequences provided in this disclosure, and variants thereof.

2.2.1.1. Kabat CDR-H3

In some embodiments, the antibody comprises a $V_H$ sequence comprising a CDR-H3 sequence, wherein the CDR-H3 sequence comprises, consists of, or consists essentially of a Kabat CDR-H3 sequence of an illustrative antibody or $V_H$ sequence provided herein. In some aspects, the Kabat CDR-H3 sequence is a Kabat CDR-H3 sequence of a $V_H$ sequence provided in SEQ ID NOs: 167-216.

In some embodiments, the antibody comprises a $V_H$ sequence comprising a Kabat CDR-H3 sequence comprising, consisting of, or consisting essentially of a sequence selected from SEQ ID NOs: 116-145. In some aspects, the antibody comprises a CDR-H3 sequence comprising, consisting of, or consisting essentially of SEQ ID NO: 116. In some aspects, the antibody comprises a CDR-H3 sequence comprising, consisting of, or consisting essentially of SEQ ID NO: 117. In some aspects, the antibody comprises a CDR-H3 sequence comprising, consisting of, or consisting essentially of SEQ ID NO: 118. In some aspects, the antibody comprises a CDR-H3 sequence comprising, consisting of, or consisting essentially of SEQ ID NO: 119. In some aspects, the antibody comprises a CDR-H3 sequence comprising, consisting of, or consisting essentially of SEQ ID NO: 120. In some aspects, the antibody comprises a CDR-H3 sequence comprising, consisting of, or consisting essentially of SEQ ID NO: 121. In some aspects, the antibody comprises a CDR-H3 sequence comprising, consisting of, or consisting essentially of SEQ ID NO: 122. In some aspects, the antibody comprises a CDR-H3 sequence comprising, consisting of, or consisting essentially of SEQ ID NO: 123. In some aspects, the antibody comprises a CDR-H3 sequence comprising, consisting of, or consisting essentially of SEQ ID NO: 124. In some aspects, the antibody comprises a CDR-H3 sequence comprising, consisting of, or consisting essentially of SEQ ID NO: 125. In some aspects, the antibody comprises a CDR-H3 sequence comprising, consisting of, or consisting essentially of SEQ ID NO: 126. In some aspects, the antibody comprises a CDR-H3 sequence comprising, consisting of, or consisting essentially of SEQ ID NO: 127. In some aspects, the antibody comprises a CDR-H3 sequence comprising, consisting of, or consisting essentially of SEQ ID NO: 128. In some aspects, the antibody comprises a CDR-H3 sequence comprising, consisting of, or consisting essentially of SEQ ID NO: 129. In some aspects, the antibody comprises a CDR-H3 sequence comprising, consisting of, or consisting essentially of SEQ ID NO: 130. In some aspects, the antibody comprises a CDR-H3 sequence comprising, consisting of, or consisting essentially of SEQ ID NO: 131. In some aspects, the antibody comprises a CDR-H3 sequence comprising, consisting of, or consisting essentially of SEQ ID NO: 132. In some aspects, the antibody comprises a CDR-H3 sequence comprising, consisting of, or consisting essentially of SEQ ID NO: 133. In some aspects, the antibody comprises a CDR-H3 sequence comprising, consisting of, or consisting essentially of SEQ ID NO: 134. In some aspects, the antibody comprises a CDR-H3 sequence comprising, consisting of, or consisting essentially of SEQ ID NO: 135. In some aspects, the antibody comprises a CDR-H3 sequence comprising, consisting of, or consisting essentially of SEQ ID NO: 136. In some aspects, the antibody comprises a CDR-H3 sequence comprising, consisting of, or consisting essentially of SEQ ID NO: 137. In some aspects, the antibody comprises a CDR-H3 sequence comprising, consisting of, or consisting essentially of SEQ ID NO: 138. In some aspects, the antibody comprises a CDR-H3 sequence comprising, consisting of, or consisting essentially of SEQ ID NO: 139. In some aspects, the antibody comprises a CDR-H3 sequence comprising, consisting of, or consisting essentially of SEQ ID NO: 140. In some aspects, the antibody comprises a CDR-H3 sequence comprising, consisting of, or consisting essentially of SEQ ID NO: 141. In some aspects, the antibody comprises a CDR-H3 sequence comprising, consisting of, or consisting essentially of SEQ ID NO: 142. In some aspects, the antibody comprises a CDR-H3 sequence comprising, consisting of, or consisting essentially of SEQ ID NO: 143. In some aspects, the antibody comprises a CDR-H3 sequence comprising, consisting of, or consisting essentially of SEQ ID NO: 144. In some aspects, the antibody comprises a CDR-H3 sequence comprising, consisting of, or consisting essentially of SEQ ID NO: 145.

2.2.1.2. Kabat CDR-H2

In some embodiments, the antibody comprises a $V_H$ sequence comprising a CDR-H2 sequence, wherein the CDR-H2 sequence comprises, consists of, or consists essentially of a Kabat CDR-H2 sequence of an illustrative antibody or $V_H$ sequence provided herein. In some aspects, the Kabat CDR-H2 sequence is a Kabat CDR-H2 sequence of a $V_H$ sequence provided in SEQ ID NOs: 167-216.

In some embodiments, the antibody comprises a $V_H$ sequence comprising a Kabat CDR-H2 sequence comprising, consisting of, or consisting essentially of a sequence selected from SEQ ID NOs: 79-115. In some aspects, the antibody comprises a CDR-H2 sequence comprising, consisting of, or consisting essentially of SEQ ID NO: 79. In some aspects, the antibody comprises a CDR-H2 sequence comprising, consisting of, or consisting essentially of SEQ ID NO: 80. In some aspects, the antibody comprises a CDR-H2 sequence comprising, consisting of, or consisting essentially of SEQ ID NO: 81. In some aspects, the antibody comprises a CDR-H2 sequence comprising, consisting of, or consisting essentially of SEQ ID NO: 82. In some aspects, the antibody comprises a CDR-H2 sequence comprising, consisting of, or consisting essentially of SEQ ID NO: 83. In some aspects, the antibody comprises a CDR-H2 sequence comprising, consisting of, or consisting essentially of SEQ ID NO: 84. In some aspects, the antibody comprises a CDR-H2 sequence comprising, consisting of, or consisting essentially of SEQ ID NO: 85. In some aspects, the antibody comprises a CDR-H2 sequence comprising, consisting of, or consisting essentially of SEQ ID NO: 86. In some aspects, the antibody comprises a CDR-H2 sequence comprising, consisting of, or consisting essentially of SEQ ID NO: 87. In some aspects, the antibody comprises a CDR-H2 sequence comprising, consisting of, or consisting essentially of SEQ ID NO: 88. In some aspects, the antibody comprises a CDR-H2 sequence comprising, consisting of, or consisting essentially of SEQ ID NO: 89. In some aspects, the antibody comprises a CDR-H2 sequence comprising, consisting of, or consisting essentially of SEQ ID NO: 90. In some aspects, the antibody comprises a CDR-H2 sequence comprising, consisting of, or consisting essentially of SEQ ID NO: 91. In some aspects, the antibody comprises a CDR-H2 sequence comprising, consisting of, or consisting essentially of SEQ ID NO: 92. In some aspects, the antibody comprises a CDR-H2 sequence comprising, consisting of, or consisting essentially of SEQ ID NO: 93. In some aspects, the antibody comprises a CDR-H2 sequence comprising, consisting of, or consisting essentially of SEQ ID NO: 94. In some aspects, the antibody comprises a CDR-H2 sequence comprising, consisting of, or consisting essentially of SEQ ID NO: 95. In some aspects, the antibody comprises a CDR-H2 sequence comprising, consisting of, or consisting essentially of SEQ ID NO: 96. In some aspects, the antibody comprises a CDR-H2 sequence comprising, consisting of, or consisting essentially of SEQ ID NO: 97. In some aspects, the antibody comprises a CDR-H2 sequence comprising, consisting of, or consisting essentially of SEQ ID NO: 98. In some aspects, the antibody comprises a CDR-H2 sequence comprising, consisting of, or consisting essentially of SEQ ID NO: 99. In some aspects, the antibody comprises a CDR-H2 sequence comprising, consisting of, or consisting essentially of SEQ ID NO: 100. In some aspects, the antibody comprises a CDR-H2 sequence comprising, consisting of, or consisting essentially of SEQ ID NO: 101. In some aspects, the antibody comprises a CDR-H2 sequence comprising, consisting of, or consisting essentially of SEQ ID NO: 102. In some aspects, the antibody comprises a CDR-H2 sequence comprising, consisting of, or consisting essentially of SEQ ID NO: 103. In some aspects, the antibody comprises a CDR-H2 sequence comprising, consisting of, or consisting essentially of SEQ ID NO: 104. In some aspects, the antibody comprises a CDR-H2 sequence comprising, consisting of, or consisting essentially of SEQ ID NO: 105. In some aspects, the antibody comprises a CDR-H2 sequence comprising, consisting of, or consisting essentially of SEQ ID NO: 106. In some aspects, the antibody comprises a CDR-H2 sequence comprising, consisting of, or consisting essentially of SEQ ID NO: 107. In some aspects, the antibody comprises a CDR-H2 sequence comprising, consisting of, or consisting essentially of SEQ ID NO: 108. In some aspects, the antibody comprises a CDR-H2 sequence comprising, consisting of, or consisting essentially of SEQ ID NO: 109. In some aspects, the antibody comprises a CDR-H2 sequence comprising, consisting of, or consisting essentially of SEQ ID NO: 110. In some aspects, the antibody comprises a CDR-H2 sequence comprising, consisting of, or consisting essentially of SEQ ID NO: 111. In some aspects, the antibody comprises a CDR-H2 sequence comprising, consisting of, or consisting essentially of SEQ ID NO: 112. In some aspects, the antibody comprises a CDR-H2 sequence comprising, consisting of, or consisting essentially of SEQ ID NO: 113. In some aspects, the antibody comprises a CDR-H2 sequence comprising, consisting of, or consisting essentially of SEQ ID NO: 114. In some aspects, the antibody comprises a CDR-H2 sequence comprising, consisting of, or consisting essentially of SEQ ID NO: 115.

2.2.1.3. Kabat CDR-H1

In some embodiments, the antibody comprises a $V_H$ sequence comprising a CDR-H1 sequence, wherein the CDR-H1 sequence comprises, consists of, or consists essentially of a Kabat CDR-H1 sequence of an illustrative antibody or $V_H$ sequence provided herein. In some aspects, the Kabat CDR-H1 sequence is a Kabat CDR-H1 sequence of a $V_H$ sequence provided in SEQ ID NOs: 167-216.

In some embodiments, the antibody comprises a $V_H$ sequence comprising a Kabat CDR-H1 sequence comprising, consisting of, or consisting essentially of a sequence selected from SEQ ID NOs: 32-56. In some aspects, the antibody comprises a CDR-H1 sequence comprising, consisting of, or consisting essentially of SEQ ID NO: 32. In some aspects, the antibody comprises a CDR-H1 sequence comprising, consisting of, or consisting essentially of SEQ ID NO: 33. In some aspects, the antibody comprises a CDR-H1 sequence comprising, consisting of, or consisting essentially of SEQ ID NO: 34. In some aspects, the antibody comprises a CDR-H1 sequence comprising, consisting of, or consisting essentially of SEQ ID NO: 35. In some aspects, the antibody comprises a CDR-H1 sequence comprising, consisting of, or consisting essentially of SEQ ID NO: 36. In some aspects, the antibody comprises a CDR-H1 sequence comprising, consisting of, or consisting essentially of SEQ ID NO: 37. In some aspects, the antibody comprises a CDR-H1 sequence comprising, consisting of, or consisting essentially of SEQ ID NO: 38. In some aspects, the antibody comprises a CDR-H1 sequence comprising, consisting of, or consisting essentially of SEQ ID NO: 39. In some aspects, the antibody comprises a CDR-H1 sequence comprising, consisting of, or consisting essentially of SEQ ID NO: 40. In some aspects, the antibody comprises a CDR-H1 sequence comprising, consisting of, or consisting essentially of SEQ ID NO: 41. In some aspects, the antibody comprises a CDR-H1 sequence comprising, consisting of, or consisting essentially of SEQ ID NO: 42. In some aspects, the antibody comprises a CDR-H1 sequence comprising, consisting of, or consisting essentially of SEQ ID NO: 43. In some aspects, the antibody comprises a CDR-H1 sequence comprising, consisting of, or consisting essentially of SEQ ID NO: 44. In some aspects, the antibody comprises a CDR-H1 sequence comprising, consisting of, or consisting essentially of SEQ ID NO: 45. In some aspects, the antibody comprises a CDR-H1 sequence comprising, consisting of, or consisting essentially of SEQ ID NO: 46. In some aspects, the antibody comprises a CDR-H1 sequence comprising, consisting of, or consisting essentially of SEQ ID NO: 47. In some aspects, the antibody comprises a CDR-H1 sequence comprising, consisting of, or consisting essentially of SEQ ID NO: 48. In some aspects, the antibody comprises a CDR-H1 sequence comprising, consisting of, or consisting essentially of SEQ ID NO: 49. In some aspects, the antibody comprises a CDR-H1 sequence comprising, consisting of, or consisting essentially of SEQ ID NO: 50. In some aspects, the antibody comprises a CDR-H1 sequence comprising, consisting of, or consisting essentially of SEQ ID NO: 51. In some aspects, the antibody comprises a CDR-H1 sequence comprising, consisting of, or consisting essentially of SEQ ID NO: 52. In some aspects, the antibody comprises a CDR-H1 sequence comprising, consisting of, or consisting essentially of SEQ ID NO: 53. In some aspects, the antibody comprises a CDR-H1 sequence comprising, consisting of, or consisting essentially of SEQ ID NO: 54. In some aspects, the antibody comprises a CDR-H1 sequence comprising, consisting of, or consisting essentially of SEQ ID NO: 55. In some aspects, the antibody comprises a CDR-H1 sequence comprising, consisting of, or consisting essentially of SEQ ID NO: 56.

2.2.1.4. Kabat CDR-H3+Kabat CDR-H2

In some embodiments, the antibody comprises a $V_H$ sequence comprising a Kabat CDR-H3 sequence comprising, consisting of, or consisting essentially of a sequence selected from SEQ ID NOs: 116-145, and a Kabat CDR-H2 sequence comprising, consisting of, or consisting essentially of a sequence selected from SEQ ID NOs: 79-115. In some aspects, the Kabat CDR-H3 sequence and the Kabat CDR-H2 sequence are both from a single illustrative $V_H$ sequence provided in this disclosure. For example, in some aspects, the Kabat CDR-H3 and Kabat CDR-H2 are both from a single illustrative $V_H$ sequence selected from SEQ ID NOs: 167-216.

2.2.1.5. Kabat CDR-H3+Kabat CDR-H1

In some embodiments, the antibody comprises a $V_H$ sequence comprising a Kabat CDR-H3 sequence comprising, consisting of, or consisting essentially of a sequence selected from SEQ ID NOs: 116-145, and a Kabat CDR-H1 sequence comprising, consisting of, or consisting essentially of a sequence selected from SEQ ID NOs: 32-56. In some aspects, the Kabat CDR-H3 sequence and the Kabat CDR-H1 sequence are both from a single illustrative $V_H$ sequence provided in this disclosure. For example, in some aspects, the Kabat CDR-H3 and Kabat CDR-H1 are both from a single illustrative $V_H$ sequence selected from SEQ ID NOs: 167-216.

2.2.1.6. Kabat CDR-H1+Kabat CDR-H2

In some embodiments, the antibody comprises a $V_H$ sequence comprising a Kabat CDR-H1 sequence comprising, consisting of, or consisting essentially of a sequence selected from SEQ ID NOs: 32-56 and a Kabat CDR-H2 sequence comprising, consisting of, or consisting essentially of a sequence selected from SEQ ID NOs: 79-115. In some aspects, the Kabat CDR-H1 sequence and the Kabat CDR-H2 sequence are both from a single illustrative $V_H$ sequence provided in this disclosure. For example, in some aspects, the Kabat CDR-H1 and Kabat CDR-H2 are both from a single illustrative $V_H$ sequence selected from SEQ ID NOs: 167-216.

2.2.1.7. Kabat CDR-H1+Kabat CDR-H2+Kabat CDR-H3

In some embodiments, the antibody comprises a $V_H$ sequence comprising a Kabat CDR-H1 sequence comprising, consisting of, or consisting essentially of a sequence selected from SEQ ID NOs: 32-56, a Kabat CDR-H2 sequence comprising, consisting of, or consisting essentially of a sequence selected from SEQ ID NOs: 79-115, and a Kabat CDR-H3 sequence comprising, consisting of, or consisting essentially of a sequence selected from SEQ ID NOs: 116-145. In some aspects, the Kabat CDR-H1 sequence, Kabat CDR-H2 sequence, and Kabat CDR-H3 sequence are all from a single illustrative $V_H$ sequence provided in this disclosure. For example, in some aspects, the Kabat CDR-H1, Kabat CDR-H2, and Kabat CDR-H3 are all from a single illustrative $V_H$ sequence selected from SEQ ID NOs: 167-216.

2.2.1.8. Variants of $V_H$ Sequences Comprising Illustrative Kabat CDRs

In some embodiments, the $V_H$ sequences provided herein comprise a variant of an illustrative Kabat CDR-H3, CDR-H2, and/or CDR-H1 sequence provided in this disclosure.

In some aspects, the Kabat CDR-H3 sequence comprises, consists of, or consists essentially of a variant of an illustrative Kabat CDR-H3 sequence provided in this disclosure. In some aspects, the Kabat CDR-H3 sequence comprises, consists of, or consists essentially of a sequence having at least 70%, 75%, 80%, 85%, 90%, or 95% identity with any of the illustrative Kabat CDR-H3 sequences provided in this disclosure. In some aspects, the Kabat CDR-H3 sequence comprises, consists of, or consists essentially of any of the illustrative Kabat CDR-H3 sequences provided in this disclosure, with 1, 2, or 3 amino acid substitutions. In some aspects, the amino acid substitutions are conservative amino acid substitutions.

In some aspects, the Kabat CDR-H2 sequence comprises, consists of, or consists essentially of a variant of an illustrative Kabat CDR-H2 sequence provided in this disclosure. In some aspects, the Kabat CDR-H2 sequence comprises, consists of, or consists essentially of a sequence having at least 70%, 75%, 80%, 85%, 90%, or 95% identity with any of the illustrative Kabat CDR-H2 sequences provided in this disclosure. In some aspects, the Kabat CDR-H2 sequence comprises, consists of, or consists essentially of any of the illustrative Kabat CDR-H2 sequences provided in this disclosure, with 1, 2, or 3 amino acid substitutions. In some aspects, the amino acid substitutions are conservative amino acid substitutions.

In some aspects, the Kabat CDR-H1 sequence comprises, consists of, or consists essentially of a variant of an illustrative Kabat CDR-H1 sequence provided in this disclosure. In some aspects, the Kabat CDR-H1 sequence comprises, consists of, or consists essentially of a sequence having at least 70%, 75%, 80%, 85%, 90%, or 95% identity with any of the illustrative Kabat CDR-H1 sequences provided in this disclosure. In some aspects, the Kabat CDR-H1 sequence comprises, consists of, or consists essentially of any of the illustrative Kabat CDR-H1 sequences provided in this disclosure, with 1, 2, or 3 amino acid substitutions. In some aspects, the amino acid substitutions are conservative amino acid substitutions.

2.2.2. $V_H$ Sequences Comprising Illustrative Chothia CDRs

In some embodiments, the antibody comprises a $V_H$ sequence comprising one or more Chothia CDR-H sequences comprising, consisting of, or consisting essentially of one or more illustrative Chothia CDR-H sequences provided in this disclosure, and variants thereof.

2.2.2.1. Chotia CDR-H3

In some embodiments, the antibody comprises a $V_H$ sequence comprising a CDR-H3 sequence, wherein the CDR-H3 sequence comprises, consists of, or consists essentially of a Chothia CDR-H3 sequence of an illustrative antibody or $V_H$ sequence provided herein. In some aspects, the Chothia CDR-H3 sequence is a Chothia CDR-H3 sequence of a $V_H$ sequence provided in SEQ ID NOs: 167-216.

In some embodiments, the antibody comprises a $V_H$ sequence comprising a Chothia CDR-H3 sequence comprising, consisting of, or consisting essentially of a sequence selected from SEQ ID NOs: 116-145. In some aspects, the antibody comprises a CDR-H3 sequence comprising, consisting of, or consisting essentially of SEQ ID NO: 116. In some aspects, the antibody comprises a CDR-H3 sequence comprising, consisting of, or consisting essentially of SEQ ID NO: 117. In some aspects, the antibody comprises a CDR-H3 sequence comprising, consisting of, or consisting essentially of SEQ ID NO: 118. In some aspects, the antibody comprises a CDR-H3 sequence comprising, consisting of, or consisting essentially of SEQ ID NO: 119. In some aspects, the antibody comprises a CDR-H3 sequence comprising, consisting of, or consisting essentially of SEQ ID NO: 120. In some aspects, the antibody comprises a CDR-H3 sequence comprising, consisting of, or consisting essentially of SEQ ID NO: 121. In some aspects, the antibody comprises a CDR-H3 sequence comprising, consisting of, or consisting essentially of SEQ ID NO: 122. In some aspects, the antibody comprises a CDR-H3 sequence comprising, consisting of, or consisting essentially of SEQ ID NO: 123. In some aspects, the antibody comprises a CDR-H3 sequence comprising, consisting of, or consisting essentially of SEQ ID NO: 124. In some aspects, the antibody comprises a CDR-H3 sequence comprising, consisting of, or consisting essentially of SEQ ID NO: 125. In some aspects, the antibody comprises a CDR-H3 sequence comprising, consisting of, or consisting essentially of SEQ ID NO: 126. In some aspects, the antibody comprises a CDR-H3 sequence comprising, consisting of, or consisting essentially of SEQ ID NO: 127. In some aspects, the antibody comprises a CDR-H3 sequence comprising, consisting of, or consisting essentially of SEQ ID NO: 128. In some aspects, the antibody comprises a CDR-H3 sequence comprising, consisting of, or consisting essentially of SEQ ID NO: 129. In some aspects, the antibody comprises a CDR-H3 sequence comprising, consisting of, or consisting essentially of SEQ ID NO: 130. In some aspects, the antibody comprises a CDR-H3 sequence comprising, consisting of, or consisting essentially of SEQ ID NO: 131. In some aspects, the antibody comprises a CDR-H3 sequence comprising, consisting of, or consisting essentially of SEQ ID NO: 132. In some aspects, the antibody comprises a CDR-H3 sequence comprising, consisting of, or consisting essentially of SEQ ID NO: 133. In some aspects, the antibody comprises a CDR-H3 sequence comprising, consisting of, or consisting essentially of SEQ ID NO: 134. In some aspects, the antibody comprises a CDR-H3 sequence comprising, consisting of, or consisting essentially of SEQ ID NO: 135. In some aspects, the antibody comprises a CDR-H3 sequence comprising, consisting of, or consisting essentially of SEQ ID NO: 136. In some aspects, the antibody comprises a CDR-H3 sequence comprising, consisting of, or consisting essentially of SEQ ID NO: 137. In some aspects, the antibody comprises a CDR-H3 sequence comprising, consisting of, or consisting essentially of SEQ ID NO: 138. In some aspects, the antibody comprises a CDR-H3 sequence comprising, consisting of, or consisting essentially of SEQ ID NO: 139. In some aspects, the antibody comprises a CDR-H3 sequence comprising, consisting of, or consisting essentially of SEQ ID NO: 140. In some aspects, the antibody comprises a CDR-H3 sequence comprising, consisting of, or consisting essentially of SEQ ID NO: 141. In some aspects, the antibody comprises a CDR-H3 sequence comprising, consisting of, or consisting essentially of SEQ ID NO: 142. In some aspects, the antibody comprises a CDR-H3 sequence comprising, consisting of, or consisting essentially of SEQ ID NO: 143. In some aspects, the antibody comprises a CDR-H3 sequence comprising, consisting of, or consisting essentially of SEQ ID NO: 144. In some aspects, the antibody comprises a CDR-H3 sequence comprising, consisting of, or consisting essentially of SEQ ID NO: 145.

2.2.2.2. Chothia CDR-H2

In some embodiments, the antibody comprises a $V_H$ sequence comprising a CDR-H2 sequence, wherein the CDR-H2 sequence comprises, consists of, or consists essentially of a Chothia CDR-H2 sequence of an illustrative antibody or $V_H$ sequence provided herein. In some aspects, the Chothia CDR-H2 sequence is a Chothia CDR-H2 sequence of a $V_H$ sequence provided in SEQ ID NOs: 167-216.

In some embodiments, the antibody comprises a $V_H$ sequence comprising a Chothia CDR-H2 sequence comprising, consisting of, or consisting essentially of a sequence selected from SEQ ID NOs: 57-78. In some aspects, the antibody comprises a CDR-H2 sequence comprising, consisting of, or consisting essentially of SEQ ID NO: 57. In some aspects, the antibody comprises a CDR-H2 sequence comprising, consisting of, or consisting essentially of SEQ ID NO: 58. In some aspects, the antibody comprises a CDR-H2 sequence comprising, consisting of, or consisting essentially of SEQ ID NO: 59. In some aspects, the antibody comprises a CDR-H2 sequence comprising, consisting of, or consisting essentially of SEQ ID NO: 60. In some aspects, the antibody comprises a CDR-H2 sequence comprising, consisting of, or consisting essentially of SEQ ID NO: 61. In some aspects, the antibody comprises a CDR-H2 sequence comprising, consisting of, or consisting essentially of SEQ ID NO: 62. In some aspects, the antibody comprises a CDR-H2 sequence comprising, consisting of, or consisting essentially of SEQ ID NO: 63. In some aspects, the antibody comprises a CDR-H2 sequence comprising, consisting of, or consisting essentially of SEQ ID NO: 64. In some aspects, the antibody comprises a CDR-H2 sequence comprising, consisting of, or consisting essentially of SEQ ID NO: 65. In some aspects, the antibody comprises a CDR-H2 sequence comprising, consisting of, or consisting essentially of SEQ ID NO: 66. In some aspects, the antibody comprises a CDR-H2 sequence comprising, consisting of, or consisting essentially of SEQ ID NO: 67. In some aspects, the antibody comprises a CDR-H2 sequence comprising, consisting of, or consisting essentially of SEQ ID NO: 68. In some aspects, the antibody comprises a CDR-H2 sequence comprising, consisting of, or consisting essentially of SEQ ID NO: 69. In some aspects, the antibody comprises a CDR-H2 sequence comprising, consisting of, or consisting essentially of SEQ ID NO: 70. In some aspects, the antibody comprises a CDR-H2 sequence comprising, consisting of, or consisting essentially of SEQ ID NO: 71. In some aspects, the antibody comprises a CDR-H2 sequence comprising, consisting of, or consisting essentially of SEQ ID NO: 72. In some aspects, the antibody comprises a CDR-H2 sequence comprising, consisting of, or consisting essentially of SEQ ID NO: 73. In some aspects, the antibody comprises a CDR-H2 sequence comprising, consisting of, or consisting essentially of SEQ ID NO: 74. In some aspects, the antibody comprises a CDR-H2 sequence comprising, consisting of, or consisting essentially of SEQ ID NO: 75. In some aspects, the antibody comprises a CDR-H2 sequence comprising, consisting of, or consisting essentially of SEQ ID NO: 76. In some aspects, the antibody comprises a CDR-H2 sequence comprising, consisting of, or consisting essentially of SEQ ID NO: 77. In some aspects, the antibody comprises a CDR-H2 sequence comprising, consisting of, or consisting essentially of SEQ ID NO: 78.

2.2.2.3. Chothia CDR-H1

In some embodiments, the antibody comprises a $V_H$ sequence comprising a CDR-H1 sequence, wherein the CDR-H1 sequence comprises, consists of, or consists essentially of a Chothia CDR-H1 sequence of an illustrative antibody or $V_H$ sequence provided herein. In some aspects, the Chothia CDR-H1 sequence is a Chothia CDR-H1 sequence of a $V_H$ sequence provided in SEQ ID NOs: 167-216.

In some embodiments, the antibody comprises a $V_H$ sequence comprising a Chothia CDR-H1 sequence comprising, consisting of, or consisting essentially of a sequence selected from SEQ ID NOs: 5-31. In some aspects, the antibody comprises a CDR-H1 sequence comprising, consisting of, or consisting essentially of SEQ ID NO: 5. In some aspects, the antibody comprises a CDR-H1 sequence comprising, consisting of, or consisting essentially of SEQ ID NO: 6. In some aspects, the antibody comprises a CDR-H1 sequence comprising, consisting of, or consisting essentially of SEQ ID NO: 7. In some aspects, the antibody comprises a CDR-H1 sequence comprising, consisting of, or consisting essentially of SEQ ID NO: 8. In some aspects, the antibody comprises a CDR-H1 sequence comprising, consisting of, or consisting essentially of SEQ ID NO: 9. In some aspects, the antibody comprises a CDR-H1 sequence comprising, consisting of, or consisting essentially of SEQ ID NO: 10. In some aspects, the antibody comprises a CDR-H1 sequence comprising, consisting of, or consisting essentially of SEQ ID NO: 11. In some aspects, the antibody comprises a CDR-H1 sequence comprising, consisting of, or consisting essentially of SEQ ID NO: 12. In some aspects, the antibody comprises a CDR-H1 sequence comprising, consisting of, or consisting essentially of SEQ ID NO: 13. In some aspects, the antibody comprises a CDR-H1 sequence comprising, consisting of, or consisting essentially of SEQ ID NO: 14. In some aspects, the antibody comprises a CDR-H1 sequence comprising, consisting of, or consisting essentially of SEQ ID NO: 15. In some aspects, the antibody comprises a CDR-H1 sequence comprising, consisting of, or consisting essentially of SEQ ID NO: 16. In some aspects, the antibody comprises a CDR-H1 sequence comprising, consisting of, or consisting essentially of SEQ ID NO: 17. In some aspects, the antibody comprises a CDR-H1 sequence comprising, consisting of, or consisting essentially of SEQ ID NO: 18. In some aspects, the antibody comprises a CDR-H1 sequence comprising, consisting of, or consisting essentially of SEQ ID NO: 19. In some aspects, the antibody comprises a CDR-H1 sequence comprising, consisting of, or consisting essentially of SEQ ID NO: 20. In some aspects, the antibody comprises a CDR-H1 sequence comprising, consisting of, or consisting essentially of SEQ ID NO: 21. In some aspects, the antibody comprises a CDR-H1 sequence comprising, consisting of, or consisting essentially of SEQ ID NO: 22. In some aspects, the antibody comprises a CDR-H1 sequence comprising, consisting of, or consisting essentially of SEQ ID NO: 23. In some aspects, the antibody comprises a CDR-H1 sequence comprising, consisting of, or consisting essentially of SEQ ID NO: 24. In some aspects, the antibody comprises a CDR-H1 sequence comprising, consisting of, or consisting essentially of SEQ ID NO: 25. In some aspects, the antibody comprises a CDR-H1 sequence comprising, consisting of, or consisting essentially of SEQ ID NO: 26. In some aspects, the antibody comprises a CDR-H1 sequence comprising, consisting of, or consisting essentially of SEQ ID NO: 27. In some aspects, the antibody comprises a CDR-H1 sequence comprising, consisting of, or consisting essentially of SEQ ID NO: 28. In some aspects, the antibody comprises a CDR-H1 sequence comprising, consisting of, or consisting essentially of SEQ ID NO: 29. In some aspects, the antibody comprises a CDR-H1 sequence comprising, consisting of, or consisting essentially of SEQ ID NO: 30. In some aspects, the antibody comprises a CDR-H1 sequence comprising, consisting of, or consisting essentially of SEQ ID NO: 31.

2.2.2.4. Chothia CDR-H3+Chothia CDR-H2

In some embodiments, the antibody comprises a $V_H$ sequence comprising a Chothia CDR-H3 sequence comprising, consisting of, or consisting essentially of a sequence selected from SEQ ID NOs: 116-145, and a Chothia CDR-H2 sequence comprising, consisting of, or consisting essentially of a sequence selected from SEQ ID NOs: 57-78. In some aspects, the Chothia CDR-H3 sequence and the Chothia CDR-H2 sequence are both from a single illustrative $V_H$ sequence provided in this disclosure. For example, in some aspects, the Chothia CDR-H3 and Chothia CDR-H2 are both from a single illustrative $V_H$ sequence selected from SEQ ID NOs: 167-216.

2.2.2.5. Chothia CDR-H3+Chothia CDR-H1

In some embodiments, the antibody comprises a $V_H$ sequence comprising a Chothia CDR-H3 sequence comprising, consisting of, or consisting essentially of a sequence selected from SEQ ID NOs: 116-145, and a Chothia CDR-H1 sequence comprising, consisting of, or consisting essentially of a sequence selected from SEQ ID NOs: 5-31. In some aspects, the Chothia CDR-H3 sequence and the Chothia CDR-H1 sequence are both from a single illustrative $V_H$ sequence provided in this disclosure. For example, in some aspects, the Chothia CDR-H3 and Chothia CDR-H1 are both from a single illustrative $V_H$ sequence selected from SEQ ID NOs: 167-216.

2.2.2.6. Chothia CDR-H1+Chothia CDR-H2

In some embodiments, the antibody comprises a $V_H$ sequence comprising a Chothia CDR-H1 sequence comprising, consisting of, or consisting essentially of a sequence selected from SEQ ID NOs: 5-31 and a Chothia CDR-H2 sequence comprising, consisting of, or consisting essentially of a sequence selected from SEQ ID NOs: 57-78. In some aspects, the Chothia CDR-H1 sequence and the Chothia CDR-H2 sequence are both from a single illustrative $V_H$ sequence provided in this disclosure. For example, in some aspects, the Chothia CDR-H1 and Chothia CDR-H2 are both from a single illustrative $V_H$ sequence selected from SEQ ID NOs: 167-216.

2.2.2.7. Chothia CDR-H1+Chothia CDR-H2+Chothia CDR-H3

In some embodiments, the antibody comprises a $V_H$ sequence comprising a Chothia CDR-H1 sequence comprising, consisting of, or consisting essentially of a sequence selected from SEQ ID NOs: 5-31, a Chothia CDR-H2 sequence comprising, consisting of, or consisting essentially of a sequence selected from SEQ ID NOs: 57-78, and a Chothia CDR-H3 sequence comprising, consisting of, or consisting essentially of a sequence selected from SEQ ID NOs: 116-145. In some aspects, the Chothia CDR-H1 sequence, Chothia CDR-H2 sequence, and Chothia CDR-H3 sequence are all from a single illustrative $V_H$ sequence provided in this disclosure. For example, in some aspects, the Chothia CDR-H1, Chothia CDR-H2, and Chothia CDR-H3 are all from a single illustrative $V_H$ sequence selected from SEQ ID NOs: 167-216.

2.2.2.8. Variants of $V_H$ Sequences Comprising Illustrative Chothia CDRs

In some embodiments, the $V_H$ sequences provided herein comprise a variant of an illustrative Chothia CDR-H3, CDR-H2, and/or CDR-H1 sequence provided in this disclosure.

In some aspects, the Chothia CDR-H3 sequence comprises, consists of, or consists essentially of a variant of an illustrative Chothia CDR-H3 sequence provided in this disclosure. In some aspects, the Chothia CDR-H3 sequence comprises, consists of, or consists essentially of a sequence having at least 70%, 75%, 80%, 85%, 90%, or 95% identity with any of the illustrative Chothia CDR-H3 sequences provided in this disclosure. In some aspects, the Chothia CDR-H3 sequence comprises, consists of, or consists essentially of any of the illustrative Chothia CDR-H3 sequences provided in this disclosure, with 1, 2, or 3 amino acid substitutions. In some aspects, the amino acid substitutions are conservative amino acid substitutions.

In some aspects, the Chothia CDR-H2 sequence comprises, consists of, or consists essentially of a variant of an illustrative Chothia CDR-H2 sequence provided in this disclosure. In some aspects, the Chothia CDR-H2 sequence comprises, consists of, or consists essentially of a sequence having at least 70%, 75%, 80%, 85%, 90%, or 95% identity with any of the illustrative Chothia CDR-H2 sequences provided in this disclosure. In some aspects, the Chothia CDR-H2 sequence comprises, consists of, or consists essentially of any of the illustrative Chothia CDR-H2 sequences provided in this disclosure, with 1, 2, or 3 amino acid substitutions. In some aspects, the amino acid substitutions are conservative amino acid substitutions.

In some aspects, the Chothia CDR-H1 sequence comprises, consists of, or consists essentially of a variant of an illustrative Chothia CDR-H1 sequence provided in this disclosure. In some aspects, the Chothia CDR-H1 sequence comprises, consists of, or consists essentially of a sequence having at least 70%, 75%, 80%, 85%, 90%, or 95% identity with any of the illustrative Chothia CDR-H1 sequences provided in this disclosure. In some aspects, the Chothia CDR-H1 sequence comprises, consists of, or consists essentially of any of the illustrative Chothia CDR-H1 sequences provided in this disclosure, with 1, 2, or 3 amino acid substitutions. In some aspects, the amino acid substitutions are conservative amino acid substitutions.

2.3. $V_H$ Sequences

In some embodiments, the antibody comprises, consists of, or consists essentially of a $V_H$ sequence provided in SEQ ID NOs: 167-216.

In some embodiments, the antibody comprises a $V_H$ sequence comprising, consisting of, or consisting essentially of a sequence selected from SEQ ID NOs: 167-216. In some aspects, the antibody comprises a $V_H$ sequence comprising, consisting of, or consisting essentially of SEQ ID NO: 167. In some aspects, the antibody comprises a $V_H$ sequence comprising, consisting of, or consisting essentially of SEQ ID NO: 168. In some aspects, the antibody comprises a $V_H$ sequence comprising, consisting of, or consisting essentially of SEQ ID NO: 169. In some aspects, the antibody comprises a $V_H$ sequence comprising, consisting of, or consisting essentially of SEQ ID NO: 170. In some aspects, the antibody comprises a $V_H$ sequence comprising, consisting of, or consisting essentially of SEQ ID NO: 171. In some aspects, the antibody comprises a $V_H$ sequence comprising, consisting of, or consisting essentially of SEQ ID NO: 172. In some aspects, the antibody comprises a $V_H$ sequence comprising, consisting of, or consisting essentially of SEQ ID NO: 173. In some aspects, the antibody comprises a $V_H$ sequence comprising, consisting of, or consisting essentially of SEQ ID NO: 174. In some aspects, the antibody comprises a $V_H$ sequence comprising, consisting of, or consisting essentially of SEQ ID NO: 175. In some aspects, the antibody comprises a $V_H$ sequence comprising, consisting of, or consisting essentially of SEQ ID NO: 176. In some aspects, the antibody comprises a $V_H$ sequence comprising, consisting of, or consisting essentially of SEQ ID NO: 177. In some aspects, the antibody comprises a $V_H$ sequence comprising, consisting of, or consisting essentially of SEQ ID NO: 178. In some aspects, the antibody comprises a $V_H$ sequence comprising, consisting of, or consisting essentially of SEQ ID NO: 179. In some aspects, the antibody comprises a $V_H$ sequence comprising, consisting of, or consisting essentially of SEQ ID NO: 180. In some aspects, the antibody comprises a $V_H$ sequence comprising, consisting of, or consisting essentially of SEQ ID NO: 181. In some aspects, the antibody comprises a $V_H$ sequence comprising, consisting of, or consisting essentially of SEQ ID NO: 182. In some aspects, the antibody comprises a $V_H$ sequence comprising, consisting of, or consisting essentially of SEQ ID NO: 183. In some aspects, the antibody comprises a $V_H$ sequence comprising, consisting of, or consisting essentially of SEQ ID NO: 184. In some aspects, the antibody comprises a $V_H$ sequence comprising, consisting of, or consisting essentially of SEQ ID NO: 185. In some aspects, the antibody comprises a $V_H$ sequence comprising, consisting of, or consisting essentially of SEQ ID NO: 186. In some aspects, the antibody comprises a $V_H$ sequence comprising, consisting of, or consisting essentially of SEQ ID NO: 187. In some aspects, the antibody comprises a $V_H$ sequence comprising, consisting of, or consisting essentially of SEQ ID NO: 188. In some aspects, the antibody comprises a $V_H$ sequence comprising, consisting of, or consisting essentially of SEQ ID NO: 189. In some aspects, the antibody comprises a $V_H$ sequence comprising, consisting of, or consisting essentially of SEQ ID NO: 190. In some aspects, the antibody comprises a $V_H$ sequence comprising, consisting of, or consisting essentially of SEQ ID NO: 191. In some aspects, the antibody comprises a $V_H$ sequence comprising, consisting of, or consisting essentially of SEQ ID NO: 192. In some aspects, the antibody comprises a $V_H$ sequence comprising, consisting of, or consisting essentially of SEQ ID NO: 193. In some aspects, the antibody comprises a $V_H$ sequence comprising, consisting of, or consisting essentially of SEQ ID NO: 194. In some aspects, the antibody comprises a $V_H$ sequence comprising, consisting of, or consisting essentially of SEQ ID NO: 195. In some aspects, the antibody comprises a $V_H$ sequence comprising, consisting of, or consisting essentially of SEQ ID NO: 196. In some aspects, the antibody comprises a $V_H$ sequence comprising, consisting of, or consisting essentially of SEQ ID NO: 197. In some aspects, the antibody comprises a $V_H$ sequence comprising, consisting of, or consisting essentially of SEQ ID NO: 198. In some aspects, the antibody comprises a $V_H$ sequence comprising, consisting of, or consisting essentially of SEQ ID NO: 199. In some aspects, the antibody comprises a $V_H$ sequence comprising, consisting of, or consisting essentially of SEQ ID NO: 200. In some aspects, the antibody comprises a $V_H$ sequence comprising, consisting of, or consisting essentially of SEQ ID NO: 201. In some aspects, the antibody comprises a $V_H$ sequence comprising, consisting of, or consisting essentially of SEQ ID NO: 202. In some aspects, the antibody comprises a $V_H$ sequence comprising, consisting of, or consisting essentially of SEQ ID NO: 203. In some aspects, the antibody comprises a $V_H$ sequence comprising, consisting of, or consisting essentially of SEQ ID NO: 204. In some aspects, the antibody comprises a $V_H$ sequence comprising, consisting of, or consisting essentially of SEQ ID NO: 205. In some aspects, the antibody comprises a $V_H$ sequence comprising, consisting of, or consisting essentially of SEQ ID NO: 206. In some aspects, the antibody comprises a $V_H$ sequence comprising, consisting of, or consisting essentially of SEQ ID NO: 207. In some aspects, the antibody comprises a $V_H$ sequence comprising, consisting of, or consisting essentially of SEQ ID NO: 208. In some aspects, the antibody comprises a $V_H$ sequence comprising, consisting of, or consisting essentially of SEQ ID NO: 209. In some aspects, the antibody comprises a $V_H$ sequence comprising, consisting of, or consisting essentially of SEQ ID NO: 210. In some aspects, the antibody comprises a $V_H$ sequence comprising, consisting of, or consisting essentially of SEQ ID NO: 211. In some aspects, the antibody comprises a $V_H$ sequence comprising, consisting of, or consisting essentially of SEQ ID NO: 212. In some aspects, the antibody comprises a $V_H$ sequence comprising, consisting of, or consisting essentially of SEQ ID NO: 213. In some aspects, the antibody comprises a $V_H$ sequence comprising, consisting of, or consisting essentially of SEQ ID NO: 214. In some aspects, the antibody comprises a $V_H$ sequence comprising, consisting of, or consisting essentially of SEQ ID NO: 215. In some aspects, the antibody comprises a $V_H$ sequence comprising, consisting of, or consisting essentially of SEQ ID NO: 216.

2.3.1. Variants of $V_H$ Sequences

In some embodiments, the $V_H$ sequences provided herein comprise, consist of, or consist essentially of a variant of an illustrative $V_H$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.5% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.4. CDR-L3 Sequences

In some embodiments, the antibody comprises a CDR-L3 sequence comprising, consisting of, or consisting essentially of a CDR-L3 sequence of an illustrative antibody or $V_L$ sequence provided herein. In some aspects, the CDR-L3 sequence is a CDR-L3 sequence of a $V_L$ sequence provided in SEQ ID NOs: 217-238.

In some embodiments, the antibody comprises a CDR-L3 sequence comprising, consisting of, or consisting essentially of a sequence selected from SEQ ID NOs: 161-166. In some aspects, the antibody comprises a CDR-L3 sequence comprising, consisting of, or consisting essentially of SEQ ID NO: 161. In some aspects, the antibody comprises a CDR-L3 sequence comprising, consisting of, or consisting essentially of SEQ ID NO: 162. In some aspects, the antibody comprises a CDR-L3 sequence comprising, consisting of, or consisting essentially of SEQ ID NO: 163. In some aspects, the antibody comprises a CDR-L3 sequence comprising, consisting of, or consisting essentially of SEQ ID NO: 164. In some aspects, the antibody comprises a CDR-L3 sequence comprising, consisting of, or consisting essentially of SEQ ID NO: 165. In some aspects, the antibody comprises a CDR-L3 sequence comprising, consisting of, or consisting essentially of SEQ ID NO: 166.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.5. $V_L$ Sequences Comprising Illustrative CDRs

In some embodiments, the antibody comprises a $V_L$ sequence comprising one or more CDR-L sequences comprising, consisting of, or consisting essentially of one or more illustrative CDR-L sequences provided in this disclosure, and variants thereof.

2.5.1. CDR-L3

In some embodiments, the antibody comprises a $V_L$ sequence comprising a CDR-L3 sequence, wherein the CDR-L3 sequence comprises, consists of, or consists essentially of a CDR-L3 sequence of an illustrative antibody or $V_L$ sequence provided herein. In some aspects, the CDR-L3 sequence is a CDR-L3 sequence of a $V_L$ sequence provided in SEQ ID NOs: 217-238.

In some embodiments, the antibody comprises a $V_L$ sequence comprising a CDR-L3 sequence comprising, consisting of, or consisting essentially of a sequence selected from SEQ ID NOs: 161-166. In some aspects, the antibody comprises a CDR-L3 sequence comprising, consisting of, or consisting essentially of SEQ ID NO: 161. In some aspects, the antibody comprises a CDR-L3 sequence comprising, consisting of, or consisting essentially of SEQ ID NO: 162. In some aspects, the antibody comprises a CDR-L3 sequence comprising, consisting of, or consisting essentially of SEQ ID NO: 163. In some aspects, the antibody comprises a CDR-L3 sequence comprising, consisting of, or consisting essentially of SEQ ID NO: 164. In some aspects, the antibody comprises a CDR-L3 sequence comprising, consisting of, or consisting essentially of SEQ ID NO: 165. In some aspects, the antibody comprises a CDR-L3 sequence comprising, consisting of, or consisting essentially of SEQ ID NO: 166.

2.5.2. CDR-L2

In some embodiments, the antibody comprises a $V_L$ sequence comprising a CDR-L2 sequence, wherein the CDR-L2 sequence comprises, consists of, or consists essentially of a CDR-L2 sequence of an illustrative antibody or $V_L$ sequence provided herein. In some aspects, the CDR-L2 sequence is a CDR-L2 sequence of a $V_L$ sequence provided in SEQ ID NOs: 217-238.

In some embodiments, the antibody comprises a $V_L$ sequence comprising a CDR-L2 sequence comprising, consisting of, or consisting essentially of a sequence selected from SEQ ID NOs: 155-160. In some aspects, the antibody comprises a $V_L$ sequence comprising a CDR-L2 sequence comprising, consisting of, or consisting essentially of SEQ ID NO: 155. In some aspects, the antibody comprises a $V_L$ sequence comprising a CDR-L2 sequence comprising, consisting of, or consisting essentially of SEQ ID NO: 156. In some aspects, the antibody comprises a $V_L$ sequence comprising a CDR-L2 sequence comprising, consisting of, or consisting essentially of SEQ ID NO: 157. In some aspects, the antibody comprises a $V_L$ sequence comprising a CDR-L2 sequence comprising, consisting of, or consisting essentially of SEQ ID NO: 158. In some aspects, the antibody comprises a $V_L$ sequence comprising a CDR-L2 sequence comprising, consisting of, or consisting essentially of SEQ ID NO: 159. In some aspects, the antibody comprises a $V_L$ sequence comprising a CDR-L2 sequence comprising, consisting of, or consisting essentially of SEQ ID NO: 160.

2.5.3. CDR-L1

In some embodiments, the antibody comprises a $V_L$ sequence comprising a CDR-L1 sequence, wherein the CDR-L1 sequence comprises, consists of, or consists essentially of a CDR-L1 sequence of an illustrative antibody or $V_L$ sequence provided herein. In some aspects, the CDR-L1 sequence is a CDR-L1 sequence of a $V_L$ sequence provided in SEQ ID NOs: 217-238.

In some embodiments, the antibody comprises a $V_L$ sequence comprising a CDR-L1 sequence comprising, consisting of, or consisting essentially of a sequence selected from SEQ ID NOs: 146-154. In some aspects, the antibody comprises a $V_L$ sequence comprising a CDR-L1 sequence comprising, consisting of, or consisting essentially of SEQ ID NO: 146. In some aspects, the antibody comprises a $V_L$ sequence comprising a CDR-L1 sequence comprising, consisting of, or consisting essentially of SEQ ID NO: 147. In some aspects, the antibody comprises a $V_L$ sequence comprising a CDR-L1 sequence comprising, consisting of, or consisting essentially of SEQ ID NO: 148. In some aspects, the antibody comprises a $V_L$ sequence comprising a CDR-L1 sequence comprising, consisting of, or consisting essentially of SEQ ID NO: 149. In some aspects, the antibody comprises a $V_L$ sequence comprising a CDR-L1 sequence comprising, consisting of, or consisting essentially of SEQ ID NO: 150. In some aspects, the antibody comprises a $V_L$ sequence comprising a CDR-L1 sequence comprising, consisting of, or consisting essentially of SEQ ID NO: 151. In some aspects, the antibody comprises a $V_L$ sequence comprising a CDR-L1 sequence comprising, consisting of, or consisting essentially of SEQ ID NO: 152. In some aspects, the antibody comprises a $V_L$ sequence comprising a CDR-L1 sequence comprising, consisting of, or consisting essentially of SEQ ID NO: 153. In some aspects, the antibody comprises a $V_L$ sequence comprising a CDR-L1 sequence comprising, consisting of, or consisting essentially of SEQ ID NO: 154.

2.5.4. CDR-L3+CDR-L2

In some embodiments, the antibody comprises a $V_L$ sequence comprising a CDR-L3 sequence comprising, consisting of, or consisting essentially of a sequence selected from SEQ ID NOs: 161-166 and a CDR-L2 sequence comprising, consisting of, or consisting essentially of a sequence selected from SEQ ID NOs: 155-160. In some aspects, the CDR-L3 sequence and the CDR-L2 sequence are both from a single illustrative $V_L$ sequence provided in this disclosure. For example, in some aspects, the CDR-L3 and CDR-L2 are both from a single illustrative $V_L$ sequence selected from SEQ ID NOs: 217-238.

2.5.5. CDR-L3+CDR-L1

In some embodiments, the antibody comprises a $V_L$ sequence comprising a CDR-L3 sequence comprising, consisting of, or consisting essentially of a sequence selected from SEQ ID NOs: 161-166 and a CDR-L1 sequence comprising, consisting of, or consisting essentially of a sequence selected from SEQ ID NOs: 146-154. In some aspects, the CDR-L3 sequence and the CDR-L1 sequence are both from a single illustrative $V_L$ sequence provided in this disclosure. For example, in some aspects, the CDR-L3 and CDR-L1 are both from a single illustrative $V_L$ sequence selected from SEQ ID NOs: 217-238.

2.5.6. CDR-L1+CDR-L2

In some embodiments, the antibody comprises a $V_L$ sequence comprising a CDR-L1 sequence comprising, consisting of, or consisting essentially of a sequence selected from SEQ ID NOs: 146-154 and a CDR-L2 sequence comprising, consisting of, or consisting essentially of a sequence selected from SEQ ID NOs: 155-160. In some aspects, the CDR-L1 sequence and the CDR-L2 sequence are both from a single illustrative $V_L$ sequence provided in this disclosure. For example, in some aspects, the CDR-L1 and CDR-L2 are both from a single illustrative $V_L$ sequence selected from SEQ ID NOs: 217-238.

2.5.7. CDR-L1+CDR-L2+CDR-L3

In some embodiments, the antibody comprises a $V_L$ sequence comprising a CDR-L1 sequence comprising, consisting of, or consisting essentially of a sequence selected from SEQ ID NOs: 146-154, a CDR-L2 sequence comprising, consisting of, or consisting essentially of a sequence selected from SEQ ID NOs: 155-160, and a CDR-L3 sequence comprising, consisting of, or consisting essentially of a sequence selected from SEQ ID NOs: 161-166. In some aspects, the CDR-L1 sequence, CDR-L2 sequence, and CDR-L3 sequence are all from a single illustrative $V_L$ sequence provided in this disclosure. For example, in some aspects, the CDR-L1, CDR-L2, and CDR-L3 are all from a single illustrative $V_L$ sequence selected from SEQ ID NOs: 217-238.

2.5.8. Variants of $V_L$ Sequences Comprising Illustrative CDR-Ls

In some embodiments, the $V_L$ sequences provided herein comprise a variant of an illustrative CDR-L3, CDR-L2, and/or CDR-L1 sequence provided in this disclosure.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

2.6. $V_L$ Sequences

In some embodiments, the antibody comprises, consists of, or consists essentially of a $V_L$ sequence provided in SEQ ID NOs: 217-238.

In some embodiments, the antibody comprises a $V_L$ sequence comprising, consisting of, or consisting essentially of a sequence selected from SEQ ID NOs: 217-238. In some aspects, the antibody comprises a $V_L$ sequence comprising, consisting of, or consisting essentially of SEQ ID NO: 217. In some aspects, the antibody comprises a $V_L$ sequence comprising, consisting of, or consisting essentially of SEQ ID NO: 218. In some aspects, the antibody comprises a $V_L$ sequence comprising, consisting of, or consisting essentially of SEQ ID NO: 219. In some aspects, the antibody comprises a $V_L$ sequence comprising, consisting of, or consisting essentially of SEQ ID NO: 220. In some aspects, the antibody comprises a $V_L$ sequence comprising, consisting of, or consisting essentially of SEQ ID NO: 221. In some aspects, the antibody comprises a $V_L$ sequence comprising, consisting of, or consisting essentially of SEQ ID NO: 222. In some aspects, the antibody comprises a $V_L$ sequence comprising, consisting of, or consisting essentially of SEQ ID NO: 223. In some aspects, the antibody comprises a $V_L$ sequence comprising, consisting of, or consisting essentially of SEQ ID NO: 224. In some aspects, the antibody comprises a $V_L$ sequence comprising, consisting of, or consisting essentially of SEQ ID NO: 225. In some aspects, the antibody comprises a $V_L$ sequence comprising, consisting of, or consisting essentially of SEQ ID NO: 226. In some aspects, the antibody comprises a $V_L$ sequence comprising, consisting of, or consisting essentially of SEQ ID NO: 227.

In some aspects, the antibody comprises a $V_L$ sequence comprising, consisting of, or consisting essentially of SEQ ID NO: 228. In some aspects, the antibody comprises a $V_L$ sequence comprising, consisting of, or consisting essentially of SEQ ID NO: 229. In some aspects, the antibody comprises a $V_L$ sequence comprising, consisting of, or consisting essentially of SEQ ID NO: 230. In some aspects, the antibody comprises a $V_L$ sequence comprising, consisting of, or consisting essentially of SEQ ID NO: 231. In some aspects, the antibody comprises a $V_L$ sequence comprising, consisting of, or consisting essentially of SEQ ID NO: 232. In some aspects, the antibody comprises a $V_L$ sequence comprising, consisting of, or consisting essentially of SEQ ID NO: 233. In some aspects, the antibody comprises a $V_L$ sequence comprising, consisting of, or consisting essentially of SEQ ID NO: 234. In some aspects, the antibody comprises a $V_L$ sequence comprising, consisting of, or consisting essentially of SEQ ID NO: 235. In some aspects, the antibody comprises a $V_L$ sequence comprising, consisting of, or consisting essentially of SEQ ID NO: 236. In some aspects, the antibody comprises a $V_L$ sequence comprising, consisting of, or consisting essentially of SEQ ID NO: 237. In some aspects, the antibody comprises a $V_L$ sequence comprising, consisting of, or consisting essentially of SEQ ID NO: 238.

2.6.1. Variants of $V_L$ Sequences

In some embodiments, the $V_L$ sequences provided herein comprise, consist of, or consist essentially of a variant of an illustrative $V_L$ sequence provided in this disclosure.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.7. Pairs 2.7.1. CDR-H3-CDR-L3 Pairs

In some embodiments, the antibody comprises a CDR-H3 sequence and a CDR-L3 sequence. In some aspects, the CDR-H3 sequence is part of a $V_H$ and the CDR-L3 sequence is part of a $V_L$.

In some aspects, the CDR-H3 sequence is a CDR-H3 sequence comprising, consisting of, or consisting essentially of any one of SEQ ID NOs: 116-145, and the CDR-L3 sequence is a CDR-L3 sequence comprising, consisting of, or consisting essentially of any one of SEQ ID NOs: 161-166.

In some aspects, the CDR-H3-CDR-L3 pairs are selected from SEQ ID NO: 116 and SEQ ID NO: 161; SEQ ID NO: 117 and SEQ ID NO: 161; SEQ ID NO: 118 and SEQ ID NO: 161; SEQ ID NO: 119 and SEQ ID NO: 161; SEQ ID NO: 120 and SEQ ID NO: 161; SEQ ID NO: 121 and SEQ ID NO: 161; SEQ ID NO: 122 and SEQ ID NO: 161; SEQ ID NO: 123 and SEQ ID NO: 161; SEQ ID NO: 124 and SEQ ID NO: 161; SEQ ID NO: 125 and SEQ ID NO: 161; SEQ ID NO: 126 and SEQ ID NO: 161; SEQ ID NO: 127 and SEQ ID NO: 161; SEQ ID NO: 128 and SEQ ID NO: 161; SEQ ID NO: 129 and SEQ ID NO: 161; SEQ ID NO: 130 and SEQ ID NO: 161; SEQ ID NO: 131 and SEQ ID NO: 161; SEQ ID NO: 132 and SEQ ID NO: 161; SEQ ID NO: 133 and SEQ ID NO: 161; SEQ ID NO: 134 and SEQ ID NO: 161; SEQ ID NO: 135 and SEQ ID NO:161; SEQ ID NO: 136 and SEQ ID NO: 161; SEQ ID NO: 137 and SEQ ID NO: 161; SEQ ID NO: 138 and SEQ ID NO: 161; SEQ ID NO: 139 and SEQ ID NO: 161; SEQ ID NO: 140 and SEQ ID NO: 161; SEQ ID NO: 141 and SEQ ID NO: 161; SEQ ID NO: 142 and SEQ ID NO: 161; SEQ ID NO: 143 and SEQ ID NO: 161; SEQ ID NO: 144 and SEQ ID NO: 161; SEQ ID NO: 145 and SEQ ID NO: 161.

In some aspects, the CDR-H3-CDR-L3 pairs are selected from SEQ ID NO: 116 and SEQ ID NO: 162; SEQ ID NO: 117 and SEQ ID NO: 162; SEQ ID NO: 118 and SEQ ID NO: 162; SEQ ID NO: 119 and SEQ ID NO: 162; SEQ ID NO: 120 and SEQ ID NO: 162; SEQ ID NO: 121 and SEQ ID NO: 162; SEQ ID NO: 122 and SEQ ID NO: 162; SEQ ID NO: 123 and SEQ ID NO: 162; SEQ ID NO: 124 and SEQ ID NO: 162; SEQ ID NO: 125 and SEQ ID NO: 162; SEQ ID NO: 126 and SEQ ID NO: 162; SEQ ID NO: 127 and SEQ ID NO: 162; SEQ ID NO: 128 and SEQ ID NO: 162; SEQ ID NO: 129 and SEQ ID NO: 162; SEQ ID NO: 130 and SEQ ID NO: 162; SEQ ID NO: 131 and SEQ ID NO: 162; SEQ ID NO: 132 and SEQ ID NO: 162; SEQ ID NO: 133 and SEQ ID NO: 162; SEQ ID NO: 134 and SEQ ID NO: 162; SEQ ID NO: 135 and SEQ ID NO:161; SEQ ID NO: 136 and SEQ ID NO: 162; SEQ ID NO: 137 and SEQ ID NO: 162; SEQ ID NO: 138 and SEQ ID NO: 162; SEQ ID NO: 139 and SEQ ID NO: 162; SEQ ID NO: 140 and SEQ ID NO: 162; SEQ ID NO: 141 and SEQ ID NO: 162; SEQ ID NO: 142 and SEQ ID NO: 162; SEQ ID NO: 143 and SEQ ID NO: 162; SEQ ID NO: 144 and SEQ ID NO: 162; SEQ ID NO: 145 and SEQ ID NO: 162.

In some aspects, the CDR-H3-CDR-L3 pairs are selected from SEQ ID NO: 116 and SEQ ID NO: 163; SEQ ID NO: 117 and SEQ ID NO: 163; SEQ ID NO: 118 and SEQ ID NO: 163; SEQ ID NO: 119 and SEQ ID NO: 163; SEQ ID NO: 120 and SEQ ID NO: 163; SEQ ID NO: 121 and SEQ ID NO: 163; SEQ ID NO: 122 and SEQ ID NO: 163; SEQ ID NO: 123 and SEQ ID NO: 163; SEQ ID NO: 124 and SEQ ID NO: 163; SEQ ID NO: 125 and SEQ ID NO: 163; SEQ ID NO: 126 and SEQ ID NO: 163; SEQ ID NO: 127 and SEQ ID NO: 163; SEQ ID NO: 128 and SEQ ID NO: 163; SEQ ID NO: 129 and SEQ ID NO: 163; SEQ ID NO: 130 and SEQ ID NO: 163; SEQ ID NO: 131 and SEQ ID NO: 163; SEQ ID NO: 132 and SEQ ID NO: 163; SEQ ID NO: 133 and SEQ ID NO: 163; SEQ ID NO: 134 and SEQ ID NO: 163; SEQ ID NO: 135 and SEQ ID NO:161; SEQ ID NO: 136 and SEQ ID NO: 163; SEQ ID NO: 137 and SEQ ID NO: 163; SEQ ID NO: 138 and SEQ ID NO: 163; SEQ ID NO: 139 and SEQ ID NO: 163; SEQ ID NO: 140 and SEQ ID NO: 163; SEQ ID NO: 141 and SEQ ID NO: 163; SEQ ID NO: 142 and SEQ ID NO: 163; SEQ ID NO: 143 and SEQ ID NO: 163; SEQ ID NO: 144 and SEQ ID NO: 163; SEQ ID NO: 145 and SEQ ID NO: 163.

In some aspects, the CDR-H3-CDR-L3 pairs are selected from SEQ ID NO: 116 and SEQ ID NO: 164; SEQ ID NO: 117 and SEQ ID NO: 164; SEQ ID NO: 118 and SEQ ID NO: 164; SEQ ID NO: 119 and SEQ ID NO: 164; SEQ ID NO: 120 and SEQ ID NO: 164; SEQ ID NO: 121 and SEQ ID NO: 164; SEQ ID NO: 122 and SEQ ID NO: 164; SEQ ID NO: 123 and SEQ ID NO: 164; SEQ ID NO: 124 and SEQ ID NO: 164; SEQ ID NO: 125 and SEQ ID NO: 164; SEQ ID NO: 126 and SEQ ID NO: 164; SEQ ID NO: 127 and SEQ ID NO: 164; SEQ ID NO: 128 and SEQ ID NO: 164; SEQ ID NO: 129 and SEQ ID NO: 164; SEQ ID NO:

130 and SEQ ID NO: 164; SEQ ID NO: 131 and SEQ ID NO: 164; SEQ ID NO: 132 and SEQ ID NO: 164; SEQ ID NO: 133 and SEQ ID NO: 164; SEQ ID NO: 134 and SEQ ID NO: 164; SEQ ID NO: 135 and SEQ ID NO:161; SEQ ID NO: 136 and SEQ ID NO: 164; SEQ ID NO: 137 and SEQ ID NO: 164; SEQ ID NO: 138 and SEQ ID NO: 164; SEQ ID NO: 139 and SEQ ID NO: 164; SEQ ID NO: 140 and SEQ ID NO: 164; SEQ ID NO: 141 and SEQ ID NO: 164; SEQ ID NO: 142 and SEQ ID NO: 164; SEQ ID NO: 143 and SEQ ID NO: 164; SEQ ID NO: 144 and SEQ ID NO: 164; SEQ ID NO: 145 and SEQ ID NO: 164.

In some aspects, the CDR-H3-CDR-L3 pairs are selected from SEQ ID NO: 116 and SEQ ID NO: 165; SEQ ID NO: 117 and SEQ ID NO: 165; SEQ ID NO: 118 and SEQ ID NO: 165; SEQ ID NO: 119 and SEQ ID NO: 165; SEQ ID NO: 120 and SEQ ID NO: 165; SEQ ID NO: 121 and SEQ ID NO: 165; SEQ ID NO: 122 and SEQ ID NO: 165; SEQ ID NO: 123 and SEQ ID NO: 165; SEQ ID NO: 124 and SEQ ID NO: 165; SEQ ID NO: 125 and SEQ ID NO: 165; SEQ ID NO: 126 and SEQ ID NO: 165; SEQ ID NO: 127 and SEQ ID NO: 165; SEQ ID NO: 128 and SEQ ID NO: 165; SEQ ID NO: 129 and SEQ ID NO: 165; SEQ ID NO: 130 and SEQ ID NO: 165; SEQ ID NO: 131 and SEQ ID NO: 165; SEQ ID NO: 132 and SEQ ID NO: 165; SEQ ID NO: 133 and SEQ ID NO: 165; SEQ ID NO: 134 and SEQ ID NO: 165; SEQ ID NO: 135 and SEQ ID NO:161; SEQ ID NO: 136 and SEQ ID NO: 165; SEQ ID NO: 137 and SEQ ID NO: 165; SEQ ID NO: 138 and SEQ ID NO: 165; SEQ ID NO: 139 and SEQ ID NO: 165; SEQ ID NO: 140 and SEQ ID NO: 165; SEQ ID NO: 141 and SEQ ID NO: 165; SEQ ID NO: 142 and SEQ ID NO: 165; SEQ ID NO: 143 and SEQ ID NO: 165; SEQ ID NO: 144 and SEQ ID NO: 165; SEQ ID NO: 145 and SEQ ID NO: 165.

In some aspects, the CDR-H3-CDR-L3 pairs are selected from SEQ ID NO: 116 and SEQ ID NO: 166; SEQ ID NO: 117 and SEQ ID NO: 166; SEQ ID NO: 118 and SEQ ID NO: 166; SEQ ID NO: 119 and SEQ ID NO: 166; SEQ ID NO: 120 and SEQ ID NO: 166; SEQ ID NO: 121 and SEQ ID NO: 166; SEQ ID NO: 122 and SEQ ID NO: 166; SEQ ID NO: 123 and SEQ ID NO: 166; SEQ ID NO: 124 and SEQ ID NO: 166; SEQ ID NO: 125 and SEQ ID NO: 166; SEQ ID NO: 126 and SEQ ID NO: 166; SEQ ID NO: 127 and SEQ ID NO: 166; SEQ ID NO: 128 and SEQ ID NO: 166; SEQ ID NO: 129 and SEQ ID NO: 166; SEQ ID NO: 130 and SEQ ID NO: 166; SEQ ID NO: 131 and SEQ ID NO: 166; SEQ ID NO: 132 and SEQ ID NO: 166; SEQ ID NO: 133 and SEQ ID NO: 166; SEQ ID NO: 134 and SEQ ID NO: 166; SEQ ID NO: 135 and SEQ ID NO:161; SEQ ID NO: 136 and SEQ ID NO: 166; SEQ ID NO: 137 and SEQ ID NO: 166; SEQ ID NO: 138 and SEQ ID NO: 166; SEQ ID NO: 139 and SEQ ID NO: 166; SEQ ID NO: 140 and SEQ ID NO: 166; SEQ ID NO: 141 and SEQ ID NO: 166; SEQ ID NO: 142 and SEQ ID NO: 166; SEQ ID NO: 143 and SEQ ID NO: 166; SEQ ID NO: 144 and SEQ ID NO: 166; SEQ ID NO: 145 and SEQ ID NO: 166.

2.7.1.1. Variants of CDR-H3-CDR-L3 Pairs

In some embodiments, the CDR-H3-CDR-L3 pairs provided herein comprise a variant of an illustrative CDR-H3 and/or CDR-L1 sequence provided in this disclosure.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.7.2. CDR-H1-CDR-L1 Pairs

In some embodiments, the antibody comprises a CDR-H1 sequence and a CDR-L1 sequence. In some aspects, the CDR-H1 sequence is part of a $V_H$ and the CDR-L1 sequence is part of a $V_L$.

In some aspects, the CDR-H1 sequence is a Chothia CDR-H1 sequence comprising, consisting of, or consisting essentially of any one of SEQ ID NOs: 5-31, and the CDR-L1 sequence is a CDR-L1 sequence comprising, consisting of, or consisting essentially of any one of SEQ ID NOs: 146-154.

In some aspects, the CDR-H1 sequence is a Kabat CDR-H1 sequence comprising, consisting of, or consisting essentially of any one of SEQ ID NOs: 32-56, and the CDR-L1 sequence is a CDR-L1 sequence comprising, consisting of, or consisting essentially of any one of SEQ ID NOs: 146-154.

2.7.2.1. Variants of CDR-H1-CDR-L1 Pairs

In some embodiments, the CDR-H1-CDR-L1 pairs provided herein comprise a variant of an illustrative CDR-H1 and/or CDR-L1 sequence provided in this disclosure.

In some aspects, the CDR-H1 sequence comprises, consists of, or consists essentially of a variant of an illustrative CDR-H1 sequence provided in this disclosure. In some aspects, the CDR-H1 sequence comprises, consists of, or consists essentially of a sequence having at least 70%, 75%, 80%, 85%, 90%, or 95% identity with any of the illustrative CDR-H1 sequences provided in this disclosure. In some aspects, the CDR-H1 sequence comprises, consists of, or consists essentially of any of the illustrative CDR-H1 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

2.7.3. CDR-H2-CDR-L2 Pairs

In some embodiments, the antibody comprises a CDR-H2 sequence and a CDR-L2 sequence. In some aspects, the CDR-H2 sequence is part of a $V_H$ and the CDR-L2 sequence is part of a $V_L$.

In some aspects, the CDR-H2 sequence is a Chothia CDR-H2 sequence comprising, consisting of, or consisting essentially of any one of SEQ ID NOs: 57-78, and the CDR-L2 sequence is a CDR-L2 sequence comprising, consisting of, or consisting essentially of any one of SEQ ID NOs: 155-160.

In some aspects, the CDR-H1 sequence is a Kabat CDR-H2 sequence comprising, consisting of, or consisting essentially of any one of SEQ ID NOs: 79-115, and the CDR-L2 sequence is a CDR-L2 sequence comprising, consisting of, or consisting essentially of any one of SEQ ID NOs: 155-160.

2.7.3.1. Variants of CDR-H2-CDR-L2 Pairs

In some embodiments, the CDR-H2-CDR-L2 pairs provided herein comprise a variant of an illustrative CDR-H2 and/or CDR-L2 sequence provided in this disclosure.

In some aspects, the CDR-H2 sequence comprises, consists of, or consists essentially of a variant of an illustrative CDR-H2 sequence provided in this disclosure. In some aspects, the CDR-H2 sequence comprises, consists of, or consists essentially of a sequence having at least 70%, 75%, 80%, 85%, 90%, or 95% identity with any of the illustrative CDR-H2 sequences provided in this disclosure. In some aspects, the CDR-H2 sequence comprises, consists of, or consists essentially of any of the illustrative CDR-H2 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

2.7.4. $V_H$-$V_L$ Pairs

In some embodiments, the antibody comprises a $V_H$ sequence and a $V_L$ sequence.

In some aspects, the $V_H$ sequence is a $V_H$ sequence comprising, consisting of, or consisting essentially of any one of SEQ ID NOs: 167-216, and the $V_L$ sequence is a $V_L$ sequence comprising, consisting of, or consisting essentially of any one of SEQ ID NOs: 217-238.

In some aspects, the $V_H$-$V_L$ pairs are selected from SEQ ID NO:167 and SEQ ID NO:217; SEQ ID NO:168 and SEQ ID NO:217; SEQ ID NO:169 and SEQ ID NO:217; SEQ ID NO:170 and SEQ ID NO:217; SEQ ID NO:171 and SEQ ID NO:217; SEQ ID NO:172 and SEQ ID NO:217; SEQ ID NO:173 and SEQ ID NO:217; SEQ ID NO:174 and SEQ ID NO:217; SEQ ID NO:175 and SEQ ID NO:217; SEQ ID NO:176 and SEQ ID NO:217; SEQ ID NO:177 and SEQ ID NO:217; SEQ ID NO:178 and SEQ ID NO:217; SEQ ID NO:179 and SEQ ID NO:217; SEQ ID NO:180 and SEQ ID NO:217; SEQ ID NO:181 and SEQ ID NO:217; SEQ ID NO:182 and SEQ ID NO:217; SEQ ID NO:183 and SEQ ID NO:217; SEQ ID NO:184 and SEQ ID NO:217; SEQ ID NO:185 and SEQ ID NO:217; SEQ ID NO:186 and SEQ ID NO:217; SEQ ID NO:187 and SEQ ID NO:217; SEQ ID NO:188 and SEQ ID NO:217; SEQ ID NO:189 and SEQ ID NO:217; SEQ ID NO:190 and SEQ ID NO:217; SEQ ID NO:191 and SEQ ID NO:217; SEQ ID NO:192 and SEQ ID NO:217; SEQ ID NO:193 and SEQ ID NO:217; SEQ ID NO:194 and SEQ ID NO:217; SEQ ID NO:195 and SEQ ID NO:217; SEQ ID NO:196 and SEQ ID NO:217; SEQ ID NO:197 and SEQ ID NO:217; SEQ ID NO:198 and SEQ ID NO:217; SEQ ID NO:199 and SEQ ID NO:217; SEQ ID NO:200 and SEQ ID NO:217; SEQ ID NO:201 and SEQ ID NO:217; SEQ ID NO:202 and SEQ ID NO:217; SEQ ID NO:203 and SEQ ID NO:217; SEQ ID NO:204 and SEQ ID NO:217; SEQ ID NO:205 and SEQ ID NO:217; SEQ ID NO:206 and SEQ ID NO:217; SEQ ID NO:207 and SEQ ID NO:217; SEQ ID NO:208 and SEQ ID NO:217; SEQ ID NO:209 and SEQ ID NO:217; SEQ ID NO:210 and SEQ ID NO:217; SEQ ID NO:211 and SEQ ID NO:217; SEQ ID NO:212 and SEQ ID NO:217; SEQ ID NO:213 and SEQ ID NO:217; SEQ ID NO:214 and SEQ ID NO:217; SEQ ID NO:215 and SEQ ID NO:217; and SEQ ID NO:216 and SEQ ID NO:217.

In some aspects, the $V_H$-$V_L$ pairs are selected from SEQ ID NO:167 and SEQ ID NO:218; SEQ ID NO:168 and SEQ ID NO:218; SEQ ID NO:169 and SEQ ID NO:218; SEQ ID NO:170 and SEQ ID NO:218; SEQ ID NO:171 and SEQ ID NO:218; SEQ ID NO:172 and SEQ ID NO:218; SEQ ID NO:173 and SEQ ID NO:218; SEQ ID NO:174 and SEQ ID NO:218; SEQ ID NO:175 and SEQ ID NO:218; SEQ ID NO:176 and SEQ ID NO:218; SEQ ID NO:177 and SEQ ID NO:218; SEQ ID NO:178 and SEQ ID NO:218; SEQ ID NO:179 and SEQ ID NO:218; SEQ ID NO:180 and SEQ ID NO:218; SEQ ID NO:181 and SEQ ID NO:218; SEQ ID NO:182 and SEQ ID NO:218; SEQ ID NO:183 and SEQ ID NO:218; SEQ ID NO:184 and SEQ ID NO:218; SEQ ID NO:185 and SEQ ID NO:218; SEQ ID NO:186 and SEQ ID NO:218; SEQ ID NO:187 and SEQ ID NO:218; SEQ ID NO:188 and SEQ ID NO:218; SEQ ID NO:189 and SEQ ID NO:218; SEQ ID NO:190 and SEQ ID NO:218; SEQ ID NO:191 and SEQ ID NO:218; SEQ ID NO:192 and SEQ ID NO:218; SEQ ID NO:193 and SEQ ID NO:218; SEQ ID NO:194 and SEQ ID NO:218; SEQ ID NO:195 and SEQ ID NO:218; SEQ ID NO:196 and SEQ ID NO:218; SEQ ID NO:197 and SEQ ID NO:218; SEQ ID NO:198 and SEQ ID NO:218; SEQ ID NO:199 and SEQ ID NO:218; SEQ ID NO:200 and SEQ ID NO:218; SEQ ID NO:201 and SEQ ID NO:218; SEQ ID NO:202 and SEQ ID NO:218; SEQ ID NO:203 and SEQ ID NO:218; SEQ ID NO:204 and SEQ ID NO:218; SEQ ID NO:205 and SEQ ID NO:218; SEQ ID NO:206 and SEQ ID NO:218; SEQ ID NO:207 and SEQ ID NO:218; SEQ ID NO:208 and SEQ ID NO:218; SEQ ID NO:209 and SEQ ID NO:218; SEQ ID NO:210 and SEQ ID NO:218; SEQ ID NO:211 and SEQ ID NO:218; SEQ ID NO:212 and SEQ ID NO:218; SEQ ID NO:213 and SEQ ID NO:218; SEQ ID NO:214 and SEQ ID NO:218; SEQ ID NO:215 and SEQ ID NO:218; and SEQ ID NO:216 and SEQ ID NO:218.

In some aspects, the $V_H$-$V_L$ pairs are selected from SEQ ID NO:167 and SEQ ID NO:219; SEQ ID NO:168 and SEQ ID NO:219; SEQ ID NO:169 and SEQ ID NO:219; SEQ ID NO:170 and SEQ ID NO:219; SEQ ID NO:171 and SEQ ID NO:219; SEQ ID NO:172 and SEQ ID NO:219; SEQ ID NO:173 and SEQ ID NO:219; SEQ ID NO:174 and SEQ ID NO:219; SEQ ID NO:175 and SEQ ID NO:219; SEQ ID NO:176 and SEQ ID NO:219; SEQ ID NO:177 and SEQ ID NO:219; SEQ ID NO:178 and SEQ ID NO:219; SEQ ID NO:179 and SEQ ID NO:219; SEQ ID NO:180 and SEQ ID NO:219; SEQ ID NO:181 and SEQ ID NO:219; SEQ ID NO:182 and SEQ ID NO:219; SEQ ID NO:183 and SEQ ID NO:219; SEQ ID NO:184 and SEQ ID NO:219; SEQ ID NO:185 and SEQ ID NO:219; SEQ ID NO:186 and SEQ ID NO:219; SEQ ID NO:187 and SEQ ID NO:219; SEQ ID NO:188 and SEQ ID NO:219; SEQ ID NO:189 and SEQ ID NO:219; SEQ ID NO:190 and SEQ ID NO:219; SEQ ID NO:191 and SEQ ID NO:219; SEQ ID NO:192 and SEQ ID NO:219; SEQ ID NO:193 and SEQ ID NO:219; SEQ ID NO:194 and SEQ ID NO:219; SEQ ID NO:195 and SEQ ID NO:219; SEQ ID NO:196 and SEQ ID NO:219; SEQ ID NO:197 and SEQ ID NO:219; SEQ ID NO:198 and SEQ ID NO:219; SEQ ID NO:199 and SEQ ID NO:219; SEQ ID NO:200 and SEQ ID NO:219; SEQ ID NO:201 and SEQ ID NO:219; SEQ ID NO:202 and SEQ ID NO:219; SEQ ID NO:203 and SEQ ID NO:219; SEQ ID NO:204 and SEQ ID NO:219; SEQ ID NO:205 and SEQ ID NO:219; SEQ ID NO:206 and SEQ ID NO:219; SEQ ID NO:207 and SEQ ID NO:219; SEQ ID NO:208 and SEQ ID NO:219; SEQ ID NO:209 and SEQ ID NO:219; SEQ ID NO:210 and SEQ ID NO:219; SEQ ID NO:211 and SEQ ID NO:219; SEQ ID NO:212 and SEQ ID NO:219; SEQ ID NO:213 and SEQ ID NO:219; SEQ ID NO:214 and SEQ ID NO:219; SEQ ID NO:215 and SEQ ID NO:219; and SEQ ID NO:216 and SEQ ID NO:219.

In some aspects, the $V_H$-$V_L$ pairs are selected from SEQ ID NO:167 and SEQ ID NO:220; SEQ ID NO:168 and SEQ ID NO:220; SEQ ID NO:169 and SEQ ID NO:220; SEQ ID NO:170 and SEQ ID NO:220; SEQ ID NO:171 and SEQ ID NO:220; SEQ ID NO:172 and SEQ ID NO:220; SEQ ID NO:173 and SEQ ID NO:220; SEQ ID NO:174 and SEQ ID NO:220; SEQ ID NO:175 and SEQ ID NO:220; SEQ ID NO:176 and SEQ ID NO:220; SEQ ID NO:177 and SEQ ID NO:220; SEQ ID NO:178 and SEQ ID NO:220; SEQ ID NO:179 and SEQ ID NO:220; SEQ ID NO:180 and SEQ ID NO:220; SEQ ID NO:181 and SEQ ID NO:220; SEQ ID NO:182 and SEQ ID NO:220; SEQ ID NO:183 and SEQ ID NO:220; SEQ ID NO:184 and SEQ ID NO:220; SEQ ID NO:185 and SEQ ID NO:220; SEQ ID NO:186 and SEQ ID NO:220; SEQ ID NO:187 and SEQ ID NO:220; SEQ ID NO:188 and SEQ ID NO:220; SEQ ID NO:189 and SEQ ID NO:220; SEQ ID NO:190 and SEQ ID NO:220; SEQ ID NO:191 and SEQ ID NO:220; SEQ ID NO:192 and SEQ ID NO:220; SEQ ID NO:193 and SEQ ID NO:220; SEQ ID NO:194 and SEQ ID NO:220; SEQ ID NO:195 and SEQ ID NO:220; SEQ ID NO:196 and SEQ ID NO:220; SEQ ID NO:197 and SEQ ID NO:220; SEQ ID NO:198 and SEQ ID NO:220; SEQ ID NO:199 and SEQ ID NO:220; SEQ ID NO:200 and SEQ ID NO:220; SEQ ID NO:201 and SEQ ID NO:220; SEQ ID NO:202 and SEQ ID NO:220; SEQ ID NO:203 and SEQ ID NO:220; SEQ ID NO:204 and SEQ ID NO:220; SEQ ID NO:205 and SEQ ID NO:220; SEQ ID NO:206 and SEQ ID NO:220; SEQ ID NO:207 and SEQ ID NO:220; SEQ ID NO:208 and SEQ ID NO:220; SEQ ID NO:209 and SEQ ID NO:220; SEQ ID NO:210 and SEQ ID NO:220; SEQ ID NO:211 and SEQ ID NO:220; SEQ ID NO:212 and SEQ ID NO:220; SEQ ID NO:213 and SEQ ID NO:220; SEQ ID NO:214 and SEQ ID NO:220; SEQ ID NO:215 and SEQ ID NO:220; and SEQ ID NO:216 and SEQ ID NO:220.

In some aspects, the $V_H$-$V_L$ pairs are selected from SEQ ID NO:167 and SEQ ID NO:221; SEQ ID NO:168 and SEQ ID NO:221; SEQ ID NO:169 and SEQ ID NO:221; SEQ ID NO:170 and SEQ ID NO:221; SEQ ID NO:171 and SEQ ID NO:221; SEQ ID NO:172 and SEQ ID NO:221; SEQ ID NO:173 and SEQ ID NO:221; SEQ ID NO:174 and SEQ ID NO:221; SEQ ID NO:175 and SEQ ID NO:221; SEQ ID NO:176 and SEQ ID NO:221; SEQ ID NO:177 and SEQ ID NO:221; SEQ ID NO:178 and SEQ ID NO:221; SEQ ID NO:179 and SEQ ID NO:221; SEQ ID NO:180 and SEQ ID NO:221; SEQ ID NO:181 and SEQ ID NO:221; SEQ ID NO:182 and SEQ ID NO:221; SEQ ID NO:183 and SEQ ID NO:221; SEQ ID NO:184 and SEQ ID NO:221; SEQ ID NO:185 and SEQ ID NO:221; SEQ ID NO:186 and SEQ ID NO:221; SEQ ID NO:187 and SEQ ID NO:221; SEQ ID NO:188 and SEQ ID NO:221; SEQ ID NO:189 and SEQ ID NO:221; SEQ ID NO:190 and SEQ ID NO:221; SEQ ID NO:191 and SEQ ID NO:221; SEQ ID NO:192 and SEQ ID NO:221; SEQ ID NO:193 and SEQ ID NO:221; SEQ ID NO:194 and SEQ ID NO:221; SEQ ID NO:195 and SEQ ID NO:221; SEQ ID NO:196 and SEQ ID NO:221; SEQ ID NO:197 and SEQ ID NO:221; SEQ ID NO:198 and SEQ ID NO:221; SEQ ID NO:199 and SEQ ID NO:221; SEQ ID NO:200 and SEQ ID NO:221; SEQ ID NO:201 and SEQ ID NO:221; SEQ ID NO:202 and SEQ ID NO:221; SEQ ID NO:203 and SEQ ID NO:221; SEQ ID NO:204 and SEQ ID NO:221; SEQ ID NO:205 and SEQ ID NO:221; SEQ ID NO:206 and SEQ ID NO:221; SEQ ID NO:207 and SEQ ID NO:221; SEQ ID NO:208 and SEQ ID NO:221; SEQ ID NO:209 and SEQ ID NO:221; SEQ ID NO:210 and SEQ ID NO:221; SEQ ID NO:211 and SEQ ID NO:221; SEQ ID NO:212 and SEQ ID NO:221; SEQ ID NO:213 and SEQ ID NO:221; SEQ ID NO:214 and SEQ ID NO:221; SEQ ID NO:215 and SEQ ID NO:221; and SEQ ID NO:216 and SEQ ID NO:221.

In some aspects, the $V_H$-$V_L$ pairs are selected from SEQ ID NO:167 and SEQ ID NO:222; SEQ ID NO:168 and SEQ ID NO:222; SEQ ID NO:169 and SEQ ID NO:222; SEQ ID NO:170 and SEQ ID NO:222; SEQ ID NO:171 and SEQ ID NO:222; SEQ ID NO:172 and SEQ ID NO:222; SEQ ID NO:173 and SEQ ID NO:222; SEQ ID NO:174 and SEQ ID NO:222; SEQ ID NO:175 and SEQ ID NO:222; SEQ ID NO:176 and SEQ ID NO:222; SEQ ID NO:177 and SEQ ID NO:222; SEQ ID NO:178 and SEQ ID NO:222; SEQ ID NO:179 and SEQ ID NO:222; SEQ ID NO:180 and SEQ ID NO:222; SEQ ID NO:181 and SEQ ID NO:222; SEQ ID NO:182 and SEQ ID NO:222; SEQ ID NO:183 and SEQ ID NO:222; SEQ ID NO:184 and SEQ ID NO:222; SEQ ID NO:185 and SEQ ID NO:222; SEQ ID NO:186 and SEQ ID NO:222; SEQ ID NO:187 and SEQ ID NO:222; SEQ ID NO:188 and SEQ ID NO:222; SEQ ID NO:189 and SEQ ID NO:222; SEQ ID NO:190 and SEQ ID NO:222; SEQ ID NO:191 and SEQ ID NO:222; SEQ ID NO:192 and SEQ ID NO:222; SEQ ID NO:193 and SEQ ID NO:222; SEQ ID NO:194 and SEQ ID NO:222; SEQ ID NO:195 and SEQ ID NO:222; SEQ ID NO:196 and SEQ ID NO:222; SEQ ID NO:197 and SEQ ID NO:222; SEQ ID NO:198 and SEQ ID NO:222; SEQ ID NO:199 and SEQ ID NO:222; SEQ ID NO:200 and SEQ ID NO:222; SEQ ID NO:201 and SEQ ID NO:222; SEQ ID NO:202 and SEQ ID NO:222; SEQ ID NO:203 and SEQ ID NO:222; SEQ ID NO:204 and SEQ ID NO:222; SEQ ID NO:205 and SEQ ID NO:222; SEQ ID NO:206 and SEQ ID NO:222; SEQ ID NO:207 and SEQ ID NO:222; SEQ ID NO:208 and SEQ ID NO:222; SEQ ID NO:209 and SEQ ID NO:222; SEQ ID NO:210 and SEQ ID NO:222; SEQ ID NO:211 and SEQ ID NO:222; SEQ ID NO:212 and SEQ ID NO:222; SEQ ID NO:213 and SEQ ID NO:222; SEQ ID NO:214 and SEQ ID NO:222; SEQ ID NO:215 and SEQ ID NO:222; and SEQ ID NO:216 and SEQ ID NO:222.

In some aspects, the $V_H$-$V_L$ pairs are selected from SEQ ID NO:167 and SEQ ID NO:223; SEQ ID NO:168 and SEQ ID NO:223; SEQ ID NO:169 and SEQ ID NO:223; SEQ ID NO:170 and SEQ ID NO:223; SEQ ID NO:171 and SEQ ID NO:223; SEQ ID NO:172 and SEQ ID NO:223; SEQ ID NO:173 and SEQ ID NO:223; SEQ ID NO:174 and SEQ ID NO:223; SEQ ID NO:175 and SEQ ID NO:223; SEQ ID NO:176 and SEQ ID NO:223; SEQ ID NO:177 and SEQ ID NO:223; SEQ ID NO:178 and SEQ ID NO:223; SEQ ID NO:179 and SEQ ID NO:223; SEQ ID NO:180 and SEQ ID NO:223; SEQ ID NO:181 and SEQ ID NO:223; SEQ ID NO:182 and SEQ ID NO:223; SEQ ID NO:183 and SEQ ID NO:223; SEQ ID NO:184 and SEQ ID NO:223; SEQ ID NO:185 and SEQ ID NO:223; SEQ ID NO:186 and SEQ ID NO:223; SEQ ID NO:187 and SEQ ID NO:223; SEQ ID NO:188 and SEQ ID NO:223; SEQ ID NO:189 and SEQ ID NO:223; SEQ ID NO:190 and SEQ ID NO:223; SEQ ID NO:191 and SEQ ID NO:223; SEQ ID NO:192 and SEQ ID NO:223; SEQ ID NO:193 and SEQ ID NO:223; SEQ ID NO:194 and SEQ ID NO:223; SEQ ID NO:195 and SEQ ID NO:223; SEQ ID NO:196 and SEQ ID NO:223; SEQ ID NO:197 and SEQ ID NO:223; SEQ ID NO:198 and SEQ ID NO:223; SEQ ID NO:199 and SEQ ID NO:223; SEQ ID NO:200 and SEQ ID NO:223; SEQ ID NO:201 and SEQ ID NO:223; SEQ ID NO:202 and SEQ ID NO:223; SEQ ID NO:203 and SEQ ID NO:223; SEQ ID NO:204 and SEQ ID NO:223; SEQ ID NO:205 and SEQ ID NO:223; SEQ ID NO:206 and SEQ ID NO:223; SEQ ID NO:207 and SEQ ID NO:223; SEQ ID NO:208 and SEQ ID NO:223; SEQ ID NO:209 and SEQ ID NO:223; SEQ ID NO:210 and SEQ ID NO:223; SEQ ID NO:211 and SEQ ID NO:223; SEQ ID NO:212 and SEQ ID NO:223; SEQ ID NO:213 and SEQ ID NO:223; SEQ ID NO:214 and SEQ ID NO:223; SEQ ID NO:215 and SEQ ID NO:223; and SEQ ID NO:216 and SEQ ID NO:223.

In some aspects, the $V_H$-$V_L$ pairs are selected from SEQ ID NO:167 and SEQ ID NO:224; SEQ ID NO:168 and SEQ ID NO:224; SEQ ID NO:169 and SEQ ID NO:224; SEQ ID NO:170 and SEQ ID NO:224; SEQ ID NO:171 and SEQ ID NO:224; SEQ ID NO:172 and SEQ ID NO:224; SEQ ID NO:173 and SEQ ID NO:224; SEQ ID NO:174 and SEQ ID NO:224; SEQ ID NO:175 and SEQ ID NO:224; SEQ ID NO:176 and SEQ ID NO:224; SEQ ID NO:177 and SEQ ID NO:224; SEQ ID NO:178 and SEQ ID NO:224; SEQ ID NO:179 and SEQ ID NO:224; SEQ ID NO:180 and SEQ ID NO:224; SEQ ID NO:181 and SEQ ID NO:224; SEQ ID NO:182 and SEQ ID NO:224; SEQ ID NO:183 and SEQ ID NO:224; SEQ ID NO:184 and SEQ ID NO:224; SEQ ID NO:185 and SEQ ID NO:224; SEQ ID NO:186 and SEQ ID NO:224; SEQ ID NO:187 and SEQ ID NO:224; SEQ ID NO:188 and SEQ ID NO:224; SEQ ID NO:189 and SEQ ID NO:224; SEQ ID NO:190 and SEQ ID NO:224; SEQ ID NO:191 and SEQ ID NO:224; SEQ ID NO:192 and SEQ ID NO:224; SEQ ID NO:193 and SEQ ID NO:224; SEQ ID NO:194 and SEQ ID NO:224; SEQ ID NO:195 and SEQ ID NO:224; SEQ ID NO:196 and SEQ ID NO:224; SEQ ID NO:197 and SEQ ID NO:224; SEQ ID NO:198 and SEQ ID NO:224; SEQ ID NO:199 and SEQ ID NO:224; SEQ ID NO:200 and SEQ ID NO:224; SEQ ID NO:201 and SEQ ID NO:224; SEQ ID NO:202 and SEQ ID NO:224; SEQ ID NO:203 and SEQ ID NO:224; SEQ ID NO:204 and SEQ ID NO:224; SEQ ID NO:205 and SEQ ID NO:224; SEQ ID NO:206 and SEQ ID NO:224; SEQ ID NO:207 and SEQ ID NO:224; SEQ ID NO:208 and SEQ ID NO:224; SEQ ID NO:209 and SEQ ID NO:224; SEQ ID NO:210 and SEQ ID NO:224; SEQ ID NO:211 and SEQ ID NO:224; SEQ ID NO:212 and SEQ ID NO:224; SEQ ID NO:213 and SEQ ID NO:224; SEQ ID NO:214 and SEQ ID NO:224; SEQ ID NO:215 and SEQ ID NO:224; and SEQ ID NO:216 and SEQ ID NO:224.

In some aspects, the $V_H$-$V_L$ pairs are selected from SEQ ID NO:167 and SEQ ID NO:225; SEQ ID NO:168 and SEQ ID NO:225; SEQ ID NO:169 and SEQ ID NO:225; SEQ ID NO:170 and SEQ ID NO:225; SEQ ID NO:171 and SEQ ID NO:225; SEQ ID NO:172 and SEQ ID NO:225; SEQ ID NO:173 and SEQ ID NO:225; SEQ ID NO:174 and SEQ ID NO:225; SEQ ID NO:175 and SEQ ID NO:225; SEQ ID NO:176 and SEQ ID NO:225; SEQ ID NO:177 and SEQ ID NO:225; SEQ ID NO:178 and SEQ ID NO:225; SEQ ID NO:179 and SEQ ID NO:225; SEQ ID NO:180 and SEQ ID NO:225; SEQ ID NO:181 and SEQ ID NO:225; SEQ ID NO:182 and SEQ ID NO:225; SEQ ID NO:183 and SEQ ID NO:225; SEQ ID NO:184 and SEQ ID NO:225; SEQ ID NO:185 and SEQ ID NO:225; SEQ ID NO:186 and SEQ ID NO:225; SEQ ID NO:187 and SEQ ID NO:225; SEQ ID NO:188 and SEQ ID NO:225; SEQ ID NO:189 and SEQ ID NO:225; SEQ ID NO:190 and SEQ ID NO:225; SEQ ID NO:191 and SEQ ID NO:225; SEQ ID NO:192 and SEQ ID NO:225; SEQ ID NO:193 and SEQ ID NO:225; SEQ ID NO:194 and SEQ ID NO:225; SEQ ID NO:195 and SEQ ID NO:225; SEQ ID NO:196 and SEQ ID NO:225; SEQ ID NO:197 and SEQ ID NO:225; SEQ ID NO:198 and SEQ ID NO:225; SEQ ID NO:199 and SEQ ID NO:225; SEQ ID NO:200 and SEQ ID NO:225; SEQ ID NO:201 and SEQ ID NO:225; SEQ ID NO:202 and SEQ ID NO:225; SEQ ID NO:203 and SEQ ID NO:225; SEQ ID NO:204 and SEQ ID NO:225; SEQ ID NO:205 and SEQ ID NO:225; SEQ ID NO:206 and SEQ ID NO:225; SEQ ID NO:207 and SEQ ID NO:225; SEQ ID NO:208 and SEQ ID NO:225; SEQ ID NO:209 and SEQ ID NO:225; SEQ ID NO:210 and SEQ ID NO:225; SEQ ID NO:211 and SEQ ID NO:225; SEQ ID NO:212 and SEQ ID NO:225; SEQ ID NO:213 and SEQ ID NO:225; SEQ ID NO:214 and SEQ ID NO:225; SEQ ID NO:215 and SEQ ID NO:225; and SEQ ID NO:216 and SEQ ID NO:225.

In some aspects, the $V_H$-$V_L$ pairs are selected from SEQ ID NO:167 and SEQ ID NO:226; SEQ ID NO:168 and SEQ ID NO:226; SEQ ID NO:169 and SEQ ID NO:226; SEQ ID NO:170 and SEQ ID NO:226; SEQ ID NO:171 and SEQ ID NO:226; SEQ ID NO:172 and SEQ ID NO:226; SEQ ID NO:173 and SEQ ID NO:226; SEQ ID NO:174 and SEQ ID NO:226; SEQ ID NO:175 and SEQ ID NO:226; SEQ ID NO:176 and SEQ ID NO:226; SEQ ID NO:177 and SEQ ID NO:226; SEQ ID NO:178 and SEQ ID NO:226; SEQ ID NO:179 and SEQ ID NO:226; SEQ ID NO:180 and SEQ ID NO:226; SEQ ID NO:181 and SEQ ID NO:226; SEQ ID NO:182 and SEQ ID NO:226; SEQ ID NO:183 and SEQ ID NO:226; SEQ ID NO:184 and SEQ ID NO:226; SEQ ID NO:185 and SEQ ID NO:226; SEQ ID NO:186 and SEQ ID NO:226; SEQ ID NO:187 and SEQ ID NO:226; SEQ ID NO:188 and SEQ ID NO:226; SEQ ID NO:189 and SEQ ID NO:226; SEQ ID NO:190 and SEQ ID NO:226; SEQ ID NO:191 and SEQ ID NO:226; SEQ ID NO:192 and SEQ ID NO:226; SEQ ID NO:193 and SEQ ID NO:226; SEQ ID NO:194 and SEQ ID NO:226; SEQ ID NO:195 and SEQ ID NO:226; SEQ ID NO:196 and SEQ ID NO:226; SEQ ID NO:197 and SEQ ID NO:226; SEQ ID NO:198 and SEQ ID NO:226; SEQ ID NO:199 and SEQ ID NO:226; SEQ ID NO:200 and SEQ ID NO:226; SEQ ID NO:201 and SEQ ID NO:226; SEQ ID NO:202 and SEQ ID NO:226; SEQ ID NO:203 and SEQ ID NO:226; SEQ ID NO:204 and SEQ ID NO:226; SEQ ID NO:205 and SEQ ID NO:226; SEQ ID NO:206 and SEQ ID NO:226; SEQ ID NO:207 and SEQ ID NO:226; SEQ ID NO:208 and SEQ ID NO:226; SEQ ID NO:209 and SEQ ID NO:226; SEQ ID NO:210 and SEQ ID NO:226; SEQ ID NO:211 and SEQ ID NO:226; SEQ ID NO:212 and SEQ ID NO:226; SEQ ID NO:213 and SEQ ID NO:226; SEQ ID NO:214 and SEQ ID NO:226; SEQ ID NO:215 and SEQ ID NO:226; and SEQ ID NO:216 and SEQ ID NO:226.

In some aspects, the $V_H$-$V_L$ pairs are selected from SEQ ID NO:167 and SEQ ID NO:227; SEQ ID NO:168 and SEQ ID NO:227; SEQ ID NO:169 and SEQ ID NO:227; SEQ ID NO:170 and SEQ ID NO:227; SEQ ID NO:171 and SEQ ID NO:227; SEQ ID NO:172 and SEQ ID NO:227; SEQ ID NO:173 and SEQ ID NO:227; SEQ ID NO:174 and SEQ ID NO:227; SEQ ID NO:175 and SEQ ID NO:227; SEQ ID NO:176 and SEQ ID NO:227; SEQ ID NO:177 and SEQ ID NO:227; SEQ ID NO:178 and SEQ ID NO:227; SEQ ID NO:179 and SEQ ID NO:227; SEQ ID NO:180 and SEQ ID NO:227; SEQ ID NO:181 and SEQ ID NO:227; SEQ ID NO:182 and SEQ ID NO:227; SEQ ID NO:183 and SEQ ID NO:227; SEQ ID NO:184 and SEQ ID NO:227; SEQ ID NO:185 and SEQ ID NO:227; SEQ ID NO:186 and SEQ ID NO:227; SEQ ID NO:187 and SEQ ID NO:227; SEQ ID NO:188 and SEQ ID NO:227; SEQ ID NO:189 and SEQ ID NO:227; SEQ ID NO:190 and SEQ ID NO:227; SEQ ID NO:191 and SEQ ID NO:227; SEQ ID NO:192 and SEQ ID NO:227; SEQ ID NO:193 and SEQ ID NO:227; SEQ ID NO:194 and SEQ ID NO:227; SEQ ID NO:195 and SEQ ID NO:227; SEQ ID NO:196 and SEQ ID NO:227; SEQ ID NO:197 and SEQ ID NO:227; SEQ ID NO:198 and SEQ ID NO:227; SEQ ID NO:199 and SEQ ID NO:227; SEQ ID NO:200 and SEQ ID NO:227; SEQ ID NO:201 and SEQ ID NO:227; SEQ ID NO:202 and SEQ ID NO:227; SEQ ID NO:203 and SEQ ID NO:227; SEQ ID NO:204 and SEQ ID NO:227; SEQ ID NO:205 and SEQ ID NO:227; SEQ ID NO:206 and SEQ ID NO:227; SEQ ID NO:207 and SEQ ID NO:227; SEQ ID NO:208 and SEQ ID NO:227; SEQ ID NO:209 and SEQ ID NO:227; SEQ ID NO:210 and SEQ ID NO:227; SEQ ID NO:211 and SEQ ID NO:227; SEQ ID NO:212 and SEQ ID NO:227; SEQ ID NO:213 and SEQ ID NO:227; SEQ ID NO:214 and SEQ ID NO:227; SEQ ID NO:215 and SEQ ID NO:227; and SEQ ID NO:216 and SEQ ID NO:227.

In some aspects, the $V_H$-$V_L$ pairs are selected from SEQ ID NO:167 and SEQ ID NO:228; SEQ ID NO:168 and SEQ ID NO:228; SEQ ID NO:169 and SEQ ID NO:228; SEQ ID NO:170 and SEQ ID NO:228; SEQ ID NO:171 and SEQ ID NO:228; SEQ ID NO:172 and SEQ ID NO:228; SEQ ID NO:173 and SEQ ID NO:228; SEQ ID NO:174 and SEQ ID NO:228; SEQ ID NO:175 and SEQ ID NO:228; SEQ ID NO:176 and SEQ ID NO:228; SEQ ID NO:177 and SEQ ID NO:228; SEQ ID NO:178 and SEQ ID NO:228; SEQ ID NO:179 and SEQ ID NO:228; SEQ ID NO:180 and SEQ ID NO:228; SEQ ID NO:181 and SEQ ID NO:228; SEQ ID NO:182 and SEQ ID NO:228; SEQ ID NO:183 and SEQ ID NO:228; SEQ ID NO:184 and SEQ ID NO:228; SEQ ID NO:185 and SEQ ID NO:228; SEQ ID NO:186 and SEQ ID NO:228; SEQ ID NO:187 and SEQ ID NO:228; SEQ ID NO:188 and SEQ ID NO:228; SEQ ID NO:189 and SEQ ID NO:228; SEQ ID NO:190 and SEQ ID NO:228; SEQ ID NO:191 and SEQ ID NO:228; SEQ ID NO:192 and SEQ ID NO:228; SEQ ID NO:193 and SEQ ID NO:228; SEQ ID NO:194 and SEQ ID NO:228; SEQ ID NO:195 and SEQ ID NO:228; SEQ ID NO:196 and SEQ ID NO:228; SEQ ID NO:197 and SEQ ID NO:228; SEQ ID NO:198 and SEQ ID NO:228; SEQ ID NO:199 and SEQ ID NO:228; SEQ ID NO:200 and SEQ ID NO:228; SEQ ID NO:201 and SEQ ID NO:228; SEQ ID NO:202 and SEQ ID NO:228; SEQ ID NO:203 and SEQ ID NO:228; SEQ ID NO:204 and SEQ ID NO:228; SEQ ID NO:205 and SEQ ID NO:228; SEQ ID NO:206 and SEQ ID NO:228; SEQ ID NO:207 and SEQ ID NO:228; SEQ ID NO:208 and SEQ ID NO:228; SEQ ID NO:209 and SEQ ID NO:228; SEQ ID NO:210 and SEQ ID NO:228; SEQ ID NO:211 and SEQ ID NO:228; SEQ ID NO:212 and SEQ ID NO:228; SEQ ID NO:213 and SEQ ID NO:228; SEQ ID NO:214 and SEQ ID NO:228; SEQ ID NO:215 and SEQ ID NO:228; and SEQ ID NO:216 and SEQ ID NO:228.

In some aspects, the $V_H$-$V_L$ pairs are selected from SEQ ID NO:167 and SEQ ID NO:229; SEQ ID NO:168 and SEQ ID NO:229; SEQ ID NO:169 and SEQ ID NO:229; SEQ ID NO:170 and SEQ ID NO:229; SEQ ID NO:171 and SEQ ID NO:229; SEQ ID NO:172 and SEQ ID NO:229; SEQ ID NO:173 and SEQ ID NO:229; SEQ ID NO:174 and SEQ ID NO:229; SEQ ID NO:175 and SEQ ID NO:229; SEQ ID NO:176 and SEQ ID NO:229; SEQ ID NO:177 and SEQ ID NO:229; SEQ ID NO:178 and SEQ ID NO:229; SEQ ID NO:179 and SEQ ID NO:229; SEQ ID NO:180 and SEQ ID NO:229; SEQ ID NO:181 and SEQ ID NO:229; SEQ ID NO:182 and SEQ ID NO:229; SEQ ID NO:183 and SEQ ID NO:229; SEQ ID NO:184 and SEQ ID NO:229; SEQ ID NO:185 and SEQ ID NO:229; SEQ ID NO:186 and SEQ ID NO:229; SEQ ID NO:187 and SEQ ID NO:229; SEQ ID NO:188 and SEQ ID NO:229; SEQ ID NO:189 and SEQ ID NO:229; SEQ ID NO:190 and SEQ ID NO:229; SEQ ID NO:191 and SEQ ID NO:229; SEQ ID NO:192 and SEQ ID NO:229; SEQ ID NO:193 and SEQ ID NO:229; SEQ ID NO:194 and SEQ ID NO:229; SEQ ID NO:195 and SEQ ID NO:229; SEQ ID NO:196 and SEQ ID NO:229; SEQ ID NO:197 and SEQ ID NO:229; SEQ ID NO:198 and SEQ ID NO:229; SEQ ID NO:199 and SEQ ID NO:229; SEQ ID NO:200 and SEQ ID NO:229; SEQ ID NO:201 and SEQ ID NO:229; SEQ ID NO:202 and SEQ ID NO:229; SEQ ID NO:203 and SEQ ID NO:229; SEQ ID NO:204 and SEQ ID NO:229; SEQ ID NO:205 and SEQ ID NO:229; SEQ ID NO:206 and SEQ ID NO:229; SEQ ID NO:207 and SEQ ID NO:229; SEQ ID NO:208 and SEQ ID NO:229; SEQ ID NO:209 and SEQ ID NO:229; SEQ ID NO:210 and SEQ ID NO:229; SEQ ID NO:211 and SEQ ID NO:229; SEQ ID NO:212 and SEQ ID NO:229; SEQ ID NO:213 and SEQ ID NO:229; SEQ ID NO:214 and SEQ ID NO:229; SEQ ID NO:215 and SEQ ID NO:229; and SEQ ID NO:216 and SEQ ID NO:229.

In some aspects, the $V_H$-$V_L$ pairs are selected from SEQ ID NO:167 and SEQ ID NO:230; SEQ ID NO:168 and SEQ ID NO:230; SEQ ID NO:169 and SEQ ID NO:230; SEQ ID NO:170 and SEQ ID NO:230; SEQ ID NO:171 and SEQ ID NO:230; SEQ ID NO:172 and SEQ ID NO:230; SEQ ID NO:173 and SEQ ID NO:230; SEQ ID NO:174 and SEQ ID NO:230; SEQ ID NO:175 and SEQ ID NO:230; SEQ ID NO:176 and SEQ ID NO:230; SEQ ID NO:177 and SEQ ID NO:230; SEQ ID NO:178 and SEQ ID NO:230; SEQ ID NO:179 and SEQ ID NO:230; SEQ ID NO:180 and SEQ ID NO:230; SEQ ID NO:181 and SEQ ID NO:230; SEQ ID NO:182 and SEQ ID NO:230; SEQ ID NO:183 and SEQ ID NO:230; SEQ ID NO:184 and SEQ ID NO:230; SEQ ID NO:185 and SEQ ID NO:230; SEQ ID NO:186 and SEQ ID NO:230; SEQ ID NO:187 and SEQ ID NO:230; SEQ ID NO:188 and SEQ ID NO:230; SEQ ID NO:189 and SEQ ID NO:230; SEQ ID NO:190 and SEQ ID NO:230; SEQ ID NO:191 and SEQ ID NO:230; SEQ ID NO:192 and SEQ ID NO:230; SEQ ID NO:193 and SEQ ID NO:230; SEQ ID NO:194 and SEQ ID NO:230; SEQ ID NO:195 and SEQ ID NO:230; SEQ ID NO:196 and SEQ ID NO:230; SEQ ID NO:197 and SEQ ID NO:230; SEQ ID NO:198 and SEQ ID NO:230; SEQ ID NO:199 and SEQ ID NO:230; SEQ ID NO:200 and SEQ ID NO:230; SEQ ID NO:201 and SEQ ID NO:230; SEQ ID NO:202 and SEQ ID NO:230; SEQ ID NO:203 and SEQ ID NO:230; SEQ ID NO:204 and SEQ ID NO:230; SEQ ID NO:205 and SEQ ID NO:230; SEQ ID NO:206 and SEQ ID NO:230; SEQ ID NO:207 and SEQ ID NO:230; SEQ ID NO:208 and SEQ ID NO:230; SEQ ID NO:209 and SEQ ID NO:230; SEQ ID NO:210 and SEQ ID NO:230; SEQ ID NO:211 and SEQ ID NO:230; SEQ ID NO:212 and SEQ ID NO:230; SEQ ID NO:213 and SEQ ID NO:230; SEQ ID NO:214 and SEQ ID NO:230; SEQ ID NO:215 and SEQ ID NO:230; and SEQ ID NO:216 and SEQ ID NO:230.

In some aspects, the $V_H$-$V_L$ pairs are selected from SEQ ID NO:167 and SEQ ID NO:231; SEQ ID NO:168 and SEQ ID NO:231; SEQ ID NO:169 and SEQ ID NO:231; SEQ ID NO:170 and SEQ ID NO:231; SEQ ID NO:171 and SEQ ID NO:231; SEQ ID NO:172 and SEQ ID NO:231; SEQ ID NO:173 and SEQ ID NO:231; SEQ ID NO:174 and SEQ ID NO:231; SEQ ID NO:175 and SEQ ID NO:231; SEQ ID NO:176 and SEQ ID NO:231; SEQ ID NO:177 and SEQ ID NO:231; SEQ ID NO:178 and SEQ ID NO:231; SEQ ID NO:179 and SEQ ID NO:231; SEQ ID NO:180 and SEQ ID NO:231; SEQ ID NO:181 and SEQ ID NO:231; SEQ ID NO:182 and SEQ ID NO:231; SEQ ID NO:183 and SEQ ID NO:231; SEQ ID NO:184 and SEQ ID NO:231; SEQ ID NO:185 and SEQ ID NO:231; SEQ ID NO:186 and SEQ ID NO:231; SEQ ID NO:187 and SEQ ID NO:231; SEQ ID NO:188 and SEQ ID NO:231; SEQ ID NO:189 and SEQ ID NO:231; SEQ ID NO:190 and SEQ ID NO:231; SEQ ID NO:191 and SEQ ID NO:231; SEQ ID NO:192 and SEQ ID NO:231; SEQ ID NO:193 and SEQ ID NO:231; SEQ ID NO:194 and SEQ ID NO:231; SEQ ID NO:195 and SEQ ID NO:231; SEQ ID NO:196 and SEQ ID NO:231; SEQ ID NO:197 and SEQ ID NO:231; SEQ ID NO:198 and SEQ ID NO:231; SEQ ID NO:199 and SEQ ID NO:231; SEQ ID NO:200 and SEQ ID NO:231; SEQ ID NO:201 and SEQ ID NO:231; SEQ ID NO:202 and SEQ ID NO:231; SEQ ID NO:203 and SEQ ID NO:231; SEQ ID NO:204 and SEQ ID NO:231; SEQ ID NO:205 and SEQ ID NO:231; SEQ ID NO:206 and SEQ ID NO:231; SEQ ID NO:207 and SEQ ID NO:231; SEQ ID NO:208 and SEQ ID NO:231; SEQ ID NO:209 and SEQ ID NO:231; SEQ ID NO:210 and SEQ ID NO:231; SEQ ID NO:211 and SEQ ID NO:231; SEQ ID NO:212 and SEQ ID NO:231; SEQ ID NO:213 and SEQ ID NO:231; SEQ ID NO:214 and SEQ ID NO:231; SEQ ID NO:215 and SEQ ID NO:231; and SEQ ID NO:216 and SEQ ID NO:231.

In some aspects, the $V_H$-$V_L$ pairs are selected from SEQ ID NO:167 and SEQ ID NO:232; SEQ ID NO:168 and SEQ ID NO:232; SEQ ID NO:169 and SEQ ID NO:232; SEQ ID NO:170 and SEQ ID NO:232; SEQ ID NO:171 and SEQ ID NO:232; SEQ ID NO:172 and SEQ ID NO:232; SEQ ID NO:173 and SEQ ID NO:232; SEQ ID NO:174 and SEQ ID NO:232; SEQ ID NO:175 and SEQ ID NO:232; SEQ ID NO:176 and SEQ ID NO:232; SEQ ID NO:177 and SEQ ID NO:232; SEQ ID NO:178 and SEQ ID NO:232; SEQ ID NO:179 and SEQ ID NO:232; SEQ ID NO:180 and SEQ ID NO:232; SEQ ID NO:181 and SEQ ID NO:232; SEQ ID NO:182 and SEQ ID NO:232; SEQ ID NO:183 and SEQ ID NO:232; SEQ ID NO:184 and SEQ ID NO:232; SEQ ID NO:185 and SEQ ID NO:232; SEQ ID NO:186 and SEQ ID NO:232; SEQ ID NO:187 and SEQ ID NO:232; SEQ ID NO:188 and SEQ ID NO:232; SEQ ID NO:189 and SEQ ID NO:232; SEQ ID NO:190 and SEQ ID NO:232; SEQ ID NO:191 and SEQ ID NO:232; SEQ ID NO:192 and SEQ ID NO:232; SEQ ID NO:193 and SEQ ID NO:232; SEQ ID NO:194 and SEQ ID NO:232; SEQ ID NO:195 and SEQ ID NO:232; SEQ ID NO:196 and SEQ ID NO:232; SEQ ID NO:197 and SEQ ID NO:232; SEQ ID NO:198 and SEQ ID NO:232; SEQ ID NO:199 and SEQ ID NO:232; SEQ ID NO:200 and SEQ ID NO:232; SEQ ID NO:201 and SEQ ID NO:232; SEQ ID NO:202 and SEQ ID NO:232; SEQ ID NO:203 and SEQ ID NO:232; SEQ ID NO:204 and SEQ ID NO:232; SEQ ID NO:205 and SEQ ID NO:232; SEQ ID NO:206 and SEQ ID NO:232; SEQ ID NO:207 and SEQ ID NO:232; SEQ ID NO:208 and SEQ ID NO:232; SEQ ID NO:209 and SEQ ID NO:232; SEQ ID NO:210 and SEQ ID NO:232; SEQ ID NO:211 and SEQ ID NO:232; SEQ ID NO:212 and SEQ ID NO:232; SEQ ID NO:213 and SEQ ID NO:232; SEQ ID NO:214 and SEQ ID NO:232; SEQ ID NO:215 and SEQ ID NO:232; and SEQ ID NO:216 and SEQ ID NO:232.

In some aspects, the $V_H$-$V_L$ pairs are selected from SEQ ID NO:167 and SEQ ID NO:233; SEQ ID NO:168 and SEQ ID NO:233; SEQ ID NO:169 and SEQ ID NO:233; SEQ ID NO:170 and SEQ ID NO:233; SEQ ID NO:171 and SEQ ID NO:233; SEQ ID NO:172 and SEQ ID NO:233; SEQ ID NO:173 and SEQ ID NO:233; SEQ ID NO:174 and SEQ ID NO:233; SEQ ID NO:175 and SEQ ID NO:233; SEQ ID NO:176 and SEQ ID NO:233; SEQ ID NO:177 and SEQ ID NO:233; SEQ ID NO:178 and SEQ ID NO:233; SEQ ID NO:179 and SEQ ID NO:233; SEQ ID NO:180 and SEQ ID NO:233; SEQ ID NO:181 and SEQ ID NO:233; SEQ ID NO:182 and SEQ ID NO:233; SEQ ID NO:183 and SEQ ID NO:233; SEQ ID NO:184 and SEQ ID NO:233; SEQ ID NO:185 and SEQ ID NO:233; SEQ ID NO:186 and SEQ ID NO:233; SEQ ID NO:187 and SEQ ID NO:233; SEQ ID NO:188 and SEQ ID NO:233; SEQ ID NO:189 and SEQ ID NO:233; SEQ ID NO:190 and SEQ ID NO:233; SEQ ID NO:191 and SEQ ID NO:233; SEQ ID NO:192 and SEQ ID NO:233; SEQ ID NO:193 and SEQ ID NO:233; SEQ ID NO:194 and SEQ ID NO:233; SEQ ID NO:195 and SEQ ID NO:233; SEQ ID NO:196 and SEQ ID NO:233; SEQ ID NO:197 and SEQ ID NO:233; SEQ ID NO:198 and SEQ ID NO:233; SEQ ID NO:199 and SEQ ID NO:233; SEQ ID NO:200 and SEQ ID NO:233; SEQ ID NO:201 and SEQ ID NO:233; SEQ ID NO:202 and SEQ ID NO:233; SEQ ID NO:203 and SEQ ID NO:233; SEQ ID NO:204 and SEQ ID NO:233; SEQ ID NO:205 and SEQ ID NO:233; SEQ ID NO:206 and SEQ ID NO:233; SEQ ID NO:207 and SEQ ID NO:233; SEQ ID NO:208 and SEQ ID NO:233; SEQ ID NO:209 and SEQ ID NO:233; SEQ ID NO:210 and SEQ ID NO:233; SEQ ID NO:211 and SEQ ID NO:233; SEQ ID NO:212 and SEQ ID NO:233; SEQ ID NO:213 and SEQ ID NO:233; SEQ ID NO:214 and SEQ ID NO:233; SEQ ID NO:215 and SEQ ID NO:233; and SEQ ID NO:216 and SEQ ID NO:233.

In some aspects, the $V_H$-$V_L$ pairs are selected from SEQ ID NO:167 and SEQ ID NO:234; SEQ ID NO:168 and SEQ ID NO:234; SEQ ID NO:169 and SEQ ID NO:234; SEQ ID NO:170 and SEQ ID NO:234; SEQ ID NO:171 and SEQ ID NO:234; SEQ ID NO:172 and SEQ ID NO:234; SEQ ID NO:173 and SEQ ID NO:234; SEQ ID NO:174 and SEQ ID NO:234; SEQ ID NO:175 and SEQ ID NO:234; SEQ ID NO:176 and SEQ ID NO:234; SEQ ID NO:177 and SEQ ID NO:234; SEQ ID NO:178 and SEQ ID NO:234; SEQ ID NO:179 and SEQ ID NO:234; SEQ ID NO:180 and SEQ ID NO:234; SEQ ID NO:181 and SEQ ID NO:234; SEQ ID NO:182 and SEQ ID NO:234; SEQ ID NO:183 and SEQ ID NO:234; SEQ ID NO:184 and SEQ ID NO:234; SEQ ID NO:185 and SEQ ID NO:234; SEQ ID NO:186 and SEQ ID NO:234; SEQ ID NO:187 and SEQ ID NO:234; SEQ ID NO:188 and SEQ ID NO:234; SEQ ID NO:189 and SEQ ID NO:234; SEQ ID NO:190 and SEQ ID NO:234; SEQ ID NO:191 and SEQ ID NO:234; SEQ ID NO:192 and SEQ ID NO:234; SEQ ID NO:193 and SEQ ID NO:234; SEQ ID NO:194 and SEQ ID NO:234; SEQ ID NO:195 and SEQ ID NO:234; SEQ ID NO:196 and SEQ ID NO:234; SEQ ID NO:197 and SEQ ID NO:234; SEQ ID NO:198 and SEQ ID NO:234; SEQ ID NO:199 and SEQ ID NO:234; SEQ ID NO:200 and SEQ ID NO:234; SEQ ID NO:201 and SEQ ID NO:234; SEQ ID NO:202 and SEQ ID NO:234; SEQ ID NO:203 and SEQ ID NO:234; SEQ ID NO:204 and SEQ ID NO:234; SEQ ID NO:205 and SEQ ID NO:234; SEQ ID NO:206 and SEQ ID NO:234; SEQ ID NO:207 and SEQ ID NO:234; SEQ ID NO:208 and SEQ ID NO:234; SEQ ID NO:209 and SEQ ID NO:234; SEQ ID NO:210 and SEQ ID NO:234; SEQ ID NO:211 and SEQ ID NO:234; SEQ ID NO:212 and SEQ ID NO:234; SEQ ID NO:213 and SEQ ID NO:234; SEQ ID NO:214 and SEQ ID NO:234; SEQ ID NO:215 and SEQ ID NO:234; and SEQ ID NO:216 and SEQ ID NO:234.

In some aspects, the $V_H$-$V_L$ pairs are selected from SEQ ID NO:167 and SEQ ID NO:235; SEQ ID NO:168 and SEQ ID NO:235; SEQ ID NO:169 and SEQ ID NO:235; SEQ ID NO:170 and SEQ ID NO:235; SEQ ID NO:171 and SEQ ID NO:235; SEQ ID NO:172 and SEQ ID NO:235; SEQ ID NO:173 and SEQ ID NO:235; SEQ ID NO:174 and SEQ ID NO:235; SEQ ID NO:175 and SEQ ID NO:235; SEQ ID NO:176 and SEQ ID NO:235; SEQ ID NO:177 and SEQ ID NO:235; SEQ ID NO:178 and SEQ ID NO:235; SEQ ID NO:179 and SEQ ID NO:235; SEQ ID NO:180 and SEQ ID NO:235; SEQ ID NO:181 and SEQ ID NO:235; SEQ ID NO:182 and SEQ ID NO:235; SEQ ID NO:183 and SEQ ID NO:235; SEQ ID NO:184 and SEQ ID NO:235; SEQ ID NO:185 and SEQ ID NO:235; SEQ ID NO:186 and SEQ ID NO:235; SEQ ID NO:187 and SEQ ID NO:235; SEQ ID NO:188 and SEQ ID NO:235; SEQ ID NO:189 and SEQ ID NO:235; SEQ ID NO:190 and SEQ ID NO:235; SEQ ID NO:191 and SEQ ID NO:235; SEQ ID NO:192 and SEQ ID NO:235; SEQ ID NO:193 and SEQ ID NO:235; SEQ ID NO:194 and SEQ ID NO:235; SEQ ID NO:195 and SEQ ID NO:235; SEQ ID NO:196 and SEQ ID NO:235; SEQ ID NO:197 and SEQ ID NO:235; SEQ ID NO:198 and SEQ ID NO:235; SEQ ID NO:199 and SEQ ID NO:235; SEQ ID NO:200 and SEQ ID NO:235; SEQ ID NO:201 and SEQ ID NO:235; SEQ ID NO:202 and SEQ ID NO:235; SEQ ID NO:203 and SEQ ID NO:235; SEQ ID NO:204 and SEQ ID NO:235; SEQ ID NO:205 and SEQ ID NO:235; SEQ ID NO:206 and SEQ ID NO:235; SEQ ID NO:207 and SEQ ID NO:235; SEQ ID NO:208 and SEQ ID NO:235; SEQ ID NO:209 and SEQ ID NO:235; SEQ ID NO:210 and SEQ ID NO:235; SEQ ID NO:211 and SEQ ID NO:235; SEQ ID NO:212 and SEQ ID NO:235; SEQ ID NO:213 and SEQ ID NO:235; SEQ ID NO:214 and SEQ ID NO:235; SEQ ID NO:215 and SEQ ID NO:235; and SEQ ID NO:216 and SEQ ID NO:235.

In some aspects, the $V_H$-$V_L$ pairs are selected from SEQ ID NO:167 and SEQ ID NO:236; SEQ ID NO:168 and SEQ ID NO:236; SEQ ID NO:169 and SEQ ID NO:236; SEQ ID NO:170 and SEQ ID NO:236; SEQ ID NO:171 and SEQ ID NO:236; SEQ ID NO:172 and SEQ ID NO:236; SEQ ID NO:173 and SEQ ID NO:236; SEQ ID NO:174 and SEQ ID NO:236; SEQ ID NO:175 and SEQ ID NO:236; SEQ ID NO:176 and SEQ ID NO:236; SEQ ID NO:177 and SEQ ID NO:236; SEQ ID NO:178 and SEQ ID NO:236; SEQ ID NO:179 and SEQ ID NO:236; SEQ ID NO:180 and SEQ ID NO:236; SEQ ID NO:181 and SEQ ID NO:236; SEQ ID NO:182 and SEQ ID NO:236; SEQ ID NO:183 and SEQ ID NO:236; SEQ ID NO:184 and SEQ ID NO:236; SEQ ID NO:185 and SEQ ID NO:236; SEQ ID NO:186 and SEQ ID NO:236; SEQ ID NO:187 and SEQ ID NO:236; SEQ ID NO:188 and SEQ ID NO:236; SEQ ID NO:189 and SEQ ID NO:236; SEQ ID NO:190 and SEQ ID NO:236; SEQ ID NO:191 and SEQ ID NO:236; SEQ ID NO:192 and SEQ ID NO:236; SEQ ID NO:193 and SEQ ID NO:236; SEQ ID NO:194 and SEQ ID NO:236; SEQ ID NO:195 and SEQ ID NO:230; SEQ ID NO:196 and SEQ ID NO:230; SEQ ID NO:197 and SEQ ID NO:236; SEQ ID NO:198 and SEQ ID NO:236; SEQ ID NO:199 and SEQ ID NO:236; SEQ ID NO:200 and SEQ ID NO:236; SEQ ID NO:201 and SEQ ID NO:236; SEQ ID NO:202 and SEQ ID NO:236; SEQ ID NO:203 and SEQ ID NO:236; SEQ ID NO:204 and SEQ ID NO:236; SEQ ID NO:205 and SEQ ID NO:236; SEQ ID NO:206 and SEQ ID NO:236; SEQ ID NO:207 and SEQ ID NO:236; SEQ ID NO:208 and SEQ ID NO:236; SEQ ID NO:209 and SEQ ID NO:236; SEQ ID NO:210 and SEQ ID NO:236; SEQ ID NO:211 and SEQ ID NO:236; SEQ ID NO:212 and SEQ ID NO:236; SEQ ID NO:213 and SEQ ID NO:236; SEQ ID NO:214 and SEQ ID NO:236; SEQ ID NO:215 and SEQ ID NO:236; and SEQ ID NO:216 and SEQ ID NO:236.

In some aspects, the $V_H$-$V_L$ pairs are selected from SEQ ID NO:167 and SEQ ID NO:237; SEQ ID NO:168 and SEQ ID NO:237; SEQ ID NO:169 and SEQ ID NO:237; SEQ ID NO:170 and SEQ ID NO:237; SEQ ID NO:171 and SEQ ID NO:237; SEQ ID NO:172 and SEQ ID NO:237; SEQ ID NO:173 and SEQ ID NO:237; SEQ ID NO:174 and SEQ ID NO:237; SEQ ID NO:175 and SEQ ID NO:237; SEQ ID NO:176 and SEQ ID NO:237; SEQ ID NO:177 and SEQ ID NO:237; SEQ ID NO:178 and SEQ ID NO:237; SEQ ID NO:179 and SEQ ID NO:237; SEQ ID NO:180 and SEQ ID NO:237; SEQ ID NO:181 and SEQ ID NO:237; SEQ ID NO:182 and SEQ ID NO:237; SEQ ID NO:183 and SEQ ID NO:237; SEQ ID NO:184 and SEQ ID NO:237; SEQ ID NO:185 and SEQ ID NO:237; SEQ ID NO:186 and SEQ ID NO:237; SEQ ID NO:187 and SEQ ID NO:237; SEQ ID NO:188 and SEQ ID NO:237; SEQ ID NO:189 and SEQ ID NO:237; SEQ ID NO:190 and SEQ ID NO:237; SEQ ID NO:191 and SEQ ID NO:237; SEQ ID NO:192 and SEQ ID NO:237; SEQ ID NO:193 and SEQ ID NO:237; SEQ ID NO:194 and SEQ ID NO:237; SEQ ID NO:195 and SEQ ID NO:237; SEQ ID NO:196 and SEQ ID NO:237; SEQ ID NO:197 and SEQ ID NO:237; SEQ ID NO:198 and SEQ ID NO:237; SEQ ID NO:199 and SEQ ID NO:237; SEQ ID NO:200 and SEQ ID NO:237; SEQ ID NO:201 and SEQ ID NO:237; SEQ ID NO:202 and SEQ ID NO:237; SEQ ID NO:203 and SEQ ID NO:237; SEQ ID NO:204 and SEQ ID NO:237; SEQ ID NO:205 and SEQ ID NO:237; SEQ ID NO:206 and SEQ ID NO:237; SEQ ID NO:207 and SEQ ID NO:237; SEQ ID NO:208 and SEQ ID NO:237; SEQ ID NO:209 and SEQ ID NO:237; SEQ ID NO:210 and SEQ ID NO:237; SEQ ID NO:211 and SEQ ID NO:237; SEQ ID NO:212 and SEQ ID NO:237; SEQ ID NO:213 and SEQ ID NO:237; SEQ ID NO:214 and SEQ ID NO:237; SEQ ID NO:215 and SEQ ID NO:237; and SEQ ID NO:216 and SEQ ID NO:237.

In some aspects, the $V_H$-$V_L$ pairs are selected from SEQ ID NO:167 and SEQ ID NO:238; SEQ ID NO:168 and SEQ ID NO:238; SEQ ID NO:169 and SEQ ID NO:238; SEQ ID NO:170 and SEQ ID NO:238; SEQ ID NO:171 and SEQ ID NO:238; SEQ ID NO:172 and SEQ ID NO:238; SEQ ID NO:173 and SEQ ID NO:238; SEQ ID NO:174 and SEQ ID NO:238; SEQ ID NO:175 and SEQ ID NO:238; SEQ ID NO:176 and SEQ ID NO:238; SEQ ID NO:177 and SEQ ID NO:238; SEQ ID NO:178 and SEQ ID NO:238; SEQ ID NO:179 and SEQ ID NO:238; SEQ ID NO:180 and SEQ ID NO:238; SEQ ID NO:181 and SEQ ID NO:238; SEQ ID NO:182 and SEQ ID NO:238; SEQ ID NO:183 and SEQ ID NO:238; SEQ ID NO:184 and SEQ ID NO:238; SEQ ID NO:185 and SEQ ID NO:238; SEQ ID NO:186 and SEQ ID NO:238; SEQ ID NO:187 and SEQ ID NO:238; SEQ ID NO:188 and SEQ ID NO:238; SEQ ID NO:189 and SEQ ID NO:238; SEQ ID NO:190 and SEQ ID NO:238; SEQ ID NO:191 and SEQ ID NO:238; SEQ ID NO:192 and SEQ ID NO:238; SEQ ID NO:193 and SEQ ID NO:238; SEQ ID NO:194 and SEQ ID NO:238; SEQ ID NO:195 and SEQ ID NO:238; SEQ ID NO:196 and SEQ ID NO:238; SEQ ID NO:197 and SEQ ID NO:238; SEQ ID NO:198 and SEQ ID NO:238; SEQ ID NO:199 and SEQ ID NO:238; SEQ ID NO:200 and SEQ ID NO:238; SEQ ID NO:201 and SEQ ID NO:238; SEQ ID NO:202 and SEQ ID NO:238; SEQ ID NO:203 and SEQ ID NO:238; SEQ ID NO:204 and SEQ ID NO:238; SEQ ID NO:205 and SEQ ID NO:238; SEQ ID NO:206 and SEQ ID NO:238; SEQ ID NO:207 and SEQ ID NO:238; SEQ ID NO:208 and SEQ ID NO:238; SEQ ID NO:209 and SEQ ID NO:238; SEQ ID NO:210 and SEQ ID NO:238; SEQ ID NO:211 and SEQ ID NO:238; SEQ ID NO:212 and SEQ ID NO:238; SEQ ID NO:213 and SEQ ID NO:238; SEQ ID NO:214 and SEQ ID NO:238; SEQ ID NO:215 and SEQ ID NO:238; and SEQ ID NO:216 and SEQ ID NO:238.

2.7.4.1. Variants of $V_H$-$V_L$ Pairs

In some embodiments, the $V_H$-$V_L$ pairs provided herein comprise a variant of an illustrative $V_H$ and/or $V_L$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.1% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.7.5. Heavy Chain-Light Chain Pairs

In some embodiments, the antibody comprises a heavy chain sequence of an antibody disclosed herein and a light chain sequence of a suitable antibody. In some embodiments, the antibody comprises a heavy chain sequence of an antibody disclosed herein and a light chain sequence of an antibody disclosed herein.

In some embodiments, the heavy chain comprises a $V_H$ sequence comprising, consisting of, or consisting essentially of any one of SEQ ID NOs: 167-216, and the light chain comprises a light chain sequence of any suitable antibody. Techniques for determining whether a particular light chain will pair with a heavy chain as described herein are well known to those of skill in the art. For example, a cell-free protein synthesis reaction comprising a nucleic acid encoding the heavy chain of interest and a nucleic acid encoding the light chain to be assessed may be performed as described, for example, in Example 1.

In some embodiments, the heavy chain comprises a $V_H$ sequence comprising, consisting of, or consisting essentially of any one of SEQ ID NOs: 167-216, and the light chain comprises a $V_L$ sequence comprising, consisting of, or consisting essentially of any one of SEQ ID NOs: 217-238.

In some embodiments, the heavy chain comprises a $V_H$ sequence comprising, consisting of, or consisting essentially of any one of SEQ ID NOs: 167-179, and the light chain comprises a $V_L$ sequence comprising, consisting of, or consisting essentially of SEQ ID NO: 217.

In some embodiments, the heavy chain comprises a $V_H$ sequence comprising, consisting of, or consisting essentially of any one of SEQ ID NOs: 180-181, and the light chain comprises a $V_L$ sequence comprising, consisting of, or consisting essentially of SEQ ID NO: 217.

In some embodiments, the heavy chain comprises a $V_H$ sequence comprising, consisting of, or consisting essentially of any one of SEQ ID NOs: 182-188, and the light chain comprises a $V_L$ sequence comprising, consisting of, or consisting essentially of SEQ ID NO: 217.

In some embodiments, the heavy chain comprises a $V_H$ sequence comprising, consisting of, or consisting essentially of any one of SEQ ID NOs: 189-195, and the light chain comprises a $V_L$ sequence comprising, consisting of, or consisting essentially of SEQ ID NO: 217.

In some embodiments, the heavy chain comprises a $V_H$ sequence comprising, consisting of, or consisting essentially of any one of SEQ ID NOs: 196-202, and the light chain comprises a $V_L$ sequence comprising, consisting of, or consisting essentially of any one of SEQ ID NOs: 218-224.

In some embodiments, the heavy chain comprises a $V_H$ sequence comprising, consisting of, or consisting essentially of any one of SEQ ID NOs: 203-207, and the light chain comprises a $V_L$ sequence comprising, consisting of, or consisting essentially of any one of SEQ ID NOs: 225-229.

In some embodiments, the heavy chain comprises a $V_H$ sequence comprising, consisting of, or consisting essentially of any one of SEQ ID NOs: 208-216, and the light chain comprises a $V_L$ sequence comprising, consisting of, or consisting essentially of any one of SEQ ID NO: 230-238.

2.8. Antibodies Comprising Six CDRs

In some embodiments, the antibody comprises a CDR-H1 sequence, a CDR-H2 sequence, a CDR-H3 sequence, a CDR-L1 sequence, a CDR-L2 sequence, and a CDR-L3 sequence. In some aspects, the CDR sequences are part of a $V_H$ (for CDR-H) or $V_L$ (for CDR-L).

In some aspects, the CDR-H1 sequence is a Chothia CDR-H1 sequence comprising, consisting of, or consisting essentially of SEQ ID NOs: 5-31; the CDR-H2 sequence is a Chothia CDR-H2 sequence comprising, consisting of, or consisting essentially of SEQ ID NOs: 57-78; the CDR-H3 sequence is a CDR-H3 sequence comprising, consisting of, or consisting essentially of SEQ ID NOs: 116-145; the CDR-L1 sequence is a CDR-L1 sequence comprising, consisting of, or consisting essentially of SEQ ID NOs: 146-154; the CDR-L2 sequence is a CDR-L2 sequence comprising, consisting of, or consisting essentially of SEQ ID NOs: 155-160; and the CDR-L3 sequence is a CDR-L3 sequence comprising, consisting of, or consisting essentially of SEQ ID NOs: 161-166.

In some aspects, the CDR-H1 sequence is a Kabat CDR-H1 sequence comprising, consisting of, or consisting essentially of SEQ ID NOs: 32-56; the CDR-H2 sequence is a Kabat CDR-H2 sequence comprising, consisting of, or consisting essentially of SEQ ID NOs: 79-115; the CDR-H3 sequence is a CDR-H3 sequence comprising, consisting of, or consisting essentially of SEQ ID NOs: 116-145; the CDR-L1 sequence is a CDR-L1 sequence comprising, consisting of, or consisting essentially of SEQ ID NOs: 146-154; the CDR-L2 sequence is a CDR-L2 sequence comprising, consisting of, or consisting essentially of SEQ ID NOs: 155-160; and the CDR-L3 sequence is a CDR-L3 sequence comprising, consisting of, or consisting essentially of SEQ ID NOs: 161-166.

In some embodiments, the antibody comprises one, two, or three of: a CDR-H1 comprising one of SEQ ID NOs: 5 and 32; a CDR-H2 comprising one of SEQ ID NOs: 57 and 79; a CDR-H3 comprising SEQ ID NO: 116; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 5 and 32; a CDR-H2 comprising one of SEQ ID NOs: 57 and 79; a CDR-H3 comprising SEQ ID NO: 116; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 5 and 32; a CDR-H2 comprising one of SEQ ID NOs: 57 and 79; a CDR-H3 comprising SEQ ID NO: 116; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 6 and 33; a CDR-H2 comprising one of SEQ ID NOs: 57 and 79; a CDR-H3 comprising SEQ ID NO: 117; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 7 and 34; a CDR-H2 comprising one of SEQ ID NOs: 57 and 79; a CDR-H3 comprising SEQ ID NO: 118; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 8 and 34; a CDR-H2 comprising one of SEQ ID NOs: 57 and 79; a CDR-H3 comprising SEQ ID NO: 119; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 9 and 35; a CDR-H2 comprising one of SEQ ID NOs: 57 and 79; a CDR-H3 comprising SEQ ID NO: 120; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 10 and 36; a CDR-H2 comprising one of SEQ ID NOs: 57 and 79; a CDR-H3 comprising SEQ ID NO: 121; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 11 and 36; a CDR-H2 comprising one of SEQ ID NOs: 58 and 80; a CDR-H3 comprising SEQ ID NO: 122; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 12 and 35; a CDR-H2 comprising one of SEQ ID NOs: 57 and 79; a CDR-H3 comprising SEQ ID NO: 116; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 13 and 36; a CDR-H2 comprising one of SEQ ID NOs: 59 and 81; a CDR-H3 comprising SEQ ID NO: 123; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 13 and 36; a CDR-H2 comprising one of SEQ ID NOs: 59 and 81; a CDR-H3 comprising SEQ ID NO: 124; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 14 and 37; a CDR-H2 comprising one of SEQ ID NOs: 57 and 79; a CDR-H3 comprising SEQ ID NO: 125; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 15 and 35; a CDR-H2 comprising one of SEQ ID NOs: 57 and 79; a CDR-H3 comprising SEQ ID NO: 126; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 16 and 38; a CDR-H2 comprising one of SEQ ID NOs: 57 and 79; a CDR-H3 comprising SEQ ID NO: 125; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 17 and 39; a CDR-H2 comprising one of SEQ ID NOs: 60 and 82; a CDR-H3 comprising SEQ ID NO: 127; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 17 and 40; a CDR-H2 comprising one of SEQ ID NOs: 61 and 83; a CDR-H3 comprising SEQ ID NO: 128; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 18 and 41; a CDR-H2 comprising one of SEQ ID NOs: 62 and 84; a CDR-H3 comprising SEQ ID NO: 129; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 19 and 42; a CDR-H2 comprising one of SEQ ID NOs: 63 and 85; a CDR-H3 comprising SEQ ID NO: 130; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 19 and 41; a CDR-H2 comprising one of SEQ ID NOs: 64 and 86; a CDR-H3 comprising SEQ ID NO: 131; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 20 and 43; a CDR-H2 comprising one of SEQ ID NOs: 65 and 87; a CDR-H3 comprising SEQ ID NO: 132; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 21 and 44; a CDR-H2 comprising one of SEQ ID NOs: 66 and 88; a CDR-H3 comprising SEQ ID NO: 133; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 22 and 42; a CDR-H2 comprising one of SEQ ID NOs: 67 and 89; a CDR-H3 comprising SEQ ID NO: 134; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 23 and 45; a CDR-H2 comprising one of SEQ ID NOs: 66 and 90; a CDR-H3 comprising SEQ ID NO: 135; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 18 and 46; a CDR-H2 comprising one of SEQ ID NOs: 68 and 91; a CDR-H3 comprising SEQ ID NO: 136; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 24 and 47; a CDR-H2 comprising one of SEQ ID NOs: 68 and 92; a CDR-H3 comprising SEQ ID NO: 137; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 19 and 48; a CDR-H2 comprising one of SEQ ID NOs: 69 and 93; a CDR-H3 comprising SEQ ID NO: 138; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 25 and 49; a CDR-H2 comprising one of SEQ ID NOs: 70 and 94; a CDR-H3 comprising SEQ ID NO: 136; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 26 and 48; a CDR-H2 comprising one of SEQ ID NOs: 70 and 95; a CDR-H3 comprising SEQ ID NO: 139; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 18 and 50; a CDR-H2 comprising one of SEQ ID NOs: 70 and 96; a CDR-H3 comprising SEQ ID NO: 140; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 26 and 48; a CDR-H2 comprising one of SEQ ID NOs: 70 and 97; a CDR-H3 comprising SEQ ID NO: 136; and/or one, two, or three of: a CDR-L1 comprising SEQ ID NO: 146; a CDR-L2 comprising SEQ ID NO: 155; and a CDR-L3 comprising SEQ ID NO: 161. In some embodiments, the antibody comprises one, two, or three of: a CDR-H1 comprising one of SEQ ID NOs: 27 and 51; a CDR-H2 comprising one of SEQ ID NOs: 71 and 98; a CDR-H3 comprising SEQ ID NO: 141; and/or one, two, or three of: a CDR-L1 comprising SEQ ID NO: 147; a CDR-L2 comprising SEQ ID NO: 156; and a CDR-L3 comprising SEQ ID NO: 162. In some embodiments, the antibody comprises one, two, or three of: a CDR-H1 comprising one of SEQ ID NOs: 27 and 51; a CDR-H2 comprising one of SEQ ID NOs: 72 and 99; a CDR-H3 comprising SEQ ID NO: 142; and/or one, two, or three of: a CDR-L1 comprising SEQ ID NO: 148; a CDR-L2 comprising SEQ ID NO: 158; and a CDR-L3 comprising SEQ ID NO: 163. In some embodiments, the antibody comprises one, two, or three of: a CDR-H1 comprising one of SEQ ID NOs: 27 and 51; a CDR-H2 comprising one of SEQ ID NOs: 73 and 100; a CDR-H3 comprising SEQ ID NO: 142; and/or one, two, or three of: a CDR-L1 comprising SEQ ID NO: 149; a CDR-L2 comprising SEQ ID NO: 158; and a CDR-L3 comprising SEQ ID NO: 164. In some embodiments, the antibody comprises one, two, or three of: a CDR-H1 comprising one of SEQ ID NOs: 27 and 51; a CDR-H2 comprising one of SEQ ID NOs: 73 and 101; and a CDR-H3 comprising SEQ ID NO: 142; and/or one, two, or three of: a CDR-L1 comprising SEQ ID NO: 149; a CDR-L2 comprising SEQ ID NO: 158; and a CDR-L3 comprising SEQ ID NO: 165. In some embodiments, the antibody comprises one, two, or three of: a CDR-H1 comprising one of SEQ ID NOs: 27 and 51; a CDR-H2 comprising one of SEQ ID NOs: 73 and 102; and a CDR-H3 comprising SEQ ID NO: 142; and/or one, two, or three of: a CDR-L1 comprising SEQ ID NO: 149; a CDR-L2 comprising SEQ ID NO: 158; and a CDR-L3 comprising SEQ ID NO: 165. In some embodiments, the antibody comprises one, two, or three of: a CDR-H1 comprising one of SEQ ID NOs: 27 and 51; a CDR-H2 comprising one of SEQ ID NOs: 73 and 102; and a CDR-H3 comprising SEQ ID NO: 142; and/or one, two, or three of: a CDR-L1 comprising SEQ ID NO: 149; a CDR-L2 comprising SEQ ID NO: 158; and a CDR-L3 comprising SEQ ID NO: 165. In some embodiments, the antibody comprises one, two, or three of: a CDR-H1 comprising one of SEQ ID NOs: 27 and 51; a CDR-H2 comprising one of SEQ ID NOs: 73 and 103; and a CDR-H3 comprising SEQ ID NO: 142; and/or one, two, or three of: a CDR-L1 comprising SEQ ID NO: 149; a CDR-L2 comprising SEQ ID NO: 158; and a CDR-L3 comprising SEQ ID NO: 165. In some embodiments, the antibody comprises one, two, or three of: a CDR-H1 comprising one of SEQ ID NOs: 28 and 52; a CDR-H2 comprising one of SEQ ID NOs: 74 and 104; and a CDR-H3 comprising SEQ ID NO: 143; and/or one, two, or three of: a CDR-L1 comprising SEQ ID NO: 150; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 28 and 52; a CDR-H2 comprising one of SEQ ID NOs: 74 and 105; and a CDR-H3 comprising SEQ ID NO: 143; and/or one, two, or three of: a CDR-L1 comprising SEQ ID NO: 150; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 28 and 52; a CDR-H2 comprising one of SEQ ID NOs: 74 and 106; and a CDR-H3 comprising SEQ ID NO: 143; and/or one, two, or three of: a CDR-L1 comprising SEQ ID NO: 150; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 28 and 52; a CDR-H2 comprising one of SEQ ID NOs: 74 and 106; and a CDR-H3 comprising SEQ ID NO: 143; and/or one, two, or three of: a CDR-L1 comprising SEQ ID NO: 150; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 28 and 52; a CDR-H2 comprising one of SEQ ID NOs: 74 and 107; and a CDR-H3 comprising SEQ ID NO: 143; and/or one, two, or three of: a CDR-L1 comprising SEQ ID NO: 150; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 29 and 53; a CDR-H2 comprising one of SEQ ID NOs: 75 and 108; and a CDR-H3 comprising SEQ ID NO: 144; and/or one, two, or three of: a CDR-L1 comprising SEQ ID NO: 151; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 30 and 54; a CDR-H2 comprising one of SEQ ID NOs: 76 and 109; and a CDR-H3 comprising SEQ ID NO: 145; and/or one, two, or three of: a CDR-L1 comprising SEQ ID NO: 152; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 30 and 53; a CDR-H2 comprising one of SEQ ID NOs:77 and 110; and a CDR-H3 comprising SEQ ID NO: 145; and/or one, two, or three of: a CDR-L1 comprising SEQ ID NO: 152; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 28 and 55; a CDR-H2 comprising one of SEQ ID NOs: 77 and 111; and a CDR-H3 comprising SEQ ID NO: 145; and/or one, two, or three of: a CDR-L1 comprising SEQ ID NO: 153; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 31 and 56; a CDR-H2 comprising one of SEQ ID NOs: 78 and 112; and a CDR-H3 comprising SEQ ID NO: 145; and/or one, two, or three of: a CDR-L1 comprising SEQ ID NO: 154; a CDR-L2 comprising SEQ ID NO: 160; and a CDR-L3 comprising SEQ ID NO: 166. In some embodiments, the antibody comprises one, two, or three of: a CDR-H1 comprising one of SEQ ID NOs: 28 and 55; a CDR-H2 comprising one of SEQ ID NOs: 77 and 113; and a CDR-H3 comprising SEQ ID NO: 145; and/or one, two, or three of: a CDR-L1 comprising SEQ ID NO: 153; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 28 and 55; a CDR-H2 comprising one of SEQ ID NOs: 77 and 114; and a CDR-H3 comprising SEQ ID NO: 145; and/or one, two, or three of: a CDR-L1 comprising SEQ ID NO: 153; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 28 and 55; a CDR-H2 comprising one of SEQ ID NOs: 77 and 114; and a CDR-H3 comprising SEQ ID NO: 145; and/or one, two, or three of: a CDR-L1 comprising SEQ ID NO: 153; a CDR-L2 comprising SEQ ID NO: 159; and a CDR-L3 comprising SEQ ID NO: 166. In some embodiments, the antibody comprises one, two, or three of: a CDR-H1 comprising one of SEQ ID NOs: 28 and 55; a CDR-H2 comprising one of SEQ ID NOs: 77 and 115; and a CDR-H3 comprising SEQ ID NO: 145; and/or one, two, or three of: a CDR-L1 comprising SEQ ID NO: 153; a CDR-L2 comprising SEQ ID NO: 159; and a CDR-L3 comprising SEQ ID NO: 166.

In certain embodiments, each antibody comprises one, two, three, four, five, or six of the listed CDRs. In certain embodiments, each antibody comprises one of the listed heavy chain CDRs. In certain embodiments, each antibody comprises two of the listed heavy chain CDRs. In certain embodiments, each antibody comprises three of the listed heavy chain CDRs. In certain embodiments, each antibody comprises one of the listed light chain CDRs. In certain embodiments, each antibody comprises two of the listed light chain CDRs. In certain embodiments, each antibody comprises three of the listed light chain CDRs. In certain embodiments, each antibody comprises the listed CDR-H3 and CDR-L3. In certain embodiments, each antibody comprises the listed CDR-H2 and CDR-L2. In certain embodiments, each antibody comprises the listed CDR-H1 and CDR-L1. In certain embodiments, each antibody comprises the listed CDR-H3, CDR-H2, CDR-L3, and CDR-L2. In certain embodiments, each antibody comprises six of the listed CDRs. In particular embodiments, the CDRs are according to Chothia. In particular embodiments, the CDRs are according to Kabat.

2.8.1. Variants of Antibodies Comprising All Six CDRs

In some embodiments, the CDR-H1, CDR-H2, CDR-H3, CDR-L1, CDR-L2, and CDR-L3 provided herein comprise a variant of an illustrative CDR-H1, CDR-H2, CDR-H3, CDR-L1, CDR-L2, and/or CDR-L3 sequence provided in this disclosure.

In some aspects, the CDR-H1 sequence comprises, consists of, or consists essentially of a variant of an illustrative Chothia or Kabat CDR-H1 sequence provided in this disclosure. In some aspects, the CDR-H1 sequence comprises, consists of, or consists essentially of a sequence having at least 70%, 75%, 80%, 85%, 90%, or 95% identity with any of the illustrative Chothia or Kabat CDR-H1 sequences provided in this disclosure. In some aspects, the CDR-H1 sequence comprises, consists of, or consists essentially of any of the illustrative Chothia or Kabat CDR-H1 sequences provided in this disclosure, with 1, 2, or 3 amino acid substitutions. In some aspects, the amino acid substitutions are conservative amino acid substitutions.

In some aspects, the CDR-H2 sequence comprises, consists of, or consists essentially of a variant of an illustrative Chothia or Kabat CDR-H2 sequence provided in this disclosure. In some aspects, the CDR-H2 sequence comprises, consists of, or consists essentially of a sequence having at least 70%, 75%, 80%, 85%, 90%, or 95% identity with any of the illustrative Chothia or Kabat CDR-H2 sequences provided in this disclosure. In some aspects, the CDR-H2 sequence comprises, consists of, or consists essentially of any of the illustrative Chothia or Kabat CDR-H2 sequences provided in this disclosure, with 1, 2, or 3 amino acid substitutions. In some aspects, the amino acid substitutions are conservative amino acid substitutions.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.9. Consensus Sequences

In some embodiments, provided herein are anti-BCMA antibodies comprising one or more sequences defined by consensus sequences. Each consensus sequence is based, at least in part, on one or more alignments of two or more useful anti-BCMA CDR sequences provided in this disclosure. Based on such alignments, a person of skill in the art would recognize that different amino acid residues may useful in certain positions of the CDRs. Accordingly, each consensus sequence encompasses two or more useful anti-BCMA CDR sequences.

In some embodiments, the antibodies comprise one to six of the consensus CDR sequences provided herein. In some embodiments, the antibodies comprise two to six of the consensus CDR sequences provided herein. In some embodiments, the antibodies comprise three to six of the consensus CDR sequences provided herein. In some embodiments, the antibodies comprise four to six of the consensus CDR sequences provided herein. In some embodiments, the antibodies comprise five to six of the consensus CDR sequences provided herein. In some embodiments, the antibodies comprise six of the consensus CDR sequences provided herein. In some embodiments, the antibodies comprise a $V_L$ comprising the CDR-L consensus sequence(s). In some embodiments, the antibodies comprise a $V_H$ comprising the CDR-H consensus sequence(s). In some embodiments, the antibodies comprise a $V_H$ comprising the CDR-H consensus sequence(s) and a $V_L$ comprising the CDR-L consensus sequence(s).

2.9.1. CDR-H3 Consensus Sequences

In some embodiments, the antibody comprises a CDR-H3 sequence defined by the consensus sequence D-$\alpha_2$-$\alpha_3$-$\alpha_4$-$\alpha_5$-Y-W-T-Y-V-L-D-Y (SEQ ID NO: 248), where $\alpha_2$ is Y or F; $\alpha_3$ is V or I; $\alpha_4$ is Y, L, N, R, Q, or P; and $\alpha_5$ is Q, A, N, or S.

In some embodiments, the antibody comprises a CDR-H3 sequence defined by the consensus sequence D-Y-$\alpha_3$-$\alpha_4$-$\alpha_5$-Y-$\alpha_7$-T-G-V-L-D-Y (SEQ ID NO: 249), where $\alpha_3$ is G or D; $\alpha_4$ is P or L; as is W or R; and a' is G or L.

In some embodiments, the antibody comprises a CDR-H3 sequence defined by the consensus sequence D-$\alpha_2$-G-$\alpha_4$-$\alpha_5$-Y-W-V-G-$\alpha_{10}$-$\alpha_{11}$-D-Y (SEQ ID NO: 250), where $\alpha_2$ is L, M, or W; $\alpha_4$ is G, V, H, Y, or S; as is G or R; an is F or V; and an is F or S.

In some embodiments, the antibody comprises a CDR-H3 sequence defined by the consensus sequence D-$\alpha_2$-$\alpha_3$-D-R-Y-$\alpha_7$-T-$\alpha_9$-V-L-D-Y (SEQ ID NO: 251), where $\alpha_2$ is F or Y; $\alpha_3$ is Y, H, or N; $\alpha_7$ is S, A, or F; and $\alpha_9$ is Y or F.

In some embodiments, the antibody comprises a CDR-H3 sequence defined by the consensus sequence T-T-C-$\alpha_4$-G-S-G-G-C-I-D-T (SEQ ID NO: 252), where $\alpha_4$ is I or V.

In some embodiments, the antibody comprises a CDR-H3 sequence defined by the consensus sequence G-G-G-L-N-S-Y-G-C-S-G-A-N-I-D-A (SEQ ID NO: 143).

In some embodiments, the antibody comprises a CDR-H3 sequence defined by the consensus sequence G-G-G-$\alpha_4$-A-S-I-D-$\alpha_9$ (SEQ ID NO: 253), where $\alpha_4$ is A or G, and $\alpha_9$ is T or G.

2.9.2. Chothia CDR-H1 Consensus Sequences

In some embodiments, the antibody comprises a Chothia CDR-H1 sequence defined by the consensus sequence G-F-N-I-$\gamma_5$-$\gamma_6$-$\gamma_7$ (SEQ ID NO: 254), where $\gamma_5$ is S, I, R, Y, or G; $\gamma_6$ is G, Y, A, V, or R; and $\gamma_7$ is S or P.

In some embodiments, the antibody comprises a Chothia CDR-H1 sequence defined by the consensus sequence G-F-N-I-N-N-S (SEQ ID NO: 17).

In some embodiments, the antibody comprises a Chothia CDR-H1 sequence defined by the consensus sequence G-F-N-I-$\gamma_5$-$\gamma_6$-$\gamma$7 (SEQ ID NO: 255), where $\gamma_5$ is S, T, A, or Q; $\gamma_6$ is S, P, Y, or T; and $\gamma_7$ is Y, D, or R.

In some embodiments, the antibody comprises a Chothia CDR-H1 sequence defined by the consensus sequence G-F-N-I-$\gamma_5$-$\gamma_6$-$\gamma_7$ (SEQ ID NO: 256), where $\gamma_5$ is S, A, K, or D; $\gamma_6$ is S, A, P, or D; and $\gamma_7$ is Y or T.

In some embodiments, the antibody comprises a Chothia CDR-H1 sequence defined by the consensus sequence G-F-T-F-S-S-F (SEQ ID NO: 27).

In some embodiments, the antibody comprises a Chothia CDR-H1 sequence defined by the consensus sequence G-F-T-F-S-G-Y (SEQ ID NO: 28).

In some embodiments, the antibody comprises a Chothia CDR-H1 sequence defined by the consensus sequence G-F-$\gamma_3$-$\gamma_4$-S-$\gamma_6$-Y (SEQ ID NO: 257), where $\gamma_3$ is S or T; $\gamma_4$ is I or F; and $\gamma_6$ is D, G, or S.

2.9.3. Chothia CDR-H2 Consensus Sequences

In some embodiments, the antibody comprises a Chothia CDR-H2 sequence defined by the consensus sequence $\varepsilon_1$-P-$\varepsilon_3$-A-$\varepsilon_5$-G-Y (SEQ ID NO: 258), where $\varepsilon_1$ is N or S; E3 is absent; and $\varepsilon_5$ is G or A.

In some embodiments, the antibody comprises a Chothia CDR-H2 sequence defined by the consensus sequence Y-P-$\varepsilon_3$-Y-$\varepsilon_5$-G-$\varepsilon_7$ (SEQ ID NO: 259), where $\varepsilon_3$ is absent; $\varepsilon_5$ is S or I; and $\varepsilon_7$ is Y or F.

In some embodiments, the antibody comprises a Chothia CDR-H2 sequence defined by the consensus sequence T-P-$\varepsilon_3$-$\varepsilon_4$-$\varepsilon_5$-G-$\varepsilon_7$ (SEQ ID NO: 260), where $\varepsilon_3$ is absent; $\varepsilon_4$ is S, P, A, or F; $\varepsilon_5$ is G, S, A, or D; and $\varepsilon_7$ is Y or F.

In some embodiments, the antibody comprises a Chothia CDR-H2 sequence defined by the consensus sequence $\varepsilon_1$-P-$\varepsilon_3$-$\varepsilon_4$-$\varepsilon_5$-G-Y (SEQ ID NO: 261), where $\varepsilon_1$ is S or F; $\varepsilon_3$ is absent; $\varepsilon_4$ is Y or S; and $\varepsilon_5$ is G or D.

In some embodiments, the antibody comprises a Chothia CDR-H2 sequence defined by the consensus sequence $\varepsilon_1$-N-D-$\varepsilon_4$-G-$\varepsilon_6$-S(SEQ ID NO: 262), where $\varepsilon_1$ is R or S; $\varepsilon_4$ is absent; and $\varepsilon_6$ is N, S, or R.

In some embodiments, the antibody comprises a Chothia CDR-H2 sequence defined by the consensus sequence T-Y-G-T-G-S-Y (SEQ ID NO: 74).

In some embodiments, the antibody comprises a Chothia CDR-H2 sequence defined by the consensus sequence $\varepsilon_1$-$\varepsilon_2$-$\varepsilon_3$-$\varepsilon_4$-$\varepsilon_5$-$\varepsilon_6$-$\varepsilon_7$, where $\varepsilon_1$ is D or N; $\varepsilon_2$ is H or S; $\varepsilon_3$ is D, A, G, or absent; $\varepsilon_4$ is G, A, or absent; $\varepsilon_5$ is G or S; $\varepsilon_6$ is R or S; and $\varepsilon_7$ is Y, G, or D.

2.9.4. Kabat CDR-H1 Consensus Sequences

In some embodiments, the antibody comprises a Kabat CDR-H1 sequence defined by the consensus sequence $\zeta_1$-$\zeta_2$-G-I-H, where $\zeta_1$ is G, Y, A, V, or R; and $\zeta_2$ is S or P.

In some embodiments, the antibody comprises a Kabat CDR-H1 sequence defined by the consensus sequence N-S-$\zeta_3$-I-H (SEQ ID NO: 263), where $\zeta_3$ is Y or W.

In some embodiments, the antibody comprises a Kabat CDR-H1 sequence defined by the consensus sequence $\zeta_1$-$\zeta_2$-W-I-H, where $\zeta_1$ is S, P, Y, or T; and $\zeta_2$ is Y, D, or R.

In some embodiments, the antibody comprises a Kabat CDR-H1 sequence defined by the consensus sequence $\zeta_1$-$\zeta_2$-$\zeta_3$-I-H; where $\zeta_1$ is S, A, P, or D; $\zeta_2$ is Y or T; and $\zeta_3$ is A, T, Y, or G.

In some embodiments, the antibody comprises a Kabat CDR-H1 sequence defined by the consensus sequence S-F-N-M-F (SEQ ID NO: 51).

In some embodiments, the antibody comprises a Kabat CDR-H1 sequence defined by the consensus sequence G-Y-N-M-G (SEQ ID NO: 52).

In some embodiments, the antibody comprises a Kabat CDR-H1 sequence defined by the consensus sequence $\zeta_1$-Y-G-$\zeta_4$-G, where $\zeta_1$ is D, G, or S; and $\zeta_4$ is M or L.

2.9.5. Kabat CDR-H2 Consensus Sequences

In some embodiments, the antibody comprises a Kabat CDR-H2 sequence defined by the consensus sequence F-I-$\theta_3$-P-A-$\theta_6$-G-Y-T-D-Y-A-$\theta_{13}$-S-V-K-G (SEQ ID NO: 264), where $\theta_3$ is N or S; $\theta_6$ is G or A; and $\theta_{13}$ is D or G.

In some embodiments, the antibody comprises a Kabat CDR-H2 sequence defined by the consensus sequence W-I-Y-P-Y-$\theta_6$-G-$\theta_8$-T-$\theta_{10}$-Y-A-D-S-V-K-G (SEQ ID NO: 265), where $\theta_6$ is S or I; $\theta_8$ is Y or F; and $\theta_{10}$ is N or E.

In some embodiments, the antibody comprises a Kabat CDR-H2 sequence defined by the consensus sequence V-I-T-P-$\theta_5$-$\theta_6$-G-$\theta_8$-T-$\theta_{10}$-Y-A-D-S-V-K-G (SEQ ID NO: 266), where $\theta_5$ is S, P, A, or F; $\theta_6$ is G, S, A, or D; $\theta_8$ is Y or F; and $\theta_{10}$ is Y or H.

In some embodiments, the antibody comprises a Kabat CDR-H2 sequence defined by the consensus sequence $\theta_1$-I-$\theta_3$-P-$\theta_5$-$\theta_6$-G-Y-T-$\theta_{10}$-Y-A-D-S-V-K-G (SEQ ID NO: 267), where $\theta_1$ is V, W, H, or F; $\theta_3$ is S or F; $\theta_5$ is Y or S; $\theta_6$ is G or D; and $\theta_{10}$ is E or D.

In some embodiments, the antibody comprises a Kabat CDR-H2 sequence defined by the consensus sequence Y-I-$\theta_3$-N-D-G-$\theta_7$-S-$\theta_9$-S-Y-$\theta_{12}$-$\theta_{13}$-$\theta_{14}$-V-K-G (SEQ ID NO: 268), where $\theta_3$ is R or S; $\theta_7$ is N, S, or R; $\theta_9$ is A or T; $\theta_{12}$ is G, V, or A; $\theta_{13}$ is P, D, or A; and $\theta_{14}$ is A, S, or P.

In some embodiments, the antibody comprises a Kabat CDR-H2 sequence defined by the consensus sequence G-I-T-Y-G-T-G-S-Y-T-A-Y-$\theta_{13}$-$\theta_{14}$-$\theta_{15}$-V-K-G (SEQ ID NO: 269), where $\theta_{13}$ is G, V, or A; $\theta_{14}$ is A or D; and $\theta_{15}$ is A, S, or P.

In some embodiments, the antibody comprises a Kabat CDR-H2 sequence defined by the consensus sequence R-I-$\theta_3$-$\theta_4$-$\theta_5$-$\theta_6$-$\theta_7$-$\theta_8$-$\theta_9$-T-$\theta_{11}$-Y-$\theta_{13}$-$\theta_{14}$-$\theta_{15}$-V-$\theta_{17}$-G (SEQ ID NO: 270), where $\theta_3$ is D or N; $\theta_4$ is H or S; $\theta_5$ is D, A, G, or absent; $\theta_6$ is G, A, or absent; $\theta_7$ is G or S; $\theta_8$ is R or S; $\theta_9$ is Y, G, or D; On is D, Y, or N; $\theta_{13}$ is G, V, or A; $\theta_{14}$ is A, S, or D; $\theta_{15}$ is V, A, S, or P; and $\theta_{17}$ is K or D.

2.9.6. CDR-L3 Consensus Sequences

In some embodiments, the antibody comprises a CDR-L3 sequence defined by the consensus sequence Q-Q-H-Y-T-T-P-P-T (SEQ ID NO: 161).

In some embodiments, In some embodiments, the antibody comprises a CDR-L3 sequence defined by the consensus sequence $\sigma_1$-$\sigma_2$-$\sigma_3$-D-$\sigma_5$-$\sigma_6$-$\sigma_7$-D-$\sigma_9$-$\sigma_{10}$, where: $\sigma_1$ is A or G; $\sigma_2$ is N or G; $\sigma_3$ is V or F; $\sigma_5$ is absent or S; $\sigma_6$ is Y, S, or F; $\sigma_7$ is T or S; $\sigma_9$ is D or A; and $\sigma_{10}$ is V or I.

In some embodiments, the antibody comprises a CDR-L3 sequence defined by the consensus sequence G-G-F-D-S-S-T-D-A-I (SEQ ID NO: 166).

In some embodiments, the antibody comprises a CDR-L3 sequence defined by the consensus sequence G-$\sigma_2$-F-D-S-S-$\sigma_7$-D-A-I (SEQ ID NO: 271), where: $\sigma_2$ is S or G; and $\sigma_7$ is T or S.

2.9.7. CDR-L2 Consensus Sequences

In some embodiments, the antibody comprises a CDR-L2 sequence defined by the consensus sequence S-A-S-F-L-Y-S(SEQ ID NO: 155).

In some embodiments, the antibody comprises a CDR-L2 sequence defined by the consensus sequence $\pi_1$-N-N-$\pi_4$-R-P-S(SEQ ID NO: 272), where: $\pi_1$ is S, Y, or R; and $\pi_4$ is Q or K.

In some embodiments, the antibody comprises a CDR-L2 sequence defined by the consensus sequence N-N-N-N-R-P-S(SEQ ID NO: 159).

In some embodiments, the antibody comprises a CDR-L2 sequence defined by the consensus sequence N-$\pi_2$-N-N-R-P-S(SEQ ID NO: 273), where: $\pi_2$ is N or S.

2.9.8. CDR-L1 Consensus Sequences

In some embodiments, the antibody comprises a CDR-L1 sequence defined by the consensus sequence R-A-S-Q-D-V-N-T-A-V-A (SEQ ID NO: 146).

In some embodiments, the antibody comprises a CDR-L1 sequence defined by the consensus sequence S-G-G-$\mu_4$-$\mu_5$-D-Y-G (SEQ ID NO: 274), where: $\mu_4$ is S or N; and $\mu_5$ is S or Y.

In some embodiments, the antibody comprises a CDR-L1 sequence defined by the consensus sequence S-G-G-G-N-Y-F-G-S-Y-Y-G (SEQ ID NO: 150).

In some embodiments, the antibody comprises a CDR-L1 sequence defined by the consensus sequence S-G-G-G-$\mu_5$-Y-$\mu_7$-G-$\mu_9$-Y-Y-Y-G (SEQ ID NO: 275), where: $\mu_5$ is S or N; to is V, Y, or A; and $\mu_9$ is G or S.

3. Germline

One of skill in the art would recognize that the CDR sequences provided herein may also be useful when combined with variable regions encoded by other variable region germline genes, or variants thereof. In particular, the CDR sequences provided herein may be useful when combined with variable regions encoded by variable region germline genes, or variants thereof, that are structurally similar to the variable region germline genes recited above. For example, in some embodiments, a CDR-H sequence provided herein may be combined with a variable region encoded by a variable region germline gene selected from the $V_H 1$, $V_H 2$, $V_H 3$, or $V_H 4$ families, or a variant thereof. In some embodiments, a CDR-L sequence provided herein may be combined with a variable region encoded by a variable region germline gene selected from the Vκ1, Vκ2, or Vκ3, or a variant thereof.

4. Affinity

In some embodiments, the affinity of the antibody for BCMA as indicated by Ku, is less than about $10^{-5}$ M, less than about $10^{-6}$ M, less than about $10^{-7}$ M, less than about $10^{-8}$ M, less than about $10^{-9}$ M, or less than about $10^{-10}$ M. In some embodiments, the affinity of the antibody is between about $10^{-7}$M and $10^{-11}$M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody is between about $10^{-8}$ M and $10^{-10}$ M. In some embodiments, the affinity of the antibody is between about $10^{-9}$ M and $10^{-11}$ M. In some embodiments, the affinity of the antibody is between about $10^{-9}$ M and $10^{-10}$ M.

In some embodiments, the affinity of the antibody for human BCMA, human BCMA extracellular domain, or for individual domains within human BCMA, as determined by surface plasmon resonance at 25° C., and as indicated by $K_D$, is from about $4.38 \times 10^{-11}$ M to about $5.23 \times 10^{-9}$ M. In some embodiments, the affinity of the antibody for human BCMA, as determined by surface plasmon resonance at 25° C., and as indicated by $K_D$, is from about $2.76 \times 10^{-10}$ M to about $2.36 \times 10^{-9}$ M. In some embodiments, the affinity of the antibody for human BCMA, as determined by surface plasmon resonance at 25° C., and as indicated by $K_D$, is from about $3.78 \times 10^{-10}$ M to about $2.08 \times 10^{-9}$ M. In some embodiments, the affinity of the antibody for human BCMA, as determined by surface plasmon resonance at 25° C., and as indicated by $K_D$, is from about $5.57 \times 10^{-10}$ M to about $1.63 \times 10^{-9}$ M. In some embodiments, the affinity of the antibody for human BCMA is about any of the $K_D$ values reported for human BCMA in the examples below.

In some embodiments, the affinity of the antibody for cynomolgous BCMA, cynomolgous BCMA extracellular domain, or for individual domains within cynomolgous BCMA, as determined by surface plasmon resonance at 25° C., and as indicated by $K_D$, is from about $3.24 \times 10^{-9}$ M to about $7.90 \times 10^{-9}$ M. In some embodiments, the affinity of the antibody for cynomolgous BCMA is about any of the $K_D$ values reported for cynomolgous BCMA in the examples below.

In some embodiments the antibody has a $k_a$ of at least about $10^4$ $M^{-1} \times sec^{-1}$. In some embodiments the antibody has a $k_a$ of at least about $10^5$ $M^{-1} \times sec^{-1}$. In some embodiments the antibody has a $k_a$ of at least about $10^6$ $M^{-1} \times sec^{-1}$. In some embodiments the antibody has a $k_a$ of between about $10^4$ $M^{-1} \times sec^{-1}$ and about $10^7$ $M^{-1} \times sec^{-1}$. In some embodiments the antibody has a $k_a$ of between about $10^5$ $M^{-1} \times sec^{-1}$ and about $10^7$ $M^{-1} \times sec^{-1}$. In some embodiments the antibody has a $k_a$ of between about $10^6$ $M^{-1} \times sec^{-1}$ and about $10^7$ $M^{-1} \times sec^{-1}$.

In some embodiments the antibody has a $k_a$ when associating with human BCMA, human BCMA extracellular domain, or for individual domains within human BCMA, as determined by surface plasmon resonance at 25° C., of from about $1.36 \times 10^5$ $M^{-1} \times sec^{-1}$ to about $1.41 \times 10^6$ $M^{-1} \times sec^{-1}$. In some embodiments the antibody has a $k_a$ when associating with human BCMA, as determined by surface plasmon resonance at 25° C., of from about $4.37 \times 10^5$ $M^{-1} \times sec^{-1}$ to about $1.36 \times 10^6 M^{-1} \times sec^{-1}$. In some embodiments the antibody has a $k_a$ when associating with human BCMA, as determined by surface plasmon resonance at 25° C., of from about $4.57 \times 10^5$ $M^{-1} \times sec^{-1}$ to about $9.27 \times 10^5$ $M^{-1} \times sec^{-1}$. In some embodiments the antibody has a $k_a$ when associating with human BCMA, as determined by surface plasmon resonance at 25° C., of from about $7.14 \times 10^5$ $M^{-1} \times sec^{-1}$ to about $7.66 \times 10^5$ $M^{-1} \times sec^{-1}$. In some embodiments the antibody has a $k_a$ when associating with human BCMA of about any of the $k_a$ values reported for human BCMA in the examples below.

In some embodiments the antibody has a $k_a$ when associating with cynomolgous BCMA, cynomolgous BCMA extracellular domain, or for individual domains within cynomolgous BCMA, as determined by surface plasmon resonance at 25° C., of from about $2.49 \times 10^5$ $M^{-1} \times sec^{-1}$ to about $3.58 \times 10^6$ $M^{-1} \times sec^{-1}$. In some embodiments the antibody has a $k_a$ when associating with cynomolgous BCMA of about any of the $k_a$ values reported for cynomolgous BCMA in the examples below.

In some embodiments the antibody has a $k_d$ of about $10^{-5}$ $sec^{-1}$ or less. In some embodiments the antibody has a $k_d$ of about $10^{-4}$ $sec^{-1}$ or less. In some embodiments the antibody has a $k_d$ of about $10^{-3}$ $sec^{-1}$ or less. In some embodiments the antibody has a $k_d$ of between about $10^{-2}$ $sec^{-1}$ and about $10^{-5}$ $sec^{-1}$. In some embodiments the antibody has a $k_d$ of between about $10^{-2}$ $sec^{-1}$ and about $10^{-4}$ $sec^{-1}$. In some embodiments the antibody has a $k_d$ of between about $10^{-3}$ $sec^{-1}$ and about $10^{-5}$ $sec^{-1}$.

In some embodiments the antibody has a $k_d$ when dissociating from human BCMA, human BCMA extracellular domain, or for individual domains within human BCMA, as determined by surface plasmon resonance at 25° C., of from about $2.82 \times 10^{-5}$ $sec^{-1}$ to about $3.32 \times 10^{-3}$ $sec^{-1}$. In some embodiments the antibody has a $k_d$ when dissociating from human BCMA, as determined by surface plasmon resonance at 25° C., of from about $1.31 \times 10^{-4}$ $sec^{-1}$ to about $2.83 \times 10^{-3}$ $sec^{-1}$. In some embodiments the antibody has aka when dissociating from human BCMA, as determined by surface plasmon resonance at 25° C., of from about $1.93 \times 10^{-4}$ $sec^{-1}$ to about $7.45 \times 10^{-4}$ $sec^{-1}$. In some embodiments the antibody has aka when dissociating from human BCMA, as determined by surface plasmon resonance at 25° C., of from about $5.16 \times 10^{-4}$ $sec^{-1}$ to about $7.12 \times 10^{-4}$ $sec^{-1}$. In some embodiments the antibody has a $k_d$ when dissociating from human BCMA of about any of the $k_d$ values reported for human BCMA in the examples below.

In some embodiments the antibody has a $k_d$ when dissociating from cynomolgous BCMA, cynomolgous BCMA extracellular domain, or for individual domains within cynomolgous BCMA, as determined by surface plasmon resonance at 25° C., of from about $1.14 \times 10^{-3}$ sec$^{-1}$ to about $2.74 \times 10^{-3}$ sec$^{-1}$. In some embodiments the antibody has a $k_d$ when dissociating from cynomolgous BCMA of about any of the $k_d$ values reported for cynomolgous BCMA in the examples below.

In some aspects, the $K_D$, $k_a$, and $k_d$ are determined at 25° C. In some embodiments, the $K_D$, $k_a$, and $k_d$ are determined by surface plasmon resonance. In some embodiments, the $K_D$, $k_a$, and $k_d$ are determined according to the methods described in the Examples provided herein.

5. Epitope Bins

In some embodiments, the antibody binds the same epitope as an antibody encompassing any of SEQ ID NOs: 167-216. In some embodiments, the antibody binds the same epitope as an antibody comprising (a) a $V_H$ sequence comprising, consisting of, or consisting essentially of SEQ ID NOs: 167-216, and (b) a $V_L$ sequence comprising, consisting of, or consisting essentially of SEQ ID NOs: 217-238. For example, in some embodiments, the antibody binds the same epitope as an antibody comprising any of the $V_H$-$V_L$ pairs, above. In some embodiments, the antibody competes for epitope binding with an antibody encompassing any of SEQ ID NOs: 167-216. In some embodiments, the antibody competes for epitope binding with an antibody comprising (a) a $V_H$ sequence comprising, consisting or, or consisting essentially of SEQ ID NOs: 167-216, and (b) a $V_L$ sequence comprising, consisting of, or consisting essentially of SEQ ID NOs: 217-238. For example, in some embodiments, the antibody competes for epitope binding with an antibody comprising any of the $V_H$-$V_L$ pairs, above.

In some embodiments, the antibody binds the same epitope as an antibody comprising (a) a $V_H$ sequence comprising, consisting of, or consisting essentially of SEQ ID NOs: 167-179, and (b) a $V_L$ sequence comprising, consisting of, or consisting essentially of SEQ ID NO: 217. In some embodiments, the antibody competes for epitope binding with an antibody comprising (a) a $V_H$ sequence comprising, consisting or, or consisting essentially of SEQ ID NOs: 167-179, and (b) a $V_L$ sequence comprising, consisting of, or consisting essentially of SEQ ID NO: 217.

In some embodiments, the antibody binds the same epitope as an antibody comprising (a) a $V_H$ sequence comprising, consisting of, or consisting essentially of SEQ ID NOs: 180-181, and (b) a $V_L$ sequence comprising, consisting of, or consisting essentially of SEQ ID NO: 217. In some embodiments, the antibody competes for epitope binding with an antibody comprising (a) a $V_H$ sequence comprising, consisting or, or consisting essentially of SEQ ID NOs: 180-181, and (b) a $V_L$ sequence comprising, consisting of, or consisting essentially of SEQ ID NO: 217.

In some embodiments, the antibody binds the same epitope as an antibody comprising (a) a $V_H$ sequence comprising, consisting of, or consisting essentially of SEQ ID NOs: 182-188, and (b) a $V_L$ sequence comprising, consisting of, or consisting essentially of SEQ ID NO: 217. In some embodiments, the antibody competes for epitope binding with an antibody comprising (a) a $V_H$ sequence comprising, consisting or, or consisting essentially of SEQ ID NOs: 182-188, and (b) a $V_L$ sequence comprising, consisting of, or consisting essentially of SEQ ID NO: 217.

In some embodiments, the antibody binds the same epitope as an antibody comprising (a) a $V_H$ sequence comprising, consisting of, or consisting essentially of SEQ ID NOs: 189-195, and (b) a $V_L$ sequence comprising, consisting of, or consisting essentially of SEQ ID NO: 217. In some embodiments, the antibody competes for epitope binding with an antibody comprising (a) a $V_H$ sequence comprising, consisting or, or consisting essentially of SEQ ID NOs: 189-195, and (b) a $V_L$ sequence comprising, consisting of, or consisting essentially of SEQ ID NO: 217.

In some embodiments, the antibody binds the same epitope as an antibody comprising (a) a $V_H$ sequence comprising, consisting of, or consisting essentially of SEQ ID NOs: 196-202, and (b) a $V_L$ sequence comprising, consisting of, or consisting essentially of SEQ ID NO: 218-224. In some embodiments, the antibody competes for epitope binding with an antibody comprising (a) a $V_H$ sequence comprising, consisting or, or consisting essentially of SEQ ID NOs: 196-202, and (b) a $V_L$ sequence comprising, consisting of, or consisting essentially of SEQ ID NO: 218-224.

In some embodiments, the antibody binds the same epitope as an antibody comprising (a) a $V_H$ sequence comprising, consisting of, or consisting essentially of SEQ ID NOs: 203-207, and (b) a $V_L$ sequence comprising, consisting of, or consisting essentially of SEQ ID NO: 225-229. In some embodiments, the antibody competes for epitope binding with an antibody comprising (a) a $V_H$ sequence comprising, consisting or, or consisting essentially of SEQ ID NOs: 203-207, and (b) a $V_L$ sequence comprising, consisting of, or consisting essentially of SEQ ID NO: 225-229.

In some embodiments, the antibody binds the same epitope as an antibody comprising (a) a $V_H$ sequence comprising, consisting of, or consisting essentially of SEQ ID NOs: 208-216, and (b) a $V_L$ sequence comprising, consisting of, or consisting essentially of SEQ ID NO: 230-238. In some embodiments, the antibody competes for epitope binding with an antibody comprising (a) a $V_H$ sequence comprising, consisting or, or consisting essentially of SEQ ID NOs: 208-216, and (b) a $V_L$ sequence comprising, consisting of, or consisting essentially of SEQ ID NO: 230-238.

6. Glycosylation Variants

In certain embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

7. Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

In some embodiments, the Fc comprises one or more modifications in at least one of the $C_H3$ sequences. In some embodiments, the Fc comprises one or more modifications in at least one of the $C_H2$ sequences. For example, the Fc can include one or modifications selected from the group consisting of: V262E, V262D, V262K, V262R, V262S, V264S, V303R, and V305R. In some embodiments, an Fc is a single polypeptide. In some embodiments, an Fc is multiple peptides, e.g., two polypeptides. Exemplary modifications in the Fc region are described, for example, in International Patent Application No. PCT/US2017/037545, filed Jun. 14, 2017.

An alteration in in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Ravetch and Kinet, *Ann. Rev. Immunol.*, 1991, 9:457-492, incorporated by reference in its entirety.

Non-limiting examples of in vitro assays to assess ADCC activity of a molecule of interest are provided in U.S. Pat. Nos. 5,500,362 and 5,821,337; Hellstrom et al., *Proc. Natl. Acad. Sci. U.S.A.*, 1986, 83:7059-7063; Hellstrom et al., *Proc. Natl. Acad. Sci. U.S.A.*, 1985, 82:1499-1502; and Bruggemann et al., *J. Exp. Med.*, 1987, 166:1351-1361; each of which is incorporated by reference in its entirety. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. *Proc. Natl. Acad. Sci. U.S.A.*, 1998, 95:652-656, incorporated by reference in its entirety.

C1q binding assays may also be carried out to confirm that the antibody is unable to bind C1q and hence lacks CDC activity. Examples of C1q binding assays include those described in WO 2006/029879 and WO 2005/100402, each of which is incorporated by reference in its entirety.

Complement activation assays include those described, for example, in Gazzano-Santoro et al., *J. Immunol. Methods*, 1996, 202:163-171; Cragg et al., *Blood*, 2003, 101: 1045-1052; and Cragg and Glennie, *Blood*, 2004, 103:2738-2743; each of which is incorporated by reference in its entirety.

FcRn binding and in vivo clearance (half-life determination) can also be measured, for example, using the methods described in Petkova et al., *Intl. Immunol.*, 2006, 18:1759-1769, incorporated by reference in its entirety.

8. Preparation of Antibodies

8.1. Antigen Preparation

The BCMA protein to be used for isolation of the antibodies may be intact BCMA or a fragment of BCMA. The intact BCMA protein, or fragment of BCMA, may be in the form of an isolated protein or protein expressed by a cell. Other forms of BCMA useful for generating antibodies will be apparent to those skilled in the art.

8.2. Monoclonal Antibodies

Monoclonal antibodies may be obtained, for example, using the hybridoma method first described by Kohler et al., *Nature*, 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* $3^{rd}$ ed. (1986) Academic Press, San Diego, CA, incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, CA), and SP-2 or X63-Ag8-653 cells (available from the American Type Culture Collection, Rockville, MD). Human myeloma and mouse-human heteromyeloma cell lines also have been described for the production of human monoclonal antibodies. See e.g., Kozbor, *J. Immunol.*, 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

8.3. Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature,* 1991, 349:293-299; Rader et al., *Proc. Nat. Acad. Sci. U.S.A.,* 1998, 95:8910-8915; Steinberger et al., *J. Biol. Chem.,* 2000, 275:36073-36078; Queen et al., *Proc. Natl. Acad. Sci. U.S.A.,* 1989, 86:10029-10033; and U.S. Pat. Nos. 5,585,089, 5,693,761, 5,693,762, and 6,180,370; each of which is incorporated by reference in its entirety.

8.4. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.,* 1993, 90:2551; Jakobovits et al., *Nature,* 1993, 362:255-258; Bruggermann et al., *Year in Immuno.,* 1993, 7:33; and U.S. Pat. Nos. 5,591,669, 5,589,369 and 5,545,807; each of which is incorporated by reference in its entirety. Human antibodies can also be derived from phage-display libraries (see e.g., Hoogenboom et al., *J. Mol. Biol.,* 1991, 227:381-388; Marks et al., *J. Mol. Biol.,* 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

9. Vectors, Host Cells, and Recombinant Methods

The invention also provides isolated nucleic acids encoding anti-BCMA antibodies, vectors and host cells comprising the nucleic acids, and recombinant techniques for the production of the antibodies.

For recombinant production of the antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella,* Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for anti-BCMA antibody-encoding vectors. *Saccharomyces cerevisiae,* or common baker's yeast, is a commonly used lower eukaryotic host microorganism. However, a number of other genera, species, and strains are available and useful, such as *Schizosaccharomyces pombe, Kluyveromyces* (*K. lactis, K. fragilis, K. bulgaricus* K. wickeramii, *K. waltii, K. drosophilarum, K. thermotolerans,* and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium,* and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-BCMA antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.,* 1979, 58:44; Barnes et al., *Anal. Biochem.,* 1980, 102:255; and U.S. Pat. Nos. 4,767,704, 4,657,866, 4,927,762, 4,560,655, and 5,122,469, or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology,* 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min Cell debris can be removed by centrifugation.

In some embodiments, the antibody is produced in a cell-free system. In some aspects, the cell-free system is an in vitro transcription and translation system as described in Yin et al., mAbs, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.*, 1983, 62:1-13, incorporated by reference in its entirety). Protein G is useful for all mouse isotypes and for human γ3 (Guss et al., *EMBO J.*, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

10. Pharmaceutical Compositions and Methods of Administration

Any of the antibodies provided herein can be provided in any appropriate pharmaceutical composition and be administered by any suitable route of administration. Suitable routes of administration include, but are not limited to, the inhalation, intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an antibody, since water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

In some embodiments lactose-free compositions are provided herein which comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre gelatinized starch, and magnesium stearate.

Also provided are pharmaceutical compositions and dosage forms that comprise one or more excipients that reduce the rate by which an antibody will decompose. Such excipients, which are referred to herein as "stabilizers," include, but are not limited to, antioxidants such as ascorbic acid, pH buffers, or salt buffers.

10.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

10.2. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

The amount of the antibody or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or for times weekly. It may be necessary to use dosages of the antibody outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

11. Therapeutic Applications

For therapeutic applications, the antibodies of the invention are administered to a mammal, generally a human, in a pharmaceutically acceptable dosage form such as those known in the art and those discussed above. For example, the antibodies of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibodies also are suitably administered by peritumoral, intralesional, or perilesional routes, to exert local as well as systemic therapeutic effects. The intraperitoneal route may be particularly useful, for example, in the treatment of ovarian tumors.

The antibodies provided herein may be useful for the treatment of any disease or condition involving BCMA. In some embodiments, the disease or condition is a disease or condition that can be diagnosed by overexpression of BCMA. In some embodiments, the disease or condition is a disease or condition that can benefit from treatment with an anti-BCMA antibody. In some embodiments, the disease or condition is a cancer. In some embodiments, the disease or condition is a leukemia, a lymphoma, or multiple myeloma.

Any suitable cancer may be treated with the antibodies provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

In some embodiments, the disease to be treated with the antibodies provided herein is gastric cancer, colorectal cancer, renal cell carcinoma, cervical cancer, non-small cell lung carcinoma, ovarian cancer, uterine cancer, endometrial carcinoma, prostate cancer, breast cancer, head and neck cancer, brain carcinoma, liver cancer, pancreatic cancer, mesothelioma, and/or a cancer of epithelial origin. In particular embodiments, the disease is colorectal cancer. In some embodiments, the disease is ovarian cancer. In some embodiments, the disease is breast cancer. In some embodiments, the disease is lung cancer. In some embodiments, the disease is head and neck cancer. In some embodiments, the disease is renal cell carcinoma. In some embodiments, the disease is brain carcinoma. In some embodiments, the disease is endometrial carcinoma.

12. Diagnostic Applications

In some embodiments, the antibodies provided herein are used in diagnostic applications. For example, an anti-BCMA antibody may be useful in assays for BCMA protein. In some aspects the antibody can be used to detect the expression of BCMA in various cells and tissues. These assays may be useful, for example, in making a diagnosis and/or prognosis for a disease, such as a cancer, a leukemia, a lymphoma, or multiple myeloma.

In some diagnostic and prognostic applications, the antibody may be labeled with a detectable moiety. Suitable detectable moieties include, but are not limited to radioisotopes, fluorescent labels, and enzyme-substrate labels. In another embodiment, the anti-BCMA antibody need not be labeled, and the presence of the antibody can be detected using a labeled antibody which specifically binds to the anti-BCMA antibody.

13. Affinity Purification Reagents

The antibodies of the invention may be used as affinity purification agents. In this process, the antibodies may be immobilized on a solid phase such a resin or filter paper, using methods well known in the art. The immobilized antibody is contacted with a sample containing the BCMA protein (or fragment thereof) to be purified, and thereafter the support is washed with a suitable solvent that will remove substantially all the material in the sample except the BCMA protein, which is bound to the immobilized antibody. Finally, the support is washed with another suitable solvent, such as glycine buffer, pH 5.0 that will release the BCMA protein from the antibody.

14. Kits

In some embodiments, an anti-BCMA antibody provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the anti-BCMA antibody. In some embodiments, the anti-BCMA antibody is provided in the form of a pharmaceutical composition.

EXAMPLES

Example 1

Generation of Anti-BCMA Antibodies

Generation and Phage Display Selection

Phage display was used to discover initial human antibody leads 2190-B01 and 2213-A06. Antibody Fab libraries were constructed using an optimized trastuzumab Fab sequence codon optimized in a modified, commercially available p3 phagemid vector (Antibody Design Labs). Briefly, the phagemid vector was modified to express Fab heavy chains as C-terminal p3 fusion proteins, and regulatory regions (start codons, restriction enzyme sites, periplasmic leader sequences) were optimized for Fab display levels. Libraries were constructed using a standard overlap extension PCR protocol with mutagenic primers targeting heavy chain complementary determining regions (CDRs). See Heckman and Pease, *Nat. Protoc.*, 2007, 2:924-932. Libraries were rescued through electroporation in M13-K07 infected SS320 *E. coli* cells. Library selections were performed using standard phage display protocols. See Rajan & Sidhu, *Methods Enzymol.*, 2012, 502:3-23; Marks & Bradbury, *Methods Mol Biol.*, 2004, 248:161-76. Following multiple selection rounds, Fab heavy chain pools were transferred into cell-free expression vectors for expression as His6 and FLAG-tagged IgG1.

Ribosome Display Selections

Ribosome display was used to discover initial human antibody leads 2137-A05 and 2137-007. Ribosome display was also used to affinity mature 2137-A05, 2137-005, 2190-B01, and 2213-A06 to generate improved derivatives 2265, 2288, 2290, and 2291 families, respectively.

Antibody Fab libraries were constructed using a standard overlap extension PCR protocol with mutagenic primers targeting complementary determining regions (CDRs). See Heckman & Pease, supra. Selections for novel antibodies were performed using standard ribosome display protocols. See Hanes & Plückthun, *Proc. Natl. Acad. Sci. U.S.A*, 1997, 94:4937-4942. Specifically, Fab-based ribosome display selections were performed according to published protocols. See Stafford et al., 2014, *Protein Eng. Des. Sel.* 27:97-109; Dreier and Plückthun, 2011, *Methods Mol Biol* 687:283-306. After multiple rounds of selection, the DNA from RT-PCR output was cloned into an optimized vector for cell-free expression using standard molecular biology techniques. See Yin et al., 2012, mAbs 4:217-225. All constructs were HIS- and FLAG-tagged to streamline purification and testing during screening Chicken HybriFree and Humanization HybriFree methods were performed as published by Kivi et al. to discover antibodies 9A8, 10G5, 11D6, 10F4, 11D11, 9A5, 9E12, 9H1, 10H1, and 10E10. See Kivi et al., 2014, *BMC Biotech* 16:2 (14 pages). Briefly, human BCMA extracellular domain fused to chicken Fc and a C-terminal His tag was cloned and expressed and purified using standard methods. Two chickens were immunized until an antibody positive titer was detected in the egg yolk as determined by an ELISA. After boosting, the spleens were isolated and used to extract mRNA. Antibodies were screened and sequenced using methods described by Kivi et al. (supra).

The CDRs for 11D6 were grafted onto human antibody frameworks VH3-30, VH3-7, Vk1-6, Vl1-51, Vl3-1, and Vl3-21 by standard methodology to yield h11D6 humanized antibodies. The CDRs for 10F4 were grafted onto human antibody frameworks VH3-23, VH3-30, VH3-21, Vk1-33, Vl1-51, Vl3-1, and Vl3-21 by standard methodology to yield h10F4 humanized antibodies. The CDRs for 10H1 were grafted onto human antibody frameworks VH3-15, VH3-23, VH3-30, VH3-74, Vk1-33, Vl1-51, Vl3-1, and Vl3-21 by standard methodology to yield h10H1 humanized antibodies. See, e.g., Kuramochi et al., 2014, *Method in Molecular Biology* 1060:123-137.

Exemplary antibodies are reported in Tables 5 and 6, below.

TABLE 5

Antibodies produced by ribosome and phage-display

| Antibody | $V_H$ | SEQ ID NO. | $V_L$ | SEQ ID NO. |
|---|---|---|---|---|
| 1 | 2137-C07 | 167 | Trastuzumab | 217 |
| 2 | 2265-F06 | 168 | Trastuzumab | 217 |
| 3 | 2265-F05 | 169 | Trastuzumab | 217 |
| 4 | 2265-F02 | 170 | Trastuzumab | 217 |
| 5 | 2265-B06 | 171 | Trastuzumab | 217 |
| 6 | 2265-A09 | 172 | Trastuzumab | 217 |
| 7 | 2265-F03 | 173 | Trastuzumab | 217 |
| 8 | 2265-E02 | 174 | Trastuzumab | 217 |
| 9 | 2265-D11 | 175 | Trastuzumab | 217 |
| 10 | 2265-D05 | 176 | Trastuzumab | 217 |
| 11 | 2265-C03 | 177 | Trastuzumab | 217 |
| 12 | 2265-C02 | 178 | Trastuzumab | 217 |
| 13 | 2265-A06 | 179 | Trastuzumab | 217 |
| 14 | 2137-A05 | 180 | Trastuzumab | 217 |
| 15 | 2288-A03 | 181 | Trastuzumab | 217 |
| 16 | 2190-B01 | 182 | Trastuzumab | 217 |
| 17 | 2290-G01 | 183 | Trastuzumab | 217 |
| 18 | 2290-D02 | 184 | Trastuzumab | 217 |
| 19 | 2290-C07 | 185 | Trastuzumab | 217 |
| 20 | 2290-D05 | 186 | Trastuzumab | 217 |
| 21 | 2290-C08 | 187 | Trastuzumab | 217 |
| 22 | 2290-A02 | 188 | Trastuzumab | 217 |
| 23 | 2213-A06 | 189 | Trastuzumab | 217 |
| 24 | 2291-G05 | 190 | Trastuzumab | 217 |
| 25 | 2291-E06 | 191 | Trastuzumab | 217 |
| 26 | 2291-D07 | 192 | Trastuzumab | 217 |
| 27 | 2291-F10 | 193 | Trastuzumab | 217 |
| 28 | 2291-A04 | 194 | Trastuzumab | 217 |
| 29 | 2291-A01 | 195 | Trastuzumab | 217 |

TABLE 6

Chicken Antibodies and Humanized Chicken Antibodies

| Antibody | $V_H$ | SEQ ID NO. | $V_L$ | SEQ ID NO. |
|---|---|---|---|---|
| 30 | 9A8 | 196 | 9A8 | 218 |
| 31 | 10G5 | 197 | 10G5 | 219 |
| 32 | 11D6 | 198 | 11D6 | 220 |
| 33 | h11D6-HC4 | 199 | h11D6-LC4 | 221 |

TABLE 6-continued

Chicken Antibodies and Humanized Chicken Antibodies

| Antibody | $V_H$ | SEQ ID NO. | $V_L$ | SEQ ID NO. |
|---|---|---|---|---|
| 34 | h11D6-HC3 | 200 | h11D6-LC3 | 222 |
| 35 | h11D6-HC2 | 201 | h11D6-LC2 | 223 |
| 36 | h11D6-HC1 | 202 | h11D6-LC1 | 224 |
| 37 | 10F4 | 203 | 10F4 | 225 |
| 38 | h10F4-HC4 | 204 | h10F4-LC4 | 226 |
| 39 | h10F4-HC3 | 205 | h10F4-LC3 | 227 |
| 40 | h10F4-HC2 | 206 | h10F4-LC2 | 228 |
| 41 | h10F4-HC1 | 207 | h10F4-LC1 | 229 |
| 42 | 9A5 | 208 | 9A5 | 230 |
| 43 | 9E12 | 209 | 9E12 | 231 |
| 44 | 9H1 | 210 | 9H1 | 232 |
| 45 | 10H1 | 211 | 10H1 | 233 |
| 46 | 10E10 | 212 | 10E10 | 234 |
| 47 | h10H1-HC4 | 213 | h10H1-LC4 | 235 |
| 48 | h10H1-HC3 | 214 | h10H1-LC3 | 236 |
| 49 | h10H1-HC2 | 215 | h10H1-LC2 | 237 |
| 50 | h10H1-HC1 | 216 | h10H1-LC1 | 238 |

Example 2

Primary Screening of Antibodies

Primary ELISA Screening of Antibody Variants

Libraries of antibody variants generated by selection workflow were transformed into *E. coli* and grown on agar plates with antibiotic (Kanamycin). Individual colonies were grown in liquid broth (TB+antibiotic Kanamycin), and used as a template for DNA amplification via rolling circle amplification (RCA). The variants were then expressed in a cell-free protein synthesis reaction as described. See Yin et al., mAbs, 2012, 4:217-225. Briefly, cell-free extracts were treated with 50 μM iodoacetamide for 30 min at RT (20° C.) and added to a premix containing cell-free components (see Cai et al., *Biotechnol Prg*, 2015, 3:823-831), 10% (v/v) RCA DNA template (approximately 10 μg/mL DNA) for HC variants of interest, and 2.5 μg/mL of the trastuzumab LC. 60 μL cell free (CF) reactions were incubated at 30° C. for 12 hr on a shaker at 650 rpm in 96-well plates. 400-1500 colonies were screened, depending on the predicted diversity of different selection campaigns. Following synthesis, each reaction was diluted 1:200 and tested for binding to human or cynomolgus BCMA-Fc protein by ELISA. Briefly, BCMA-Fc (R&D Systems, Minneapolis, MN) was coated on 384-well Maxisorp plates in 0.1M bicarbonate (pH 8.9) and blocked with 1% BSA in PBST. Antibodies from a 1:200 diluted CF reaction were incubated on the plates, washed, and detected with HRP-conjugated anti-human Fab antibodies (Jackson ImmunoResearch, West Grove, PA) and Pierce Pico Supersignal ELISA substrate (ThermoFisher Scientific).

High-throughput Cell Binding

A high-throughput primary screen was performed to rapidly assess cell binding of antibodies produced in small-scale (60 μL) cell-free reactions. In this screen, four components were combined in equal volumes to a final volume of 100 μL/well in a U-bottom 96-well plate (Greiner Cat #650201) or flat bottom 384-well plate (Greiner Cat #781201). These components are: 1) BCMA-expressing NCI-H929 cells diluted in assay buffer (1×PBS+0.2% BSA, sterile filtered) to achieve a final concentration of 500,000 cells/well, 2) BCMA-negative MOLT-4 cells stained with CellTrace Oregon Green (Invitrogen Cat #34555) and diluted in assay buffer to achieve a final concentration of 500,000 cells/well, 3) a 1:50 dilution of cell-free reaction producing the antibody of interest diluted in assay buffer, and 4) a secondary anti-human antibody (AlexaFluor 647 AffiniPure F(ab')$_2$ Donkey anti-human IgG, Fc specific; Jackson ImmunoResearch Cat #709-606-098) diluted 1:100 in assay buffer. Plates were then incubated on ice for one hour. Cells were pelleted by spinning at 1500×g for 5 minutes and resuspended in assay buffer. High-throughput flow cytometry was then performed on resuspended cells on a FACS instrument (BD Biosciences FACSCanto II or BD Biosciences LSR II), and data was analyzed with FlowJo software. Antibody binding was assessed by the proportional level of secondary antibody signal (presumably due to binding to the antibody of interest) on NCIH929 BCMA-positive cells compared to the signal on MOLT-4 BCMA-negative cells.

Example 3

Secondary Screening of Antibodies

Preparation of IgGs

The top leads from the initial round of screening were cultured and miniprepped via the Qiaprep 96 Turbo miniprep kit (Qiagen) according to manufacturer's instructions. 7.5 μg/mL miniprepped HC DNA and 2.5 μg/mL of the trastuzumab LC was added to 4 mL cell-free reactions and incubated overnight for 12 hr at 30° C., 650 rpm. Expressed variants from clarified cell-free reactions were purified via IMAC purification using a semi-automated high throughput batch purification method. Briefly, purifications were performed in a 96-well plate format where 50 μL/well of IMAC resin (Ni Sepharose High Performance, GE Healthcare) was equilibrated in IMAC binding buffer (50 mM Tris pH 8.0, 300 mM NaCl, 10 mM imidazole), incubated with 1 mL cell-free reaction for 15 minutes followed by two washes in IMAC binding buffer. His-tagged antibody variants were then eluted using 200 μL IMAC elution buffer (50 mM Tris pH 8.0, 300 mM NaCl, 500 mM imidazole) and buffer exchanged into PBS using a 96-well Zeba plate (7 kD MWCO, Thermofisher). Purified antibodies were quantified via high throughput capillary electrophoresis using the Labchip GXII (Perkin Elmer) against a Herceptin standard curve, according to manufacturer's instructions.

Preparation of scFvs

A single-chain antibody is made in either the $V_HV_L$ or $V_LV_H$ orientation with a linker sequence between the $V_H$ and $V_L$ domains. Typically scFv linkers are composed of (GGGGS)n repeats where n=3, 4, 5, or 6 for linkers of 15, 20, 25, or 30 residues respectively. For cell-free expression, an N-terminal Met is added, but for mammalian expression a leader peptide is added. On the C-terminal end of the scFv, an Fc sequence can be added to extend in vivo half-life or the scFv can be used directly. An optional linker sequence can be incorporated between the scFv and the Fc. An exemplary scFv-Fc linker sequence is AAGSDQEPKSS (SEQ ID NO: 247). C-terminal affinity tags can optionally be added to facilitate purification and assay development. An exemplary affinity tag is a C-terminal FlagHis tag GSGDYKDDDDKGSGHHHHHH (SEQ ID NO: 245). A stop codon is typically inserted at the end of the sequence. An exemplary scFv can include an N-terminal Met residue, a $V_H$ domain, a GGGGSGGGGSGGGGS (SEQ ID NO: 246) linker, a $V_L$ domain, an AAGSDQEPKSS (SEQ ID NO: 247) linker, an Fc domain, a FlagHis tag, and a stop codon.

Differential Scanning Fluorimetry

A protein thermal shift assay was carried out by mixing the protein to be assayed with an environmentally sensitive dye (SYPRO Orange, Life Technologies Cat #S-6650) in a phosphate buffered solution (PBS), and monitoring the fluorescence of the mixture in real time as it underwent controlled thermal denaturation. Protein solutions between 0.2-2 mg/mL were mixed at a 1:1 volumetric ratio with a 1:500 PBS-diluted solution of SYPRO Orange (SYPRO Orange stock dye is 5000× in DMSO). 10 µL aliquots of the protein-dye mixture were dispensed in quadruplicate in a 384-well microplate (Bio-Rad Cat #MSP-3852), and the plate was sealed with an optically clear sealing film (Bio-Rad Cat #MSB-1001) and placed in a 384-well plate real-time thermocycler (Bio-Rad CFX384 Real Time System). The protein-dye mixture was heated from 25° C. to 95° C., at increments of 0.1° C. per cycle (~1.5° C. per minute), allowing 3 seconds of equilibration at each temperature before taking a fluorescence measurement. At the end of the experiment, the transition melting temperatures (TM1 and TM2) were determined using the Bio-Rad CFX manager software. TM1 represents the melting temperature of the Fc domain. TM2 represents the melting temperature of the Fab domain.

Biacore Off-Rate and Kinetic Analysis

Anti-Fab or anti-Fc polyclonal antibodies were immobilized onto a CM5 chip (GE Life Sciences) using amine coupling chemistry (from Amine Coupling Kit, GE Life Sciences). The immobilization steps were carried out at a flow rate of 25 µL/min in 1×HBS-EP+ buffer (GE Life Sciences; 10× Stock diluted before use). The sensor surfaces were activated for 7 min with a mixture of NHS (0.05 M) and EDC (0.2 M). The anti-Fab or anti-Fc antibodies were injected over all 4 flow cells at a concentration of 25 ug/ml in 10 mM sodium acetate, pH 4.5, for 7 min. Ethanolamine (1 M, pH 8.5) was injected for 7 min to block any remaining activated groups. An average of 12,000 response units (RU) of capture antibody was immobilized on each flow cell.

Off-rate and kinetic binding experiments were performed at 25° C. using 1×HBS-EP+ buffer. Test and control antibodies were injected over the anti-Fab or anti-Fc surface at concentrations of 5-10 µg/mL for 12 seconds at a flow rate of 10 µL/min on flow cells 2, 3 and 4, followed by a buffer wash for 30 seconds at the same flow rate. Kinetic characterization of antibody samples was carried out with a range of antigen concentrations from 1-100 nM and 1 injection of 0 nM antigen (for example, 100, 50, 25, 6.25, 1.56 and 0 nM). After capturing ligand (antibody) on the anti-Fab or anti-Fc surface, the analyte (human BCMA-Fc, cyno BCMA-Fc, or human BCMA from R&D Systems, custom protein production, or Sigma Aldrich, respectively) was bound for 180 seconds, followed by a 600 second dissociation phase at a flow rate of 50 µL/min. Between each ligand capture and analyte binding cycle, regeneration was carried out using 2 injections of 10 mM glycine pH 2.0 for 30 seconds at 30 µL/min, followed by a 30 second buffer wash step.

The data was fit with the Biacore T200 Evaluation software, using a 1-1 *Langmuir* binding model. $K_D$ (affinity, nM) was determined as a ratio of the kinetic rate constants calculated from the fits of the association and dissociation phases.

Cell Lines and Cell Culture Conditions

NCI-H929, U266B1, MOLT-4 and ARP-1, were obtained from ATCC and the Keats Lab (Tgen, Phoenix, AZ). 293T-cynoBCMA and 293T-ratBCMA recombinant cells were generated by transfecting 293T cells with a plasmid containing cynomolgus or rat BCMA cDNA sequences and selecting for the highest stable expression of cynomolgus BCMA or rat BCMA on the cell surface. NCI-H929, U266B1, and MOLT-4 cells were maintained in RPMI-1640 (Cellgro-Mediatech; Manassas, VA) supplemented with 20% heat-inactivated fetal bovine serum (Hyclone; Thermo Scientific; Waltham, MA), 1% Penicillin/Streptomycin (Cellgro-Mediatech; Manassas, VA), and 2 mmol/L-glutamax (Life Technology; Carlsbad, CA). 293T-cynoBCMA and 293T-ratBCMA cells were maintained in Ham's F-12-high glucose DMEM (50-50) (Cellgro-Mediatech; Manassas, VA) supplemented with 10% heat-inactivated fetal bovine serum (Hyclone; Thermo Scientific; Waltham, MA), 1% Penicillin/Streptomycin (Cellgro-Mediatech; Manassas, VA), and 2 mmol/L-glutamax (Life Technology; Carlsbad, CA).

Cell Binding Experiments

Variants for which sufficient protein was purified in secondary screening were tested in a fluorescence-activated cell sorting (FACS) cell-binding assay. BCMA positive NCI-H929 and 293T-cynoBCMA cells and BCMA negative 293T cells were used to screen for FACS binders. 293T cells were treated with 1 µM DAPT 24 hours prior to cell binding to prevent BCMA shedding. 6-12 point dilutions of anti-BCMA variants starting from concentrations of about 100-200 nM antibody were dispensed into each well using a BioMekFX (Beckman Coulter). Cells were then incubated on ice for 1 hr, washed with FACS buffer and incubated for 1 hr on ice with 50 mL FACS buffer containing 2.5 µg/ml Alexa647-conjugated Goat Anti-Human IgG dispensed using BioMekFX (Beckman Coulter). Cells were then washed 2× with FACS buffer and fixed for 10 minutes in 200 ml PBS with 2% PFA prior to fluorescence detection. Samples were acquired using a Beckton Dickinson LSRII FACS. Geometric Mean Fluorescence Intensity of BCMA antibody binding was analyzed using FlowJo® software (Tree Star, Inc.).

Cell-killing Analysis

The internalization of the antibodies was evaluated by drugs conjugated to secondary antibodies in a cell killing assay on BCMA positive cells. BCMA-positive cell lines ARP-1 and U266B1 were used to screen for internalizing leads. Cells were washed twice with calcium and magnesium-free Dulbecco's phosphate-buffered saline (DPBS), harvested with Accutase® (Innovative Cell Technologies; San Diego, CA) and counted by the Vi-CELL Cell Viability Analyzers (Beckman Coulter. Brea. CA), A total of 625 cells in a volume of 25 µL were seeded in each well of a 384-well half area flat bottom tissue culture-coated white polystyrene plate (Greiner Bio-One, Monroe, NC). Lead antibodies were formulated at 4× starting concentration in the cell culture medium and filtered through MultiScreenHTS 96-Well Filter Plates (Millipore; Billerica, MA). 12.5 µL of the serial diluted antibody (1:3 serial dilution starting from 100 nM) was added into treatment wells and 12.5 µL of an anti-human nanobody conjugated to SC239 (hemiasterlin via a cleavable linker) or SC225 (maytansinoid via a non-cleavable linker) was then added into each well at a fixed final concentration of 20 UM. Assay plates were cultured at 37° C. in a $CO_2$ incubator for 72 hrs before assay. For cell viability measurement, 30 µL of Cell Titer-Gb® reagent (Promega Corp. Madison, WI) was added into each well, and plates were processed as per product instructions. Relative luminescence was measured on an ENVISION® plate reader (Perkin-Elmer; Waltham, MA). Relative luminescence readings were converted to % viability using untreated cells as controls. Data was fitted with non-linear regression analysis, using a log(inhibitor) vs. response-variable slope, 4 parameter fit with GraphPad Prism (GraphPad v 5.0, Software; San Diego, CA). Data was expressed as relative cell viability (ATP content) % vs. dose of antibody.

Example 4

Characteristics of Illustrative Anti-BCMA Antibodies

Tables 7 through 9 show results obtained using the illustrative antibodies described herein. Tables 7 and 8 show results obtained with antibodies produced by ribosome and phage-display of initial leads. Table 9 shows results obtained with antibodies isolated from affinity maturation of initial antibody leads constructed with a trastuzumab light chain.

TABLE 7A

Antibodies from ribosome and phage-display.

| Fab-HC Variant ID | NCI-H929 (BCMA + cells) cell binding | | 293T-cynoBCMA cell binding | | ARP-1, SC225-conjugated 2° antibody cell killing | | U266B1, SC225-conjugated 2° antibody cell killing | |
|---|---|---|---|---|---|---|---|---|
| | $B_{max}$ (MFI) | Kd (nM) | $B_{max}$ (MFI) | Kd (nM) | $EC_{50}$ (nM) | Span (%) | $EC_{50}$ (nM) | Span (%) |
| SRP2137-C07 | — | — | 18519 | 10.1 | NK | NK | NK | NK |
| SRP2265-F06 | 11434 | 4.5 | 25786 | 3.4 | 1.2 | 62 | 0.9 | 59 |
| SRP2265-F05 | 12685 | 10.3 | 18484 | 3.0 | 1.8 | 52 | 1.2 | 61 |
| SRP2265-F02 | 12211 | 4.5 | 21843 | 5.0 | 1.6 | 62 | 1.0 | 62 |
| SRP2265-B06 | 11856 | 6.2 | 26591 | 3.4 | 1.6 | 67 | 0.6 | 59 |
| SRP2265-A09 | 11728 | 5.2 | 23759 | 6.2 | 1.9 | 55 | 0.9 | 58 |
| SRP2265-F03 | 12522 | 5.3 | — | — | 2.3 | 57 | 0.8 | 56 |
| SRP2265-E02 | 11629 | 4.5 | 26694 | 5.1 | 1.5 | 55 | 0.8 | 53 |
| SRP2265-D11 | 9617 | 4.4 | 21925 | 2.5 | 1.9 | 51 | 1.0 | 54 |
| SRP2265-D05 | 10944 | 4.0 | 21324 | 3.8 | 1 | 50 | 0.8 | 53 |
| SRP2265-C03 | 11519 | 4.4 | 24116 | 4.9 | 2.2 | 70 | 1.1 | 61 |
| SRP2265-C02 | 11248 | 4.3 | 17431 | 2.5 | 1.5 | 55 | 0.7 | 51 |
| SRP2265-A06 | 11072 | 5.7 | 22100 | 3.8 | 2.9 | 68 | 1.3 | 59 |

NK = no killing

TABLE 7B

Antibodies from ribosome and phage-display.

| Fab-HC Variant ID | Thermo-stability Fab TM2 (° C.) | Biacore, human BCMA-Fc | | | Biacore, cyno BCMA-Fc | | |
|---|---|---|---|---|---|---|---|
| | | $k_a$ (1/Ms) | $k_d$ (1/s) | $K_D$ (M) | $k_a$ (1/Ms) | $k_d$ (1/s) | $K_D$ (M) |
| SRP2137-C07 | 88.9 | 4.57E+05 | 7.45E−04 | 1.63E−09 | ND | ND | ND |
| SRP2265-F06 | 87.0 | 6.99E+05 | 1.93E−04 | 2.76E−10 | 3.47E+05 | 1.33E−03 | 3.84E−09 |
| SRP2265-F05 | 86.9 | 5.12E+05 | 2.40E−04 | 4.69E−10 | 2.60E+05 | 1.14E−03 | 4.39E−09 |
| SRP2265-F02 | 85.0 | 5.87E+05 | 2.93E−04 | 4.99E−10 | 3.15E+05 | 1.16E−03 | 3.68E−09 |
| SRP2265-B06 | 86.7 | 7.05E+05 | 3.85E−04 | 5.46E−10 | 3.54E+05 | 1.30E−03 | 3.67E−09 |
| SRP2265-A09 | 86.0 | 5.39E+05 | 3.18E−04 | 5.89E−10 | 2.70E+05 | 1.73E−03 | 6.43E−09 |
| SRP2265-F03 | 83.3 | 7.49E+05 | 4.74E−04 | 6.33E−10 | 3.46E+05 | 2.74E−03 | 7.90E−09 |
| SRP2265-E02 | 87.3 | 5.71E+05 | 3.83E−04 | 6.70E−10 | 2.66E+05 | 1.53E−03 | 5.75E−09 |
| SRP2265-D11 | 87.5 | 7.66E+05 | 5.37E−04 | 7.01E−10 | 3.58E+05 | 1.16E−03 | 3.24E−09 |
| SRP2265-D05 | 87.0 | 6.91E+05 | 4.85E−04 | 7.02E−10 | 3.25E+05 | 1.47E−03 | 4.53E−09 |
| SRP2265-C03 | 88.0 | 5.87E+05 | 4.25E−04 | 7.24E−10 | 3.04E+05 | 1.77E−03 | 5.83E−09 |
| SRP2265-C02 | 87.3 | 7.47E+05 | 5.67E−04 | 7.58E−10 | 3.25E+05 | 1.37E−03 | 4.22E−09 |
| SRP2265-A06 | 86.6 | 4.97E+05 | 3.92E−04 | 7.89E−10 | 2.49E+05 | 1.56E−03 | 6.24E−09 |

ND = not detected

TABLE 8A

Antibodies from ribosome and phage-display.

| Fab-HC Variant ID | NCI-H929 (BCMA + cells) cell binding | | 293T-cynoBCMA cell binding | | U266B1, SC225-conjugated 2° antibody cell killing | |
|---|---|---|---|---|---|---|
| | $B_{max}$ (MFI) | Kd (nM) | $B_{max}$ (MFI) | Kd (nM) | $EC_{50}$ (nM) | Span (%) |
| SRP2137-A05 | 2689 | 10.0 | 1906 | 18.3 | NK | NK |
| SRP2288-A03 | 16291 | 4.8 | 46759 | 1.8 | 2.3 | 42 |
| SRP2190-B01 | NSB | NSB | NSB | NSB | NK | NK |
| SRP2290-C08 | 37810 | 11.0 | 70959 | 2.3 | 1.1 | 73 |
| SRP2290-G01 | NSB | NSB | 77116 | 4.7 | 1.4 | 70 |
| SRP2290-A02 | 33585 | 4.9 | 70302 | 2.3 | 1.6 | 70 |
| SRP2290-C07 | NSB | NSB | 78098 | 6.7 | 0.93 | 75 |

TABLE 8A-continued

Antibodies from ribosome and phage-display.

| Fab-HC Variant ID | NCI-H929 (BCMA + cells) cell binding | | 293T-cynoBCMA cell binding | | U266B1, SC225-conjugated 2° antibody cell killing | |
|---|---|---|---|---|---|---|
| | $B_{max}$ (MFI) | Kd (nM) | $B_{max}$ (MFI) | Kd (nM) | $EC_{50}$ (nM) | Span (%) |
| SRP2290-D05 | 21841 | 4.6 | 57580 | 1.7 | 0.96 | 50 |
| SRP2290-D02 | 33647 | 19.2 | 75785 | 3.5 | 1.4 | 60 |
| SRP2213-A06 | 2506 | 5.3 | 3622 | 15.1 | NK | NK |
| SRP2291-D07 | 28671 | 3.8 | 67897 | 0.5 | 16 | 2.0 |
| SRP2291-G05 | 23164 | 1.4 | 62738 | 1.0 | 20 | 0.8 |
| SRP2291-E06 | 34417 | 5.8 | 68318 | 1.4 | 27 | 1.1 |
| SRP2291-F10 | 33846 | 5.4 | 66502 | 0.7 | 46 | 1.0 |
| SRP2291-A04 | 33916 | 5.0 | 63767 | 1.2 | 49 | 0.8 |
| SRP2291-A01 | 32503 | 4.9 | 67229 | 1.0 | 58 | 1.1 |

NK = no killing
NSB = non-saturating binding

TABLE 8B

Antibodies from ribosome and phage-display.

| Fab-HC Variant ID | huBCMA-Fc ELISA | | cynoBCMA-Fc ELISA | | Biacore, human BCMA-Fc kinetics | | | Thermo-stability |
|---|---|---|---|---|---|---|---|---|
| | $B_{max}$ | $EC_{50}$ (nM) | $B_{max}$ | $EC_{50}$ (nM) | $k_a$ (1/Ms) | $k_d$ (1/s) | $K_D$ (M) | Fab TM2 (° C.) |
| SRP2137-A05 | 3302000 | 0.52 | 2198000 | 419.2 | 1.41E+06 | 3.32E−03 | 2.36E−09 | 85.6 |
| SRP2288-A03 | 4245000 | 0.56 | 3022000 | 0.57 | 9.27E+05 | 5.16E−04 | 5.57E−10 | 81.1 |
| SRP2190-B01 | 3678000 | 0.3 | 2154000 | 19.3 | 1.36E+06 | 7.12E−04 | 5.23E−09 | 75.3 |
| SRP2290-C08 | 4334000 | 0.3 | 4135000 | 0.2 | 6.66E+05 | 2.52E−04 | 3.78E−10 | 80.3 |
| SRP2290-G01 | 4828000 | 0.3 | 4599000 | 0.3 | 7.14E+05 | 3.18E−04 | 4.45E−10 | 70.9 |
| SRP2290-A02 | 4871000 | 0.4 | 4471000 | 0.4 | 2.31E+05 | 1.31E−04 | 5.67E−10 | 84.8 |
| SRP2290-C07 | 4116000 | 0.2 | 3810000 | 0.2 | 3.61E+05 | 2.21E−04 | 6.12E−10 | 74.3 |
| SRP2290-D05 | 3943000 | 0.3 | 3606000 | 0.2 | 4.76E+05 | 4.46E−04 | 9.37E−10 | 81.2 |
| SRP2290-D02 | 4539000 | 0.3 | 3913000 | 0.2 | 2.92E+05 | 2.77E−04 | 9.49E−10 | 85.6 |
| SRP2213-A06 | 3685000 | 0.2 | 2230000 | 39.04 | 1.36E+06 | 2.83E−03 | 2.08E−09 | 87 |
| SRP2291-D07 | 4080000 | 0.03 | 3942000 | 0.03 | 4.37E+05 | 4.14E−04 | 9.48E−10 | 84.1 |
| SRP2291-G05 | 3906000 | 0.13 | 3385000 | 0.09 | 4.40E+05 | 4.23E−04 | 9.62E−10 | 85.7 |
| SRP2291-E06 | 4107000 | 0.21 | 3360000 | 0.13 | 4.68E+05 | 3.57E−04 | 7.63E−10 | 84.6 |
| SRP2291-F10 | 3724000 | 0.1 | 3432000 | 0.06 | 5.41E+05 | 9.65E−05 | 1.78E−10 | 84.7 |
| SRP2291-A04 | 4604000 | 0.23 | 4227000 | 0.2 | 4.87E+05 | 3.49E−04 | 7.16E−10 | 86.7 |
| SRP2291-A01 | 4999000 | 0.39 | 4772000 | 0.33 | 6.44E+05 | 2.82E−05 | 4.38E−11 | 82.3 |

TABLE 9A

Chicken HybriFree-derived antibodies.

| Fab-HC Variant ID | NCI-H929 (BCMA + cells) cell binding | | 293T-cynoBCMA cell binding | | 293T-ratBCMA cell binding | | Biacore, human BCMA-Fc kinetics | | |
|---|---|---|---|---|---|---|---|---|---|
| | $B_{max}$ (MFI) | Kd (nM) | $B_{max}$ (MFI) | Kd (nM) | $B_{max}$ (MFI) | Kd (nM) | $k_a$ (1/Ms) | $k_d$ (1/s) | $K_D$ (M) |
| 9A8 | 21148 | 32.99 | 17799 | 8.87 | NB | NB | not determined | not determined | not determined |
| 10G5 | 25759 | 65.84 | 24439 | 7.33 | NB | NB | not determined | not determined | not determined |
| 11D6 | 26365 | 47.55 | 27672 | 12.17 | NB | NB | 1.02E+06 | 3.18E−04 | 3.13E−10 |
| 10F4 | 18715 | 10.51 | 12768 | 5.94 | 410 | 5.47 | not detected | not detected | not detected |
| 9A5 | 19686 | 1.01 | 18234 | 0.64 | 2780 | 7.13 | not determined | not determined | not determined |
| 9E12 | 8137 | 0.52 | 13204 | 0.34 | 4692 | 2.61 | not determined | not determined | not determined |
| 9H1 | 6156 | 1 | 11443 | 0.39 | 3452 | 1.32 | not determined | not determined | not determined |
| 10H1 | 22498 | 0.36 | 21201 | 0.25 | 4353 | 0.39 | 6.14E+09 | 1.79E+01 | 2.92E−09 |
| 10E10 | 3435 | 4.67 | 4543 | 18.91 | 906 | 6.83 | not determined | not determined | not determined |

TABLE 9B

Chicken HybriFree-derived antibodies.

| Fab-HC Variant ID | ARP-1, SC239-conjugated 2° antibody cell killing | | U266B1, SC239-conjugated 2° antibody cell killing | |
|---|---|---|---|---|
| | EC50 (nM) | Span (%) | EC50 (nM) | Span (%) |
| 9A8 | 2.4 | 82 | 2.3 | 42 |
| 10G5 | 3.5 | 82 | 1.9 | 63 |
| 11D6 | 3.8 | 83 | 1.1 | 67 |
| 10F4 | 1 | 87 | 0.36 | 81 |
| 9A5 | 0.7 | 93 | 0.29 | 84 |
| 9E12 | 1.2 | 80 | 1.4 | 47 |
| 9H1 | 1.3 | 74 | 1.1 | 50 |
| 10H1 | 0.86 | 88 | 0.29 | 89 |
| 10E10 | 3 | 46 | 2.5 | 20 |

Example 5

Sequences

Table 10 provides sequences referred to herein.

TABLE 10

Sequences

| SEQ ID NO: | Molecule | Region | Scheme | Sequence |
|---|---|---|---|---|
| 1 | Human BCMA (Isoform 1, UniprotKB-Q02223) | | | MLQMAGQCSQNEYFDSLLHACIPCQLRCSSNTPPLTCQRYCNASVTNSVKGTNAILWTCLGLSLIISLAVFVLMFLLRKINSEPLKDEFKNTGSGLLGMANIDLEKSRTGDEIILPRGLEYTVEECTCEDCIKSKPKVDSDHCFPLPAMEEGATILVTTKTNDYCKSLPAALSATEIEKSISAR |
| 2 | Human BCMA (Isoform 2, UniprotKB-Q02223) | | | MLQMAGQCSQNEYFDSLLHACIPCQLRCSSNTPPLTCQRYCNARSGLLGMANIDLEKSRTGDEIILPRGLEYTVEECTCEDCIKSKPKVDSDHCFPLPAMEEGATILVTTKTNDYCKSLPAALSATEIEKSISAR |
| 3 | Cynomolgus BCMA (Predicted NCBI Reference Sequence: XP_001106892.1) | | | MLQMARQCSQNEYFDSLLHDCKPCQLRCSSTPPLTCQRYCNASMTNSVKGMNAILWTCLGLSLIISLAVFVLTFLLRKMSSEPLKDEFKNTGSGLLGMANIDLEKGRTGDEIVLPRGLEYTVEECTCEDCIKNKPKVDSDHCFPLPAMEEGATILVTTKTNDYCNSLSAALSVTEIEKSISAR |
| 4 | Murine BCMA (NBCI Reference Sequence: NP_035738.1) | | | MAQQCFHSEYFDSLLHACKPCHLRCSNPPATCQPYCDPSVTSSVKGTYTVLWIFLGLTLVLSLALFTISFLLRKMNPEALKDEPQSPGQLDGSAQLDKADTELTRIRAGDDRIFPRSLEYTVEECTCEDCVKSKPKGDSDHFFPLPAMEEGATILVTTKTGDYGKSSVPTALQSVMGMEKPTHTR |
| 5 | 2137-C07 | CDR-H1 | Chothia | GFNISGS |
| 6 | 2265-F06 | CDR-H1 | Chothia | GFNISYP |
| 7 | 2265-F05 | CDR-H1 | Chothia | GFNIIAP |
| 8 | 2265-F02 | CDR-H1 | Chothia | GFNISAP |
| 9 | 2265-B06 | CDR-H1 | Chothia | GFNIRVS |
| 10 | 2265-A09 | CDR-H1 | Chothia | GFNIIGP |
| 11 | 2265-F03 | CDR-H1 | Chothia | GFNIRGP |
| 12 | 2265-E02 | CDR-H1 | Chothia | GFNIYVS |
| 13 | 2265-D11 | CDR-H1 | Chothia | GFNISGP |
| 14 | 2265-C03 | CDR-H1 | Chothia | GFNISVP |
| 15 | 2265-C02 | CDR-H1 | Chothia | GFNIGVS |

TABLE 10-continued

Sequences

| SEQ ID NO: | Molecule | Region | Scheme | Sequence |
|---|---|---|---|---|
| 16 | 2265-A06 | CDR-H1 | Chothia | GFNIYRS |
| 17 | 2137-A05 | CDR-H1 | Chothia | GFNINNS |
| 18 | 2190-B01 | CDR-H1 | Chothia | GFNISSY |
| 19 | 2290-G01 | CDR-H1 | Chothia | GFNISPY |
| 20 | 2290-C07 | CDR-H1 | Chothia | GFNITYD |
| 21 | 2290-D05 | CDR-H1 | Chothia | GFNIASR |
| 22 | 2290-C08 | CDR-H1 | Chothia | GFNIQPY |
| 23 | 2290-A02 | CDR-H1 | Chothia | GFNISTR |
| 24 | 2291-G05 | CDR-H1 | Chothia | GFNIAAY |
| 25 | 2291-D07 | CDR-H1 | Chothia | GFNIKDT |
| 26 | 2291-F10 | CDR-H1 | Chothia | GFNIDPY |
| 27 | 9A8 | CDR-H1 | Chothia | GFTFSSF |
| 28 | 10F4 | CDR-H1 | Chothia | GFTFSGY |
| 29 | 9A5 | CDR-H1 | Chothia | GFSISDY |
| 30 | 9E12 | CDR-H1 | Chothia | GFTFSDY |
| 31 | 10E10 | CDR-H1 | Chothia | GFTFSSY |
| 32 | 2137-C07 | CDR-H1 | Kabat | GSGIH |
| 33 | 2265-F06 | CDR-H1 | Kabat | YPGIH |
| 34 | 2265-F05 | CDR-H1 | Kabat | APGIH |
| 35 | 2265-B06 | CDR-H1 | Kabat | VSGIH |
| 36 | 2265-A09 | CDR-H1 | Kabat | GPGIH |
| 37 | 2265-C03 | CDR-H1 | Kabat | VPGIH |
| 38 | 2265-A06 | CDR-H1 | Kabat | RSGIH |
| 39 | 2137-A05 | CDR-H1 | Kabat | NSYIH |
| 40 | 2288-A03 | CDR-H1 | Kabat | NSWIH |
| 41 | 2190-B01 | CDR-H1 | Kabat | SYWIH |
| 42 | 2290-G01 | CDR-H1 | Kabat | PYWIH |
| 43 | 2290-C07 | CDR-H1 | Kabat | YDWIH |
| 44 | 2290-D05 | CDR-H1 | Kabat | SRWIH |
| 45 | 2290-A02 | CDR-H1 | Kabat | TRWIH |
| 46 | 2213-A06 | CDR-H1 | Kabat | SYAIH |
| 47 | 2291-G05 | CDR-H1 | Kabat | AYTIH |
| 48 | 2291-E06 | CDR-H1 | Kabat | PYTIH |
| 49 | 2291-D07 | CDR-H1 | Kabat | DTYIH |
| 50 | 2291-A04 | CDR-H1 | Kabat | SYGIH |
| 51 | 9A8 | CDR-H1 | Kabat | SFNMF |
| 52 | 10F4 | CDR-H1 | Kabat | GYNMG |
| 53 | 9A5 | CDR-H1 | Kabat | DYGMG |

TABLE 10-continued

| SEQ ID NO: | Molecule | Region | Scheme | Sequence |
|---|---|---|---|---|
| 54 | 9E12 | CDR-H1 | Kabat | DYGLG |
| 55 | 10H1 | CDR-H1 | Kabat | GYGMG |
| 56 | 10E10 | CDR-H1 | Kabat | SYGMG |
| 57 | 2137-C07 | CDR-H2 | Chothia | NPAGGY |
| 58 | 2265-F03 | CDR-H2 | Chothia | SPAAGY |
| 59 | 2265-D11 | CDR-H2 | Chothia | NPAAGY |
| 60 | 2137-A05 | CDR-H2 | Chothia | YPYSGY |
| 61 | 2288-A03 | CDR-H2 | Chothia | YPYIGF |
| 62 | 2190-B01 | CDR-H2 | Chothia | TPSGGY |
| 63 | 2290-G01 | CDR-H2 | Chothia | TPPSGF |
| 64 | 2290-D02 | CDR-H2 | Chothia | TPAAGY |
| 65 | 2290-C07 | CDR-H2 | Chothia | TPFDGY |
| 66 | 2290-D05 | CDR-H2 | Chothia | TPSAGY |
| 67 | 2290-C08 | CDR-H2 | Chothia | TPPSGY |
| 68 | 2213-A06 | CDR-H2 | Chothia | SPYGGY |
| 69 | 2291-E06 | CDR-H2 | Chothia | FPSGGY |
| 70 | 2291-D07 | CDR-H2 | Chothia | SPYDGY |
| 71 | 9A8 | CDR-H2 | Chothia | RNDGNS |
| 72 | 10G5 | CDR-H2 | Chothia | SNDGSS |
| 73 | 11D6 | CDR-H2 | Chothia | RNDGRS |
| 74 | 10F4 | CDR-H2 | Chothia | TYGTGSY |
| 75 | 9A5 | CDR-H2 | Chothia | DHDGRY |
| 76 | 9E12 | CDR-H2 | Chothia | NSAGSG |
| 77 | 9H1 | CDR-H2 | Chothia | NSAGSD |
| 78 | 10E10 | CDR-H2 | Chothia | NSGGSSY |
| 79 | 2137-C07 | CDR-H2 | Kabat | FINPAGGYTDYADSVKG |
| 80 | 2265-F03 | CDR-H2 | Kabat | FISPAAGYTDYADSVKG |
| 81 | 2265-D11 | CDR-H2 | Kabat | FINPAAGYTDYADSVKG |
| 82 | 2137-A05 | CDR-H2 | Kabat | WIYPYSGYTNYADSVKG |
| 83 | 2288-A03 | CDR-H2 | Kabat | WIYPYIGFTEYADSVKG |
| 84 | 2190-B01 | CDR-H2 | Kabat | VITPSGGYTYYADSVKG |
| 85 | 2290-G01 | CDR-H2 | Kabat | VITPPSGFTYYADSVKG |
| 86 | 2290-D02 | CDR-H2 | Kabat | vITPAAGYTYYADSVKG |
| 87 | 2290-C07 | CDR-H2 | Kabat | VITPFDGYTYYADSVKG |
| 88 | 2290-D05 | CDR-H2 | Kabat | VITPSAGYTYYADSVKG |
| 89 | 2290-C08 | CDR-H2 | Kabat | VITPPSGYTYYADSVKG |
| 90 | 2290-A02 | CDR-H2 | Kabat | VITPSAGYTHYADSVKG |

TABLE 10-continued

Sequences

| SEQ ID NO: | Molecule | Region | Scheme | Sequence |
|---|---|---|---|---|
| 91 | 2213-A06 | CDR-H2 | Kabat | VISPYGGYTEYADSVKG |
| 92 | 2291-G05 | CDR-H2 | Kabat | WISPYGGYTEYADSVKG |
| 93 | 2291-E06 | CDR-H2 | Kabat | HIFPSGGYTDYADSVKG |
| 94 | 2291-D07 | CDR-H2 | Kabat | vlSPYDGYTEYADSVKG |
| 95 | 2291-F10 | CDR-H2 | Kabat | WISPYDGYTEYADSVKG |
| 96 | 2291-A04 | CDR-H2 | Kabat | FISPYDGYTEYADSVKG |
| 97 | 2291-A01 | CDR-H2 | Kabat | HISPYDGYTDYADSVKG |
| 98 | 9A8 | CDR-H2 | Kabat | YIRNDGNSASYGPAVKG |
| 99 | 10G5 | CDR-H2 | Kabat | YISNDGSSTSYGPAVKG |
| 100 | 11D6 | CDR-H2 | Kabat | YIRNDGRSTSYGPAVKG |
| 101 | h11D6-Hc4 | CDR-H2 | Kabat | YIRNDGRSTSYVDSVKG |
| 102 | h11D6-Hc3 | CDR-H2 | Kabat | YIRNDGRSTSYADSVKG |
| 103 | h11D6-Hc1 | CDR-H2 | Kabat | YIRNDGRSTSYAAPVKG |
| 104 | 10F4 | CDR-H2 | Kabat | GITYGTGSYTAYGAAVKG |
| 105 | h10F4-Hc4 | CDR-H2 | Kabat | GITYGTGSYTAYVDSVKG |
| 106 | h10F4-Hc3 | CDR-H2 | Kabat | GITYGTGSYTAYADSVKG |
| 107 | h10F4-Hc1 | CDR-H2 | Kabat | GITYGTGSYTAYAAPVKG |
| 108 | 9A5 | CDR-H2 | Kabat | RIDHDGRYTDYGAVVKG |
| 109 | 9E12 | CDR-H2 | Kabat | RINSAGSGTYYGSAVDG |
| 110 | 9H1 | CDR-H2 | Kabat | RINSAGSDTNYGSAVKG |
| 111 | 11H1 | CDR-H2 | Kabat | RINSAGSDTDYGAAVKG |
| 112 | 10E10 | CDR-H2 | Kabat | RINSGGSSYTDYGSAVKG |
| 113 | h10H1-Hc4 | CDR-H2 | Kabat | RINSAGSDTDYVDSVKG |
| 114 | h10H1-Hc3 | CDR-H2 | Kabat | RINSAGSDTDYADSVKG |
| 115 | h10H1-Hc1 | CDR-H2 | Kabat | RINSAGSDTDYAAPVKG |
| 116 | 2137-C07 | CDR-H3 | | DYVYQYWTYVLDY |
| 117 | 2265-F06 | CDR-H3 | | DYILQYWTYVLDY |
| 118 | 2265-F05 | CDR-H3 | | DYVNAYWTYVLDY |
| 119 | 2265-F02 | CDR-H3 | | DYIRQYWTYVLDY |
| 120 | 2265-B06 | CDR-H3 | | DYVQAYWTYVLDY |
| 121 | 2265-A09 | CDR-H3 | | DYVNYWTYVLDY |
| 122 | 2265-F03 | CDR-H3 | | DFVQSYWTYVLDY |
| 123 | 2265-D11 | CDR-H3 | | DYIYQYWTYVLDY |
| 124 | 2265-D05 | CDR-H3 | | DFVYAYWTYVLDY |
| 125 | 2265-C03 | CDR-H3 | | DYVPQYWTYVLDY |
| 126 | 2265-C02 | CDR-H3 | | DYIYSYWTYVLDY |
| 127 | 2137-A05 | CDR-H3 | | DYGPWYGTGVLDY |
| 128 | 2288-A03 | CDR-H3 | | DYDLRYLTGVLDY |

TABLE 10-continued

| SEQ ID NO: | Molecule | Region | Scheme | Sequence |
|---|---|---|---|---|
| 129 | 2190-B01 | CDR-H3 | | DLGGGYWVGFFDY |
| 130 | 2290-G01 | CDR-H3 | | DLGVGYWVGFSDY |
| 131 | 2290-D02 | CDR-H3 | | DLGHRYWVGVFDY |
| 132 | 2290-C07 | CDR-H3 | | DMGVGYWVGFSDY |
| 133 | 2290-D05 | CDR-H3 | | DLGYGYWVGFSDY |
| 134 | 2290-C08 | CDR-H3 | | DWGVGYWVGFSDY |
| 135 | 2290-A02 | CDR-H3 | | DLGSRYWVGVFDY |
| 136 | 2213-A06 | CDR-H3 | | DFYDRYSTYVLDY |
| 137 | 2291-G05 | CDR-H3 | | DFHDRYATFVLDY |
| 138 | 2291-E06 | CDR-H3 | | DFYDRYATYVLDY |
| 139 | 2291-F10 | CDR-H3 | | DYYDRYSTYVLDY |
| 140 | 2291-A04 | CDR-H3 | | DFNDRYFTYVLDY |
| 141 | 9A8 | CDR-H3 | | TTCIGSGGCIDT |
| 142 | 11D6 | CDR-H3 | | TTCVGSGGCIDT |
| 143 | 10F4 | CDR-H3 | | GGGLNSYGCSGANIDA |
| 144 | 9A5 | CDR-H3 | | GGGAASIDT |
| 145 | 9E12 | CDR-H3 | | GGGGASIDG |
| 146 | trastuzumab | CDR-L1 | | RASQDVNTAVA |
| 147 | 9A8 | CDR-L1 | | SGGSSDYG |
| 148 | 10G5 | CDR-L1 | | SGGNYDYG |
| 149 | 11D6 | CDR-L1 | | SGGNSDYG |
| 150 | 10F4 | CDR-L1 | | SGGGNYFGSYYYG |
| 151 | 9A5 | CDR-L1 | | SGGGNYVGGYYYG |
| 152 | 9E12 | CDR-L1 | | SGGGSYYGSYYYG |
| 153 | 10H1 | CDR-L1 | | SGGGNYYGSYYYG |
| 154 | 10E10 | CDR-L1 | | SGGGNYAGSYYYG |
| 155 | trastuzumab | CDR-L2 | | SASFLYS |
| 156 | 9A8 | CDR-L2 | | SNNQRPS |
| 157 | 10G5 | CDR-L2 | | YNNKRPS |
| 158 | 11D6 | CDR-L2 | | RNNQRPS |
| 159 | 10F4 | CDR-L2 | | NNNNRPS |
| 160 | 10E10 | CDR-L2 | | NSNNRPS |
| 161 | trastuzumab | CDR-L3 | | QQHYTTPPT |
| 162 | 9A8 | CDR-L3 | | ANVDYTDDV |
| 163 | 10G5 | CDR-L3 | | ANVDSTDDV |
| 164 | 11D6 | CDR-L3 | | GNVDFTDDV |
| 165 | h11D6-Lc4 | CDR-L3 | | GGFDSSSDAI |

TABLE 10-continued

Sequences

| SEQ ID NO: | Molecule | Region | Scheme | Sequence |
| --- | --- | --- | --- | --- |
| 166 | 10F4 | CDR-L3 | | GGFDSSTDAI |
| 167 | 2137-C07 | $V_H$ | | EVQLVESGGGLVQPGGSLRLSCAASGFN ISGSGIHWVRQAPGKGLEWVGFINPAGG YTDYADSVKGRFTISADTSKNTAYLQMN SLRAEDTAVYYCARDYVYQYWTYVLDYW GQGTLVTVSS |
| 168 | 2265-F06 | $V_H$ | | EVQLVESGGGLVQPGGSLRLSCAASGFN ISYPGIHWVRQAPGKGLEWVGFINPAGG YTDYADSVKGRFTISADTSKNTAYLQMN SLRAEDTAVYYCARDYILQYWTYVLDYW GQGTLVTVSS |
| 169 | 2265-F05 | $V_H$ | | EVQLVESGGGLVQPGGSLRLSCAASGFN IIAPGIHWVRQAPGKGLEWVGFINPAGG YTDYADSVKGRFTISADTSKNTAYLQMN SLRAEDTAVYYCARDYVNAYWTYVLDYW GQGTLVTVSS |
| 170 | 2265-F02 | $V_H$ | | EVQLVESGGGLVQPGGSLRLSCAASGFN ISAPGIHWVRQAPGKGLEWVGFINPAGG YTDYADSVKGRFTISADTSKNTAYLQMN SLRAEDTAVYYCARDYIRQYWTYVLDYW GQGTLVTVSS |
| 171 | 2265-B06 | $V_H$ | | EVQLVESGGGLVQPGGSLRLSCAASGFN IRVSGIHWVRQAPGKGLEWVGFINPAGG YTDYADSVKGRFTISADTSKNTAYLQMN SLRAEDTAVYYCARDYVQAYWTYVLDYW GQGTLVTVSS |
| 172 | 2265-A09 | $V_H$ | | EVQLVESGGGLVQPGGSLRLSCAASGFN IIGPGIHWVRQAPGKGLEWVGFINPAGG YTDYADSVKGRFTISADTSKNTAYLQMN SLRAEDTAVYYCARDYVNYWTYVLDYW GQGTLVTVSS |
| 173 | 2265-F03 | $V_H$ | | EVQLVESGGGLVQPGGSLRLSCAASGFN IRGPGIHWVRQAPGKGLEWVGFISPAAG YTDYADSVKGRFTISADTSKNTAYLQMN SLRAEDTAVYYCARDFVQSYWTYVLDYW GQGTLVTVSS |
| 174 | 2265-E02 | $V_H$ | | EVQLVESGGGLVQPGGSLRLSCAASGFN IYVSGIHWVRQAPGKGLEWVGFINPAGG YTDYADSVKGRFTISADTSKNTAYLQTN SLRAEDTAVYYCARDYVYQYWTYVLDYW GQGTLVTVSS |
| 175 | 2265-D11 | $V_H$ | | EVQLVESGGGLVQPGGSLRLSCAASGFN ISGPGIHWVRQAPGKGLEWVGFINPAAG YTDYADSVKGRFTISADTSKNTAYLQMN SLRAEDTAVYYCARDYIYQYWTYVLDYW GQGTLVTVSS |
| 176 | 2265-D05 | $V_H$ | | EVQLVESGGGLVQPGGSLRLSCAASGFN ISGPGIHWVRQAPGKGLEWVGFINPAAG YTDYADSVKGRFAISADTSKNTAYLQMN SLRAEDTAVYYCARDFVYAYWTYVLDYW GQGTLVTVSS |
| 177 | 2265-C03 | $V_H$ | | EVQLVESGGGLVQPGGSLRLSCAAPGFN ISVPGIHWVRQAPGKGLEWVGFINPAGG YTDYADSVKGRFTISADTSKNTAYLQMN SLRAEDTAVYYCARDYVPQYWTYVLDYW GQGTLVTVSS |
| 178 | 2265-C02 | $V_H$ | | EVQLVESGGGLVQPGGSLRLSCAASGFN IGVSGIHWVRQAPGKGLEWVGFINPAGG YTDYAGSVKGRFTISADTSKNTAYLQMN SLRAEDTAVYYCARDYTSYWTYVLDYW GQGTLVTVSS |

TABLE 10-continued

Sequences

| SEQ ID NO: | Molecule | Region | Scheme | Sequence |
|---|---|---|---|---|
| 179 | 2265-A06 | $V_H$ | | EVQLVESGGGLVQPGGSLRLSCAASGFN IYRSGIHWVRQAPGKGLEWVGINPAGG YTDYADSVKGRFTISADTSKNTAYLQMN SLRAEDTAVYYCARDYVPQYWTYVLDYW GQGTLVTVSS |
| 180 | 2137-A05 | $V_H$ | | EVQLVESGGGLVQPGGSLRLSCAASGFN INNSYIHWVRQAPGKGLEWVGWIYPYSG YTNYADSVKGRFTISADTSKNTAYLQMN SLRAEDTAVYYCARDYGPWYGTGVLDYW GQGTLVTVSS |
| 181 | 2288-A03 | $V_H$ | | EVQLVESGGGLVQPGGSLRLSCAASGFN INNSWIHWVRQAPGKGLEWVGWIYPYIG FTEYADSVKGRFTISADTSKNTAYLQMN SLRAEDTAVYYCARDYDLRYLTGVLDYW GQGTLVTVSS |
| 182 | 2190-B01 | $V_H$ | | EVQLVESGGGLVQPGGSLRLSCAASGFN ISSYWIHWVRQAPGKGLEWVGITPSGG YTYYADSVKGRFTISADTSKNTAYLQMN SLRAEDTAVYYCARDLGGGYWVGFFDYW GQGTLVTVSS |
| 183 | 2290-G01 | $V_H$ | | EVQLVESGGGLVQPGGSLRLSCAASGFN ISPYWIHWVRQAPGKGLEWVGITPPSG FTYYADSVKGRFTISADTSKNTAYLQVN SLRAEDTAVYYCARDLGVGYWVGFSDYW GQGTLVTVSS |
| 184 | 2290-D02 | $V_H$ | | EVQLVESGGGLVQPGGSLRLSCAASGFN ISSYWIHWVRQAPGKGLEWMGVITPAAG YTYYADSVKGRFTISADTSKNTAYLQMN SLRAEDTAVYYCARDLGHRYWVGVFDYW GQGTLVTVSS |
| 185 | 2290-C07 | $V_H$ | | EVQLVESGGGLVQPGGSLRLSCAASGFN ITYDWIHWVRQAPGKGLEWVGITPFDG YTYYADSVKGHFTISADTSKNTAYLQMN SLRAEDTAVYYCARDMGVGYWVGFSDYW GQGTLVTVSS |
| 186 | 2290-D05 | $V_H$ | | EVQLVESGGGLVQPGGSLRLSCAASGFN IASRWIHWVRQAPGKGLEWVGITPSAG YTYYADSVKGRFTISADTSKNTAYLQMN SLRAEDTAVYYCARDLGYGYWVGFSDYW GQGTLVTVSS |
| 187 | 2290-C08 | $V_H$ | | EVQLVESGGGLVQPGGSLRLSCAASGFN IQPYWIHWVRQAPGKGLEWVGITPPSG YTYYADSVKGRFTISADTSKNTAYLQMN SLRAEDTAVYYCARDWGVGYWVGFSDYW GQGTLVTVSS |
| 188 | 2290-A02 | $V_H$ | | EVQLVESGGGLVQPGGSLRLSCAASGFN ISTRWIHWVRQAPGKGLEWVGITPSAG YTHYADSVKGRFTISAGTSKNTAYLQMN SLRAEDTAVYYCARDLGSRYWVGVFDYW GQGTLVTVSS |
| 189 | 2213-A06 | $V_H$ | | EVQLVESGGGLVQPGGSLRLSCAASGFN ISSYAIHWVRQAPGKGLEWVGVISPYGG YTEYADSVKGRFTISADTSKNTAYLQMN SLRAEDTAVYYCARDFYDRYSTYVLDYW GQGTLVTVSS |
| 190 | 2291-G05 | $V_H$ | | EVQLVESGGGLVQPGGSLRLSCAASGFN IAAYTIHWVRQAPGKGLEWVGWISPYGG YTEYADSVKGRFTISADTSKNTAYLQMN SLRAEDTAVYYCARDFHDRYATFVLDYW GQGTLVTVSS |

TABLE 10-continued

Sequences

| SEQ ID NO: | Molecule | Region | Scheme | Sequence |
|---|---|---|---|---|
| 191 | 2291-E06 | $V_H$ | | EVQLVESGGGLVQPGGSLRLSCAASGFN ISPYTIHWVRQAPGKGLEWVAHIFPSGG YTDYADSVKGRFTISADTSKNTAYLQMN SLRAEDTAVYYCARDFYDRYATYVLDYW GQGTLVTVSS |
| 192 | 2291-D07 | $V_H$ | | EVQLVESGGGLVQPGGSLRLSCAASGFN IKDTYIHWVRQAPGKGLEWVGVISPYDG YTEYADSVKGRFTISADTSKNTAYLQMN SLRAEDTAVYYCAHDFYDRYSTYVLDYW GQGTLVTVSS |
| 193 | 2291-F10 | $V_H$ | | EVQLVESGGGLVQPGGSLRLSCAASGFN IDPYTIHWVRQAPGKGLEWVGWISPYDG YTEYADSVKGRFTISADTSKNTAYLQMN SLRAEDTAVYYCARDYYDRYSTYVLDYW GRGTLVTVSS |
| 194 | 2291-A04 | $V_H$ | | EVQLVESGGGLVQPGGSLRLSCAASGFN ISSYGIHWVRQAPGKGLEWVGFISPYDG YTEYADSVKGRFTISAGTSKNTAYLQMN SLRAEDTAVYYCARDFNDRYFTYVLDYW GQGTLVTVSS |
| 195 | 2291-A01 | $V_H$ | | EVQLVESGGGLVQPGGSLRLSCAASGFN IDPYTIHWARQAPGKGLEWVAHISPYDG YTDYADSVKGRFTISADTSKNTAYLQMN SLRAEDTAVYYCARDFYDRYSTYVLDYW GQGTLVTVSS |
| 196 | 9A8 | $V_H$ | | AVTLDESGGGLQTPGGTLSLVCKASGFT FSSFNMFWVRQAPGKGLEWVAYIRNDGN SASYGPAVKGRATISRDNGQSTVRLQLN NLRAEDTATYYCAKTTCIGSGGCIDTWG HGTEVIVSS |
| 197 | 10G5 | $V_H$ | | AVTLDESGGGLQTPGGVLSLVCKASGFT FSSFNMFWVRQAPGKGLEWVAYISNDGS STSYGPAVKGRATISRDNGQSTVRLQLN NLRAEDTATYFCAKTTCIGSGGCIDTWG HGTEVIVSS |
| 198 | 11D6 | $V_H$ | | AVTLDESGGGLQTPGGTLSLVCKASGFT FSSFNMFWVRQAPGEGLEWVAYIRNDGR STSYGPAVKGRATISRDNGQSTVRLQLN NLRAEDTGTYFCAKTTCVGSGGCIDTWG HGTEVIVSS |
| 199 | h11D6-HC4 | $V_H$ | | EVQLVESGGGLVQPGGSLRLSCAASGFT FSSFNMFWVRQAPGKGLEWVAYIRNDGR STSYVDSVKGRFTISRDNAKSSVYLQMN SLRAEDTAVYYCAKTTCVGSGGCIDTWG QGTLVTVSS |
| 200 | h11D6-HC3 | $V_H$ | | QVQLVESGGGVVQPGRSLRLSCAASGFT FSSFNMFWVRQAPGKGLEWVAYIRNDGR STSYADSVKGRFTISRDNSKSTVYLQMN SLRAEDTAVYYCAKTTCVGSGGCIDTWG QGTLVTVSS |
| 201 | h11D6-HC2 | $V_H$ | | EVQLLESGGGLVQPGGSLRLSCAASGFT FSSFNMFWVRQAPGKGLEWVAYIRNDGR STSYADSVKGRFTISRDNSKSTVYLQMN SLRAEDTAVYYCAKTTCVGSGGCIDTWG QGTLVTVSS |
| 202 | h11D6-HC1 | $V_H$ | | EVQLVESGGGLVKPGGSLRLSCAASGFT FSSFNMFWVRQAPGKGLEWVAYIRNDGR STSYAAPVKGRFTISRDNSKSTVYLQMN SLKTEDTAVYYCAKTTCVGSGGCIDTWG QGTLVTVSS |

TABLE 10-continued

Sequences

| SEQ ID NO: | Molecule | Region | Scheme | Sequence |
|---|---|---|---|---|
| 203 | 10F4 | $V_H$ | | AVTLDESGGGLQTPGGALSLVCKASGFTFSGYNMGWVRQAPGKGLEYVAGITYGTGSYTAYGAAVKGRATISRDNGQSTLRLQLNNLRAEDTATYYCARGGGLNSYGCSGANIDAWGHGTEVIVSS |
| 204 | h10F4-HC4 | $V_H$ | | EVQLVESGGGLVQPGGSLRLSCAASGFTFSGYNMGWVRQAPGKGLEWVAGITYGTGSYTAYVDSVKGRFTISRDNAKSSLYLQMNSLRAEDTAVYYCARGGGLNSYGCSGANIDAWGQGTLVTVSS |
| 205 | h10F4-HC3 | $V_H$ | | QVQLVESGGGVVQPGRSLRLSCAASGFTFSGYNMGWVRQAPGKGLEWVAGITYGTGSYTAYADSVKGRFTISRDNSKSTLYLQMNSLRAEDTAVYYCARGGGLNSYGCSGANIDAWGQGTLVTVSS |
| 206 | h10F4-HC2 | $V_H$ | | EVQLLESGGGLVQPGGSLRLSCAASGFTFSGYNMGWVRQAPGKGLEWVAGITYGTGSYTAYADSVKGRFTISRDNSKSTLYLQMNSLRAEDTAVYYCARGGGLNSYGCSGANIDAWGQGTLVTVSS |
| 207 | h10F4-HC1 | $V_H$ | | EVQLVESGGGLVKPGGSLRLSCAASGFTFSGYNMGWVRQAPGKGLEWVAGITYGTGSYTAYAAPVKGRFTISRDNSKSTLYLQMNSLKTEDTAVYYCARGGGLNSYGCSGANIDAWGQGTLVTVSS |
| 208 | 9A5 | $V_H$ | | AVTLDESGGGLQTPGGAVSLVCKASGFSISDYGMGWMRQAPGKGLQYVARIDHDGRYTDYGAVVKGRATISRDNGQSTVRLQLNNLRAEDTGTYYCTRGGGAASIDTWGHGTEVIVSS |
| 209 | 9E12 | $V_H$ | | AVTLDESGGGLQTPGGGLSLVCKASGFTFSDYGLGWMRQAPGKGLEYVARINSAGSGTYYGSAVDGRATISRDNGQSTVRLQLNNLRAEDTGTYYCTRGGGASIDGWGHGTEVIVSS |
| 210 | 9H1 | $V_H$ | | AVTLDESGGGLQTPGGALSLVCKGSGFTFSDYGMGWMRQAPGKGLQYVARINSAGSDTNYGSAVKGRATISRDDGQSTVRLQLSSLRAEDTGIYYCTRGGGASIDGWGHGTEVIVSS |
| 211 | 10H1 | $V_H$ | | AVTLDESGGGLQTPGGALSLVCKASGFTFSGYGMGWMRQAPGKGLEYVARINSAGSDTDYGAAVKGRATISRDNGQSTVRLQLNNLRAEDTATYFCTRGGGASIDGWGHGTEVIVSS |
| 212 | 10E10 | $V_H$ | | AVTLDESGGGLQTPGGGLSLVCKASGFTFSSYGMGWMRQAPGKGLEFVARINSGGSSYTDYGSAVKGRATISRDDGQSTVRLQLNNLRAEDTGIYYCTRGGGASIDGWGHGTEVIVSS |
| 213 | h10H1-HC4 | $V_H$ | | EVQLVESGGGLVQPGGSLRLSCAASGFTFSGYGMGWVRQAPGKGLEWVARINSAGSDTDYVDSVKGRFTISRDNAKSSVYLQMNSLRAEDTAVYYCTRGGGASIDGWGQGTLVTVSS |
| 214 | h10H1-HC3 | $V_H$ | | QVQLVESGGGVVQPGRSLRLSCAASGFTFSGYGMGWVRQAPGKGLEWVARINSAGSDTDYADSVKGRFTISRDNSKSTVYLQMNSLRAEDTAVYYCTRGGGASIDGWGQGTLVTVSS |

TABLE 10-continued

Sequences

| SEQ ID NO: | Molecule | Region | Scheme | Sequence |
|---|---|---|---|---|
| 215 | h10H1-HC2 | $V_H$ | | EVQLLESGGGLVQPGGSLRLSCAASGFTFSGYGMGWVRQAPGKGLEWVARINSAGSDTDYADSVKGRFTISRDNSKSTVYLQMNSLRAEDTAVYYCTRGGGASIDGWGQGTLVTVSS |
| 216 | h10H1-HC1 | $V_H$ | | EVQLVESGGGLVKPGGSLRLSCAASGFTFSGYGMGWVRQAPGKGLEWVARINSAGSDTDYAAPVKGRFTISRDNSKSTVYLQMNSLKTEDTAVYYCTRGGGASIDGWGQGTLVTVSS |
| 217 | trastuzumab | $V_L$ | | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIK |
| 218 | 9A8 | $V_L$ | | ALTQPSSVSANPGETVKITCSGGSSDYGWFQQKSPGSAPVTVIYSNNQRPSGIPSRFSGSKSGSTGTLTITGVQAEDEAIYYCANVDYTDDVFGAGTTLTVL |
| 219 | 10G5 | $V_L$ | | ALTQPSSVSANPGETVKITCSGGNYDYGWYQQKSPGSAPVTLIYYNNKRPSDIPSRFSGSKSGSTGTLTITGVQAEDEAIYYCANVDSTDDVFGAGTTLTVL |
| 220 | 11D6 | $V_L$ | | ALTQPSSVSANPGETVEITCSGGNSDYGWFQQKSPGSAPVTVIYRNNQRPSDIPSRFSGSGSGSTNTLTITGVQAEDEAIYYCGNVDFTDDVFGAGTTLTVL |
| 221 | h11D6-LC4 | $V_L$ | | SYVLTQPPSVSVAPGKTARITCSGGNSDYGWYQQKPGQAPVLVVYRNNQRPSGIPERFSGSGSGSTNTLTISGTQAMDEADYYCGGFDSSSDAIFGGGTKLTVL |
| 222 | h11D6-LC3 | $V_L$ | | SYELTQPPSVSVSPGQTASITCSGGNSDYGWYQQKPGQSPVLVIYRNNQRPSGIPERFSGSGSGSTNTLTISGTQAMDEADYYCGGFDSSSDAIFGGGTKLTVL |
| 223 | h11D6-LC2 | $V_L$ | | QSVLTQPPSVSAAPGQKVTISCSGGNSDYGWYQQLPGTAPKLLIYRNNQRPSGIPDRFSGSGSGSTNTLGITGLQTGDEADYYCGGFDSSSDAIFGGGTKLTVL |
| 224 | h11D6-LC1 | $V_L$ | | DIQMTQSPSSVSASVGDRVTITCSGGNSDYGWYQQKPGKAPKLLIYRNNQRPSGVPSRFSGSGSGSTNTLTISSLQPEDFATYYCGGFDSSSDAIFGQGTKVEIK |
| 225 | 10F4 | $V_L$ | | ALTQPSSVSANLGGTVKITCSGGGNYFGSYYYGWYQQKAPGSAPVTVIYNNNNRPSDIPSRFSGSTSGSTSTLTISGVRAEDEAVYFCGGFDSSTDAIFGAGTTLTVL |
| 226 | h10F4-LC4 | $V_L$ | | SYVLTQPPSVSVAPGKTARITCSGGGNYFGSYYYGWYQQKPGQAPVLVVYNNNNRPSGIPERFSGSTSGSTSTLTISGTQAMDEADYYCGGFDSSTDAIFGGGTKLTVL |
| 227 | h10F4-LC3 | $V_L$ | | SYELTQPPSVSVSPGQTASITCSGGGNYFGSYYYGWYQQKPGQSPVLVIYNNNNRPSGIPERFSGSTSGSTSTLTISGTQAMDEADYYCGGFDSSTDAIFGGGTKLTVL |
| 228 | h10F4-LC2 | $V_L$ | | QSVLTQPPSVSAAPGQKVTISCSGGGNYFGSYYYGWYQQLPGTAPKLLIYNNNNRPSGIPDRFSGSTSGSTSTLGITGLQTGDEADYYCGGFDSSTDAIFGGGTKLTVL |

TABLE 10-continued

Sequences

| SEQ ID NO: | Molecule | Region | Scheme | Sequence |
|---|---|---|---|---|
| 229 | h10F4-LC1 | $V_L$ | | DIQMTQSPSSVSASVGDRVTITCSGGGN YFGSYYYGWYQQKPGKAPKLLIYNNNNR PSGVPSRFSGSTSGSTSTLTISSLQPED FATYYCGGFDSSTDAIFGQGTKVEIK |
| 230 | 9A5 | $V_L$ | | ALTQPSSVSANPGETVKITCSGGGNYVG GYYYGWYQQKAPGSALVTLIYNNNNRPS NIPSRFSGSTSGSTSTLTITGVRAEDEA VYFCGSFDSSTDAIFGAGTTLTVL |
| 231 | 9E12 | $V_L$ | | ALTQPSSVSANPGETVKITCSGGGSYYG SYYYGWYQQKSPGSAPVTLIYNNNNRPS DIPSRFSGSTSGSTGTLTITGVRAEDEA VYYCGSFDSSTDAIFGAGTTLTVL |
| 232 | 9H1 | $V_L$ | | ALTQPSSVSANPGETVKITCSGGGSYYG SYYYGWYQQKSPGSAPVTLIYNNNNRPS DIPSRFSGSTSGSTGTLTITGVRAEDEA VYYCGSFDSSTDAIFGAGTTLTVL |
| 233 | 10H1 | $V_L$ | | ALTQPSSVSANPGETVKITCSGGGNYYG SYYYGWYQQKAPGSAPVTIYNNNNRPS NIPSRFSGSKSGSTGTLTITGVQAEDEA VYFCGGFDSSSDAIFGAGTTLTVL |
| 234 | 10E10 | $V_L$ | | ALTQPSSVSANPGETVKITCSGGGNYAG SYYYGWYQQKSPGSAPLTVIYNSNNRPS DIPSRFSGSLSGSTGTLTITGVRAEDEA VYFCGGFDSSTDAIFGAGTTLTVL |
| 235 | h10H1-LC4 | $V_L$ | | SYVLTQPPSVSVAPGKTARITCSGGGNY YGSYYYGWYQQKPGQAPVLVVYNNNNRP SGIPERFSGSKSGSTGTLTISGTQAMDE ADYYCGGFDSSSDAIFGGGTKLTVL |
| 236 | h10H1-LC3 | $V_L$ | | SYELTQPPSVSVSPGQTASITCSGGGNY YGSYYYGWYQQKPGQSPVLVIYNNNNRP SGIPERFSGSKSGSTGTLTISGTQAMDE ADYYCGGFDSSSDAIFGGGTKLTVL |
| 237 | h10H1-LC2 | $V_L$ | | QSVLTQPPSVSAAPGQKVTISCSGGGNY YGSYYYGWYQQLPGTAPKLLIYNNNNRP SGIPDRFSGSKSGSTGTLGITGLQTGDE ADYYCGGFDSSSDAIFGGGTKLTVL |
| 238 | h10H1-LC1 | $V_L$ | | DIQMTQSPSSVSASVGDRVTITCSGGGN YYGSYYYGWYQQKPGKAPKLLIYNNNNR PSGVPSRFSGSKSGSTGTLTISSLQPED FATYYCGGFDSSSDAIFGQGTKVEIK |
| 239 | Human IgG1 HC Constant | | | ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCDKTHTCPPC PAPELLGGPSVFLFPPKPKDTLMISRTP EVTCVVVDVSHEDPEVKFNWYVDGVEVH NAKTKPREEQYNSTYRVVSVLTVLHQDW LNGKEYKCKVSNKALPAPIEKTISKAKG QPREPQVYTLPPSREEMTKNQVSLTCLV KGFYPSDIAVEWESNGQPENNYKTTPPV LDSDGSFFLYSKLTVDKSRWQQGNVFSC SVMHEALHNHYTQKSLSLSPGK |
| 240 | Human IgG LC Constant Ckappa | | | RTVAAPSVFIFPPSDEQLKSGTASVVCL LNNFYPREAKVQWKVDNALQSGNSQESV TEQDSKDSTYSLSSTLTLSKADYEKHKV YACEVTHQGLSSPVTKSFNRGEC |
| 241 | Mouse IgG1 HC Constant | | | AKTTPPSVYPLAPGSAAQTNSMVTLGCL VKGYFPEPVTVTWNSGSLSSGVHTFPAV LQSDLYTLSSSVTVPSSTWPSETVTCNV AHPASSTKVDKKIVPRDCGCKPCICTVP EVSSVFIFPPKPKDVLTITLTPKVTCVV VDISKDDPEVQFSWFVDDVEVHTAQTQP |

TABLE 10-continued

Sequences

| SEQ ID NO: | Molecule | Region | Scheme | Sequence |
|---|---|---|---|---|
| | | | | REEQFNSTFRSVSELPIMHQDWLNGKEF KCRVNSAAFPAPIEKTISKTKGRPKAPQ VYTIPPPKEQMAKDKVSLTCMITDFFPE DITVEWQWNGQPAENYKNTQPIMDTDGS YFVYSKLNVQKSNWEAGNTFTCSVLHEG LHNHHTEKSLSHSPG |
| 242 | Mouse IgG LC Constant Ckappa | | | RADAAPTVSIFPPSSEQLTSGGASVVCF LNNFYPKDINVKWKIDGSERQNGVLNSW TDQDSKDSTYSMSSTLTLTKDEYERHNS YTCEATHKTSTSPIVKSFNRNEC |
| 243 | Kappa LC | | | HMTVAAPSVFIFPPSDEQLKSGTASVVC LLNNFYPREAKVQWKVDNALQSGNSQES VTEQDSKDSTYSLSSTLTLSKADYEKHK VYACEVTHQGLSSPVTKSFNRGEC |
| 244 | Lambda LD | | | GQPKAAPSVTLFPPSSEELQANKATLVC LISDFYPGAVTVAWKADSSPVKAGVETT TPSKQSNNKYAASSYLSLTPEQWKSHRS YSCQVTHEGSTVEKTVAPTECS |
| 245 | FlagHis Tag | | | GSGDYKDDDDKGSGHHHHHH |
| 246 | Linker | | | GGGGSGGGGSGGGGS |
| 247 | Linker | | | AAGSDQEPKSS |

TABLE 11 provides sequences referred to herein.

| | SEQ ID NO | CDR H1 Chothia | SEQ ID NO | CDR H1 Kabat | SEQ ID NO | CDR H2 Chothia | SEQ ID NO | CDR H2 Kabat | SEQ ID NO | CDR H3 |
|---|---|---|---|---|---|---|---|---|---|---|
| 2137-C07 | 5 | GFNISGS | 32 | GSGIH | 57 | NPAGGY | 79 | FINPAGGYTDYADSVKG | 116 | DYVYQYWTYVLDY |
| 2265-F06 | 6 | GFNISYP | 33 | YPGIH | 57 | NPAGGY | 79 | FINPAGGYTDYADSVKG | 117 | DYILQYWTYVLDY |
| 2265-F05 | 7 | GFNIIAP | 34 | APGIH | 57 | NPAGGY | 79 | FINPAGGYTDYADSVKG | 118 | DYVNAYWTYVLDY |
| 2265-F02 | 8 | GFNISAP | 34 | APGIH | 57 | NPAGGY | 79 | FINPAGGYTDYADSVKG | 119 | DYIRQYWTYVLDY |
| 2265-B06 | 9 | GFNIRVS | 35 | VSGIH | 57 | NPAGGY | 79 | FINPAGGYTDYADSVKG | 120 | DYVQAYWTYVLDY |
| 2265-A09 | 10 | GFNIIGP | 36 | GPGIH | 57 | NPAGGY | 79 | FINPAGGYTDYADSVKG | 121 | DYVYNYWTYVLDY |
| 2265-F03 | 11 | GFNIRGP | 36 | GPGIH | 58 | SPAAGY | 80 | FISPAAGYTDYADSVKG | 122 | DFVQSYWTYVLDY |
| 2265-E02 | 12 | GFNIYVS | 35 | VSGIH | 57 | NPAGGY | 79 | FINPAGGYTDYADSVKG | 116 | DYVYQYWTYVLDY |
| 2265-D11 | 13 | GFNISGP | 36 | GPGIH | 59 | NPAAGY | 81 | FINPAAGYTDYADSVKG | 123 | DYIYQYWTYVLDY |
| 2265-D05 | 13 | GFNISGP | 36 | GPGIH | 59 | NPAAGY | 81 | FINPAAGYTDYADSVKG | 124 | DFVYAYWTYVLDY |
| 2265-C03 | 14 | GFNISVP | 37 | VPGIH | 57 | NPAGGY | 79 | FINPAGGYTDYADSVKG | 125 | DYVPQYWTYVLDY |
| 2265-C02 | 15 | GFNIGVS | 35 | VSGIH | 57 | NPAGGY | 79 | FINPAGGYTDYADSVKG | 126 | DYIYSYWTYVLDY |
| 2265-A06 | 16 | GFNIYRS | 38 | RSGIH | 57 | NPAGGY | 79 | FINPAGGYTDYADSVKG | 125 | DYVPQYWTYVLDY |
| 2137-A05 | 17 | GFNINNS | 39 | NSYIH | 60 | YPYSGY | 82 | WIYPYSGYTNYADSVKG | 127 | DYGPWYGTGVLDY |
| 2288-A03 | 17 | GFNINNS | 40 | NSWIH | 61 | YPYIGF | 83 | WIYPYIGFTEYADSVKG | 128 | DYDLRYLTGVLDY |
| 2190-B01 | 18 | GFNISSY | 41 | SYWIH | 62 | TPSGGY | 84 | VITPSGGYTYADSVKG | 129 | DLGGGYWVGFFDY |
| 2290-G01 | 19 | GFNISPY | 42 | PYWIH | 63 | TPPSGF | 85 | VITPPSGFTYADSVKG | 130 | DLGVGYWVGFSDY |
| 2290-D02 | 19 | GFNISSY | 41 | SYWIH | 64 | TPAAGY | 86 | VITPAAGYTYYADSVKG | 131 | DLGHRYWVGVFDY |

TABLE 11-continued provides sequences referred to herein.

|  | SEQ ID NO | CDR H1 Chothia | SEQ ID NO | CDR H1 Kabat | SEQ ID NO | CDR H2 Chothia | SEQ ID NO | CDR H2 Kabat | SEQ ID NO | CDR H3 |
|---|---|---|---|---|---|---|---|---|---|---|
| 2290-C07 | 20 | GFNITYD | 43 | YDWIH | 65 | TPFDGY | 87 | VITPFDGYTYYADSVKG | 132 | DMGVGYWVGFSDY |
| 2290-D05 | 21 | GFNIASR | 44 | SRWIH | 66 | TPSAGY | 88 | VITPSAGYTYYADSVKG | 133 | DLGYGYWVGFSDY |
| 2290-C08 | 22 | GFNIQPY | 42 | PYWIH | 67 | TPPSGY | 89 | VITPPSGYTYYADSVKG | 134 | DWGVGYWVGFSDY |
| 2290-A02 | 23 | GFNISTR | 45 | TRWIH | 66 | TPSAGY | 90 | VITPSAGYTHYADSVKG | 135 | DLGSRYWVGVFDY |
| 2213-A06 | 18 | GFNISSY | 46 | SYAIH | 68 | SPYGGY | 91 | VISPYGGYTEYADSVKG | 136 | DFYDRYSTYVLDY |
| 2291-G05 | 24 | GFNIAAY | 47 | AYTIH | 68 | SPYGGY | 92 | WISPYGGYTEYADSVKG | 137 | DFHDRYATFVLDY |
| 2291-E06 | 19 | GFNISPY | 48 | PYTIH | 69 | FPSGGY | 93 | HIFPSGGYTDYADSVKG | 138 | DFYDRYATYVLDY |
| 2291-D07 | 25 | GFNIKDT | 49 | DTYIH | 70 | SPYDGY | 94 | VISPYDGYTEYADSVKG | 136 | DFYDRYSTYVLDY |
| 2291-F10 | 26 | GFNIDPY | 48 | PYTIH | 70 | SPYDGY | 95 | WISPYDGYTEYADSVKG | 139 | DYYDRYSTYVLDY |
| 2291-A04 | 18 | GFNISSY | 50 | SYGIH | 70 | SPYDGY | 96 | FISPYDGYTEYADSVKG | 140 | DFNDRYFTYVLDY |
| 2291-A01 | 26 | GFNIDPY | 48 | PYTIH | 70 | SPYDGY | 97 | HISPYDGYTDYADSVKG | 136 | DFYDRYSTYVLDY |
| 9A8 | 27 | GFTFSSF | 51 | SFNMF | 71 | RNDGNS | 98 | YIRNDGNSASYGPAVKG | 141 | TTCIGSGGCIDT |
| 10g5 | 27 | GFTFSSF | 51 | SFNMF | 72 | SNDGSS | 99 | YISNDGSSTSYGPAVKG | 142 | TTCVGSGGCIDT |
| 11D6 | 27 | GFTFSSF | 51 | SFNMF | 73 | RNDGRS | 100 | YIRNDGRSTSYGPAVKG | 142 | TTCVGSGGCIDT |
| H11D6-HC4 | 27 | GFTFSSF | 51 | SFNMF | 73 | RNDGRS | 101 | YIRNDGRSTSYVDSVKG | 142 | TTCVGSGGCIDT |
| H11D6-HC3 | 27 | GFTFSSF | 51 | SFNMF | 73 | RNDGRS | 102 | YIRNDGRSTSYADSVKG | 142 | TTCVGSGGCIDT |
| H11D6-HC2 | 27 | GFTFSSF | 51 | SFNMF | 73 | RNDGRS | 102 | YIRNDGRSTSYADSVKG | 142 | TTCVGSGGCIDT |
| H11D6-HC1 | 27 | GFTFSSF | 51 | SFNMF | 73 | RNDGRS | 103 | YIRNDGRSTSYAAPVKG | 142 | TTCVGSGGCIDT |
| 10F4 | 28 | GFTFSGY | 52 | GYNMG | 74 | TYGTGSY | 104 | GITYGTGSYTAYGAAVKG | 143 | GGGLNSYGCSGANIDA |
| H10F4-HC4 | 28 | GFTFSGY | 52 | GYNMG | 74 | TYGTGSY | 105 | GITYGTGSYTAYVDSVKG | 143 | GGGLNSYGCSGANIDA |
| H10F4-HC3 | 28 | GFTFSGY | 52 | GYNMG | 74 | TYGTGSY | 106 | GITYGTGSYTAYADSVKG | 143 | GGGLNSYGCSGANIDA |
| H10F4-HC2 | 28 | GFTFSGY | 52 | GYNMG | 74 | TYGTGSY | 106 | GITYGTGSYTAYADSVKG | 143 | GGGLNSYGCSGANIDA |
| H10F4-HC1 | 28 | GFTFSGY | 52 | GYNMG | 74 | TYGTGSY | 107 | GITYGTGSYTAYAAPVKG | 143 | GGGLNSYGCSGANIDA |
| 9A5 | 29 | GFSISDY | 53 | DYGMG | 75 | DHDGRY | 108 | RIDHDGRYTDYGAVVKG | 144 | GGGAASIDT |
| 9E12 | 30 | GFTFSDY | 54 | DYGLG | 76 | NSAGSG | 109 | RINSAGSGTYYGSAVDG | 145 | GGGGASIDG |
| 9H1 | 30 | GFTFSDY | 53 | DYGMG | 77 | NSAGSD | 110 | RINSAGSDTNYGSAVKG | 145 | GGGGASIDG |
| 10H1 | 28 | GFTFSGY | 55 | GYGMG | 77 | NSAGSD | 111 | RINSAGSDTDYGAAVKG | 145 | GGGGASIDG |
| 10E10 | 31 | GFTFSSY | 56 | SYGMG | 78 | NSGSSY | 112 | RINSGGSSYTDYGSAVKG | 145 | GGGGASIDG |
| H10H1-HC4 | 28 | GFTFSGY | 55 | GYGMG | 77 | NSAGSD | 113 | RINSAGSDTDYVDSVKG | 145 | GGGGASIDG |
| H10H1-HC3 | 28 | GFTFSGY | 55 | GYGMG | 77 | NSAGSD | 114 | RINSAGSDTDYADSVKG | 145 | GGGGASIDG |
| H10H1-HC2 | 28 | GFTFSGY | 55 | GYGMG | 77 | NSAGSD | 114 | RINSAGSDTDYADSVKG | 145 | GGGGASIDG |

TABLE 11-continued provides sequences referred to herein.

| | SEQ ID NO | CDR H1 Chothia | SEQ ID NO | CDR H1 Kabat | SEQ ID NO | CDR H2 Chothia | SEQ ID NO | CDR H2 Kabat | SEQ ID NO | CDR H3 |
|---|---|---|---|---|---|---|---|---|---|---|
| H10H1-HC1 | 28 | GFTFSGY | 55 | GYGMG | 77 | NSAGSD | 115 | RINSAGSDTDYAAPVKG | 145 | GGGGASIDG |

TABLE 12 provides sequences referred to herein.

| | SEQ ID NO | CDR L1 | SEQ ID NO | CDR L2 | SEQ ID NO | CDR L3 |
|---|---|---|---|---|---|---|
| trastuzumab | 146 | RASQDVNTAVA | 155 | SASFLYS | 161 | QQHYTTPPT |
| 9A8 | 147 | SGGSSDYG | 156 | SNNQRPS | 162 | ANVDYTDDV |
| 10G5 | 148 | SGGNYDYG | 157 | YNNKRPS | 163 | ANVDSTDDV |
| 11D6 | 149 | SGGNSDYG | 158 | RNNQRPS | 164 | GNVDFTDDV |
| H11D6-LC4 | 149 | SGGNSDYG | 158 | RNNQRPS | 165 | GGFDSSSDAI |
| H11D6-LC3 | 149 | SGGNSDYG | 158 | RNNQRPS | 165 | GGFDSSSDAI |
| H11D6-LC2 | 149 | SGGNSDYG | 158 | RNNQRPS | 165 | GGFDSSSDAI |
| H11D6-LC1 | 149 | SGGNSDYG | 158 | RNNQRPS | 165 | GGFDSSSDAI |
| 10F4 | 150 | SGGGNYFGSYYYG | 159 | NNNNRPS | 166 | GGFDSSTDAI |
| H10F4-LC4 | 150 | SGGGNYFGSYYYG | 159 | NNNNRPS | 166 | GGFDSSTDAI |
| H10F4-LC3 | 150 | SGGGNYFGSYYYG | 159 | NNNNRPS | 166 | GGFDSSTDAI |
| H10F4-LC2 | 150 | SGGGNYFGSYYYG | 159 | NNNNRPS | 166 | GGFDSSTDAI |
| H10F4-LC1 | 150 | SGGGNYFGSYYYG | 159 | NNNNRPS | 166 | GGFDSSTDAI |
| 9A5 | 151 | SGGGNYVGGYYYG | 159 | NNNNRPS | 166 | GGFDSSTDAI |
| 9E12 | 152 | SGGGSYYGSYYYG | 159 | NNNNRPS | 166 | GGFDSSTDAI |
| 9H1 | 152 | SGGGSYYGSYYYG | 159 | NNNNRPS | 166 | GGFDSSTDAI |
| 10H1 | 153 | SGGGNYYGSYYYG | 159 | NNNNRPS | 166 | GGFDSSTDAI |
| 10E10 | 154 | SGGGNYAGSYYYG | 160 | NSNNRPS | 166 | GGFDSSTDAI |
| H10H1-LC4 | 153 | SGGGNYYGSYYYG | 159 | NNNNRPS | 166 | GGFDSSTDAI |
| H10H1-LC3 | 153 | SGGGNYYGSYYYG | 159 | NNNNRPS | 166 | GGFDSSTDAI |
| H10H1-LC2 | 153 | SGGGNYYGSYYYG | 159 | NNNNRPS | 166 | GGFDSSTDAI |
| H10H1-LC1 | 153 | SGGGNYYGSYYYG | 159 | NNNNRPS | 166 | GGFDSSTDAI |

TABLE 13 provides sequences referred to herein.

| | CDR H1 Chothia SEQ ID NO | CDR H1 Kabat SEQ ID NO | CDR H2 Chothia SEQ ID NO | CDR H2 Kabat SEQ ID NO | CDR H3 SEQ ID NO | CDR L1 SEQ ID NO | CDR 12 SEQ ID NO | CDR 13 SEQ ID NO |
|---|---|---|---|---|---|---|---|---|
| 2137-C07 | 5 | 32 | 57 | 79 | 116 | 146 | 155 | 161 |
| 2265-F06 | 6 | 33 | 57 | 79 | 117 | 146 | 155 | 161 |
| 2265-F05 | 7 | 34 | 57 | 79 | 118 | 146 | 155 | 161 |

TABLE 13-continued provides sequences referred to herein.

| | CDR H1 Chothia SEQ ID NO | CDR H1 Kabat SEQ ID NO | CDR H2 Chothia SEQ ID NO | CDR H2 Kabat SEQ ID NO | CDR H3 SEQ ID NO | CDR L1 SEQ ID NO | CDR 12 SEQ ID NO | CDR 13 SEQ ID NO |
|---|---|---|---|---|---|---|---|---|
| 2265-F02 | 8 | 34 | 57 | 79 | 119 | 146 | 155 | 161 |
| 2265-B06 | 9 | 35 | 57 | 79 | 120 | 146 | 155 | 161 |
| 2265-A09 | 10 | 36 | 57 | 79 | 121 | 146 | 155 | 161 |
| 2265-F03 | 11 | 36 | 58 | 80 | 122 | 146 | 155 | 161 |
| 2265-E02 | 12 | 35 | 57 | 79 | 116 | 146 | 155 | 161 |
| 2265-D11 | 13 | 36 | 59 | 81 | 123 | 146 | 155 | 161 |
| 2265-D05 | 13 | 36 | 59 | 81 | 124 | 146 | 155 | 161 |
| 2265-C03 | 14 | 37 | 57 | 79 | 125 | 146 | 155 | 161 |
| 2265-C02 | 15 | 35 | 57 | 79 | 126 | 146 | 155 | 161 |
| 2265-A06 | 16 | 38 | 57 | 79 | 125 | 146 | 155 | 161 |
| 2137-A05 | 17 | 39 | 60 | 82 | 127 | 146 | 155 | 161 |
| 2288-A03 | 17 | 40 | 61 | 83 | 128 | 146 | 155 | 161 |
| 2190-B01 | 18 | 41 | 62 | 84 | 129 | 146 | 155 | 161 |
| 2290-G01 | 19 | 42 | 63 | 85 | 130 | 146 | 155 | 161 |
| 2290-D02 | 19 | 41 | 64 | 86 | 131 | 146 | 155 | 161 |
| 2290-C07 | 20 | 43 | 65 | 87 | 132 | 146 | 155 | 161 |
| 2290-D05 | 21 | 44 | 66 | 88 | 133 | 146 | 155 | 161 |
| 2290-C08 | 22 | 42 | 67 | 89 | 134 | 146 | 155 | 161 |
| 2290-A02 | 23 | 45 | 66 | 90 | 135 | 146 | 155 | 161 |
| 2213-A06 | 18 | 46 | 68 | 91 | 136 | 146 | 155 | 161 |
| 2291-G05 | 24 | 47 | 68 | 92 | 137 | 146 | 155 | 161 |
| 2291-E06 | 19 | 48 | 69 | 93 | 138 | 146 | 155 | 161 |
| 2291-D07 | 25 | 49 | 70 | 94 | 136 | 146 | 155 | 161 |
| 2291-F10 | 26 | 48 | 70 | 95 | 139 | 146 | 155 | 161 |
| 2291-A04 | 18 | 50 | 70 | 96 | 140 | 146 | 155 | 161 |
| 2291-A01 | 26 | 48 | 70 | 97 | 136 | 146 | 155 | 161 |
| 9A8 | 27 | 51 | 71 | 98 | 141 | 147 | 156 | 162 |
| 10g5 | 27 | 51 | 72 | 99 | 142 | 148 | 157 | 163 |
| 11D6 | 27 | 51 | 73 | 100 | 142 | 149 | 158 | 164 |
| H11D6-HC4-LC4 | 27 | 51 | 73 | 101 | 142 | 149 | 158 | 165 |
| H11D6-HC3-LC3 | 27 | 51 | 73 | 102 | 142 | 149 | 158 | 165 |
| H11D6-HC2-LC2 | 27 | 51 | 73 | 102 | 142 | 149 | 158 | 165 |
| H11D6-HC1-LC1 | 27 | 51 | 73 | 103 | 142 | 149 | 158 | 165 |
| 10F4 | 28 | 52 | 74 | 104 | 143 | 150 | 159 | 166 |
| H10F4-HC4-LC4 | 28 | 52 | 74 | 105 | 143 | 150 | 159 | 166 |
| H10F4-HC3-LC3 | 28 | 52 | 74 | 106 | 143 | 150 | 159 | 166 |
| H10F4-HC2-LC2 | 28 | 52 | 74 | 106 | 143 | 150 | 159 | 166 |
| H10F4-HC1-LC1 | 28 | 52 | 74 | 107 | 143 | 150 | 159 | 166 |
| 9A5 | 29 | 53 | 75 | 108 | 144 | 151 | 159 | 166 |
| 9E12 | 30 | 54 | 76 | 109 | 145 | 152 | 159 | 166 |
| 9H1 | 30 | 53 | 77 | 110 | 145 | 152 | 159 | 166 |
| 10H1 | 28 | 55 | 77 | 111 | 145 | 153 | 159 | 166 |
| 10E10 | 31 | 56 | 78 | 112 | 145 | 154 | 160 | 166 |
| H10H1-HC4-LC4 | 28 | 55 | 77 | 113 | 145 | 153 | 159 | 166 |
| H10H1-HC3-LC3 | 28 | 55 | 77 | 114 | 145 | 153 | 159 | 166 |
| H10H1-HC2-LC2 | 28 | 55 | 77 | 114 | 145 | 153 | 159 | 166 |
| H10H1-HC1-LC1 | 28 | 55 | 77 | 115 | 145 | 153 | 159 | 166 |

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

One or more features from any embodiments described herein or in the figures may be combined with one or more features of any other embodiments described herein or in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated antibody of the IgG class that specifically binds to B-cell maturation antigen (BCMA), wherein the antibody comprises a CDR-H1, a CDR-H2, a CDR-H3, a CDR-LI, a CDR-L2, and a CDR-L3, of the $V_H$-$V_L$ (heavy chain variable region-light chain variable region) pair of SEQ ID NO: 170 and 217.

2. The antibody of claim 1 comprising a $V_H$ region of SEQ ID NO: 170, or a variant thereof having 20 or fewer amino acid substitutions, and a $V_L$ region of SEQ ID NO: 217, or a variant thereof having 20 or fewer amino acid substitutions.

3. The antibody of claim 1, wherein the antibody comprises at least one constant region domain selected from SEQ ID NO: 239-242.

4. The antibody of claim 1, wherein the antibody is humanized.

5. The antibody of claim 1, wherein the antibody is aglycosylated.

6. The antibody of claim 1, wherein the antibody is an antibody fragment.

7. The antibody of claim 6, wherein the antibody fragment is selected from an FIT fragment, a Fab fragment, a F(ab')$_2$ fragment, a Fab' fragment, an scFv (sFv) fragment, and an scFv-Fc fragment.

8. The antibody of claim 7, wherein the antibody is an scFv fragment.

9. The antibody of claim 1 that specifically binds to B-cell maturation antigen (BCMA), wherein the antibody comprises:

a V$_H$ comprising: a CDR-H1 comprising one of SEQ ID NO: 8 and 34; a CDR-H2 comprising one of SEQ ID NO: 57 and 79; and a CDR-H3 comprising SEQ ID NO: 119.

10. The antibody of claim 9, wherein the antibody comprises:
(a) a V$_L$ comprising: a CDR-L1 comprising SEQ ID NO: 146; a CDR-L2 comprising SEQ ID NO: 155; and a CDR-L3 comprising SEQ ID NO: 161.

11. The antibody of claim 9, wherein the antibody comprises:
a V$_H$ comprising: a CDR-H1 comprising one of SEQ ID NO: 8 and 34; a CDR-H2 comprising one of SEQ ID NO: 57 and 79; a CDR-H3 comprising SEQ ID NO: 119; a CDR-L1 comprising SEQ ID NO: 146; a CDR-L2 comprising SEQ ID NO: 155; and a CDR-L3 comprising SEQ ID NO: 161.

12. The antibody of claim 9, wherein the antibody has a k$_a$ of about $4.57 \times 10^5$ M$^{-1}$×sec$^{-1}$ to about $7.66 \times 10^5$ M$^{-1}$×sec$^{-1}$ when associating with human BCMA at a temperature of 25° C.

13. A kit comprising an antibody of claim 1, and instructions for use of the antibody.

14. A pharmaceutical composition comprising the antibody of claim 1 and a pharmaceutically acceptable carrier.

15. A method of treating a disease or condition in a subject in need thereof, comprising administering to the subject an effective amount of an antibody of claim 1, or a pharmaceutical composition of claim 14, wherein the disease or condition is a BCMA-expressing cancer.

16. The method of claim 15, the BCMA-expressing cancer is leukemia, lymphoma, multiple myeloma, a plasmacytoid dendritic cell tumor, a B-cell lineage malignancy, or a plasma cell neoplasm, and optionally wherein the lymphoma is diffuse large B-cell lymophoma (DLBCL), a low-grade B-cell lymphoma, Burkitt's lymphoma, a plasmablastic lymphoma, or a follicular lymphoma.

* * * * *